United States Patent
McCall et al.

(10) Patent No.: US 11,459,307 B2
(45) Date of Patent: *Oct. 4, 2022

(54) HETEROCYCLIC COMPOUNDS FOR THE INHIBITION OF PASK

(71) Applicant: BioEnergenix LLC, San Francisco, CA (US)

(72) Inventors: John M. McCall, Boca Grande, FL (US); Donna L. Romero, Chesterfield, MO (US); John McKearn, St. Louis, MO (US); Michael Clare, Skokie, IL (US)

(73) Assignee: BioEnergenix LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/991,726

(22) Filed: Aug. 12, 2020

(65) Prior Publication Data

US 2021/0198216 A1    Jul. 1, 2021

Related U.S. Application Data

(63) Continuation of application No. 15/833,565, filed on Dec. 6, 2017, now Pat. No. 10,781,185, which is a continuation of application No. 14/886,751, filed on Oct. 19, 2015, now Pat. No. 9,868,708, which is a continuation of application No. 14/499,981, filed on Sep. 29, 2014, now Pat. No. 9,193,693, which is a continuation of application No. 13/408,893, filed on Feb. 29, 2012, now Pat. No. 8,916,560, which is a continuation of application No. PCT/US2010/047736, filed on Sep. 2, 2010.

(60) Provisional application No. 61/239,744, filed on Sep. 3, 2009.

(51) Int. Cl.
| | | |
|---|---|---|
| *C07D 241/44* | (2006.01) |
| *A61K 45/06* | (2006.01) |
| *C07D 401/04* | (2006.01) |
| *C07D 401/12* | (2006.01) |
| *C07D 403/04* | (2006.01) |
| *C07D 405/04* | (2006.01) |
| *C07D 409/04* | (2006.01) |
| *C07D 241/54* | (2006.01) |
| *C07D 403/12* | (2006.01) |
| *C07D 405/14* | (2006.01) |
| *C07D 413/04* | (2006.01) |
| *C07D 471/04* | (2006.01) |
| *C07D 401/14* | (2006.01) |
| *C07D 405/12* | (2006.01) |

(52) U.S. Cl.
CPC .......... *C07D 241/44* (2013.01); *A61K 45/06* (2013.01); *C07D 241/54* (2013.01); *C07D 401/04* (2013.01); *C07D 401/12* (2013.01); *C07D 401/14* (2013.01); *C07D 403/04* (2013.01); *C07D 403/12* (2013.01); *C07D 405/04* (2013.01); *C07D 405/12* (2013.01); *C07D 405/14* (2013.01); *C07D 409/04* (2013.01); *C07D 413/04* (2013.01); *C07D 471/04* (2013.01)

(58) Field of Classification Search
None
See application file for complete search history.

(56) References Cited

U.S. PATENT DOCUMENTS

| | | |
|---|---|---|
| 6,245,760 B1 | 6/2001 | He |
| 6,319,679 B1 | 11/2001 | Mcknight |
| 6,331,555 B1 | 12/2001 | Hirth |
| 7,189,724 B2 | 3/2007 | An |
| 8,912,188 B2 | 12/2014 | McCall |
| 8,916,560 B2 | 12/2014 | McCall |
| 8,916,561 B2 | 12/2014 | McCall |
| 9,073,902 B2 | 7/2015 | McCall |
| 9,193,693 B2 | 11/2015 | McCall |
| 9,868,708 B2 | 1/2018 | McCall |
| 10,781,185 B2 | 9/2020 | McCall |
| 2003/0059917 A1 | 3/2003 | McKnight |
| 2003/0207886 A1 | 11/2003 | Pluecker |
| 2004/0034028 A1 | 2/2004 | Guevel |
| 2004/0176426 A1 | 9/2004 | Houze |
| 2005/0101565 A1 | 5/2005 | Dasseux |
| 2006/0122224 A1 | 6/2006 | Bechle |
| 2008/0194803 A1 | 8/2008 | Sinclair |
| 2009/0082356 A1 | 3/2009 | Gaillard |
| 2009/0317359 A1 | 12/2009 | Ramurthy |

(Continued)

FOREIGN PATENT DOCUMENTS

| | | |
|---|---|---|
| CH | 419399 | 8/1966 |
| DE | 1177642 | 9/1964 |

(Continued)

OTHER PUBLICATIONS

Beccalli, E. et al., "v-Triazolines. Part 37. Rearrangement reactions of 5-amino-1-(2-formyl-, -benzoyl-, -cyano-aryl)-?-triazolines: new synthesis of 2-amino- and 2,4-diamino-quinolines and 2,4-diamino-1,7-naphthyridines", J Chem Soc.,12:1359-64, (1996).

(Continued)

*Primary Examiner* — Leslie A. Royds Draper
(74) *Attorney, Agent, or Firm* — Dennis A. Bennett; Brock Levin

(57) ABSTRACT

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

1 Claim, 1 Drawing Sheet

(56) References Cited

U.S. PATENT DOCUMENTS

| | | |
|---|---|---|
| 2012/0225863 A1 | 9/2012 | McCall |
| 2012/0232056 A1 | 9/2012 | McCall |
| 2015/0031679 A1 | 1/2015 | McCall |

FOREIGN PATENT DOCUMENTS

| | | |
|---|---|---|
| JP | 2002534512 A | 10/2002 |
| JP | 2004346016 | 12/2004 |
| JP | 2014500323 A | 1/2014 |
| WO | 1999042463 | 8/1999 |
| WO | 2005007099 | 1/2005 |
| WO | 2005051308 | 6/2005 |
| WO | 2005056547 | 6/2005 |
| WO | 2006076681 | 7/2006 |
| WO | 2006078283 | 7/2006 |
| WO | 2006079021 | 7/2006 |
| WO | 2006091395 | 8/2006 |
| WO | 2007128568 | 11/2007 |
| WO | 2007146747 | 12/2007 |
| WO | 2008148867 | 12/2008 |
| WO | 2010093808 | 8/2010 |
| WO | 2010101230 | 9/2010 |
| WO | 2010143168 | 12/2010 |
| WO | 2010143169 | 12/2010 |
| WO | 2010143170 | 12/2010 |
| WO | 2011028947 | 3/2011 |
| WO | 2011114148 | 9/2011 |
| WO | 2012094462 | 7/2012 |

OTHER PUBLICATIONS

Delamatar, A., "Clinical Use of Hemoglobin A1C to Improve Diabetes Management", Clinical Diabetes, 24(1):6-8, (2006).

Hackam, et al.. Translation of Research Evidence from Animals to Humans, JAMA 296(14), 2006, 1731-1732.

Hao, H-X, et al. 'PAS kinase is required for normal cellular energy balance.' Proceedings of the National Academy of Sciences 104.39 (2007): 15466-15471.

Hui, X, Synthesis and antiprotozoal activity of some new synthetic substituted quinoxalines, Bioorganic & Medicinal Chemistry Letters 16 (2006) 815-820.

International Application No. PCT/US2010/047736; International Preliminary Report on Patentability, dated Mar. 6, 2012; 5 pages.

International Application No. PCT/US2010/047736; International Search Report and Written Opinion of the International Search Authority, dated Jun. 16, 2011; 8 pages.

Jordan V. C, Tamoxifen: A most unlikely pioneering medicine Nature Reviewa: Drug Discovery, 2, 2003, 205.

Lee, B. et al., "Syntheses and Binding Affinities of 6-nitroquipazine Analogues for Serotonin Transporter: Part 3. A Potential 5-HT Transporter Imaging Agent, 3-(3-[18F]fluoropropyl)-6-nitroquipazine", Bioorg Med Chem., 11 (23):4949-58, (2003).

Loriga, Mario et al., Quinoxaline chemistry. Part 4. 2-(R)-Anilinoquinoxalines as nonclassicalantifolate agents. Synthes, Il Farmaco, vol. 50 No. 5, , 1995 pp. 289-301.

Loriga, Mario et al., Quinoxaline chemistry. Part 5. 2-(Substituted benzylamino)quinoxalines as nonclassical antifolate ag, Il Farmaco, vol. 51 No. 8,9 1996 pp. 559-568.

Loriga, Mario et al.. Quinoxaline chemistry. Part 7. Quinoxalines containing 2-(aminobenzoate)and 2-[(aminobenzoyl) gluta, Il Farmaco, vol. 52 No. 3, , 1997 pp. 157-166.

Lundholt, BK, Identification of Akt Pathway Inhibitors Using Redistribution Screening on the FLIPR and the IN Cell 3000 Analyzer, Journal of Biomolecular Screening, 2005, 20-29.

Rong, F, Structure-activity relationship (SAR) studies of quinoxalines as novel HCV NS5B RNA-dependent RNA polymerase inhibitors, Bioorganic & Medicinal Chemistry Letters 17 (2007) 1663-1666.

Sanchez Maya, AB, New naphthylcombretastatins. Modifications on the ethylene bridge, Bioorganic & Medicinal Chemistry 13 (2005) 2097-2107.

U.S. Appl. No. 12/874,967; Application as filed dated Sep. 2, 2010; 283 pages.

U.S. Appl. No. 14/499,981; Examiner Initiated Interview Summary dated Jul. 17, 2015; 1 page.

U.S. Appl. No. 14/499,981; Non-Final Office Action dated Feb. 9, 2015; 16 pages.

U.S. Appl. No. 14/499,981; Notice of Allowance dated Jul. 17, 2015; 10 pages.

U.S. Appl. No. 14/499,981; Notice of Allowance dated Oct. 15, 2015; 6 pages.

U.S. Appl. No. 15/833,565; Final Office Action, dated Oct. 10, 2019; 7 pages.

U.S. Appl. No. 15/833,565; Non-Final Office Action dated Jan. 31, 2019; 34 pages.

U.S. Appl. No. 15/833,565; Notice of Allowance, dated May 13, 2020; pages.

Vitale, Gabriella et al., Quinoxaline chemistry. Part 10. Quinoxaline 10-oxa-analogs of trimetrexate(TMQ) and of 5,8-dideaza, Il Farmaco, vol. 53 No. 2, , 1998 pp. 150-159.

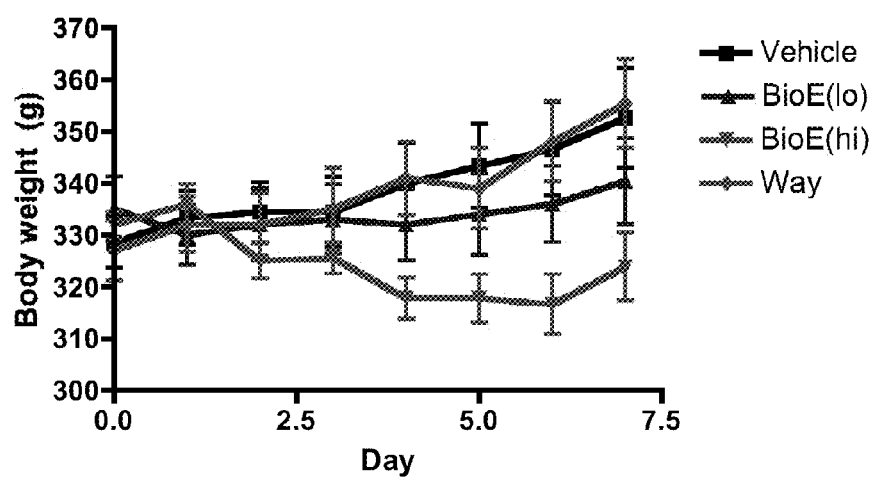

HETEROCYCLIC COMPOUNDS FOR THE INHIBITION OF PASK

This application is a continuation of U.S. patent application Ser. No. 15/833,565, filed Dec. 6, 2017, which is a continuation of U.S. patent application Ser. No. 14/886,751, filed Oct. 19, 2015, now U.S. Pat. No. 9,868,708, which is a continuation of U.S. patent application Ser. No. 14/499,981, filed Sep. 29, 2014, now U.S. Pat. No. 9,193,693, which is a continuation of U.S. patent application Ser. No. 13/408,893, filed Feb. 29, 2012, now U.S. Pat. No. 8,916,560, which is a bypass continuation application claiming priority to parent application no. PCT/US2010/047736, filed Sep. 2, 2010, which claims the benefit of priority of U.S. Provisional Application No. 61/239,744, filed Sep. 3, 2009, the disclosures of which are hereby incorporated by reference as if written herein in their entireties.

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

The regulation of glycogen metabolism is critical for the maintenance of glucose and energy homeostasis in mammals. Glycogen, a large branched polymer of glucose, acts as a reserve of carbon and energy in a variety of organisms. In mammals, the most important stores are found in the liver and skeletal muscle (1). Liver glycogen is required to efficiently buffer blood glucose levels during fasting, whereas muscle glycogen is primarily used locally as a fuel for muscle contraction (2). Dysregulation of glycogen metabolism has been implicated in the development of many diseases, including type 2 diabetes mellitus (3, 4).

The synthesis of glycogen is primarily controlled through regulation of the enzyme glycogen synthase (GYS, various isoforms), which catalyzes bulk glycogen synthesis (5, 6, 7). The muscle isoform of glycogen synthase (GYS1) is inactivated by reversible phosphorylation that occurs at nine distinct sites within the enzyme (8, 9, 10). In the best characterized form of glycogen synthase, the phosphorylation sites are clustered at the N and C termini (14). Glycogen synthase kinase-3 (GSK-3), an insulin-dependent kinase which has long been implicated in the stepwise phosphorylation of four key sites in the C terminus of glycogen synthase including Ser-640 (one of the most important endogenous regulatory phosphorylation sites in mammalian glycogen synthase (15, 32) and Ser-644 (10, 11-13, 24, 25). GSK-3, however, is not the sole kinase that phosphorylates C-terminal regulatory sites; GSK-3-independent mechanisms also exist, since serine-to-alanine substitutions at Ser-7 and Ser-10 block GSK-3-mediated phosphorylation of the important regulatory sites Ser-640 and Ser-644, and phosphorylation at these sites still occurs.

PASK (purine-analog sensitive kinase, PAS kinase) is a PAS domain-containing serine/threonine kinase, and genetic experiments in S. cerevisiae yeast have implicated PASK as a physiological regulator of glycogen synthase and glycogen accumulation (16, 17). As with the entire glycogen synthase regulatory system, PASK is highly conserved from yeast to man. Human PASK (hPASK) phosphorylates glycogen synthase primarily at Ser-640, causing near complete inactivation. It is interesting to note that the exact site of PASK-dependent phosphorylation is similar but not identical in yeast and mammalian glycogen synthase (18, 19); yeast PASK phosphorylates glycogen synthase at the site analogous to Ser-644, four residues C-terminal (18). It appears that the hPASK mid region (residues 444-955) is required for efficient phosphorylation of glycogen synthase in vitro and for interaction with glycogen synthase in cells: an hPASK mutant (Δ955) lacking the noncatalytic N terminus was unable to efficiently phosphorylate glycogen synthase. Since this region is not required for the phosphorylation of generic, nonphysiological substrates, such as histones and synthetic peptides, it has been proposed that the mid region of hPASK is essential for substrate-targeting. A similar substrate region has been discovered in many protein kinases (26-29). Unlike GSK-3, the activity of hPASK has been shown to be independent of insulin and probably regulated instead by a more direct metabolic signal (23).

Genetic and proteomic screens using yeast PASK identified a number of substrates and implicated this kinase in the regulation of carbohydrate metabolism and translation (18). It has previously been shown that yeast PASK phosphorylates glycogen synthase in vitro and that strains lacking the PASK genes (PSK1 and PSK2) had elevated glycogen synthase activity and an approximately 5- to 10-fold accumulation of glycogen relative to wild-type strains, consistent with impaired ability to phosphorylate glycogen synthase in vivo (18). Because glycogen synthesis and translation are two processes tightly regulated in response to nutrient availability and because PAS domains are frequently involved in metabolic sensing, a role for PASK in the cellular response to metabolic status has been proposed. Indeed, it was recently demonstrated that mammalian PASK plays a role in the cellular response to nutrients. The catalytic activity of PASK in pancreatic islet 3-cells is rapidly increased in response to glucose addition, and PASK is required for the glucose-responsive expression of some 3-cell genes, including preproinsulin (23).

PASK catalytic activity is not responsive to glucose alone, however. The interaction between the hPASK midregion and glycogen synthase is regulated by at least two factors. First, the PAS domain of PAS kinase plays a negative role in regulating this interaction. If the PAS domain is deleted or disrupted, hPASK associates more stably with glycogen synthase. PAS domain function is usually controlled by the metabolic status of the host cell, as has been suggested for the PASK PAS domain (23). This observation raises the intriguing possibility that the hPASK-glycogen synthase interaction is regulated by the metabolic status of the cell, thereby enabling an additional layer of metabolic regulation of glycogen synthesis. Second, glycogen negatively regulates the hPASK-glycogen synthase interaction, which would initially seem counterintuitive, since glycogen would thereby stimulate its own continued synthesis. It is possible, however, that this mechanism exists to spatially coordinate the synthesis of glycogen. It is becoming increasingly apparent that glycogen is synthesized in cells in a highly organized spatial pattern (30). Perhaps one function of hPASK is to maintain free, unlocalized glycogen synthase in a phosphorylated, inactive form until it is properly localized to an existing, properly organized glycogen particle. These data strongly suggest that the hPASK midregion plays an important role in targeting hPASK catalytic activity to specific substrates within the cell.

Since hPASK has been recently implicated in glucose-sensing and glucose-responsive transcription, it appears likely that glucose signaling by means of hPASK affects glycogen metabolism in vivo. It is well-established that derangement in glycogen metabolism is one of the hallmarks of both Type 1 and Type 2 diabetes (20) and related conditions (21), including a panoply of life-threatening cardiovascular conditions (22). Using PASK1 mice, it has further been demonstrated that PASK is indeed required for normal insulin secretion by pancreatic β cells, and that PASK deletion results in nearly complete resistance to the phenotypes caused by a high-fat diet, including obesity, insulin resistance and hepatic fat accumulation. Therefore, PASK inhibition would comprise a system for the metabolic control of glucose utilization and storage in mammalian cells, and offer a new method to treat metabolic diseases including but not limited to diabetes and its complications, the metabolic syndrome, insulin resistance, and various cardiovascular conditions.

The hallmarks of cancer, cellular overgrowth and hyperproliferation, require the rapid synthesis of all cellular materials, including protein and lipids. Both of these synthetic processes are controlled, to some extent, by PASK. As a result of these observations, it is possible that inhibition of PASK could be a viable therapeutic strategy for many cancers. By preventing the rapid synthesis of proteins and lipids, such an inhibitor should prevent the rapid and uncontrolled growth and division of cells that characterizes many cancers.

Novel compounds and pharmaceutical compositions, certain of which have been found to inhibit PASK have been discovered, together with methods of synthesizing and using the compounds including methods for the treatment of PASK-mediated diseases in a patient by administering the compounds.

In certain embodiments of the present invention, a compound has structural Formula I:

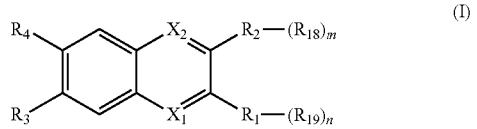

or a pharmaceutically acceptable salt, ester, or prodrug thereof, wherein:
$X_1$ and $X_2$ are each independently chosen from CH and N;
$R_1$ and $R_2$ are each independently chosen from alkyl, cycloalkyl, heterocycloalkyl, aryl, heteroaryl, and $NR_5R_6$, any of which may be optionally substituted, with the proviso that at least one of $R_1$ or $R_2$ is $NR_5R_6$;
$R_3$ is chosen from hydrogen, halogen, trifluoromethyl, hydroxyl, $C_1$-$C_5$ alkyl, and $C_1$-$C_5$ alkoxy, any of which may be optionally substituted;
$R_4$ is chosen from $COOR_7$, $NO_2$, $CONR_8R_9$, $CONR_{10}OR_{11}$, and tetrazolyl;
$R_5$ and $R_6$ are each independently chosen from hydrogen, alkyl, cycloalkyl, heterocycloalkyl, alkenyl, alkynyl, aryl, heteroaryl, aralkyl, and heteroaralkyl, any of which may be optionally substituted; or taken together, $R_5$ and $R_6$ may form a heterocycloalkyl or heteroaryl, either of which may be optionally substituted;
$R_7$, $R_8$, $R_9$, $R_{10}$, and $R_{11}$ are each independently chosen from hydrogen, $C_1$-$C_6$ alkyl, aryl, heteroaryl, aralkyl and heteroaralkyl, any of which may be optionally substituted;
$R_{18}$ and $R_{19}$ are independently chosen from cycloalkyl, heterocycloalkyl, aryl, and heteroaryl, any of which may be optionally substituted; and
m and n are each independently an integer from 0 to 2.

Certain compounds disclosed herein may possess useful PASK modulating activity, and may be used in the treatment or prophylaxis of a disease or condition in which PASK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating PASK. Other embodiments provide methods for treating a PASK-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PASK.

In certain embodiments of the present invention, a compound has structural Formula I:

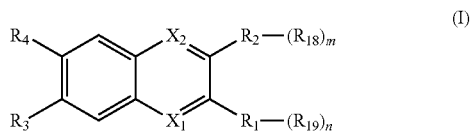

or a pharmaceutically acceptable salt, ester, or prodrug thereof, wherein:
$X_1$ and $X_2$ are each independently chosen from CH and N;
$R_1$ and $R_2$ are each independently chosen from alkyl, cycloalkyl, heterocycloalkyl, aryl, heteroaryl, and $NR_5R_6$, any of which may be optionally substituted, with the proviso that at least one of $R_1$ or $R_2$ is $NR_5R_6$;
$R_3$ is chosen from hydrogen, halogen, trifluoromethyl, hydroxyl, $C_1$-$C_5$ alkyl, and $C_1$-$C_5$ alkoxy, any of which may be optionally substituted;
$R_4$ is chosen from $COOR_7$, $NO_2$, $CONR_8R_9$, $CONR_{10}OR_{11}$, and tetrazolyl;
$R_5$ and $R_6$ are each independently chosen from hydrogen, $C_1$-$C_6$ alkyl, $C_1$-$C_7$ cycloalkyl, $C_1$-$C_7$ heterocycloalkyl, $C_1$-$C_6$ alkenyl, $C_1$-$C_6$ alkynyl, aryl, heteroaryl, aralkyl, and heteroaralkyl, any of which may be optionally substituted; or taken together, $R_5$ and $R_6$ may form a heterocycloalkyl or heteroaryl, either of which may be optionally substituted;
$R_7$, $R_8$, $R_9$, $R_{10}$, and $R_{11}$ are each independently chosen from hydrogen, $C_1$-$C_6$ alkyl, aryl, heteroaryl, aralkyl and heteroaralkyl, any of which may be optionally substituted;
$R_{18}$ and $R_{19}$ are independently chosen from cycloalkyl, heterocycloalkyl, aryl, and heteroaryl, any of which may be optionally substituted; and m and n are each independently an integer from 0 to 2.

In certain embodiments compounds of Formula I are provided wherein $X_1$ and $X_2$ are N.

In certain embodiments compounds of Formula I are provided wherein $R_4$ is $COOR_7$.

In certain embodiments compounds of Formula I are provided wherein
$R_1$ is chosen from alkyl, phenyl and heteroaryl, and has one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy and $OCF_3$; and $R_{12}$, $R_{12a}$ and $R_{12b}$ are independently chosen from hydrogen, $C_1$-$C_6$ alkyl, aryl, heteroaryl, aralkyl and heteroaralkyl, any of which may be optionally substituted.

In certain embodiments compounds of Formula I are provided wherein $R_2$ is chosen from phenyl and heteroaryl and has one or more substituents selected from the following group: hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{13}$, $NHSO_2NHR_{13}$, $NHCOR_{13}$, $NHCONHR_{13}$, $CONHR_{13}$, $CONR_{13a}R_{13b}$, hydroxy and $OCF_3$; and $R_{13}$, $R_{13a}$ and $R_{13b}$ are independently chosen from hydrogen, $C_1$-$C_6$ alkyl, aryl, heteroaryl, aralkyl and heteroaralkyl, any of which may be optionally substituted.

In certain embodiments compounds of Formula I are provided wherein $R_{18}$ and $R_{19}$ are optionally substituted with one or more substituents chosen from hydrogen, halogen, alkoxy, haloalkoxy, alkyl, and amino.

In certain embodiments compounds of Formula I are provided wherein $R_7$ is hydrogen.

In certain embodiments compounds of Formula I are provided wherein m is 0.

In certain embodiments compounds of Formula I are provided wherein n is 0.

In certain embodiments of the present invention, a compound has structural Formula II:

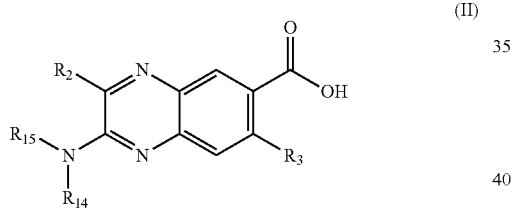

(II)

or a salt, ester or prodrug thereof, wherein:

$R_2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{13}$, $NHSO_2NHR_{13}$, $NHCOR_{13}$, $NHCONHR_{13}$, $CONHR_{13}$, $CONR_{13a}R_{13b}$, hydroxy, and $OCF_3$;

$R_3$ is chosen from hydrogen, hydroxyl, $C_1$-$C_5$ alkyl, and $C_1$-$C_5$ alkoxy, any of which may be optionally substituted;

$R_{14}$ and $R_{15}$ are independently chosen from hydrogen, $C_1$-$C_6$ alkyl, aryl, heteroaryl, aralkyl, and heteroaralkyl, or taken together, $R_{14}$ and $R_{15}$ may form a heterocycloalkyl, any of which may be optionally substituted; and $R_{13}$, $R_{13a}$ and $R_{13b}$ are independently chosen from hydrogen, $C_1$-$C_6$ alkyl, aryl, heteroaryl, aralkyl and heteroaralkyl, any of which may be optionally substituted.

In certain embodiments of the present invention, a compound has structural Formula III:

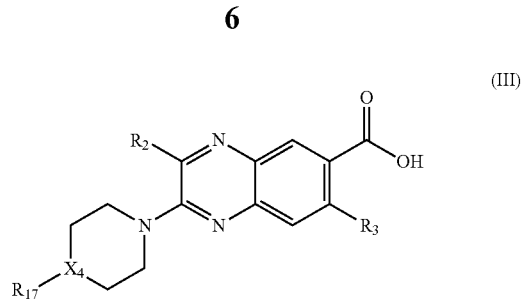

(III)

or a salt, ester or prodrug thereof, wherein:

$R_2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{13}$, $NHSO_2NHR_{13}$, $NHCOR_{13}$, $NHCONHR_{13}$, $CONHR_{13}$, $CONR_{13a}R_{13b}$, hydroxy, and $OCF_3$;

$R_3$ is chosen from hydrogen and hydroxyl;

$R_{13}$, $R_{13a}$ and $R_{13b}$ are independently chosen from hydrogen, $C_1$-$C_6$ alkyl, aryl, heteroaryl, aralkyl and heteroaralkyl, any of which may be optionally substituted;

$R_{17}$ is chosen from null, hydrogen, alkyl, cycloalkyl, heterocycloalkyl, aryl, and heteroaryl, any of which may be optionally substituted; and $X_4$ is chosen from CH, N, and O.

In certain embodiments of the present invention, a compound has structural Formula IV:

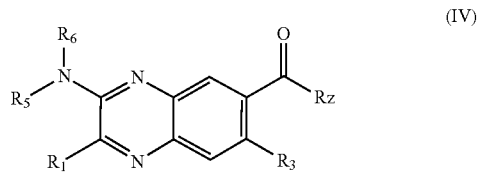

(IV)

or a salt, ester or prodrug thereof, wherein:

Rz is chosen from OH, $NR_8$, $R_9$, $NR_8OR_9$;

$R_1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, $SO_2NHR_{12}$, $CF_3$, and $OCF_3$;

$R_3$ is chosen from hydrogen, hydroxyl, $C_1$-$C_5$ alkyl, and $C_1$-$C_5$ alkoxy, any of which may be optionally substituted;

$R_5$ and $R_6$ are independently chosen from hydrogen, $C_1$-$C_6$ alkyl, $C_1$-$C_7$ cycloalkyl, $C_1$-$C_7$ heterocycloalkyl, $C_1$-$C_6$ alkenyl, $C_1$-$C_6$ alkynyl, aryl, heteroaryl, aralkyl, and heteroaralkyl, or taken together, $R_5$ and $R_6$ may form a heterocycloalkyl or heteroaryl, any of which may be optionally substituted;

$R_8$ and $R_9$ are each independently chosen from hydrogen, $C_1$-$C_6$ alkyl, aryl, heteroaryl, aralkyl and heteroaralkyl, any of which may be optionally substituted; and $R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted.

In certain embodiments compounds of Formula IV are provided wherein
R₁ is phenyl and has one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, NHSO₂R₁₂, NHSO₂NHR₁₂, NHCOR₁₂, NHCONHR₁₂, CONHR₁₂, CONR₁₂ₐR₁₂ᵦ, hydroxy and OCF₃; and
R₁₂, R₁₂ₐ and R₁₂ᵦ are independently chosen from hydrogen, C₁-C₆ alkyl, aryl, heteroaryl, aralkyl and heteroaralkyl, any of which may be optionally substituted.

In certain embodiments compounds of Formula IV are provided wherein R₅ and R₆ are independently C₁-C₆ alkyl.

In certain embodiments compounds of Formula IV are provided wherein R₃ is hydrogen.

In certain embodiments the compound is as recited in Claim 13 wherein R₅ and R₆ are independently C₁-C₆ alkyl.

In certain embodiments of the present invention, a compound has structural Formula V:

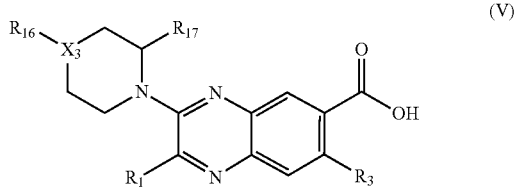

(V)

or a salt, ester or prodrug thereof, wherein:
R₁ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, NHSO₂R₁₂, NHSO₂NHR₁₂, NHCOR₁₂, NHCONHR₁₂, CONHR₂, CONR₁₂ₐR₁₂ᵦ, hydroxy, CF₃, SO₂R₁₂, NHSO₂R₁₂, and OCF₃;
R₃ is chosen from hydrogen and hydroxyl;
R₁₂, R₁₂ₐ and R₁₂ᵦ are independently chosen from hydrogen, C₁-C₆ alkyl, aryl, heteroaryl, aralkyl and heteroaralkyl, any of which may be optionally substituted;
R₁₆ is chosen from null, hydrogen, alkyl, cycloalkyl, heterocycloalkyl, aryl, and heteroaryl any of which may be optionally substituted;
R₁₇ is chosen from hydrogen and C₁-C₆ alkyl; and
X₃ is chosen from CH, N, and O.

In certain embodiments of the present invention, a compound has structural Formula VI:

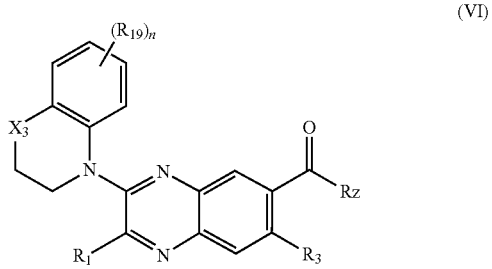

(VI)

or a salt, ester or prodrug thereof, wherein:
Rz is chosen from OH, NR, R₉, NR₈OR₉;

R₁ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, NHSO₂R₁₂, NHSO₂NHR₁₂, NHCOR₂, NHCONHR₂, CONHR₂, CONR₁₂ₐR₁₂ᵦ, hydroxy, and CF₃, SO₂R₁₂, SO₂NHR₁₂, SO₂NR₁₂ₐR₁₂ᵦ, COOH, and OCF₃;
R₃ is chosen from hydrogen and hydroxyl;
R₈ and R₉ are each independently chosen from hydrogen, C₁-C₆ alkyl, aryl, heteroaryl, aralkyl and heteroaralkyl, any of which may be optionally substituted;
R₁₂, R₁₂ₐ and R₁₂ᵦ are independently chosen from hydrogen, C₁-C₆ alkyl, aryl, heteroaryl, aralkyl and heteroaralkyl, any of which may be optionally substituted;
R₁₉ is chosen from null, hydrogen, alkyl, alkoxy, CF₃, OCF₃, COOH, halo, alkenyl, alkynyl, hydroxy, alkyllsulfonyl, cyano, nitro, alkylamino, dialkylamino, NHSO₂R₁₂, NHSO₂NHR₁₂, NHCOR₁₂, NHCONHR₁₂, CONR₁₂ₐR₁₂ᵦ, aryl, and heteroaryl;
n is an integer from 0 to 3; and
X₃ is chosen from CH₂, NR₁₂, S, SO₂, and O.

Further provided is a compound as recited in Claim 1 for use as a medicament.

Further provided is a compound as recited in Claim 1 for use in the manufacture of a medicament for the prevention or treatment of a disease or condition ameliorated by the inhibition of PASK.

Further provided is a compound as recited in Claim 9 for use in the manufacture of a medicament for the prevention or treatment of a disease or condition ameliorated by the inhibition of PASK.

Further provided is a compound chosen from
2-phenyl-3-(4-(4-(trifluoromethyl)phenyl)piperazin-1-yl)quinoxaline-6-carboxylic acid,
2-phenyl-3-(4-(4-(trifluoromethyl)phenyl)piperazin-1-yl)quinoxaline-6-carboxylic acid,
3-(4-(3-chlorophenyl)piperazin-1-yl)-2-phenylquinoxaline-6-carboxylic acid,
3-(4-methylpiperazin-1-yl)-2-phenylquinoxaline-6-carboxylic acid,
2-phenyl-3-(piperazin-1-yl)quinoxaline-6-carboxylic acid,
2-phenyl-3-(4-phenylpiperazin-1-yl)quinoxaline-6-carboxylic acid,
2-phenyl-3-(4-(4-(trifluoromethyl)phenyl)piperidin-1-yl)quinoxaline-6-carboxylic acid,
3-(4-(4-chlorophenyl)piperazin-1-yl)-2-phenylquinoxaline-6-carboxylic acid,
3-(4-(4-methoxyphenyl)piperazin-1-yl)-2-phenylquinoxaline-6-carboxylic acid,
3-(4-(3-chlorophenyl)piperidin-1-yl)-2-phenylquinoxaline-6-carboxylic acid,
3-(4-(4-methoxyphenyl)piperidin-1-yl)-2-phenylquinoxaline-6-carboxylic acid,
2-phenyl-3-(piperidin-1-yl)quinoxaline-6-carboxylic acid,
2-phenyl-3-(4-phenylpiperidin-1-yl)quinoxaline-6-carboxylic acid,
3-(azepan-1-yl)-2-phenylquinoxaline-6-carboxylic acid,
3-(4-(4-chlorophenyl)piperidin-1-yl)-2-phenylquinoxaline-6-carboxylic acid,
3-morpholino-2-phenylquinoxaline-6-carboxylic acid,
3-(4-methyl-1,4-diazepan-1-yl)-2-phenylquinoxaline-6-carboxylic acid,
3-(isopropylamino)-2-phenylquinoxaline-6-carboxylic acid,
2-phenyl-3-(4-(pyrimidin-2-yl)piperazin-1-yl)quinoxaline-6-carboxylic acid, 2-phenyl-3-(4-(5-(trifluoromethyl)pyridin-2-yl)piperazin-1-yl)quinoxaline-6-carboxylic acid,
2-phenyl-3-(4-(quinolin-2-yl)piperazin-1-yl)quinoxaline-6-carboxylic acid,
2-(azepan-1-yl)-3-phenylquinoxaline-6-carboxylic acid,
3-phenyl-2-(piperidin-1-yl)quinoxaline-6-carboxylic acid,
2-(4-(4-chlorophenyl)piperidin-1-yl)-3-(4-fluorophenyl)quinoxaline-6-carboxylic acid,
2-(4-(3-chlorophenyl)piperidin-1-yl)-3-(4-fluorophenyl)quinoxaline-6-carboxylic acid,
3-(4-fluorophenyl)-2-(4-(4-methoxyphenyl)piperidin-1-yl)quinoxaline-6-carboxylic acid,
3-(4-fluorophenyl)-2-(4-(pyridin-2-yl)piperazin-1-yl)quinoxaline-6-carboxylic acid,
2-phenyl-3-(4-(3-(trifluoromethyl)pyridin-2-yl)piperazin-1-yl)quinoxaline-6-carboxylic acid,
3-(4-fluorophenyl)-2-(4-(4-(trifluoromethyl)phenyl)piperidin-1-yl)quinoxaline-6-carboxylic acid,
2,3-bis(4-phenylpiperidin-1-yl)quinoxaline-6-carboxylic acid,
2,3-bis(4-methoxyphenyl)-6-(1H-tetrazol-5-yl)quinoxaline,
3-(4-(N-methylmethan-3-ylsulfonamido)piperidin-1-yl)-2-phenylquinoxaline-6-carboxylic acid,
3-(4-(methylsulfonyl)piperazin-1-yl)-2-phenylquinoxaline-6-carboxylic acid,
3-(4-(N-methylacetamido)piperidin-1-yl)-2-phenylquinoxaline-6-carboxylic acid,
3-(4-(methyl(phenyl)amino)piperidin-1-yl)-2-phenylquinoxaline-6-carboxylic acid,
3-(diethylamino)-2-phenylquinoxaline-6-carboxylic acid,
3-(N-methylmethan-5-ylsulfonamido)-2-phenylquinoxaline-6-carboxylic acid,
3-(3,4-dihydroisoquinolin-2(1H)-yl)-2-phenylquinoxaline-6-carboxylic acid,
3-(3,4-dihydroquinolin-1(2H)-yl)-2-phenylquinoxaline-6-carboxylic acid,
3-(phenethylamino)-2-phenylquinoxaline-6-carboxylic acid,
3-(methyl(phenethyl)amino)-2-phenylquinoxaline-6-carboxylic acid,
3-(isopropyl(methyl)amino)-2-phenylquinoxaline-6-carboxylic acid,
3-(cyclohexylamino)-2-phenylquinoxaline-6-carboxylic acid,
3-(2-methylpiperidin-1-yl)-2-phenylquinoxaline-6-carboxylic acid,
3-(cyclopropyl(methyl)amino)-2-phenylquinoxaline-6-carboxylic acid,
3-(2-methylpyrrolidin-1-yl)-2-phenylquinoxaline-6-carboxylic acid,
3-(sec-butyl(methyl)amino)-2-phenylquinoxaline-6-carboxylic acid,
(R)-3-(3-hydroxypyrrolidin-1-yl)-2-phenylquinoxaline-6-carboxylic acid,
(S)-3-(3-hydroxypyrrolidin-1-yl)-2-phenylquinoxaline-6-carboxylic acid,
(R)-3-(2-(methoxymethyl)pyrrolidin-1-yl)-2-phenylquinoxaline-6-carboxylic acid,
(R)-3-(2-(hydroxymethyl)pyrrolidin-1-yl)-2-phenylquinoxaline-6-carboxylic acid,
(S)-3-(2-(hydroxymethyl)pyrrolidin-1-yl)-2-phenylquinoxaline-6-carboxylic acid,
3-(3-methylmorpholino)-2-phenylquinoxaline-6-carboxylic acid,
(S)-3-(2-methylpyrrolidin-1-yl)-2-phenylquinoxaline-6-carboxylic acid,
(S)-3-(2-methylpyrrolidin-1-yl)-2-phenylquinoxaline-6-carboxylic acid,
2-(4-fluorophenyl)-3-(isopropyl(methyl)amino)quinoxaline-6-carboxylic acid,
3-(isopropyl(methyl)amino)-2-(4-methoxyphenyl)quinoxaline-6-carboxylic acid,
(R)-3-(methyl(1-phenylethyl)amino)-2-phenylquinoxaline-6-carboxylic acid.
(S)-3-(methyl(1-phenylethyl)amino)-2-phenylquinoxaline-6-carboxylic acid,
(R)-3-(sec-butyl(methyl)amino)-2-phenylquinoxaline-6-carboxylic acid,
3-(1H-indol-1-yl)-2-phenylquinoxaline-6-carboxylic acid,
2-(3,4-difluorophenyl)-3-(isopropyl(methyl)amino)quinoxaline-6-carboxylic acid,
2-(4-chlorophenyl)-3-(isopropyl(methyl)amino)quinoxaline-6-carboxylic acid,
(R)-2-phenyl-3-(2-(trifluoromethyl)pyrrolidin-1-yl)quinoxaline-6-carboxylic acid,
3-(6-methoxy-3,4-dihydroquinolin-1(2H)-yl)-2-phenylquinoxaline-6-carboxylic acid,
3-(indolin-1-yl)-2-phenylquinoxaline-6-carboxylic acid,
3-(2,3-dihydrobenzo[b][1,4]oxazin-4-yl)-2-phenylquinoxaline-6-carboxylic acid,
3-(isopropyl(methyl)amino)-2-(3-methoxyphenyl)quinoxaline-6-carboxylic acid,
2-(3-fluorophenyl)-3-(isopropyl(methyl)amino)quinoxaline-6-carboxylic acid,
2-(2-fluorophenyl)-3-(isopropyl(methyl)amino)quinoxaline-6-carboxylic acid,
3-(cyclopentyl(methyl)amino)-2-phenylquinoxaline-6-carboxylic acid,
3-(isopropyl(methyl)amino)-2-(4-methoxyphenyl)quinoxaline-6-carboxylic acid,
(S)-2-(4-fluorophenyl)-3-(2-methylpyrrolidin-1-yl)quinoxaline-6-carboxylic acid,
butyl 2-(4-fluorophenyl)-3-(piperidin-1-yl)quinoxaline-6-carboxylate,
3-(azepan-1-yl)-2-(4-fluorophenyl)quinoxaline-6-carboxylic acid,
2-(benzo[d][1,3]dioxol-5-yl)-3-(isopropyl(methyl)amino)quinoxaline-6-carboxylic acid,
2-(4-fluorophenyl)-3-(3-(methoxymethyl)piperidin-1-yl)quinoxaline-6-carboxylic acid,
3-(3,3-dimethylpiperidin-1-yl)-2-(4-fluorophenyl)quinoxaline-6-carboxylic acid,
2-(4-fluorophenyl)-3-(3-methylpiperidin-1-yl)quinoxaline-6-carboxylic acid,
2-(2,3-dihydrobenzo[b][1,4]dioxin-6-yl)-3-(isopropyl(methyl)amino)quinoxaline-6-carboxylic acid,
3-(isopropyl(methyl)amino)-2-(4-(methylsulfonyl)phenyl)quinoxaline-6-carboxylic acid,
2-(benzo[d][1,3]dioxol-5-yl)-3-((S)-2-methylpyrrolidin-1-yl)quinoxaline-6-carboxylic acid,
2-(1H-indol-5-yl)-3-(isopropyl(methyl)amino)quinoxaline-6-carboxylic acid,
3-(isopropyl(methyl)amino)-2-(4-(trifluoromethoxy)phenyl)quinoxaline-6-carboxylic acid,
2-(4-cyanophenyl)-3-(isopropyl(methyl)amino)quinoxaline-6-carboxylic acid,
3-(isopropyl(methyl)amino)-2-(pyridin-4-yl)quinoxaline-6-carboxylic acid,
2-(H-imidazo[1,2-a]pyridin-6-yl)-3-(isopropyl(methyl)amino)quinoxaline-6-carboxylic acid,
2-(benzofuran-2-yl)-3-(isopropyl(methyl)amino)quinoxaline-6-carboxylic acid, (S)-2-(4-fluorophenyl)-3-(2-methyl-4-(pyridin-2-yl)piperazin-1-yl)quinoxaline-6-carboxylic acid,
(S)-2-(4-fluorophenyl)-3-(2-methylpiperidin-1-yl)quinoxaline-6-carboxylic acid,
3-(cyclopropyl(methyl)amino)-2-(4-fluorophenyl)quinoxaline-6-carboxylic acid,
(R)-2-(4-fluorophenyl)-3-(2-(methoxymethyl)pyrrolidin-1-yl)quinoxaline-6-carboxylic acid,
(S)-3-(2-methyl-4-(pyridin-2-yl)piperazin-1-yl)-2-phenylquinoxaline-6-carboxylic acid,
2-(benzo[d][1,3]dioxol-5-yl)-3-(3,4-dihydroquinolin-1(2H)-yl)quinoxaline-6-carboxylic acid,
3-(octahydroquinolin-1(2H)-yl)-2-phenylquinoxaline-6-carboxylic acid,
3-(isopropyl(methyl)amino)-2-(pyridin-3-yl)quinoxaline-6-carboxylic acid,
2-(furan-2-yl)-3-(isopropyl(methyl)amino)quinoxaline-6-carboxylic acid,
3-(isopropyl(methyl)amino)-2-(quinolin-3-yl)quinoxaline-6-carboxylic acid,
3-(isopropyl(methyl)amino)-2-(4-morpholinophenyl)quinoxaline-6-carboxylic acid,
3-(1,1-dioxidothiomorpholino)-2-(4-fluorophenyl)quinoxaline-6-carboxylic acid,
3-(1,1-dioxidothiomorpholino)-2-phenylquinoxaline-6-carboxylic acid,
2-(4-fluorophenyl)-3-(3-oxopiperazin-1-yl)quinoxaline-6-carboxylic acid,
2-(4-fluorophenyl)-3-(methyl(piperidin-4-yl)amino)quinoxaline-6-carboxylic acid,
2-(4-fluorophenyl)-3-(methyl(tetrahydro-2H-pyran-4-yl)amino)quinoxaline-6-carboxylic acid,
3-(cyclopentyl(methyl)amino)-2-(4-fluorophenyl)quinoxaline-6-carboxylic acid,
3-(isopropyl(methyl)amino)-2-(5-methylthiophen-2-yl)quinoxaline-6-carboxylic acid,
3-(isopropyl(methyl)amino)-2-(thiophen-2-yl)quinoxaline-6-carboxylic acid,
3-(isopropyl(methyl)amino)-2-(6-methoxypyridin-3-yl)quinoxaline-6-carboxylic acid,
2-(furan-2-yl)-3-(isopropyl(methyl)amino)quinoxaline-6-carboxylic acid,
2-(4-fluorophenyl)-3-(4-(N-methylacetamido)piperidin-1-yl)quinoxaline-6-carboxylic acid,
2-(4-fluorophenyl)-3-(4-methyl-3-oxopiperazin-1-yl)quinoxaline-6-carboxylic acid,
3-(4-acetamidopiperidin-1-yl)-2-phenylquinoxaline-6-carboxylic acid,
2-phenyl-3-(2,3,4,5-tetrahydro-1H-benzo[b]azepin-1-yl)quinoxaline-6-carboxylic acid,
2-(4-fluorophenyl)-3-(2,3,4,5-tetrahydro-1H-benzo[b]azepin-1-yl)quinoxaline-6-carboxylic acid,
(S)-3-(sec-butyl(methyl)amino)-2-(4-fluorophenyl)quinoxaline-6-carboxylic acid,
3-(sec-butyl(methyl)amino)-2-(furan-3-yl)quinoxaline-6-carboxylic acid,
3-(isopropyl(methyl)amino)-2-(1H-pyrazol-4-yl)quinoxaline-6-carboxylic acid,
3-(isopropyl(methyl)amino)-2-(6-methoxypyridin-3-yl)quinoxaline-6-carboxylic acid,
2-(1H-indazol-6-yl)-3-(isopropyl(methyl)amino)quinoxaline-6-carboxylic acid,
3-(isopropyl(methyl)amino)-2-(1-methyl-1H-indazol-6-yl)quinoxaline-6-carboxylic acid,
2-(1H-indol-6-yl)-3-(isopropyl(methyl)amino)quinoxaline-6-carboxylic acid,
2-(1-(tert-butoxycarbonyl)-1H-indol-2-yl)-3-(isopropyl(methyl)amino)quinoxaline-6-carboxylic acid,
2-(1H-indol-2-yl)-3-(isopropyl(methyl)amino)quinoxaline-6-carboxylic acid,
2-(1-(tert-butoxycarbonyl)-5-methoxy-1H-indol-2-yl)-3-(isopropyl(methyl)amino)quinoxaline-6-carboxylic acid,
3-(isopropyl(methyl)amino)-2-(5-methoxy-1H-indol-2-yl)quinoxaline-6-carboxylic acid,
2-(5-fluoro-1H-indol-2-yl)-3-(isopropyl(methyl)amino)quinoxaline-6-carboxylic acid,
2-(5-bromopyridin-3-yl)-3-(isopropyl(methyl)amino)quinoxaline-6-carboxylic acid,
2-(1H-indazol-5-yl)-3-(isopropyl(methyl)amino)quinoxaline-6-carboxylic acid,
3-(isopropyl(methyl)amino)-2-(3-(trifluoromethyl)-1H-pyrazol-4-yl)quinoxaline-6-carboxylic acid,
2-(6-(tert-butoxycarbonylamino)pyridin-3-yl)-3-(isopropyl(methyl)amino)quinoxaline-6-carboxylic acid,
2-(5-fluoropyridin-2-yl)-3-(isopropyl(methyl)amino)quinoxaline-6-carboxylic acid,
3-(isopropyl(methyl)amino)-2-(5-(trifluoromethyl)pyridin-2-yl)quinoxaline-6-carboxylic acid,
3-(isopropyl(methyl)amino)-2-(6-(trifluoromethyl)pyridin-3-yl)quinoxaline-6-carboxylic acid,
2-(5-cyanopyridin-2-yl)-3-(isopropyl(methyl)amino)quinoxaline-6-carboxylic acid,
3-(isopropyl(methyl)amino)-2-(6-(pyrrolidin-1-yl)pyridin-3-yl)quinoxaline-6-carboxylic acid,
2-(6-fluoropyridin-3-yl)-3-(isopropyl(methyl)amino)quinoxaline-6-carboxylic acid,
(S)-2-(benzofuran-2-yl)-3-(2-methylpyrrolidin-1-yl)quinoxaline-6-carboxylic acid,
2-(benzofuran-2-yl)-3-(cyclopropyl(methyl)amino)quinoxaline-6-carboxylic acid,
2-(5-fluorobenzofuran-2-yl)-3-(isopropyl(methyl)amino)quinoxaline-6-carboxylic acid,
2-(5-chlorobenzofuran-2-yl)-3-(isopropyl(methyl)amino)quinoxaline-6-carboxylic acid, and
2-(benzofuran-2-yl)-3-(sec-butyl(methyl)amino)quinoxaline-6-carboxylic acid.

Further provided is a pharmaceutical composition comprising a compound as recited above together with a pharmaceutically acceptable carrier.

Further provided is a method of inhibiting PASK comprising contacting PASK with a compound as disclosed above.

Further provided is a method of treatment of a disease comprising the administration of a therapeutically effective amount of a compound as disclosed above to a patient in need thereof.

Further provided is the method as recited above wherein said disease is chosen from cancer and a metabolic disease.

Further provided is the method as recited above wherein said disease is a metabolic disease.

Further provided is the method as recited above wherein said metabolic disease is chosen from metabolic syndrome, diabetes, dyslipidemia, fatty liver disease, non-alcoholic steatohepatitis, obesity, and insulin resistance.

Further provided is the method disclosed above wherein said diabetes is Type II diabetes.

Further provided is the method as disclosed above wherein said dyslipidemia is hyperlipidemia.

Further provided is a method for achieving an effect in a patient comprising the administration of a therapeutically effective amount of a compound as disclosed above to a patient, wherein the effect is selected from the group consisting of reduction of triglycerides, reduction of cholesterol, and reduction of hemoglobin A1c.

Further provided is the method as disclosed above wherein said cholesterol is chosen from LDL and VLDL cholesterol.

Further provided is the method as disclosed above wherein said triglycerides are chosen from plasma triglycerides and liver triglycerides.

Further provided is a method of treatment of a PASK-mediated disease comprising the administration of:
a. a therapeutically effective amount of a compound as disclosed above; and
b. another therapeutic agent.

Not to be bound by any theory or mechanism, the compounds disclosed herein can be used to treat or modulate metabolic disease (including but not limited to diabetes, metabolic disorder, dyslipidemia, fatty liver disease, nonalcoholic steatohepatitis, obesity, and insulin resistance, as well as to reduce triglycerides, cholesterol, and hemoglobin A1c) and cancer.

BRIEF DESCRIPTION OF THE DRAWINGS

FIG. 1 shows change in body weight over time for the Vehicle-, WAY-, and subject compound-treated rats during the in vivo studies.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups. The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 3 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be substituted or quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like. The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, 3,4-methylenedioxyphenyl and the like. The heterocycle groups may be optionally substituted unless specifically prohibited.

The term "hydrazinyl" as used herein, alone or in combination, refers to two amino groups joined by a single bond, i.e., —N—N— and not embodied in a ring.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a $X_3CO-$ group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aralkyl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as $-C(O)N(R)-$ may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein. "PASK inhibitor" as used herein refers to a compound that exhibits an ($IC_{50}$/$EC_{50}$) with respect to PASK activity of no more than about 10 µM and more typically not more than about 5 µM, as measured in the PASK assay described generally hereinbelow. $IC_{50}$ is that concentration of inhibitors which reduces the activity of PASK to half-maximal level. Certain compounds disclosed herein have been discovered to exhibit inhibition against PASK.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002). The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described. Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity. In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of a compound as disclosed herein, and at least one other agent selected from the group comprising:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPAR6 agonist e.g. GI-262570;

b) hypolipidemic agents such as 3-hydroxy-3-methylglutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin n antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) an HDL increasing compound;

f) cholesterol absorption modulator such as etizimibe and KT6-971;

g) Apo-Al analogues and mimetics;

h) thrombin inhibitors such as Ximelagatran;

i) aldosterone inhibitors such as anastrazole, fadrazole, and eplerenone;

j) inhibitors of platelet aggregation such as aspirin, and clopidogrel bisulfate;

k) estrogen, testosterone, a selective estrogen receptor modulator, and a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, and compounds decreasing the protein kinase activity such as a PDGF receptor tyrosine kinase inhibitor such as miatinib; and m) an agent interacting with a 5-HT3 receptor and/or an agent interacting with 5-HT4 receptor such as tegaserod described in the U.S. Pat. No. 5,510,353 as example 13, tegaserod hydrogen maleate, cisapride, and cilansetron.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PASK-mediated disorders in a human or animal subject in need of such treatment comprising administering to said subject an amount of a compound disclosed herein effective to reduce or prevent said disorder in the subject, optionally in combination with at least one additional agent that is known in the art. In a related aspect, certain embodiments provide therapeutic compositions comprising at least one compound disclosed herein in combination with one or more additional agents for the treatment of PASK-mediated disorders.

Recent studies have found that elevated medium glucose concentrations caused post-translational activation of PASK. It has also been demonstrated that PASK activity is required for glucose-stimulated insulin expression, as shown by studies in PASK1 mice. It has also been demonstrated that PASK deletion results in nearly complete resistance to the phenotypes caused by a high-fat diet, including obesity, insulin resistance and hepatic fat accumulation. It appears that PASK inhibition can provide an effective therapeutic strategy for the treatment of diseases, for example Type 2 diabetes, insulin resistance in general, and the metabolic syndrome.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL—less than 40 mg/dL; pro-thrombotic state (e.g. high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men. As described above, insulin resistance can be manifested in several ways, including type 2 diabetes. Type 2 diabetes is the condition most obviously linked to insulin resistance. Compensatory hyperinsulinemia helps maintain normal glucose levels-often for decades, before overt diabetes develops. Eventually the beta cells of the pancreas are unable to overcome insulin resistance through hypersecretion. Glucose levels rise, and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance.

Hyperlipidemia, too, is associated with insulin resistance. The lipid profile of patients with type 2 diabetes includes increased serum very-low-density lipoprotein cholesterol and triglyceride levels and, sometimes, a decreased low-density lipoprotein cholesterol level. Insulin resistance has been found in persons with low levels of high-density lipoprotein. Insulin levels have also been linked to very-low-density lipoprotein synthesis and plasma triglyceride levels.

Accordingly, also disclosed are methods of treating insulin resistance in a subject comprising selecting a subject in need of treatment for insulin resistance; and administering to the subject an effective amount of a compound that inhibits PASK. Specific diseases to be treated by the compounds, compositions, and methods disclosed herein are those mediated at least in part by PASK. Accordingly, disclosed herein are methods: for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; for reducing hemoglobin A1c in a subject; or for treating disease; all comprising the administration of a therapeutic amount of a compound as described herein, to a patient in need thereof. In further embodiments, the disease to be treated may be a metabolic disease. In further embodiments, the metabolic disease may be chosen from: obesity, diabetes melitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be chosen from: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state. In further embodiments, the metabolic disease may be a neurological disease known to be associated with metabolic disease and/or insulin resistance, such as Alzheimer's disease.

Additionally, the PASK modulators disclosed herein may be used to treat proliferative disorders such as cancers. Hematological and non-hematological cancers which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia (CLL), lymphomas, including Hodgkin's lymphoma and non-Hodgkin's lymphoma (low, intermediate, and high grade), malignancies of the brain, head and neck, breast, lung, reproductive tract, upper digestive tract, pancreas, liver, renal, bladder, prostate and colon/rectum.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

REFERENCES CITED

The following is a list of references cited herein which, while not necessarily comprehensive, is provided for the convenience of the reader. All references, patents, and patent applications cited herein are hereby incorporated by reference as if written herein in their entireties. When the teachings of these references contradict the teachings presented expressly herein, the present disclosure controls.

1. Roach, P. J. et al. (2001) in The Endocrine Pancreas and Regulation of Metabolism, eds. Cherrington, A. D. & Jefferson, L. S. (Oxford Univ. Press, New York), pp. 609-647.
2. Bergstrom, J. et al. (1967) Acta Physiol. Scand. 71: 140-150.
3. Cline, G. W. et al. (1994) J. Clin. Invest. 94: 2369-2376.
4. Shulman, G. I. et al. G. (1990) N. Engl. J. Med. 322: 223-228.
5. Cohen, P. (1982) Nature 296: 613-620.
6. Roach, P. J. (1986) in The Enzymes, eds. Boyer, P. D. & Krebs, E. G. (Academic, Orlando, Fla.), Vol. 17: pp. 499-539.
7. Cohen, P. (1986) in The Enzymes, eds. Boyer, P. D. & Krebs, E. G. (Academic, Orlando, Fla.), Vol. 17: pp. 461-497.
8. Friedman, D. L. & Lamer, J. (1963) Biochemistry 128: 669-675.
9. Larner, J. (1990) Adv. Enzymol. Relat. Areas Mol. Biol. 63: 173-231.
10. Roach, P. J. (1990) FASEB J. 4: 2961-2968.
11. Skurat, A. V., et al. (1994) J. Biol. Chem. 269: 25534-25542.
12. Flotow, H. & Roach, P. J. (1989) J. Biol. Chem. 264: 9126-9128.
13. Nakielny, S., Campbell, D. G. & Cohen, P. (1991) Eur. J. Biochem. 199: 713-722.
14. Wilson W A et al., *Proc Natl Acad Sci USA*. 2005 Nov. 15; 102(46):16596-601, FIG. 6

15. Skurat, A. V. & Roach, P. J. (1995) J. Biol. Chem. 270: 12491-12497.
16. Hardy, T. A. & Roach, P. J. (1993) J. Biol. Chem. 268: 23799-23805
17. Francois, J. & Parrou, J. L. (2001) FEMS Microbiol. Rev. 25: 125-145.
18. Rutter, J., Probst, B. L. & McKnight, S. L. (2002) Cell 111: 17-28.
19. Rutter, J et al. (2001) Proc. Natl. Acad. Sci. USA 98: 8991-8996.
20. Roden M, Bernroider E: *Best Pract Res Clin Endocrinol Metab.* 2003 September; 17(3):365-83
21. Van Steenbergen W, Lanckmans S: *Int J Obes Relat Metab Disord.* 1995 September; 19 Suppl 3:S27-36.
22. Arad M et al., *Circ Res.* 2007 Mar. 2; 100(4):474-88
23. da Silva Xavier, G. et al. (2004) Proc. Natl. Acad. Sci. USA 101: 8319-8324.
24. Picton, C. et al. (1982) FEBS Lett. 150: 191-196.
25. DePaoli-Roach, A. A. et al., (1983) J. Biol. Chem. 258: 10702-10709.
26. Elia, A. E. et al. (2003) Science 299: 1228-1231.
27. Gao, T. et al. (1997) Neuron 19: 185-196.
28. Wilson, W. A. et al. (1999) Mol. Cell. Biol. 19: 7020-7030.
29. Yedovitzky, M. et al. (1997) J. Biol. Chem. 272: 1417-1420.
30. Fernandez-Novell, J. M., et al. (2002) FEBS Lett. 531: 222-228.
31. Hao H-X. et al., "PAS kinase is required for normal cellular energy balance," *Proc. Nat. Acad. Sci.* (USA) v104, pp 15466-15471, 2007.
32. Horton J D. et al., "Regulation of sterol regulatory element binding proteins in livers of fasted and refed mice," *Proc. Nat. Acad. Sci.* (USA) v95, pp5987-5992, 1998.
33. Evans M J et al., "A synthetic farnesoid X receptor (FXR) agonist promotes cholesterol lowering in models of dyslipidemia," *Am. J. Physiol. Gastrointest. Liver Physiol.* V296, G543-G552, 2009.
34. Hartman, H B. Et al., "Activation of farnesoid X receptor prevents atherosclerotic lesion formation in $LDLR^{-/-}$ and $apoE^{-/-}$ mice," *J. Lipid Res.*, v50, 1090-1100, 2009.
35. Zhang, S. et al., "Farnesoid X receptor agonist WAY-362450 attenuates liver inflammation and fibrosis in murine model of non-alcoholic steatohepatitis," *J. of Hepatology*, v51, 380-388, 2009.
36. Flatt, B. et al., "Discovery of XL335 (WAY-362450), a Highly Potent, Selective, and Orally Active Agonist of the Farnesoid X Receptor," *J. Med. Chem.*, v52, 904-907, 2009.

General Synthetic Methods for Preparing Compounds

The following schemes can generally be used to practice the present invention.

Scheme I

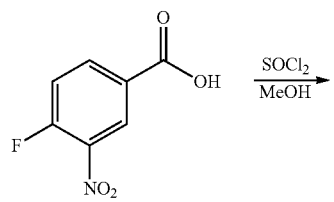

Step 1.
Synthesis of methyl 4-fluoro-3-nitrobenzoate. Thionyl chloride (6.5 g, 54.62 mmol, 1.01 equiv) was added dropwise, with stirring at 0° C., to a methanolic solution (60 mL) of 4-fluoro-3-nitrobenzoic acid (10 g, 54.05 mmol, 1.00 equiv) in a 250-mL round-bottom flask, then stirred for 3 hr at reflux in an oil bath. The resulting mixture was concentrated under vacuum, diluted with 100 mL of EtOAc, and the pH of the solution adjusted to 7-8 with aqueous $NaHCO_3$ (saturated). The solution was then extracted with 6×50 mL of ethyl acetate, the organic layers combined and dried over anhydrous sodium sulfate, and concentrated under vacuum, affording 12.42 g (crude) of methyl 4-fluoro-3-nitrobenzoate as a white solid.

Step 2.
Synthesis of methyl 4-(2-methoxy-2-oxo-1-phenylethylamino)-3-nitrobenzoate. A solution of methyl 2-amino-2-phenylacetate hydrochloride (2.5 g, 12.38 mmol, 1.00 equiv) in DMF (30 mL), methyl 4-fluoro-3-nitrobenzoate (5 g, 25.13 mmol, 2.00 equiv), and DIEA (5 g, 38.76 mmol, 3.13 equiv) was reacted overnight at 30° C. in a 100-mL round-bottom flask. The reaction was then quenched by the addition of 200 mL of water, and the solids were collected by filtration. Purification via silica gel column (petroleum ether/EtOAc (50:1)) yielded 3.82 g (90%) of methyl 4-(2-methoxy-2-oxo-1-phenylethylamino)-3-nitrobenzoate as a yellow solid. LC-MS (ES, m/z): 345 [M+H]$^+$.

Step 3.

Synthesis of methyl 3-oxo-2-phenyl-1,2,3,4-tetrahydroquinoxaline-6-carboxylate. Iron (34.89 g, 623.04 mmol, 5.00 equiv) was added portionwise to a stirred solution of methyl 4-(2-methoxy-2-oxo-1-phenylethylamino)-3-nitrobenzoate (42.87 g, 124.62 mmol, 1.00 equiv) and aqueous NH$_4$Cl (32.1 g, 600.00 mmol, 5.00 equiv, 80 mL) in methanol (300 mL). The resulting solution was heated under reflux for 5 h. Upon cooling, the solids were filtered out. The resulting filtrate was concentrated under vacuum, affording 19.81 g (56%) of methyl 3-oxo-2-phenyl-1,2,3,4-tetrahydroquinoxaline-6-carboxylate as a yellow solid. LC-MS (ES, m/z): 283 [M+H]$^+$.

Step 4.

Synthesis of methyl 3-oxo-2-phenyl-3,4-dihydroquinoxaline-6-carboxylate. DDQ (21.25 g, 93.6 mmol, 2.62 equiv) was added to a stirred solution of methyl 3-oxo-2-phenyl-1,2,3,4-tetrahydroquinoxaline-6-carboxylate (10.07 g, 35.7 mmol, 1.00 equiv) in dioxane (750 mL) and allowed to react, with stirring, overnight at room temperature.

The solids were collected by filtration. The filter cake was washed with 2×500 mL of aqueous K$_2$CO$_3$ (saturated). This resulted in 7.29 g (crude) of methyl 3-oxo-2-phenyl-3,4-dihydroquinoxaline-6-carboxylate as an off-white solid. LC-MS (ES, m/z): 281 [M+H]$^+$.

Step 5.

Synthesis of methyl 3-bromo-2-phenylquinoxaline-6-carboxylate. A solution of methyl 3-oxo-2-phenyl-3,4-dihydroquinoxaline-6-carboxylate (2.1 g, 7.50 mmol, 1.00 equiv) and POBr$_3$ (21.5 g, 74.91 mmol, 10.00 equiv) in CH$_3$CN (120 mL) in a 1000-mL round-bottom flask was heated under reflux overnight in an oil bath. The resulting mixture was concentrated under vacuum; the pH value was adjusted to 7-8 with aqueous sodium bicarbonate (saturated), and the solution extracted with 4×100 mL of dichloromethane. The organic layers were combined, dried over anhydrous sodium sulfate and concentrated under vacuum, giving 2 g (78%) of methyl 3-bromo-2-phenylquinoxaline-6-carboxylate as a white solid. LC-MS (ES, m/z): 343 [M+H]$^+$. $^1$H-NMR (300 MHz, DMSO-d$_6$) 8.620-8.615 (d, J=1.5 Hz, 1H), 8.38-8.35 (q, J=3.3 Hz, 1H), 8.28-8.25 (d, J=8.7 Hz, 1H), 7.85-7.82 (q, J=6 Hz, 2H), 7.60-7.58 (t, J=2.4 Hz, 3H), 3.99 (s, 3H).

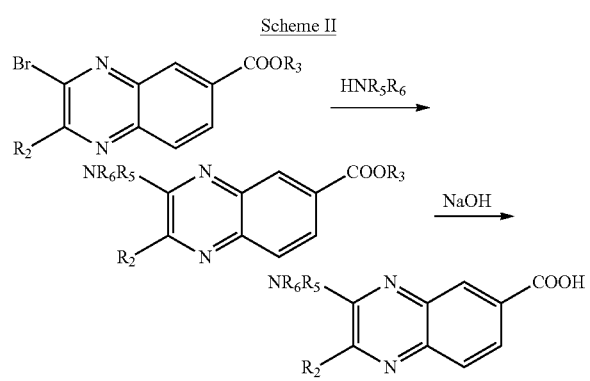

Scheme II

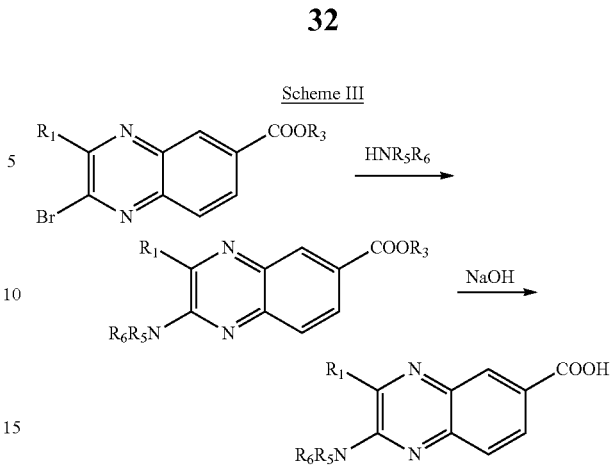

Scheme III wherein R$_1$ and R$_2$ are each independently chosen from alkyl, cycloalkyl, heterocycloalkyl, aryl, heteroaryl, and amino any of which may be optionally substituted; and R$_3$ is chosen from hydrogen and optionally substituted alkyl. The invention is further illustrated by the following examples, which can be made by the methods described herein or by one skilled in the art without undue experimentation, or can be purchased from commercial sources. Throughout the experimental protocols, the following abbreviations may be used. The list below is provided for convenience and is not intended to be inclusive.

| Abbreviation/Acronym | Meaning |
| --- | --- |
| Ar | Aryl |
| Pd$_2$(dba)$_3$ | Tris(dibenzylideneacetone)dipalladium(0) |
| BINAP | 2,2'-bis(diphenylphosphino)-1,1'-binaphthyl |
| NaOt-Bu | Sodium t-Butoxide |
| PE | Petroleum Ether |
| EA | Ethyl Acetate |
| DCM | Dichloromethane |
| TFA | Trifluoroacetic Acid |
| AcOH | Acetic Acid |
| DMF | N,N-Dimethylformamide |
| DIEA | N,N-Diisopropylethylamine |
| MeOH | Methanol |
| THF | Tetrahydrofuran |
| BOC | N-t-butoxycarbonyl |
| Tol | Toluene |
| DMSO | Dimethyl Sulfoxide |
| PCy3 | Tricyclohexylphosphine |
| TLC | Thin Layer Chromatography |
| X-Phos | 2-Dicyclohexylphosphino-2',4',6'-triisopropylbiphenyl |
| DDQ | 2,3-dichloro-5,6-dicyanobenzoquinone |

EXAMPLE 1

2-Phenyl-3-(4-(4-(trifluoromethyl)phenyl)piperazin-1-yl)quinoxaline-6-carboxylic Acid

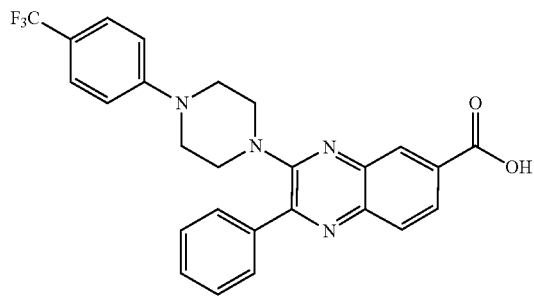 [SMILES: O=C(O)c1ccc2nc(-c3ccccc3)c(N3CCN(c4ccc(C(F)(F)F)cc4)CC3)nc2c1]

Step 1. t-Butyl 4-(4-(trifluoromethyl)phenyl)piperazine-1-carboxylate

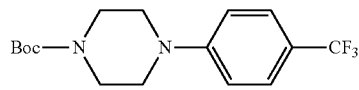

t-Butyl piperazine-1-carboxylate (1.52 g, 8.17 mmol, 2.00 equiv), 1-bromo-4-(trifluoromethyl)benzene (1 g, 4.10 mmol, 1.00 equiv), BINAP (124 mg, 0.40 mmol, 0.10 equiv), Pd$_2$(dba)$_3$ (184 mg, 0.20 mmol, 0.05 equiv), NaOt-Bu (1.2 g, 12.50 mmol, 3.00 equiv), and toluene (15 mL) were combined in a 100-mL round-bottom flask, stirred overnight at 100° C. in an oil bath, and concentrated under vacuum. Purification by silica gel column with PE/EA (50:1) yielded 1.06 g (78%) of t-butyl 4-(4-(trifluoromethyl)phenyl)piperazine-1-carboxylate as a yellow solid.

LC-MS (ES, m/z): 331 [M+H]+

Step 2. 1-(4-(Trifluoromethyl)phenyl)piperazine

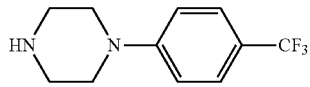

A solution of t-butyl 4-(4-(trifluoromethyl)phenyl)piperazine-1-carboxylate (1.06 g, 3.21 mmol, 1.00 equiv) in dichloromethane (10 mL) and trifluoroacetic acid (6 mL) was placed in a 50-mL round-bottom flask and stirred for 2 h at 30° C. in an oil bath. The pH value of the solution was adjusted to 7-8 with saturated aqueous sodium bicarbonate. The resulting solution was extracted with 4×30 mL of dichloromethane and the organic layers combined and dried over anhydrous sodium sulfate, followed by filtration to remove the solids. The resulting solution was concentrated under vacuum, resulting in 740 mg (crude) of 1-(4-(trifluoromethyl)phenyl)piperazine as a yellow solid.

LC-MS (ES, m/z): 231 [M+H]+

Step 3. Methyl 2-phenyl-3-(4-(4-(trifluoromethyl)phenyl)piperazin-1-yl)quinoxaline-6-carboxylate

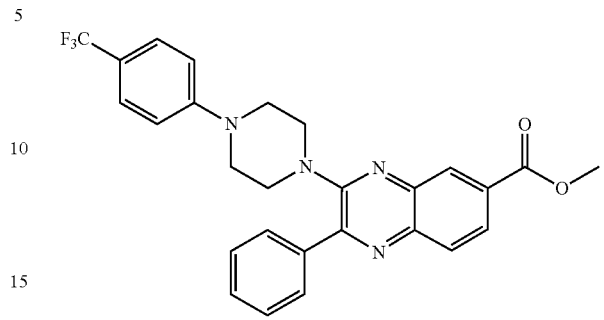

A solution of methyl 3-bromo-2-phenylquinoxaline-6-carboxylate (150 mg, 0.44 mmol, 1.00 equiv) in DMF (8 mL), 1-(4-(trifluoromethyl)phenyl)piperazine (202 mg, 0.88 mmol, 2.00 equiv), DIEA (170.3 mg, 1.32 mmol, 3.00 equiv) were placed in a 20-mL sealed tube and stirred overnight at 100° C. in an oil bath. The reaction was then quenched by the addition of water. The resulting solution was extracted with 4×50 mL of ethyl acetate and the organic layers combined and dried over anhydrous sodium sulfate followed by filtration to remove solids. The resulting mixture was concentrated under vacuum, resulting in 177.4 mg (78%) of methyl 2-phenyl-3-(4-(4-(trifluoromethyl)phenyl)piperazin-1-yl)quinoxaline-6-carboxylate as a yellow solid.

LC-MS (ES, m/z): 492 [M+H]+

Step 4. 2-Phenyl-3-(4-(4-(trifluoromethyl)phenyl)piperazin-1-yl)quinoxaline-6-carboxylic Acid

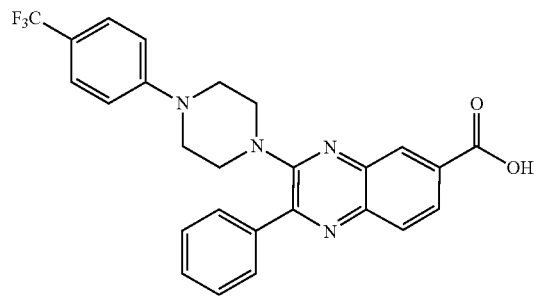 [SMILES: O=C(O)c1ccc2nc(-c3ccccc3)c(N3CCN(c4ccc(C(F)(F)F)cc4)CC3)nc2c1]

A solution of methyl 2-phenyl-3-(4-(4-(trifluoromethyl)phenyl)piperazin-1-yl)quinoxaline-6-carboxylate (137.7 mg, 0.28 mmol, 1.00 equiv) in methanol/THF (1:1) (10 mL), and sodium hydroxide (56 mg, 1.40 mmol, 5.00 equiv) in water (3 mL) were placed in a 50-mL round bottom flask and stirred for 2 h at 40° C. in an oil bath. The mixture was concentrated by vacuum and filtered. The resulting solution was concentrated under vacuum, and the resulting solid washed with DCM/MeOH (5:1) resulting in 45 mg (33%) of 2-phenyl-3-(4-(4-(trifluoromethyl)phenyl)piperazin-1-yl)quinoxaline-6-carboxylic acid as a yellow solid.

LC-MS (ES, m/z): 478 [M+H]+

$^1$H-NMR (300 MHz, DMSO, ppm) δ 13.37 (1H, s), 8.341 (1H, s), 8.029 (4H, s), 7.578, 7.566 (4H, d, J=6.3 Hz), 7.528, 7.499 (2H, d, J=8.7 Hz), 7.101, 7.072 (2H, d, J=8.7 Hz), 3.367 (8H, s).

EXAMPLE 2

2-Phenyl-3-(4-(pyridin-2-yl)piperazin-1-yl)quinoxaline-6-carboxylic Acid

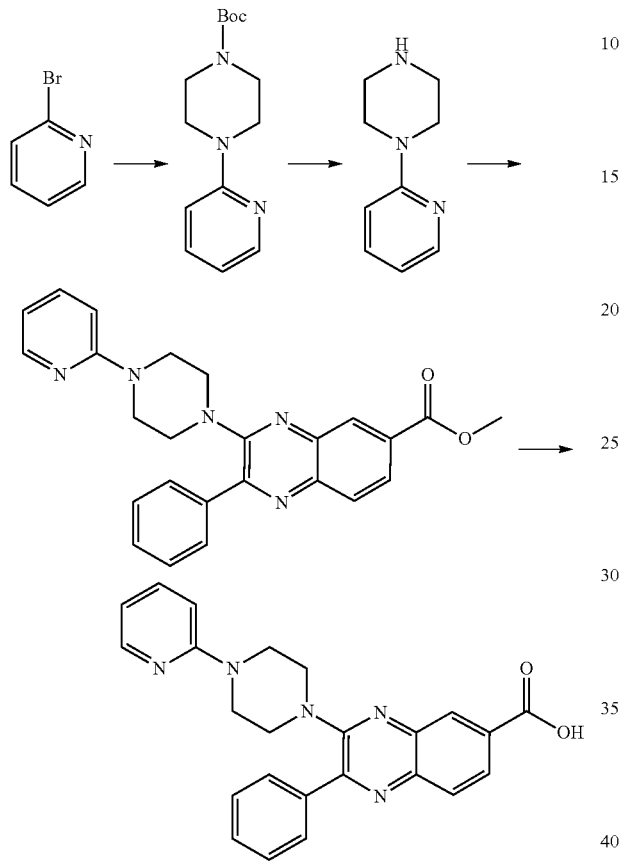

Step 1. t-Butyl 4-(pyridin-2-yl)piperazine-1-carboxylate

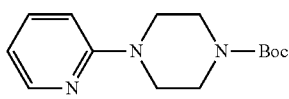

A solution of 2-bromopyridine (1.0 g, 6.33 mmol, 1.00 equiv), t-butyl piperazine-1-carboxylate (2.35 g, 12.62 mmol, 2.00 equiv), BINAP (196 mg, 0.63 mmol, 0.10 equiv), Pd₂(dba)₃ (290 mg, 0.32 mmol, 0.05 equiv), and NaOt-Bu (1.89 g, 18.90 mmol, 3.00 equiv) in toluene (20 mL) was placed in a 100-mL round bottom flask under an inert atmosphere and stirred overnight at 100° C. in an oil bath. The resulting mixture was concentrated under vacuum. Purification by silica gel column (ethyl acetate/petroleum ether (1:40)) yielded 1.4 g (84%) of t-butyl 4-(pyridin-2-yl)piperazine-1-carboxylate as a yellow solid.

Step 2. 1-(Pyridin-2-yl)piperazine

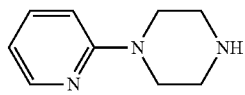 [SMILES: c1ccc(N2CCNCC2)nc1]

A solution of t-butyl 4-(pyridin-2-yl)piperazine-1-carboxylate (500 mg, 1.90 mmol, 1.00 equiv) in DCM/CF₃COOH (10/3 mL) was placed in a 50-mL round bottom flask and stirred for 1 h at 30° C. in an oil bath. The pH value of the solution was adjusted to 9 with aqueous sodium hydroxide (1M), then extracted with 3×10 mL of dichloromethane. The organic layers combined, dried over anhydrous sodium sulfate, and filtered to remove solids. The resulting solution was concentrated under vacuum, yielding 300 mg (97%) of 1-(pyridin-2-yl)piperazine as yellow oil.

Step 3. Methyl 2-phenyl-3-(4-(pyridin-2-yl)piperazin-1-yl)quinoxaline-6-carboxylate

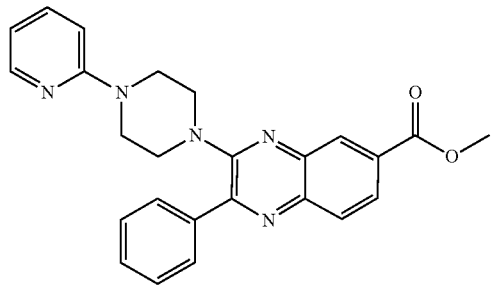 [SMILES: COC(=O)c1ccc2nc(-c3ccccc3)c(N3CCN(c4ccccn4)CC3)nc2c1]

A solution of methyl 3-bromo-2-phenylquinoxaline-6-carboxylate (50 mg, 0.15 mmol, 1.00 equiv), 1-(pyridin-2-yl)piperazine (50 mg, 0.31 mmol, 2.00 equiv), and DIEA (100 mg, 0.78 mmol, 3.00 equiv) in DMF (10 mL) was placed in a 20-mL sealed tube under an inert atmosphere and stirred overnight at 100° C. in an oil bath and then concentrated under vacuum. Purification via silica gel column (ethyl acetate/petroleum ether (1:10)) yielded 68 mg (crude) of methyl 2-phenyl-3-(4-(pyridin-2-yl)piperazin-1-yl)quinoxaline-6-carboxylate as a yellow solid

Step 4. 2-Phenyl-3-(4-(pyridin-2-yl)piperazin-1-yl)quinoxaline-6-carboxylic Acid

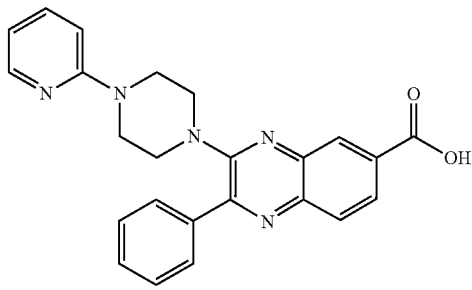 [SMILES: O=C(O)c1ccc2nc(-c3ccccc3)c(N3CCN(c4ccccn4)CC3)nc2c1]

A solution of methyl 2-phenyl-3-(4-(pyridin-2-yl)piperazin-1-yl)quinoxaline-6-carboxylate (100 mg, 0.24 mmol, 1.00 equiv) and sodium hydroxide (47 mg, 1.18 mmol, 5.00 equiv) in methanol (10 mL) was placed in a 100-mL round bottom flask and stirred for 2 h at 50° C. in an oil bath. The pH of the solution was adjusted to 4-5 with hydrochloric acid (1 M), followed by extractions with 3×10 mL of dichloromethane. The organic layers were combined and concentrated under vacuum yielding 80 mg (83%) of 2-phenyl-3-(4-(pyridin-2-yl)piperazin-1-yl)quinoxaline-6-carboxylic acid as a yellow solid.

LC-MS (ES, m/z): 412 [M+H]+

$^1$H-NMR (300 MHz, CDCl$_3$, ppm) δ 8.507 (s, 1H), 7.970-8.159 (m, 5H), 7.574-7.617 (m, 4H), 6.846-6.875 (m, 1H), 6.694-6.733 (m, 1H), 3.540-3.559 (m, 4H), 3.437-3.454 (m, 4H).

EXAMPLE 3

3-(4-(3-Chlorophenyl)piperazin-1-yl)-2-phenylquinoxaline-6-carboxylic Acid

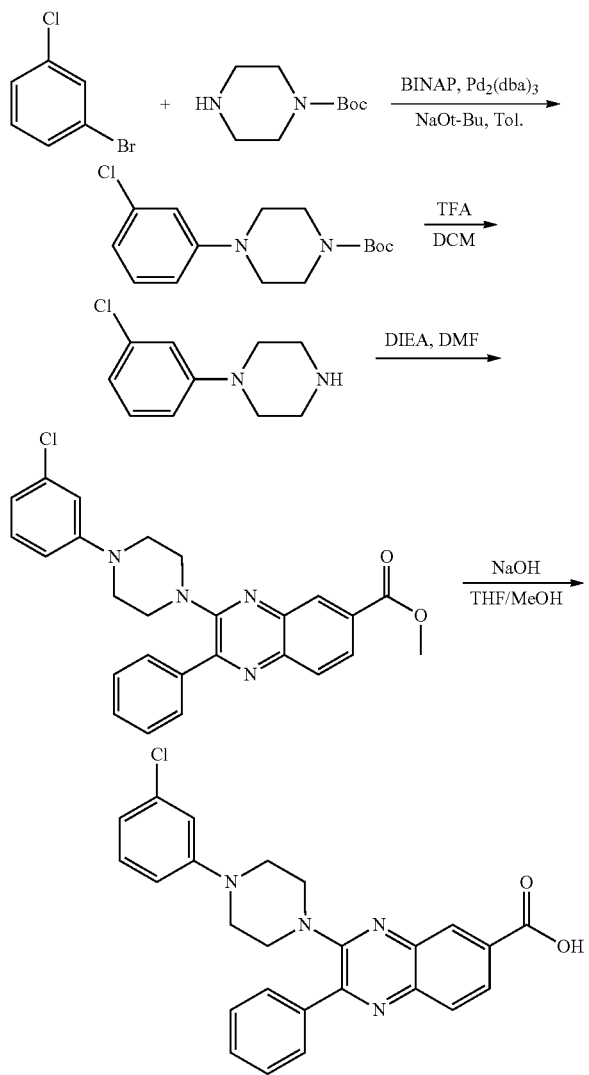

Step 1. t-Butyl 4-(3-chlorophenyl)piperazine-1-carboxylate

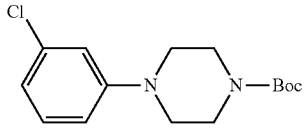 [SMILES: CC(C)(C)OC(=O)N1CCN(c2cccc(Cl)c2)CC1]

A solution of t-butyl piperazine-1-carboxylate (1.96 g, 10.54 mmol, 2.00 equiv), 1-bromo-3-chlorobenzene (1 g, 5.26 mmol, 1.00 equiv), BINAP (330 mg, 0.53 mmol, 0.10 equiv), Pd$_2$(dba)$_3$ (243.8 mg, 0.27 mmol, 0.05 equiv), NaOt-Bu (1.59 g, 16.56 mmol, 3.00 equiv), and toluene (17 mL) was placed in a 100-mL round bottom flask, stirred overnight at 100° C. in an oil bath, and concentrated under vacuum. Purification via silica gel column (PE/EA (50:1)) yielded 1.3 g (83%) of t-butyl 4-(3-chlorophenyl)piperazine-1-carboxylate as a yellow solid.

LC-MS (ES, m/z): 297 [M+H]+

Step 2. 1-(3-Chlorophenyl)piperazine

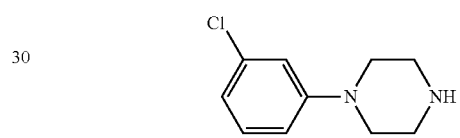

A solution of t-butyl 4-(4-methoxyphenyl)piperazine-1-carboxylate (1.3 g, 4.39 mmol, 1.00 equiv) in dichloromethane (11 mL) and trifluoroacetic acid (6 mL) was placed in a 50-mL round bottom flask and stirred for 3 h at 20° C. in an oil bath. The solution was adjusted to a pH value of 7-8 with a saturated aqueous solution of sodium bicarbonate, and extracted with 6×15 mL of dichloromethane. The organic layers combined and dried over anhydrous sodium sulfate, filtered to remove solids, and concentrated under vacuum yielding 430 mg (50%) of 1-(3-chlorophenyl)piperazine as a yellow solid.

LC-MS (ES, m/z): 197 [M+H]+

Step 3. Methyl 3-(4-(3-chlorophenyl)piperazin-1-yl)-2-phenylquinoxaline-6-carboxylate

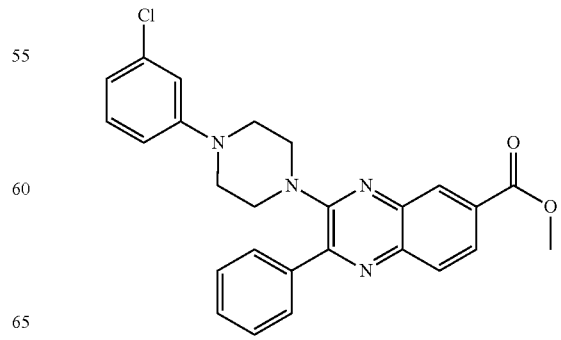

A solution of methyl 3-bromo-2-phenylquinoxaline-6-carboxylate (150 mg, 0.44 mmol, 1.00 equiv), 1-(3-chlorophenyl)piperazine (172.5 mg, 0.88 mmol, 2.00 equiv), and DIEA (170.3 mg, 1.32 mmol, 3.00 equiv) in DMF (4 mL) was placed in a 20-mL sealed tube and stirred overnight at 100° C. in an oil bath, then quenched with water.

The resulting solution was extracted with 6×20 mL of ethyl acetate, the organic layers combined and dried over anhydrous sodium sulfate, filtered to remove solids, and concentrated under vacuum. Purification via silica gel column (PE/EA (30:1)) yielded 186.7 mg (89%) of methyl 3-(4-(3-chlorophenyl)piperazin-1-yl)-2-phenylquinoxaline-6-carboxylate as a yellow solid.

LC-MS (ES, m/z): 459 [M+H]+

Step 4. 3-(4-(3-Chlorophenyl)piperazin-1-yl)-2-phenylquinoxaline-6-carboxylic Acid

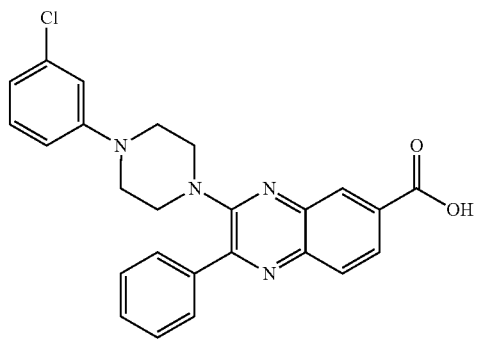

A solution of methyl 3-(4-(3-chlorophenyl)piperazin-1-yl)-2-phenylquinoxaline-6-carboxylate (186.7 mg, 0.41 mmol, 1.00 equiv) and sodium hydroxide (82 mg, 2.05 mmol, 5.00 equiv) in tetrahydrofuran/MeOH (1:1) (25 mL) was placed in a 50-mL round bottom flask, stirred for 8 h at 50° C. in an oil bath, and then concentrated under vacuum. This resulted in 177.7 mg (95%) of 3-(4-(3-chlorophenyl)piperazin-1-yl)-2-phenylquinoxaline-6-carboxylic acid as a yellow solid.

LC-MS (ES, m/z): 445 [M+H]+

¹H-NMR (300 MHz, DMSO, ppm) δ 8.340 (1H, s), 8.029 (4H, s), 7.587, 7.565 (3H, d, J=6.6 Hz), 7.217, 7.190 (1H, d, J=8.1 Hz), 6.972, 6.935 (2H, d, J=11.1 Hz), 6.818, 6.789 (2H, d, J=8.7 Hz), 3.3.246 (4H, s).

EXAMPLE 4

3-(4-Methylpiperazin-1-yl)-2-phenylquinoxaline-6-carboxylic Acid

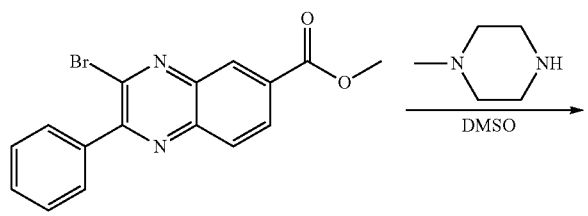

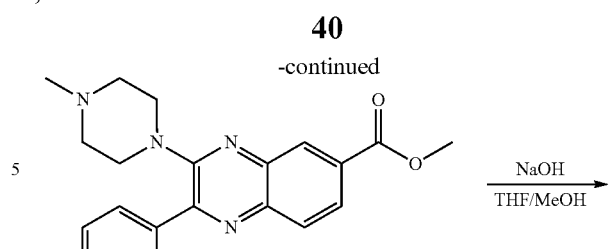

Step 1. Methyl 3-(4-methylpiperazin-1-yl)-2-phenylquinoxaline-6-carboxylate

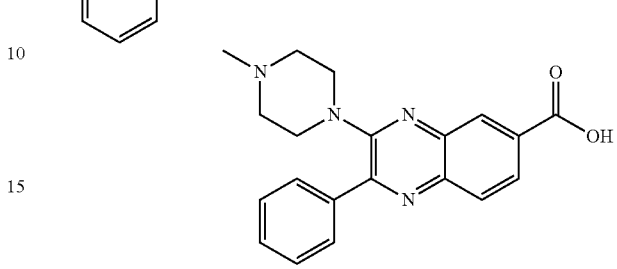

Methyl 3-bromo-2-phenylquinoxaline-6-carboxylate (150 mg, 0.44 mmol, 1.00 equiv) in DMSO (8 mL) and 1-methylpiperazine (90 mg, 0.90 mmol, 2.00 equiv) were stirred for 2 hours at 125° C. in an oil bath in a 20-mL sealed tube. The resulting solution was diluted with 20 ml of DCM/H₂O (1:1), extracted with 4×40 mL of DCM, and the organic layers combined. The mixture was dried over Na₂SO₄, filtered to remove solids, and then concentrated under vacuum, resulting in 200 mg (crude) of methyl 3-(4-methylpiperazin-1-yl)-2-phenylquinoxaline-6-carboxylate as a brown solid.

LC-MS (ES, m/z): 363 [M+H]+

Step 2. 3-(4-Methylpiperazin-1-yl)-2-phenylquinoxaline-6-carboxylic Acid

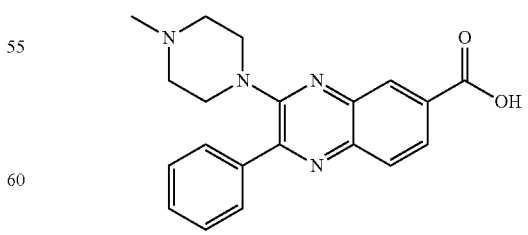

Solutions of methyl 3-(4-methylpiperazin-1-yl)-2-phenylquinoxaline-6-carboxylate (249.7 mg, 0.55 mmol, 1.00 equiv.) in THF/MeOH (1:1) (20 mL) and sodium hydroxide (138 mg, 3.45 mmol, 5.00 equiv) in water (1.5 mL) were placed in a 50-mL round bottom flask, stirred for 3 hrs at 30° C. in an oil bath, concentrated under vacuum, and washed with DCM. This resulted in 90 mg (45%) of 3-(4-methylpiperazin-1-yl)-2-phenylquinoxaline-6-carboxylic acid as a yellow solid.

LC-MS (ES, m/z): 348 [M+H]+

$^1$H-NMR (300 MHz, DMSO, ppm) 8.355 (1H, s), 8.083-8.017 (4H, t), 8.585-8.572 (3H, d, J=3.9 Hz), 3.341-3.202 (8H, d, J=41.7 Hz), 2.737 (3H, s).

EXAMPLE 5

2-Phenyl-3-(piperazin-1-yl)quinoxaline-6-carboxylic Acid

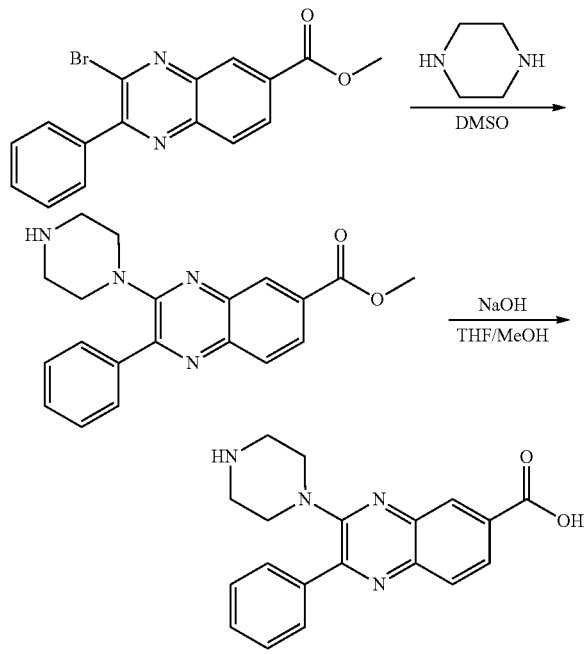

Step 1. Methyl 2-phenyl-3-(piperazin-1-yl)quinoxaline-6-carboxylate

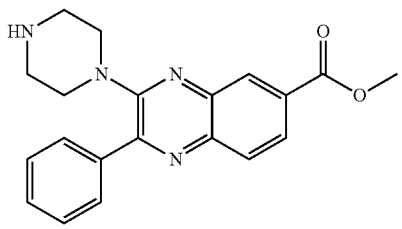 [SMILES: COC(=O)c1ccc2nc(-c3ccccc3)c(N3CCNCC3)nc2c1]

A solution of methyl 3-bromo-2-phenylquinoxaline-6-carboxylate (150 mg, 0.44 mmol, 1.00 equiv) and piperazine (77.4 mg, 0.90 mmol, 2.00 equiv) in DMSO (8 mL) was placed in a 20-mL sealed tube, stirred for 3 hrs at 125° C. in an oil bath, and then quenched by the addition of 50 mL of water. The resulting solution was extracted with 6×50 mL of dichloromethane, the organic layers combined and dried over anhydrous sodium sulfate, and the solution filtered to remove solids. Concentration under vacuum yielded 160 mg (91%) of methyl 2-phenyl-3-(piperazin-1-yl)quinoxaline-6-carboxylate as a yellow solid.

LC-MS (ES, m/z): 348 [M+H]+

Step 2. 2-Phenyl-3-(piperazin-1-yl)quinoxaline-6-carboxylic Acid

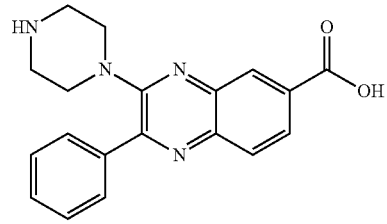 [SMILES: O=C(O)c1ccc2nc(-c3ccccc3)c(N3CCNCC3)nc2c1]

Solutions of methyl 2-phenyl-3-(piperazin-1-yl)quinoxaline-6-carboxylate (160 mg, 0.42 mmol, 1.00 equiv.) in THF/MeOH (1:1) (20 mL) and sodium hydroxide (91.9 mg, 2.30 mmol, 5.00 equiv) in water (1.5 mL) were placed in a 50-mL round bottom flask, stirred for 3 hrs at 30° C. in an oil bath, and then concentrated under vacuum. The residue was dissolved in 4 mL of DMSO and purified via silica gel column (DCM/MeOH (5:1)) yielding 42 mg (29%) of 2-phenyl-3-(piperazin-1-yl)quinoxaline-6-carboxylic acid as a yellow solid.

LC-MS (ES, m/z): 334 [M+H]+

$^1$H-NMR (300 MHz, DMSO, ppm) 8.346-8.342 (1H, d, H=1.2 Hz), 8.150 (1H, s), 8.054-8.007 (3H, q), 7.584-7.560 (3H, t), 3.420 (4H, s), 3.112 (4H, s).

EXAMPLE 6

2-Phenyl-3-(4-phenylpiperazin-1-yl)quinoxaline-6-carboxylic Acid

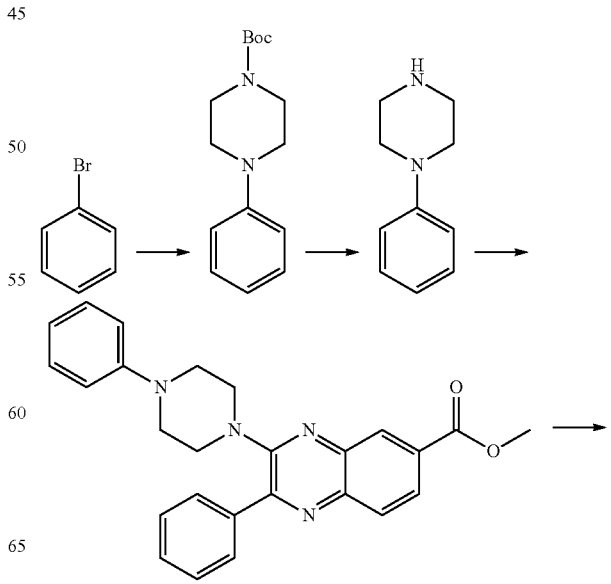

-continued

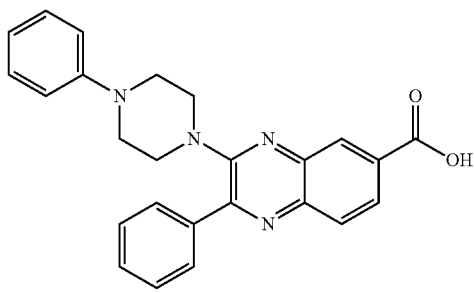

Step 1. t-Butyl 4-phenylpiperazine-1-carboxylate

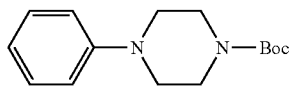 [SMILES: CC(C)(C)OC(=O)N1CCN(c2ccccc2)CC1]

A solution of 1-bromobenzene (1 g, 6.37 mmol, 1.00 equiv), t-butyl piperazine-1-carboxylate (2.35 g, 12.62 mmol, 2.00 equiv), BINAP (196 mg, 0.63 mmol, 0.10 equiv), Pd$_2$(dba)$_3$ (290 mg, 0.32 mmol, 0.05 equiv), and NaOt-Bu (1.89 g, 18.90 mmol, 3.00 equiv) in toluene (20 mL) was placed in a 100-mL 3-necked round bottom flask and stirred overnight at 100° C. in an oil bath under an inert atmosphere. The resulting mixture was concentrated under vacuum and purified via silica gel column (ethyl acetate/petroleum ether (1:40)) yielding 1.3 g (78%) of t-butyl 4-phenylpiperazine-1-carboxylate as a yellow solid.

Step 2. 1-Phenylpiperazine

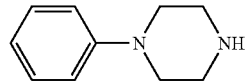 [SMILES: c1ccc(N2CCNCC2)cc1]

A solution of t-butyl 4-phenylpiperazine-1-carboxylate (500 mg, 1.91 mmol, 1.00 equiv) in DCM/CF$_3$COOH (10/3 mL) was placed in a 50-mL round bottom flask and stirred for 1 h at 30° C. in an oil bath. The pH value of the solution was adjusted to 9 with aqueous sodium hydroxide (1 M), and the solution was extracted with 3×10 mL of dichloromethane, the organic layers combined and dried over anhydrous sodium sulfate. Solids were removed via filtration, and the resulting solution concentrated under vacuum yielding 300 mg (97%) of 1-phenylpiperazine as yellow oil.

Step 3. Methyl 2-phenyl-3-(4-phenylpiperazin-1-yl)quinoxaline-6-carboxylate

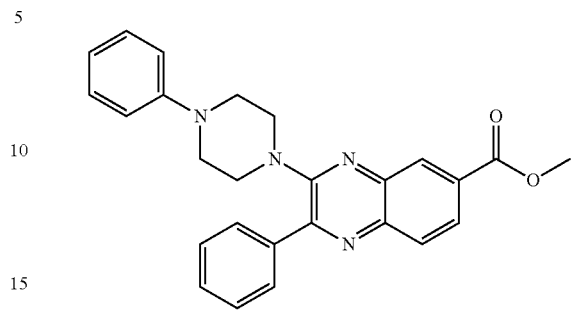

To a solution of methyl 3-bromo-2-phenylquinoxaline-6-carboxylate (50 mg, 0.15 mmol, 1.00 equiv) in DMF (10 mL) was added 1-phenylpiperazine (50 mg, 0.31 mmol, 2.00 equiv) and DIEA (100 mg, 0.78 mmol, 5.3 equiv). The resulting solution was placed in a 20-mL sealed tube, stirred overnight at 100° C. in an oil bath, then concentrated under vacuum. Purification via silica gel column (ethyl acetate/petroleum ether (1:10)) yielded 70 mg (crude) of methyl 2-phenyl-3-(4-phenylpiperazin-1-yl)quinoxaline-6-carboxylate as a yellow solid.

Step 4. 2-Phenyl-3-(4-phenylpiperazin-1-yl)quinoxaline-6-carboxylic Acid

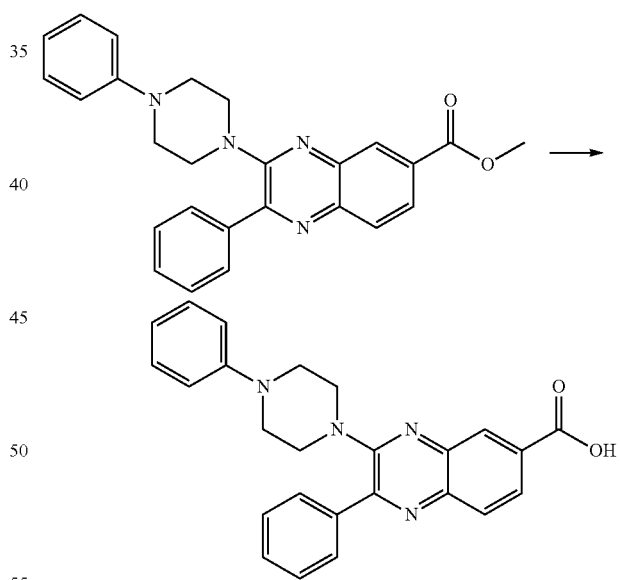

A solution of methyl 2-phenyl-3-(4-phenylpiperazin-1-yl)quinoxaline-6-carboxylate (100 mg, 0.24 mmol, 1.00 equiv) and sodium hydroxide (47 mg, 1.18 mmol, 5.00 equiv) in methanol (10 mL) was placed in a 100-mL round bottom flask and stirred for 2 h at 50° C. in an oil bath. The pH value of the solution was adjusted to 4-5 with hydrochloric acid (1 M). The resulting solution was extracted with 3×10 mL of dichloromethane, and the organic layers combined and concentrated under vacuum, yielding 70 mg (72%) of 2-phenyl-3-(4-phenylpiperazin-1-yl)quinoxaline-6-carboxylic acid as a yellow solid.

LC-MS (ES, m/z): 411 [M+H]+

¹H-NMR (300 MHz, CDCl₃, ppm) δ 8.472 (s, 1H), 8.118-8.147 (m, 1H), 8.009-8.041 (m, 2H), 7.923-7.952 (m, 1H), 7.536-7.596 (m, 3H), 7.218-7.271 (m, 2H), 6.961-6.987 (m, 2H), 6.830-6.879 (m, 1H), 3.434-3.466 (m, 4H), 3.170-3.202 (m, 4H).

EXAMPLE 7

2-Phenyl-3-(4-(4-(trifluoromethyl)phenyl)piperidin-1-yl)quinoxaline-6-carboxylic Acid

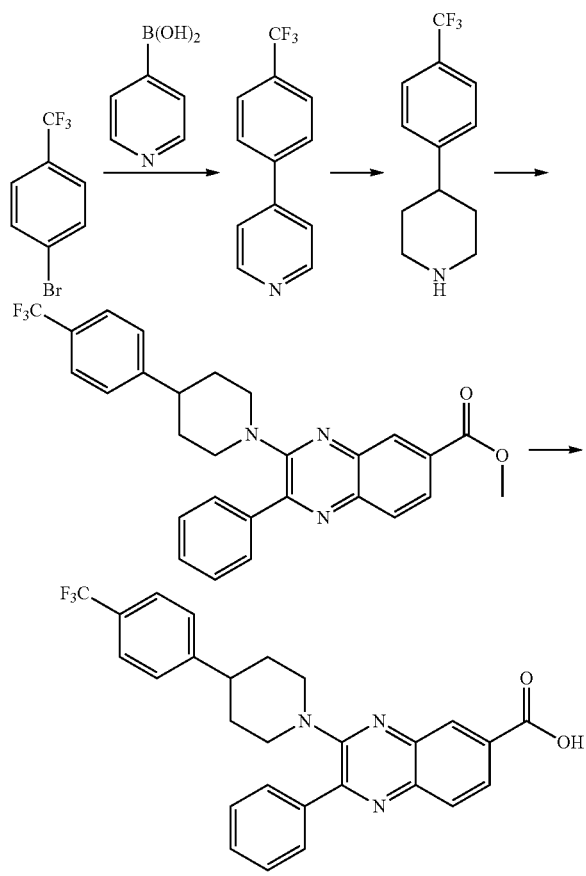

Step 1. 4-(4-(Trifluoromethyl)phenyl)pyridine.

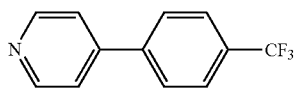

A solution of 1-bromo-4-(trifluoromethyl)benzene (1.0 g, 4.44 mmol, 1.00 equiv), pyridin-4-ylboronic acid (820 mg, 6.67 mmol, 1.50 equiv), PCy₃ (156 mg, 0.56 mmol, 0.14 equiv), Pd₂(dba)₃ (220 mg, 0.24 mmol, 0.06 equiv), and K₃PO₄ (2.5 g, 11.79 mmol, 3.00 equiv) in 1,4-dioxane (10 mL) was placed in a 20-mL sealed tube under inert atmosphere stirred overnight at 100° C. in an oil bath, and then concentrated under vacuum. Purification via silica gel column (ethyl acetate/petroleum ether (1:20)) yielded 1.2 g (crude) of 4-(4-(trifluoromethyl)phenyl)pyridine as a yellow solid.

Step 2. 4-(4-(Trifluoromethyl)phenyl)piperidine

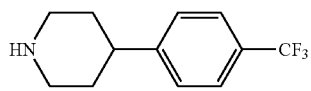

A suspension of 4-(4-(trifluoromethyl)phenyl)pyridine (500 mg, 2.24 mmol, 1.00 equiv), CF₃COOH (1.27 g, 11.14 mmol, 5.00 equiv), and palladium carbon (100 mg, 5%) in methanol (50 mL) was hydrogenated overnight under an atmosphere of H2(g) at 30° C. in an oil bath. The reaction mixture was filtered and washed with methanol and concentrated in vacuo. The pH value of the solution was adjusted to 8-9 with aqueous sodium hydroxide (1 M). The resulting solution was extracted with 3×20 mL of dichloromethane and the organic layers combined and concentrated under vacuum, yielding 350 mg (68%) of 4-(4-(trifluoromethyl)phenyl)piperidine as brown oil. LC-MS (ES, m/z) [M+H]⁺: 230

Step 3. Methyl 2-phenyl-3-(4-(4-(trifluoromethyl)phenyl)piperidin-1-yl)quinoxaline-6-carboxylate

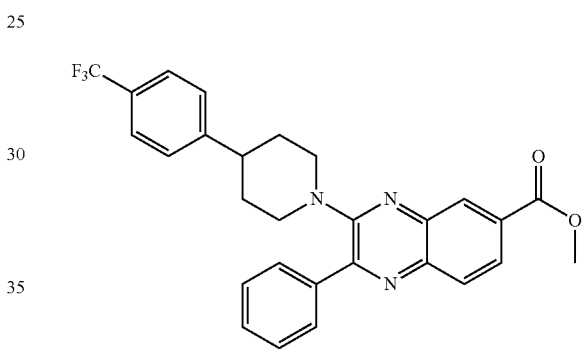

A solution of 4-(4-(trifluoromethyl)phenyl)piperidine (200 mg, 0.87 mmol, 2.00 equiv), methyl 3-bromo-2-phenylquinoxaline-6-carboxylate (150 mg, 0.44 mmol, 1.00 equiv), and DIEA (169 mg, 1.31 mmol, 3.00 equiv) in DMF (10 mL) was placed in a 20-mL sealed tube and stirred overnight at 100° C. in an oil bath. The resulting mixture was concentrated under vacuum and purified via silica gel column (ethyl acetate/petroleum ether (1:20)), yielding 180 mg (84%) of methyl 2-phenyl-3-(4-(4-(trifluoromethyl)phenyl)piperidin-1-yl)quinoxaline-6-carboxylate as a yellow solid.

Step 4. 2-Phenyl-3-(4-(4-(trifluoromethyl)phenyl)piperidin-1-yl)quinoxaline-6-carboxylic Acid

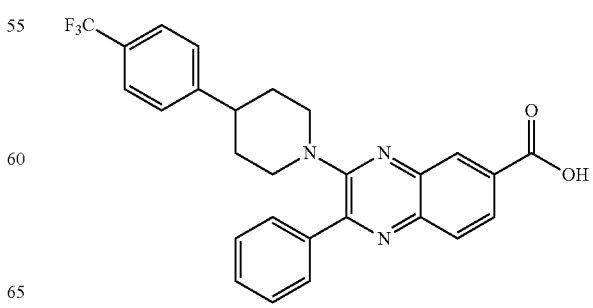

A solution of methyl 2-phenyl-3-(4-(4-(trifluoromethyl)phenyl)piperidin-1-yl)quinoxaline-6-carboxylate (50 mg, 0.10 mmol, 1.00 equiv) and sodium hydroxide (20 mg, 0.50 mmol, 5.00 equiv) in methanol (10 mL) was placed in a 50-mL round bottom flask and stirred for 2 h at 50° C. in an oil bath. The pH value of the solution was adjusted to 4-5 with aqueous sodium hydroxide (1 M). The resulting solution was extracted with 3×10 mL of dichloromethane, and the organic layers combined, concentrated under vacuum, and purified by prep-TLC (DCM:CH$_3$OH 10:1) yielding 25 mg (51%) of 2-phenyl-3-(4-(4-(trifluoromethyl)phenyl)piperidin-1-yl)quinoxaline-6-carboxylic acid as a white solid.

LC-MS (ES, m/z): 478 [M+H]+

$^1$H-NMR (300 MHz, CDCl$_3$, ppm) δ 8.319 (s, 1H), 7.964-8.056 (m, 4H), 7.496-7.688 (m, 7H), 3.862-3.906 (m, 2H), 2.862-2.934 (m, 4H), 1.770 (m, 3H).

EXAMPLE 8

3-(4-(4-Chlorophenyl)piperazin-1-yl)-2-phenylquinoxaline-6-carboxylic Acid

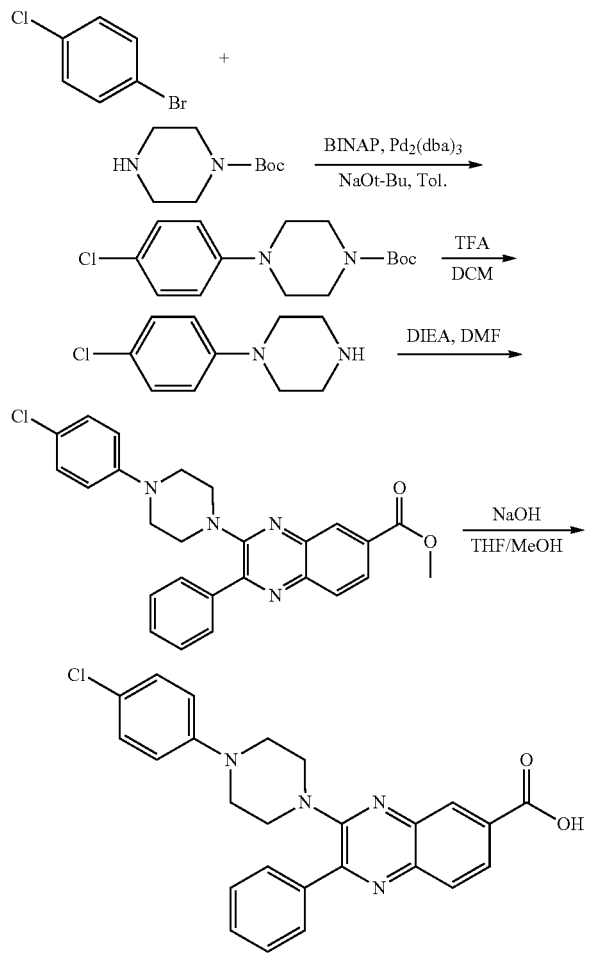

Step 1. t-Butyl 4-(4-chlorophenyl)piperazine-1-carboxylate

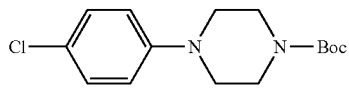

A suspension of 1-bromo-4-chlorobenzene (500 mg, 2.63 mmol, 1.00 equiv), t-butyl piperazine-1-carboxylate (725 mg, 3.90 mmol, 1.50 equiv), BINAP (48.6 mg, 0.08 mmol, 0.03 equiv), Pd$_2$(dba)$_3$ (23.9 mg, 0.03 mmol, 0.01 equiv), and NaOt-Bu (780 mg, 8.12 mmol, 3.00 equiv) in toluene (20 mL) was placed in a 50-mL round bottom flask, stirred overnight at 100° C. in an oil bath, then concentrated under vacuum. Purification via silica gel column (PE/EA (50:1)) yielded 360.6 mg (46%) of t-butyl 4-(4-chlorophenyl)piperazine-1-carboxylate as a yellow solid.

LC-MS (ES, m/z): 297 [M+H]+

Step 2. 1-(4-Chlorophenyl)piperazine

Trifluoroacetic acid (3 mL) was added dropwise with stirring at 0° C. to a solution of t-butyl 4-(4-chlorophenyl)piperazine-1-carboxylate (360.6 mg, 1.21 mmol, 1.00 equiv) in dichloromethane (12 mL). The resulting solution was stirred for 3 h at 20° C. in an oil bath. The pH value of the solution was adjusted to 7-8 with a saturated solution of sodium bicarbonate. The resulting solution was extracted with 6×20 mL of dichloromethane, the organic layers combined and dried over anhydrous sodium sulfate and concentrated under vacuum. This resulted in 264.5 mg (102%) of 1-(4-chlorophenyl)piperazine as a yellow solid.

LC-MS (ES, m/z): 197 [M+H]+

Step 3. Methyl 3-(4-(4-chlorophenyl)piperazin-1-yl)-2-phenylquinoxaline-6-carboxylate

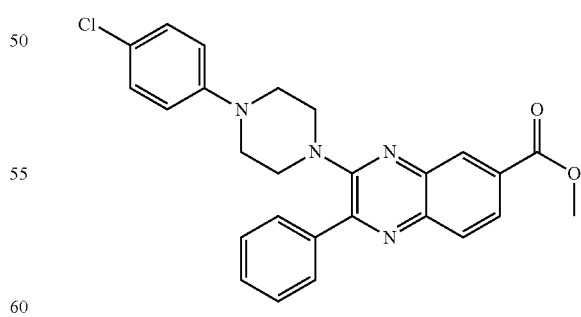

A solution of methyl 3-bromo-2-phenylquinoxaline-6-carboxylate (150 mg, 0.44 mmol, 1.00 equiv), 1-(4-chlorophenyl)piperazine (172.5 mg, 0.88 mmol, 5.00 equiv), and DIEA (170.3 mg, 1.32 mmol, 3.00 equiv) in DMF (4 mL) was placed in a 8-mL sealed tube, stirred overnight at 100° C. in an oil bath, then concentrated under vacuum. Purification via silica gel column (ethyl acetate/petroleum ether (1:50)) afforded 153.4 mg (69%) of methyl 3-(4-(4-chlorophenyl)piperazin-1-yl)-2-phenylquinoxaline-6-carboxylate as a yellow solid.

LC-MS (ES, m/z): 459 [M+H]+

Step 4. 3-(4-(4-Chlorophenyl)piperazin-1-yl)-2-phenylquinoxaline-6-carboxylic Acid

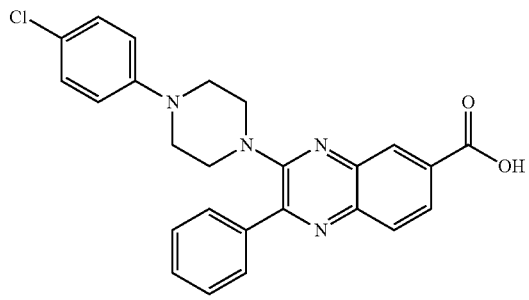 [SMILES: O=C(O)c1ccc2nc(-c3ccccc3)c(N3CCN(c4ccc(Cl)cc4)CC3)nc2c1]

A solution of methyl 3-(4-(4-chlorophenyl)piperazin-1-yl)-2-phenylquinoxaline-6-carboxylate (153.4 mg, 0.33 mmol, 1.00 equiv) and sodium hydroxide (66 mg, 1.65 mmol, 5.00 equiv) in tetrahydrofuran/MeOH (1:1) (12 mL) was placed in a 50-mL round bottom flask and stirred for 5 h at 50° C. in an oil bath. The pH value of the solution was adjusted to 3-4 with 1N hydrochloric acid, then concentrated under vacuum. The resulting solid was washed with methanol affording 47 mg (31%) of 3-(4-(4-chlorophenyl)piperazin-1-yl)-2-phenylquinoxaline-6-carboxylic acid as a yellow solid.

LC-MS (ES, m/z): 445 [M+H]+

$^1$H-NMR (300 MHz, DMSO, ppm) δ 13.305 (1H, s), 8.342 (1H, s), 8.031 (4H, s), 7.585, 7.566 (3H, d, J=5.7 Hz), 7.256, 7.228 (2H, d, J=8.4 Hz), 6.984, 6.956 (2H, d, J=8.4 Hz), 3.359 (4H, s), 3.204 (4H, s).

EXAMPLE 9

3-(4-(4-Methoxyphenyl)piperazin-1-yl)-2-phenylquinoxaline-6-carboxylic Acid

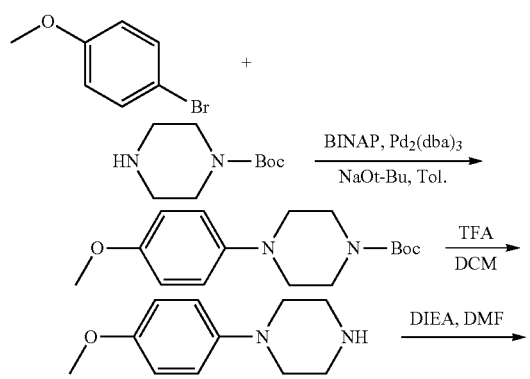

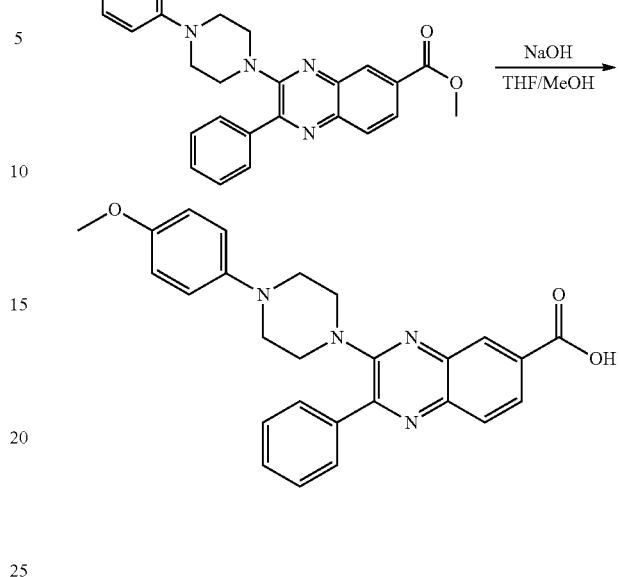

Step 1. t-Butyl 4-(4-methoxyphenyl)piperazine-1-carboxylate

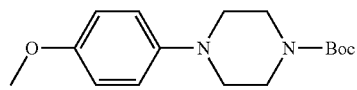 [SMILES: COc1ccc(N2CCN(C(=O)OC(C)(C)C)CC2)cc1]

A suspension of t-butyl piperazine-1-carboxylate (2 g, 10.75 mmol, 2.00 equiv), 1-bromo-4-methoxybenzene (1 g, 5.38 mmol, 1.00 equiv), X-phos (257.2 mg, 0.54 mmol, 0.10 equiv), Pd$_2$(dba)$_3$ (248.4 mg, 0.27 mmol, 0.05 equiv), and NaOt-Bu (1.62 g, 16.88 mmol, 3.00 equiv) in toluene (15 mL) was placed in a 100-mL round bottom flask, stirred overnight at 100° C. in an oil bath, then concentrated under vacuum. Purification via silica gel column (PE/EA (50:1)) yielded 1.412 g (81%) of t-butyl 4-(4-methoxyphenyl)piperazine-1-carboxylate as a yellow solid.

LC-MS (ES, m/z): 293 [M+H]+

Step 2. 1-(4-Methoxyphenyl)piperazine

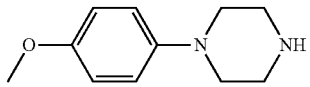

A solution of t-butyl 4-(4-methoxyphenyl)piperazine-1-carboxylate (1.412 g, 4.84 mmol, 1.00 equiv) in dichloromethane (17 mL) and trifluoroacetic acid (6 mL) was placed in a 50-mL round bottom flask and stirred for 2 h at 20° C. in an oil bath. The pH of the solution was adjusted to 7-8 with saturated aqueous sodium bicarbonate. The resulting mixture was concentrated under vacuum yielding 0.92 g (65%) of 1-(4-methoxyphenyl)piperazine as a yellow solid.

LC-MS (ES, m/z): 193 [M+H]+

Step 3. Methyl 3-(4-(4-methoxyphenyl)piperazin-1-yl)-2-phenylquinoxaline-6-carboxylate

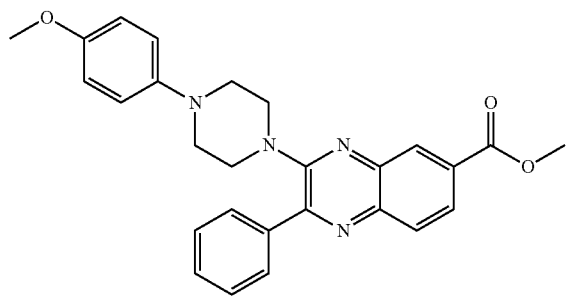

A solution of methyl 3-bromo-2-phenylquinoxaline-6-carboxylate (200 mg, 0.58 mmol, 1.00 equiv), 1-(4-methoxyphenyl)piperazine (230.4 mg, 1.20 mmol, 2.00 equiv) and DIEA (232.3 mg, 1.80 mmol, 3.00 equiv) in DMF (6 mL) was placed in a 20-mL sealed tube and stirred overnight at 100° C. in an oil bath, then concentrated under vacuum. Purification via prep-HPLC yielded 117.1 mg (42%) of methyl 3-(4-(4-methoxyphenyl)piperazin-1-yl)-2-phenylquinoxaline-6-carboxylate as a yellow solid. LC-MS (ES, m/z): 455 [M+H]+

Step 4. 3-(4-(4-Methoxyphenyl)piperazin-1-yl)-2-phenylquinoxaline-6-carboxylic Acid

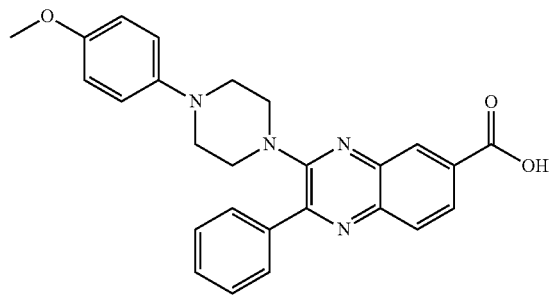 [SMILES: COc1ccc(N2CCN(c3nc4cc(C(=O)O)ccc4nc3-c3ccccc3)CC2)cc1]

A solution of methyl 3-(4-(4-methoxyphenyl)piperazin-1-yl)-2-phenylquinoxaline-6-carboxylate (117.1 mg, 0.26 mmol, 1.00 equiv) and sodium hydroxide (51.6 mg, 1.29 mmol, 5.00 equiv) in methanol (15 mL) was placed in a 50-mL round bottom flask and stirred for 5 h at 50° C. in an oil bath. The solution was adjusted to a pH of 3-4 with 1N hydrochloric acid, and then concentrated under vacuum. The resulting solids were washed with methanol yielding 80 mg (70%) of 3-(4-(4-methoxyphenyl)piperazin-1-yl)-2-phenylquinoxaline-6-carboxylic acid as a yellow solid.

LC-MS (ES, m/z): 441 [M+H]+

$^1$H-NMR (300 MHz, DMSO, ppm) δ 13.330 (1H, s), 8.331 (1H, s), 8.019 (4H, s), 7.579, 7.557 (3H, d, J=6.6 Hz), 6.922-6.802 (4H, q, J=9 Hz), 3.683 (4H, s), 3.068 (4H, s).

EXAMPLE 10

3-(4-(3-Chlorophenyl)piperidin-1-yl)-2-phenylquinoxaline-6-carboxylic Acid

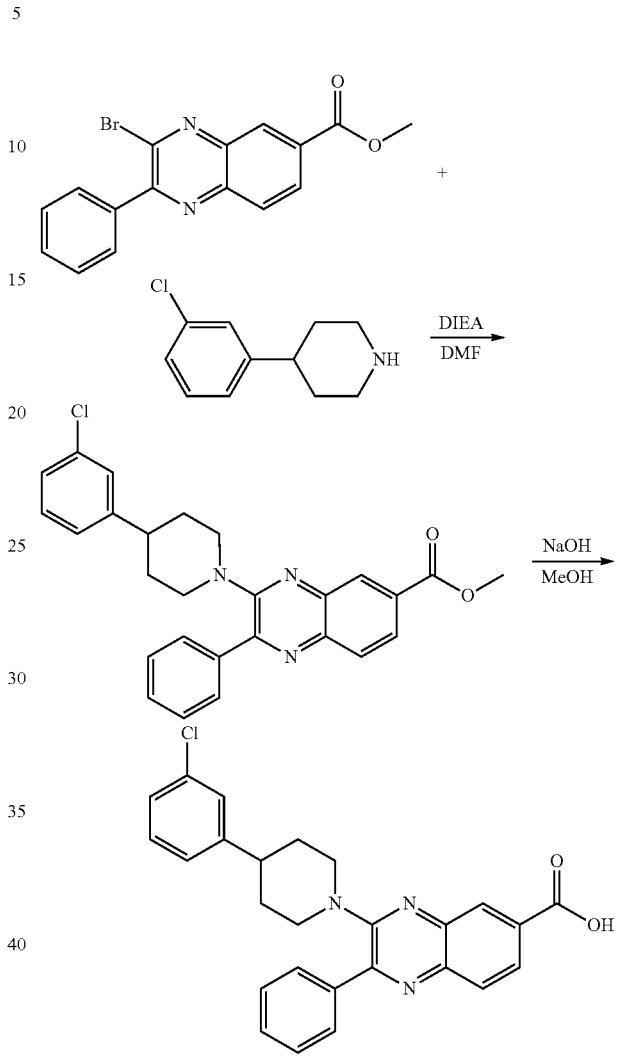

Step 1. Methyl 3-(4-(3-chlorophenyl)piperidin-1-yl)-2-phenylquinoxaline-6-carboxylate

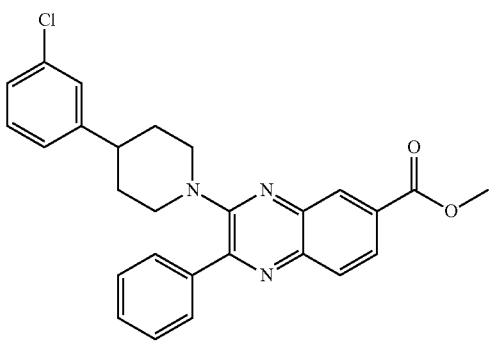 [SMILES: COC(=O)c1ccc2nc(-c3ccccc3)c(N3CCC(c4cccc(Cl)c4)CC3)nc2c1]

A solution of methyl 3-bromo-2-phenylquinoxaline-6-carboxylate (150 mg, 0.44 mmol, 1.00 equiv, 4-(3-chlorophenyl)piperidine hydrochloride (204.2 mg, 0.88 mmol, 2.00 equiv), and DIEA (194.8 mg, 1.51 mmol, 5.00 equiv) in DMF (4 mL) was placed in an 8-mL sealed tube and stirred overnight at 100° C. in an oil bath. The reaction was then quenched by the addition of water, then concentrated under vacuum. Purification via silica gel column (ethyl acetate/petroleum ether (1:100)) yielded 143.5 mg (64%) of methyl 3-(4-(3-chlorophenyl)piperidin-1-yl)-2-phenylquinoxaline-6-carboxylate as a yellow solid.

LC-MS (ES, m/z): 457 [M+H]+

Step 2. 3-(4-(3-Chlorophenyl)piperidin-1-yl)-2-phenylquinoxaline-6-carboxylic Acid

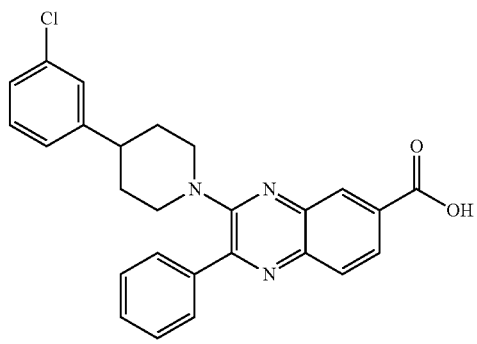 [SMILES: O=C(O)c1ccc2nc(-c3ccccc3)c(N3CCC(c4cccc(Cl)c4)CC3)nc2c1]

To a solution of methyl 3-(4-(3-chlorophenyl)piperidin-1-yl)-2-phenylquinoxaline-6-carboxylate (143.5 mg, 0.29 mmol, 1.00 equiv, 91%) in methanol (15 mL) was added a solution of sodium hydroxide (62.8 mg, 1.57 mmol, 5.00 equiv) in water (2 mL) dropwise with stirring. The resulting solution was stirred overnight at 50° C. in an oil bath, then concentrated under vacuum. The resulting solids were washed with methanol yielding 44 mg (34%) of 3-(4-(3-chlorophenyl)piperidin-1-yl)-2-phenylquinoxaline-6-carboxylic acid as a yellow solid.

LC-MS (ES, m/z): 443 [M+H]+

$^1$H-NMR (300 MHz, DMSO, ppm) δ 13.272 (1H, s), 8.312 (1H, s), 8.050-8.000 (4H, t), 7.611-7.528 (3H, t), 7.370-7.228 (4H, m) 3.941-3.864 (2H, t), 2.907-2.717 (3H, m), 1.738-1.631 (4H, t).

EXAMPLE 11

3-(4-(4-Methoxyphenyl)piperidin-1-yl)-2-phenylquinoxaline-6-carboxylic Acid

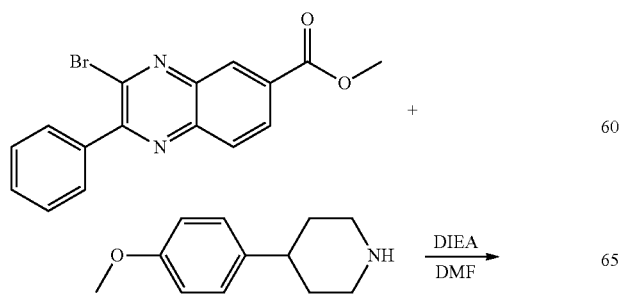

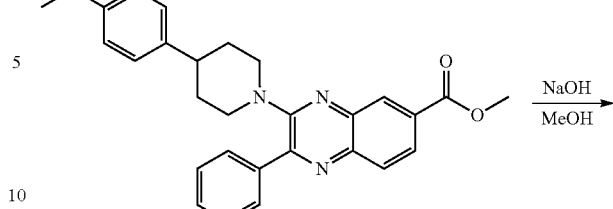

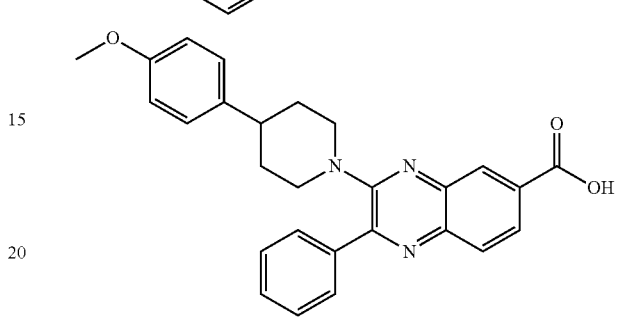

Step 1. Methyl 3-(4-(4-methoxyphenyl)piperidin-1-yl)-2-phenylquinoxaline-6-carboxylate

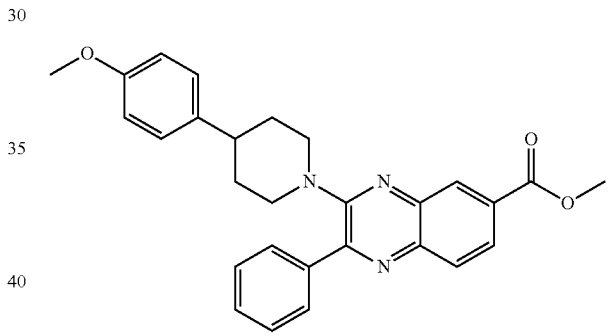

A solution of methyl 3-chloro-2-phenylquinoxaline-6-carboxylate (150 mg, 0.50 mmol, 1.00 equiv), 4-(4-methoxyphenyl)piperidine (191 mg, 1.00 mmol, 2.00 equiv), and DIEA (194.8 mg, 1.51 mmol, 5.00 equiv) in DMF (4 mL) was placed in an 8-mL sealed tube and stirred overnight at 100° C. in an oil bath. The reaction was then quenched by the addition of water, and the resulting mixture was concentrated under vacuum. Purification via silica gel column (ethyl acetate/petroleum ether (1:50)) yielded 179.6 mg (63%) of methyl 3-(4-(4-methoxyphenyl)piperidin-1-yl)-2-phenylquinoxaline-6-carboxylate as a yellow solid.

LC-MS (ES, m/z): 454 [M+H]+

Step 2. 3-(4-(4-Methoxyphenyl)piperidin-1-yl)-2-phenylquinoxaline-6-carboxylic Acid

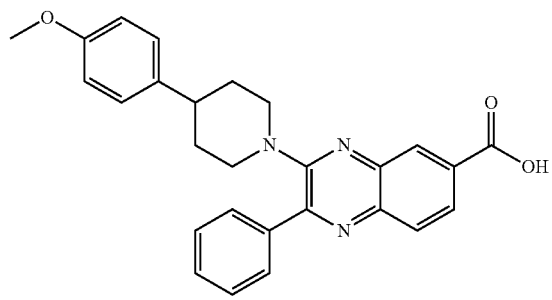 [SMILES: COc1ccc(C2CCN(c3nc4cc(C(=O)O)ccc4nc3-c3ccccc3)CC2)cc1]

To a solution of methyl 3-(4-(4-methoxyphenyl)piperidin-1-yl)-2-phenylquinoxaline-6-carboxylate (179.6 mg, 0.36 mmol, 1.00 equiv, 90%) in methanol (17 mL) was added a solution of sodium hydroxide (80 mg, 2.00 mmol, 5.00 equiv) in water (2 mL) dropwise with stirring. The resulting solution was stirred for 7 h at 50° C. in an oil bath, then the pH of the solution was adjusted to 3-4 with 1N hydrochloric acid. The resulting mixture was concentrated under vacuum, followed by washing with methanol yielding 81.9 mg (50%) of 3-(4-(4-methoxyphenyl)piperidin-1-yl)-2-phenylquinoxaline-6-carboxylic acid as a yellow solid.

LC-MS (ES, m/z): 440 [M+H]+

$^1$H-NMR (300 MHz, DMSO, ppm) δ 8.302 (1H, s), 8.035-7.991 (4H, m), 7.607-7.519 (3H, m), 7.177, 7.148 (2H, d, J=8.7 Hz), 6.873-6.844 (2H, d, J=8.7 Hz), 3.889, 3.846 (2H, d, J=12.9 Hz), 3.717 (3H, s), 2.899-2.825 (2H, t), 2.661-2.610 (1H, t), 1.732-1.619 (4H, m).

EXAMPLE 12

2-Phenyl-3-(piperidin-1-yl)quinoxaline-6-carboxylic Acid

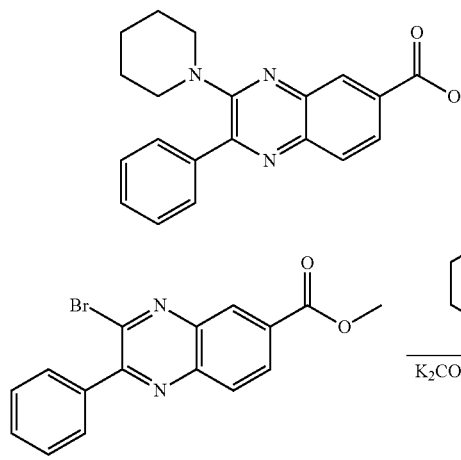

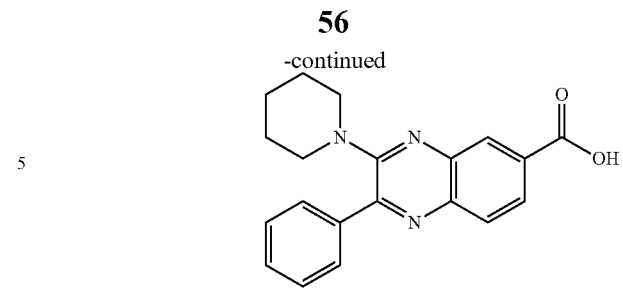

Into a 8-mL sealed tube, were placed a solution of methyl 3-bromo-2-phenylquinoxaline-6-carboxylate (200 mg, 0.58 mmol, 1.00 equiv) piperidine (149 mg, 1.75 mmol, 3.01 equiv), potassium carbonate (404 mg, 2.93 mmol, 5.02 equiv), H$_2$O (1 mL) and DMF (3 mL). The resulting mixture was stirred for overnight at 100° C.

The resulting mixture was concentrated under vacuum. The residue was dissolved in 20 mL of H$_2$O. The pH value of the aqueous solution was adjusted to 5 with hydrogen chloride (1 mol/L). The resulting solids were collected by filtration and washed with water and dried in an oven under reduced pressure. This resulted in 105 mg (54%) of 2-phenyl-3-(piperidin-1-yl)quinoxaline-6-carboxylic acid as a yellow solid.

LC-MS:(ES, m/z): 334 [M+H]+

$^1$H-NMR (300 MHz, DMSO, ppm): δ 8.28 (d, J=1.2 Hz, 1H), 8.02-7.94 (m, 4H), 7.60-7.52 (m, 3H), 3.22 (s, 4H), 1.53 (s, 6H).

EXAMPLE 13

2-Phenyl-3-(4-phenylpiperidin-1-yl)quinoxaline-6-carboxylic Acid

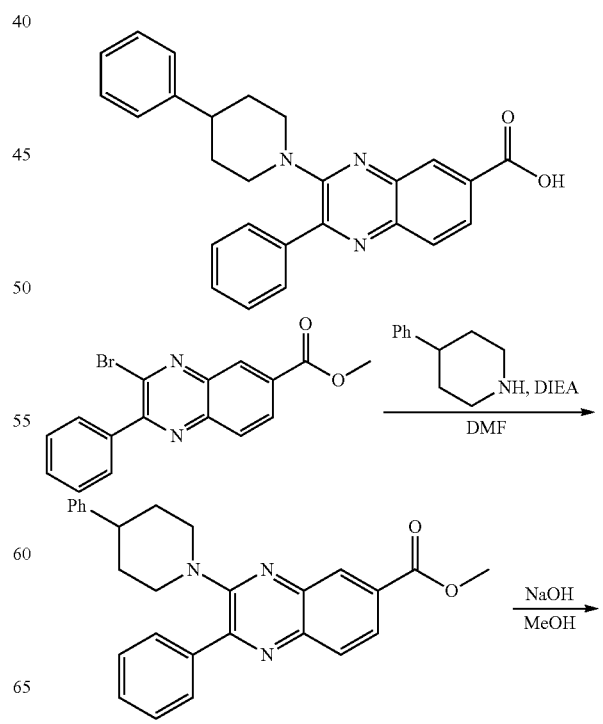

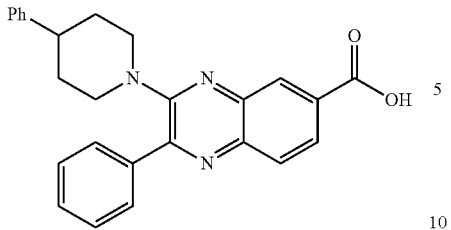

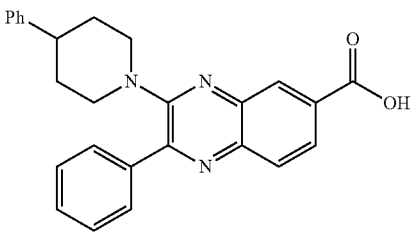

Step 1. Methyl 2-phenyl-3-(4-phenylpiperidin-1-yl)quinoxaline-6-carboxylate

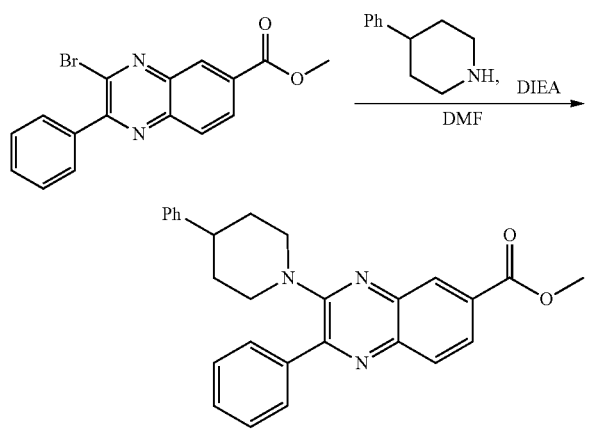

Into a 8-mL sealed tube, was placed methyl 3-bromo-2-phenylquinoxaline-6-carboxylate (150 mg, 0.44 mmol, 1.00 equiv), 4-phenylpiperidine (141.68 mg, 0.88 mmol, 2.00 equiv), DIEA (170.3 mg, 1.32 mmol, 3.00 equiv), N,N-dimethylformamide (4 mL). The resulting solution was stirred overnight at 100° C. in an oil bath. The resulting mixture was concentrated under vacuum. The residue was applied onto a silica gel column with PE/EA (100:1). This resulted in 92.9 mg (49%) of methyl 2-phenyl-3-(4-phenylpiperidin-1-yl)quinoxaline-6-carboxylate as a yellow solid.

LC-MS:(ES, m/z): 424 [M+H]+

Step 2. 2-Phenyl-3-(4-phenylpiperidin-1-yl)quinoxaline-6-carboxylic Acid

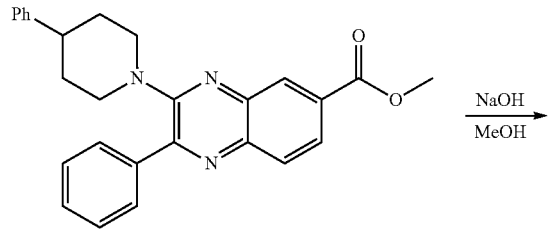

Into a 50-mL round-bottom flask, was placed a solution of methyl 2-phenyl-3-(4-phenylpiperidin-1-yl)quinoxaline-6-carboxylate (92.9 mg, 0.22 mmol, 1.00 equiv) in methanol (15 mL), a solution of sodium hydroxide (44 mg, 1.10 mmol, 5.00 equiv) in water (1.5 mL). The resulting solution was stirred overnight at 50° C. in an oil bath. The pH value of the solution was adjusted to 3-4 with 1N hydrogen chloride. The resulting mixture was concentrated under vacuum. The resulting mixture was washed with methanol. This resulted in 85 mg (93%) of 2-phenyl-3-(4-phenylpiperidin-1-yl)quinoxaline-6-carboxylic acid as a yellow solid.

LC-MS:(ES, m/z): 410 [M+H]+

$^1$H-NMR (300 MHz, DMSO, ppm): δ 13.291 (1H, s), 8.311 (1H, s), 8.041-7.942 (4H, m), 7.611-7.503 (3H, m), 7.336-7.179 (5H, m), 3.903, 3.861 (2H, d, J=12.6 Hz), 2.918-2.844 (2H, t), 2.708-2.676 (1H, t), 1.733-1.628 (4H, m)

EXAMPLE 14

3-(Azepan-1-yl)-2-phenylquinoxaline-6-carboxylic Acid

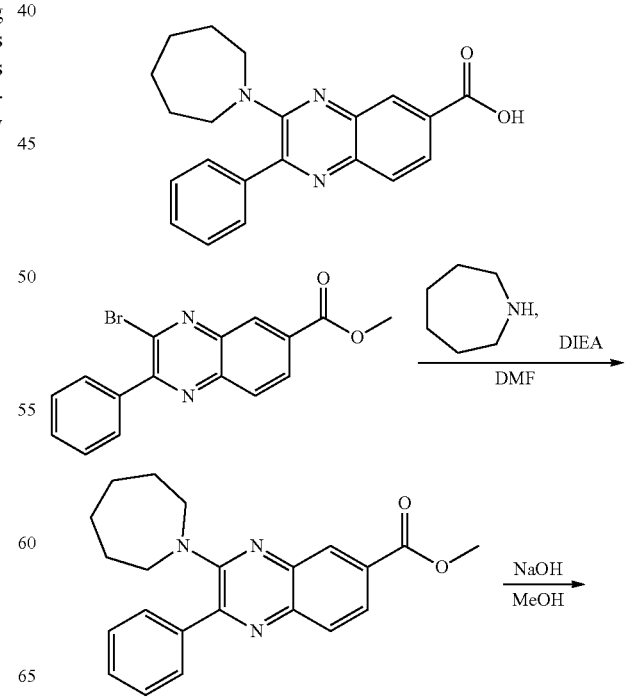

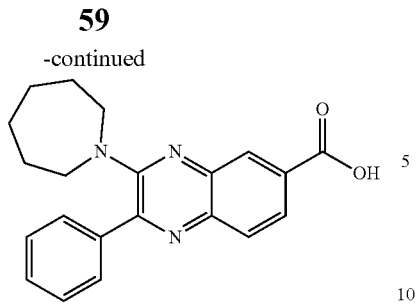

Step 1. Methyl 3-(azepan-1-yl)-2-phenylquinoxaline-6-carboxylate-8

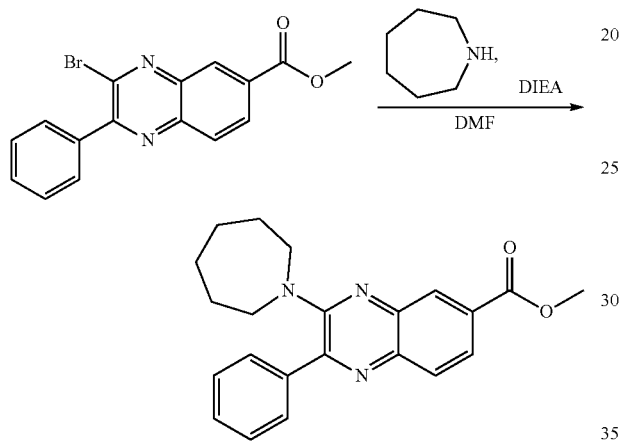

Into a 8-mL sealed tube, was placed methyl 3-bromo-2-phenylquinoxaline-6-carboxylate (150 mg, 0.44 mmol, 1.00 equiv), HMI (87.27 mg, 0.88 mmol, 2.00 equiv), DIEA (170.3 mg, 1.32 mmol, 3.00 equiv), N,N-dimethylformamide (4 mL). The resulting solution was stirred overnight at 100° C. in an oil bath. The solids were filtered out. The resulting mixture was concentrated under vacuum. The residue was applied onto a silica gel column with ethyl acetate/petroleum ether (1:100). This resulted in 132.4 mg (81%) of methyl 3-(azepan-1-yl)-2-phenylquinoxaline-6-carboxylate as a yellow solid.

LC-MS:(ES, m/z): 362 [M+H]+

Step 2. 3-(Azepan-1-yl)-2-phenylquinoxaline-6-carboxylic Acid

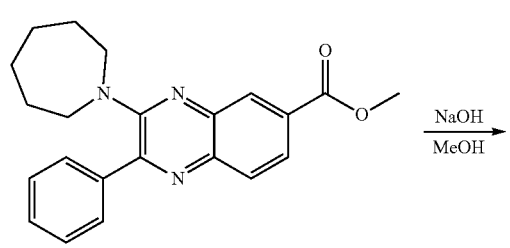

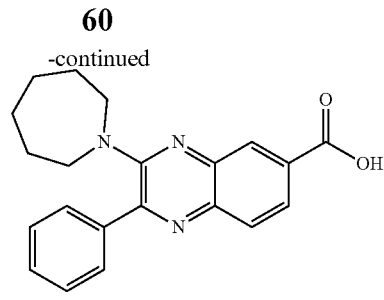

Into a 50-mL round-bottom flask, was placed a solution of methyl 3-(azepan-1-yl)-2-phenylquinoxaline-6-carboxylate (132.4 mg, 0.37 mmol, 1.00 equiv) in methanol (15 mL), a solution of sodium hydroxide (73.4 mg, 1.83 mmol, 5.00 equiv) in water (2 mL). The resulting solution was stirred overnight at 50° C. in an oil bath. The pH value of the solution was adjusted to 3-4 with 1N hydrogen chloride. The resulting mixture was concentrated under vacuum. The resulting mixture was washed with methanol. This resulted in 80 mg (61%) of 3-(azepan-1-yl)-2-phenylquinoxaline-6-carboxylic acid as a yellow solid.

LC-MS:(ES, m/z): 347 [M+H]+

$^1$H-NMR (300 MHz, DMSO, ppm): δ 13.204 (1H, s), 8.233 (1H, s), 7.939-7.873 (2H, m), 7.743-7.712 (2H, m), 7.565-7.493 (3H, m), 3.446-3.408 (4H, t), 1.624 (4H, s), 1.407 (4H, s).

EXAMPLE 15

3-(4-(4-Chlorophenyl)piperidin-1-yl)-2-phenylquinoxaline-6-carboxylic Acid

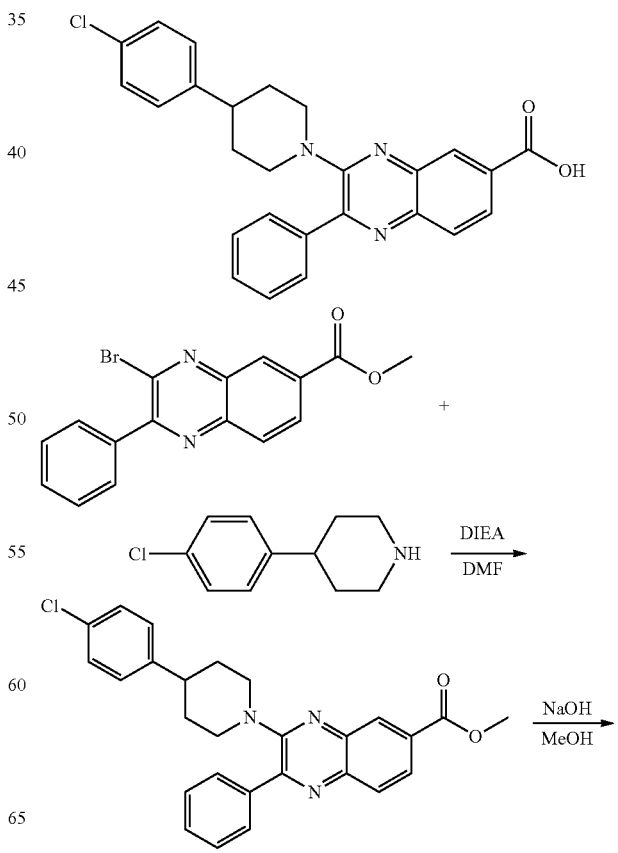

-continued

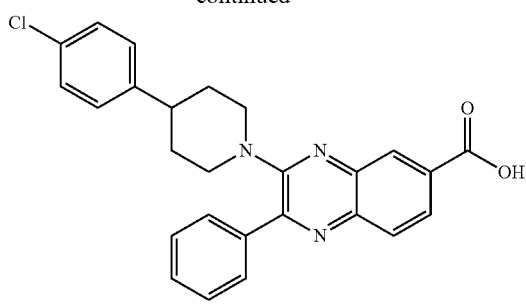

Step 1. Methyl 3-(4-(4-chlorophenyl)piperidin-1-yl)-2-phenylquinoxaline-6-carboxylate

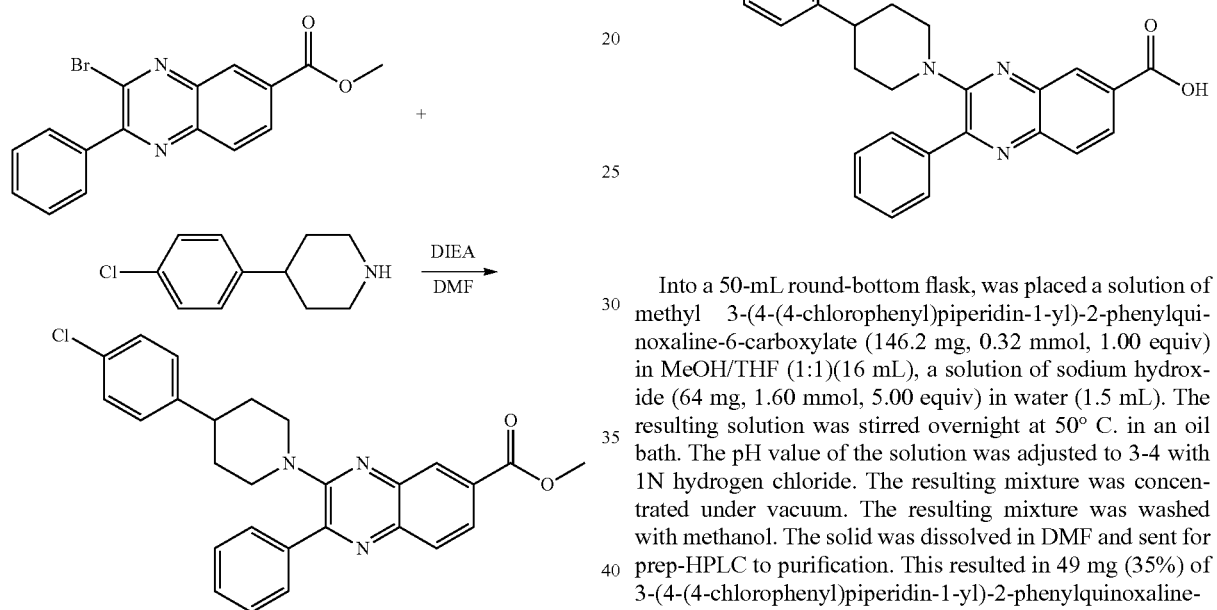

Into a 8-mL sealed tube, was placed methyl 3-bromo-2-phenylquinoxaline-6-carboxylate (150 mg, 0.44 mmol, 1.00 equiv), 4-(4-chlorophenyl)piperidine hydrochloride (204.2 mg, 0.88 mmol, 2.00 equiv), DIEA (170.3 mg, 1.32 mmol, 3.00 equiv), N,N-dimethylformamide (4 mL). The resulting solution was stirred overnight at 100° C. in an oil bath. The reaction was then quenched by the addition of water. The resulting solution was extracted with 6×15 mL of dichloromethane and the organic layers combined and dried over anhydrous sodium sulfate. The solids were filtered out. The resulting mixture was concentrated under vacuum. The residue was applied onto a silica gel column with ethyl acetate/petroleum ether (1:50). This resulted in 146.2 mg (71%) of methyl 3-(4-(4-chlorophenyl)piperidin-1-yl)-2-phenylquinoxaline-6-carboxylate as a yellow solid.

LC-MS:(ES, m/z): 458 [M+H]+

Step 2. 3-(4-(4-Chlorophenyl)piperidin-1-yl)-2-phenylquinoxaline-6-carboxylic Acid Into a 50-mL round-bottom flask, was placed a solution of methyl 3-(4-(4-chlorophenyl)piperidin-1-yl)-2-phenylquinoxaline-6-carboxylate (146.2 mg, 0.32 mmol, 1.00 equiv) in MeOH/THF (1:1)(16 mL), a solution of sodium hydroxide (64 mg, 1.60 mmol, 5.00 equiv) in water (1.5 mL). The resulting solution was stirred overnight at 50° C. in an oil bath. The pH value of the solution was adjusted to 3-4 with 1N hydrogen chloride. The resulting mixture was concentrated under vacuum. The resulting mixture was washed with methanol. The solid was dissolved in DMF and sent for prep-HPLC to purification. This resulted in 49 mg (35%) of 3-(4-(4-chlorophenyl)piperidin-1-yl)-2-phenylquinoxaline-6-carboxylic acid as a yellow solid.

LC-MS:(ES, m/z): 444 [M+H]+

$^1$H-NMR (300 MHz, DMSO, ppm): δ 13.264 (1H, s), 8.313 (1H, s), 8.046-8.004 (4H, t), 7.586-7.530 (3H, t), 7.377-7.280 (4H, m), 3.902, 3.861 (2H, d, J=12.3 Hz), 2.916-2.842 (3H, t), 2.514 (1H, s), 1.721-1.644 (4H, t).

EXAMPLE 16

3-Morpholino-2-phenylquinoxaline-6-carboxylic Acid

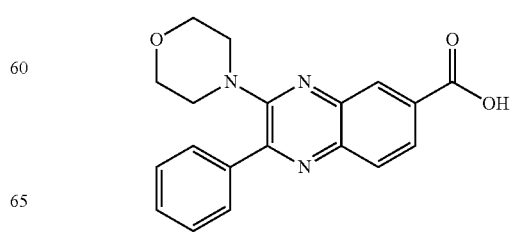

Step 2. 3-Morpholino-2-phenylquinoxaline-6-carboxylic Acid

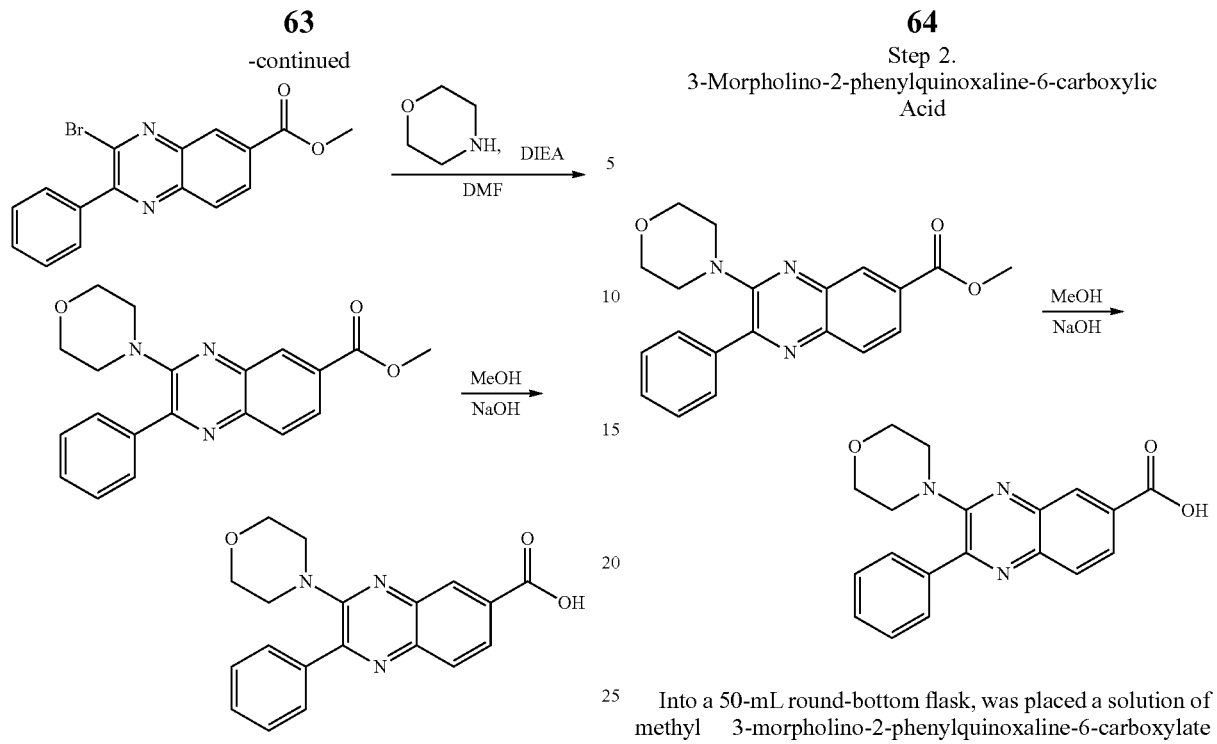

Into a 50-mL round-bottom flask, was placed a solution of methyl 3-morpholino-2-phenylquinoxaline-6-carboxylate (136.4 mg, 0.39 mmol, 1.00 equiv) in methanol (12 mL), a solution of sodium hydroxide (78.2 mg, 1.96 mmol, 5.00 equiv) in water (2 mL). The resulting solution was stirred overnight at 50° C. in an oil bath. The pH value of the solution was adjusted to 3-4 with 1N hydrogen chloride. The resulting mixture was concentrated under vacuum. The resulting mixture was sent for prep-HPLC. This resulted in 56 mg (41%) of 3-morpholino-2-phenylquinoxaline-6-carboxylic acid as a yellow solid.

LC-MS:(ES, m/z): 336 [M+H]+

$^1$H-NMR (300 MHz, DMSO, ppm): δ 8.323 (s, 1H), 8.026-7.995 (m, 4H), 7.609-7.537 (m, 3H), 3.652-3.622 (t, J=9 Hz, 4H), 3.247-3.233 (d, J=4.2 Hz, 4H).

EXAMPLE 17

3-(4-Methyl-1,4-diazepan-1-yl)-2-phenylquinoxaline-6-carboxylic Acid

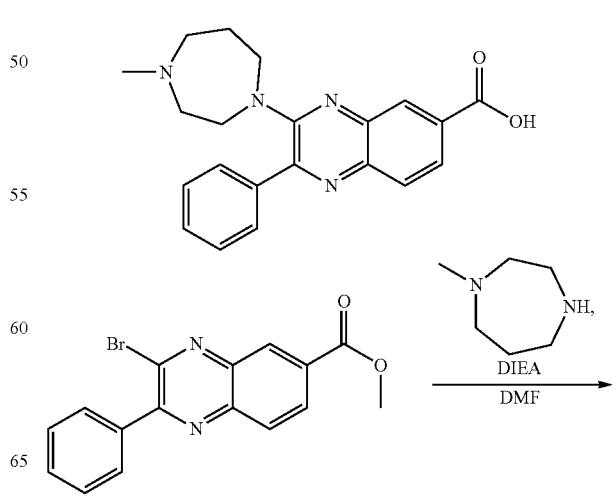

Step 1. Methyl 3-morpholino-2-phenylquinoxaline-6-carboxylate

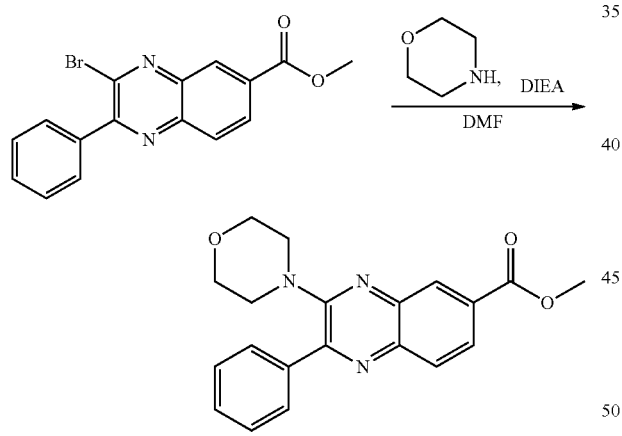

Into a 8-mL sealed tube, was placed a solution of methyl 3-bromo-2-phenylquinoxaline-6-carboxylate (150 mg, 0.44 mmol, 1.00 equiv) in N,N-dimethylformamide (4 mL), morpholine (76.6 mg, 0.88 mmol, 2.00 equiv), DIEA (170.3 mg, 1.32 mmol, 3.00 equiv). The resulting solution was stirred overnight at 100° C. in an oil bath. The resulting solution was concentrated under vacuum. The residue was applied onto a silica gel column with ethyl acetate/petroleum ether (1:10). This resulted in 136.4 mg (86%) of methyl 3-morpholino-2-phenylquinoxaline-6-carboxylate as a yellow solid.

LC-MS:(ES, m/z): 350 [M+H]+

Step 1. Methyl 3-(4-methyl-1,4-diazepan-1-yl)-2-phenylquinoxaline-6-carboxylate

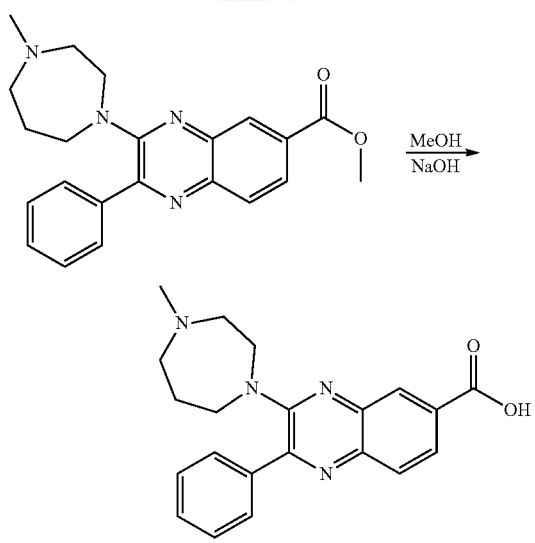

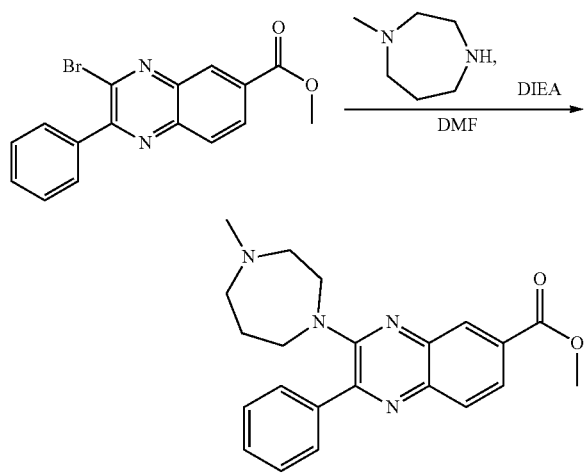

Into a 8-mL sealed tube, was placed a solution of methyl 3-bromo-2-phenylquinoxaline-6-carboxylate (150 mg, 0.44 mmol, 1.00 equiv) in N,N-dimethylformamide (4 mL), 1-methyl-1,4-diazepane (100.3 mg, 0.88 mmol, 2.00 equiv), DIEA (170.3 mg, 1.32 mmol, 3.00 equiv). The resulting solution was stirred overnight at 100° C. in an oil bath. The resulting solution was concentrated under vacuum. The residue was applied onto a silica gel column with dichloromethane/methanol (20:1). This resulted in 126.6 mg (77%) of methyl 3-(4-methyl-1,4-diazepan-1-yl)-2-phenylquinoxaline-6-carboxylate as yellow oil.

LC-MS:(ES, m/z): 377 [M+H]+

Step 2. 3-(4-Methyl-1,4-diazepan-1-yl)-2-phenylquinoxaline-6-carboxylic Acid

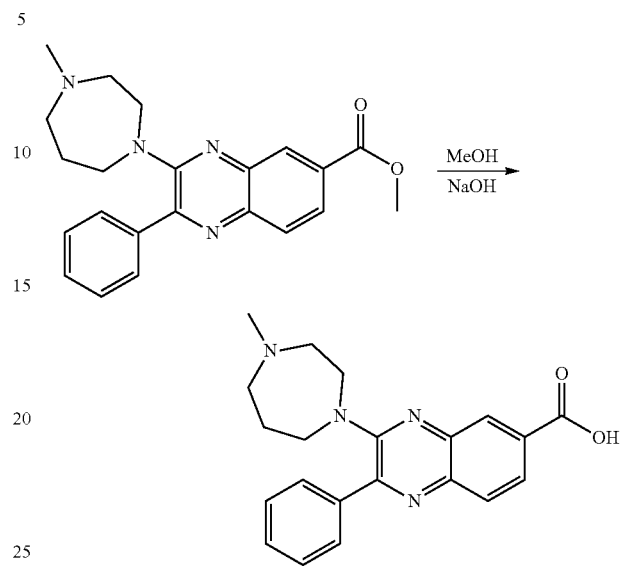

Into a 50-mL round-bottom flask, was placed a solution of methyl 3-(4-methyl-1,4-diazepan-1-yl)-2-phenylquinoxaline-6-carboxylate (126.6 mg, 0.34 mmol, 1.00 equiv) in methanol (12 mL), a solution of sodium hydroxide (72.6 mg, 1.81 mmol, 5.00 equiv) in water (2.5 mL). The resulting solution was stirred overnight at 50° C. in an oil bath. The pH value of the solution was adjusted to 3-4 with 1N hydrogen chloride. The resulting mixture was concentrated under vacuum. The resulting mixture was sent for prop-HPLC. This resulted in 46 mg (38%) of 3-(4-methyl-1,4-diazepan-1-yl)-2-phenylquinoxaline-6-carboxylic acid as a yellow solid.

LC-MS:(ES, m/z): 363 [M+H]+

$^1$H NMR (300 MHz, CD$_3$OD, ppm): δ 8.470-8.465 (d, J=1.5 Hz, 1H), 8.102-8.068 (m, 1H), 7.994-7.965 (d, J=8.7 Hz, 1H), 7.807-7.776 (m, 2H), 7.588-7.523 (m, 2H), 3.620 (s, 2H), 3.250-3.177 (m, 2H), 2.906 (s, 3H), 2.069 (s, 2H), 1.338-1.289 (t, J=14.7 Hz, 4H).

EXAMPLE 18

3-(Isopropylamino)-2-phenylquinoxaline-6-carboxylic Acid

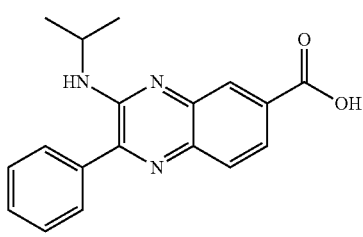

Step 1. Methyl 3-(isopropylamino)-2-phenylquinoxaline-6-carboxylate

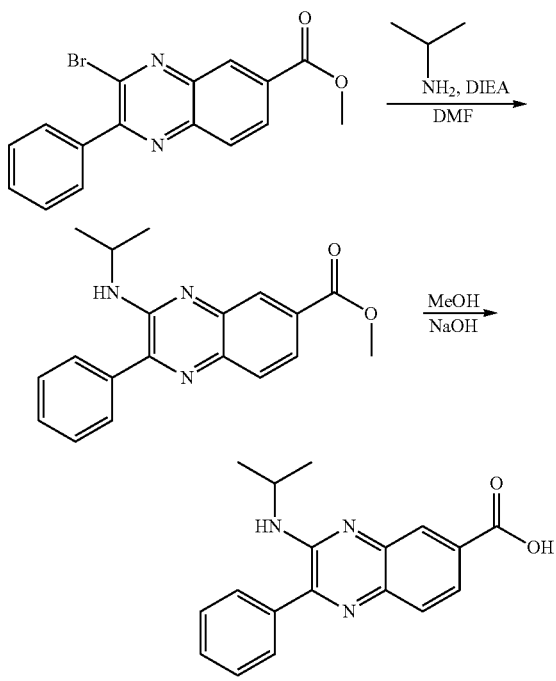

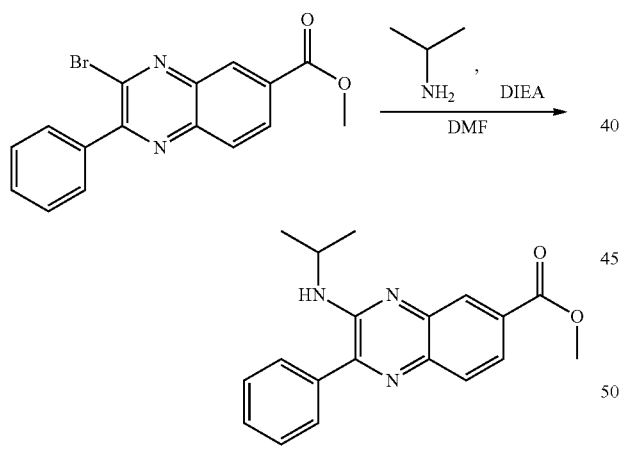

Into a 8-mL sealed tube, was placed a solution of methyl 3-bromo-2-phenylquinoxaline-6-carboxylate (100 mg, 0.29 mmol, 1.00 equiv, 99%) in N,N-dimethylformamide (4 mL), propan-2-amine (34.5 mg, 0.58 mmol, 2.00 equiv), DIEA (112.23 mg, 0.87 mmol, 3.00 equiv). The resulting solution was stirred overnight at 100° C. in an oil bath. The residue was applied onto a silica gel column with ethyl acetate/petroleum ether (1:50). This resulted in 95.6 mg (100%) of methyl 3-(isopropylamino)-2-phenylquinoxaline-6-carboxylate as a yellow solid.

LC-MS:(ES, m/z): 322 [M+H]+

Step 2. 3-(Isopropylamino)-2-phenylquinoxaline-6-carboxylic Acid

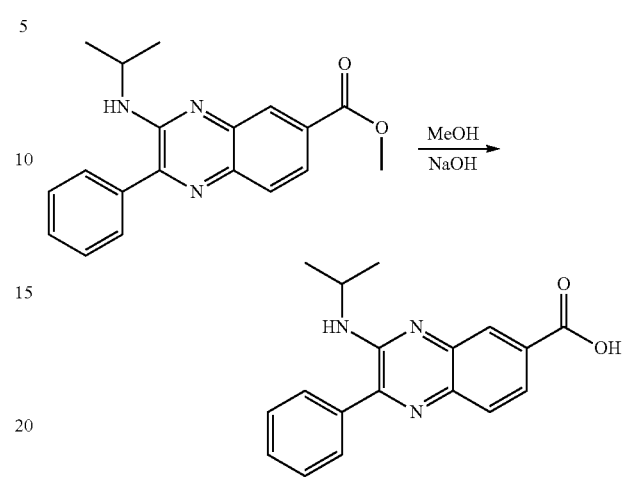

Into a 50-mL round-bottom flask, was placed a solution of methyl 3-(isopropylamino)-2-phenylquinoxaline-6-carboxylate (95.6 mg, 0.30 mmol, 1.00 equiv) in methanol (19 mL). This was followed by the addition of a solution of sodium hydroxide (60 mg, 1.50 mmol, 5.00 equiv) in water (3 mL) dropwise with stirring. The resulting solution was stirred overnight at 50° C. in an oil bath. The resulting mixture was concentrated under vacuum. The crude product was sent for prep-HPLC to get the product. This resulted in 55 mg (58%) of 3-(isopropylamino)-2-phenylquinoxaline-6-carboxylic acid as a yellow solid.

LC-MS:(ES, m/z): 308 [M+H]+

$^1$H-NMR (300 MHz, CDCl$_3$, ppm): 8.624 (s, 1H), 8.091-8.057 (m, 2H), 7.881-7.550 (m, 3H), 7.678-7.601 (m, 3H), 5.283 (s, 1H), 4.541-4.521 (d, J=6 Hz, 1H), 1.333-1.312 (d, J=6.3 Hz, 6H).

EXAMPLE 19

2-Phenyl-3-(4-(pyrimidin-2-yl)piperazin-1-yl)quinoxaline-6-carboxylic Acid

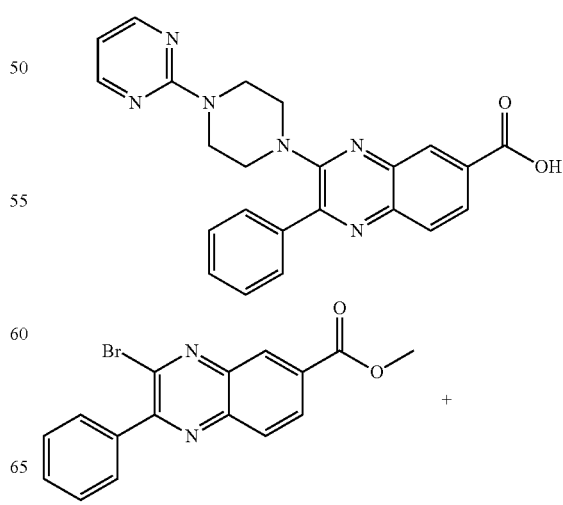

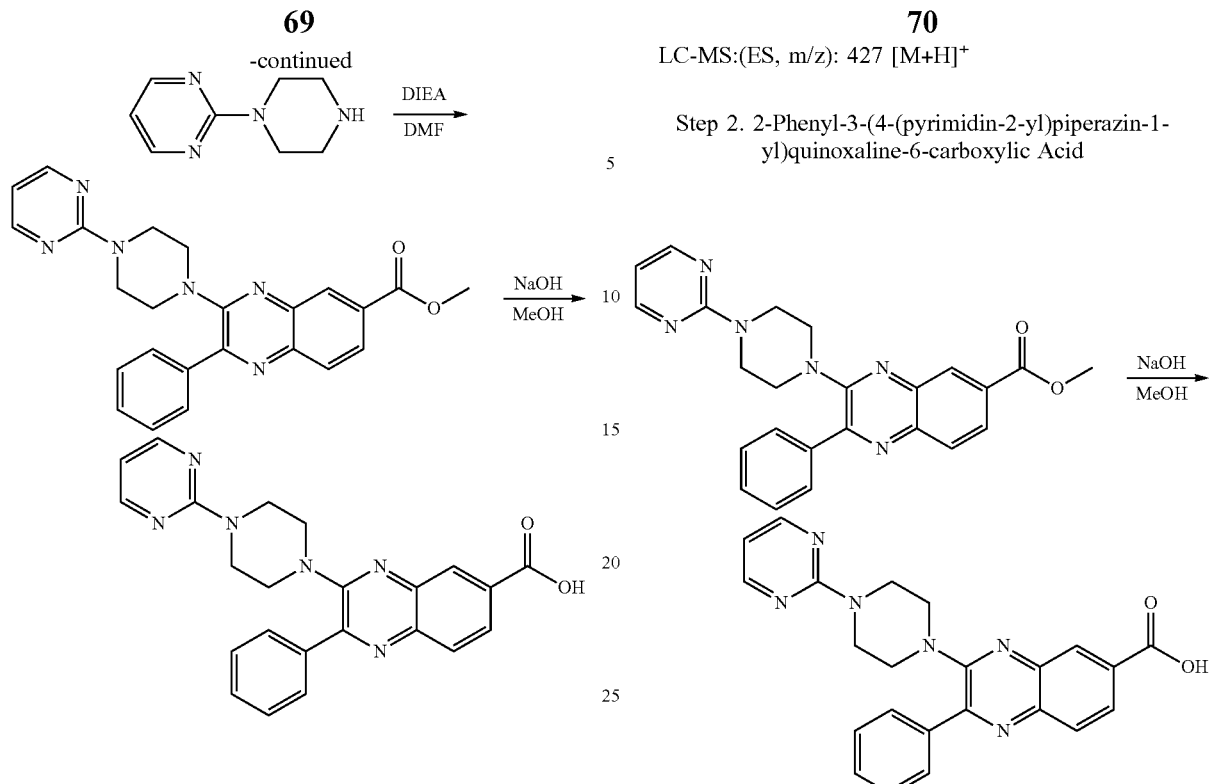

Step 1. Methyl 2-phenyl-3-(4-(pyrimidin-2-yl)piperazin-1-yl)quinoxaline-6-carboxylate

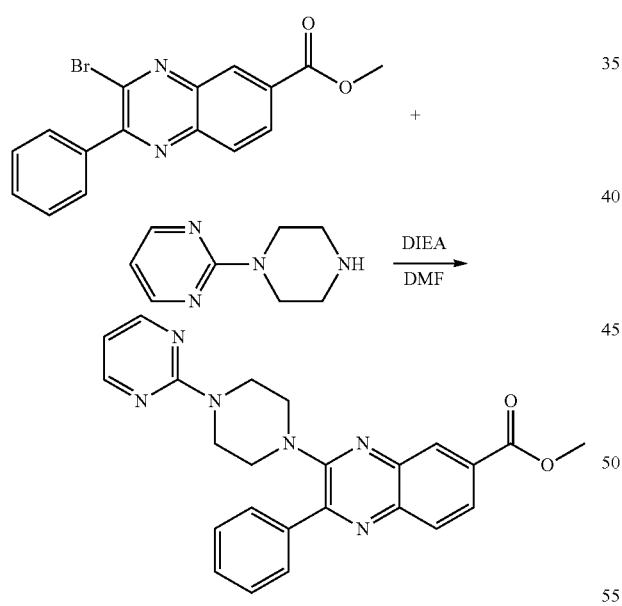

Into a 8-mL sealed tube, was placed methyl 3-bromo-2-phenylquinoxaline-6-carboxylate (150 mg, 0.44 mmol, 1.00 equiv), 2-(piperazin-1-yl)pyrimidine (144.3 mg, 0.88 mmol, 2.00 equiv), DIEA (170.3 mg, 1.32 mmol, 3.00 equiv), N,N-dimethylformamide (3 mL). The resulting solution was stirred overnight at 100° C. in an oil bath. The resulting solution was concentrated under vacuum. The residue was applied onto a silica gel column with ethyl acetate/petroleum ether (1:50). This resulted in 192 mg (95%) of methyl 2-phenyl-3-(4-(pyrimidin-2-yl)piperazin-1-yl)quinoxaline-6-carboxylate as a yellow solid.

LC-MS:(ES, m/z): 427 [M+H]$^+$

Step 2. 2-Phenyl-3-(4-(pyrimidin-2-yl)piperazin-1-yl)quinoxaline-6-carboxylic Acid Into a 50-mL round-bottom flask, was placed a solution of methyl 2-phenyl-3-(4-(pyrimidin-2-yl)piperazin-1-yl)quinoxaline-6-carboxylate (192 mg, 0.41 mmol, 1.00 equiv, 90%) in methanol (10 mL), a solution of sodium hydroxide (80 mg, 2.00 mmol, 5.00 equiv) in water (2 mL). The resulting solution was stirred overnight at 50° C. in an oil bath. The resulting mixture was concentrated under vacuum. The resulting mixture was washed with methanol. This resulted in 80 mg (47%) of 2-phenyl-3-(4-(pyrimidin-2-yl)piperazin-1-yl)quinoxaline-6-carboxylic acid as a yellow solid.

LC-MS:(ES, m/z): 413 [M+H]$^+$ $^1$H-NMR (300 MHz, DMSO, ppm): δ 13.275 (s, 1H), 8.389-8.336 (t, 3H), 8.062-8.026 (t, 4H), 7.609-7.571 (t, 3H), 6.685-6.654 (t, 1H), 3.774 (s, 4H).

EXAMPLE 20

2-Phenyl-3-(4-(5-(trifluoromethyl)pyridin-2-yl)piperazin-1-yl)quinoxaline-6-carboxylic Acid

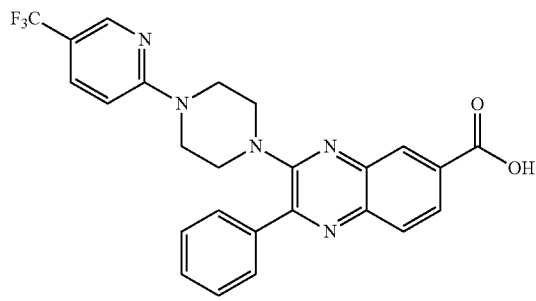

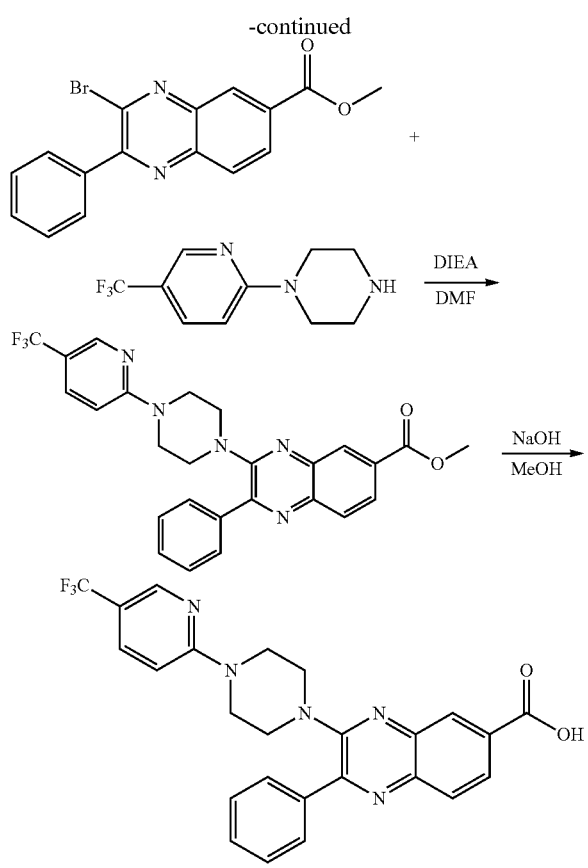

Step 1. Methyl 2-phenyl-3-(4-(5-(trifluoromethyl)pyridin-2-yl)piperazin-1-yl)quinoxaline-6-carboxylate

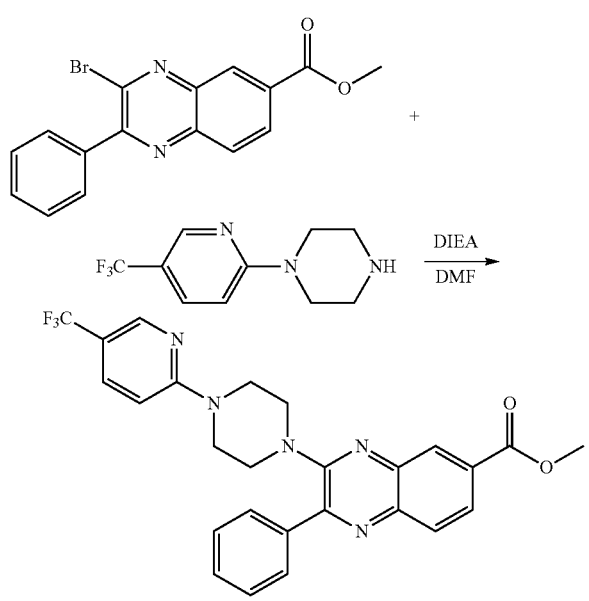

Into a 8-mL sealed tube, was placed methyl 3-bromo-2-phenylquinoxaline-6-carboxylate (150 mg, 0.44 mmol, 1.00 equiv), 1-(5-(trifluoromethyl)pyridin-2-yl)piperazine (203.28 mg, 0.88 mmol, 2.00 equiv), DIEA (170.3 mg, 1.32 mmol, 3.00 equiv), N,N-dimethylformamide (3 mL). The resulting solution was stirred overnight at 100° C. in an oil bath. The reaction was then quenched by the addition of water. The resulting solution was extracted with 4×30 mL of dichloromethane and the organic layers combined and dried over anhydrous sodium sulfate. The solids were filtered out. The residue was applied onto a silica gel column with ethyl acetate/petroleum ether (1:50). This resulted in 210.8 mg (97%) of methyl 2-phenyl-3-(4-(5-(trifluoromethyl)pyridin-2-yl)piperazin-1-yl)quinoxaline-6-carboxylate as a yellow solid.

LC-MS:(ES, m/z): 494 [M+H]$^+$

Step 2. 2-Phenyl-3-(4-(5-(trifluoromethyl)pyridin-2-yl)piperazin-1-yl)quinoxaline-6-carboxylic Acid

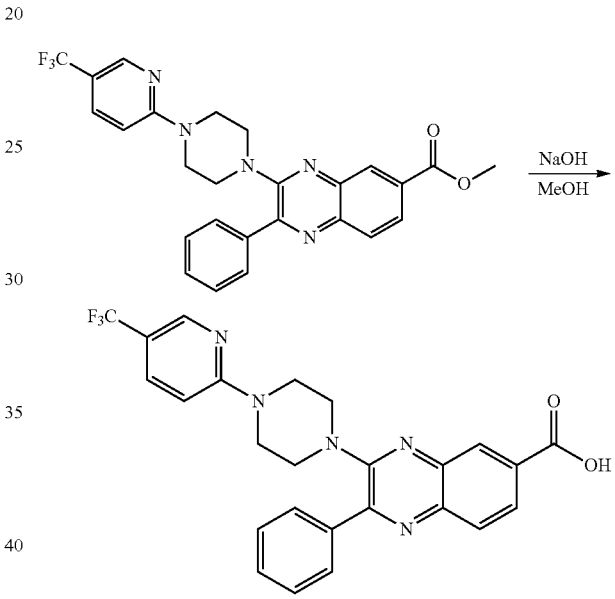

Into a 50-mL round-bottom flask, was placed a solution of methyl 2-phenyl-3-(4-(5-(trifluoromethyl)pyridin-2-yl)piperazin-1-yl)quinoxaline-6-carboxylate (210.8 mg, 0.43 mmol, 1.00 equiv) in methanol (15 mL). This was followed by the addition of a solution of sodium hydroxide (85.5 mg, 2.14 mmol, 5.00 equiv) in water (1.5 mL), which was added dropwise with stirring. The salting solution was stirred overnight at 50° C. in an oil bath. The pH value of the solution was adjusted to 3-4 with 1N hydrochloric acid. The mixture was concentrated under vacuum. The resulting mixture was washed with methanol. This resulted in 78 mg (38%) of 2-phenyl-3-(4-(5-(trifluoromethyl)pyridin-2-yl)piperazin-1-yl)quinoxaline-6-carboxylic acid as a yellow solid.

LC-MS:(ES, m/z): 480 [M+H]$^+$ $^1$H-NMR (300 MHz, DMSO, ppm): δ 13.310 (s, 1H), 8.425-8.337 (d, J=26.4 Hz, 2H), 8.026 (s, 4H), 7.829-7.800 (d, J=8.7 Hz, 1H), 7.589-7.570 (d, J=5.7 Hz, 3H) 6.993-6.963 (d, J=9 Hz, 1H), 3.694 (s, 4H), 3.372 (s, 4H).

EXAMPLE 21

2-phenyl-3-(4-(quinolin-2-yl)piperazin-1-yl)quinoxaline-6-carboxylic Acid

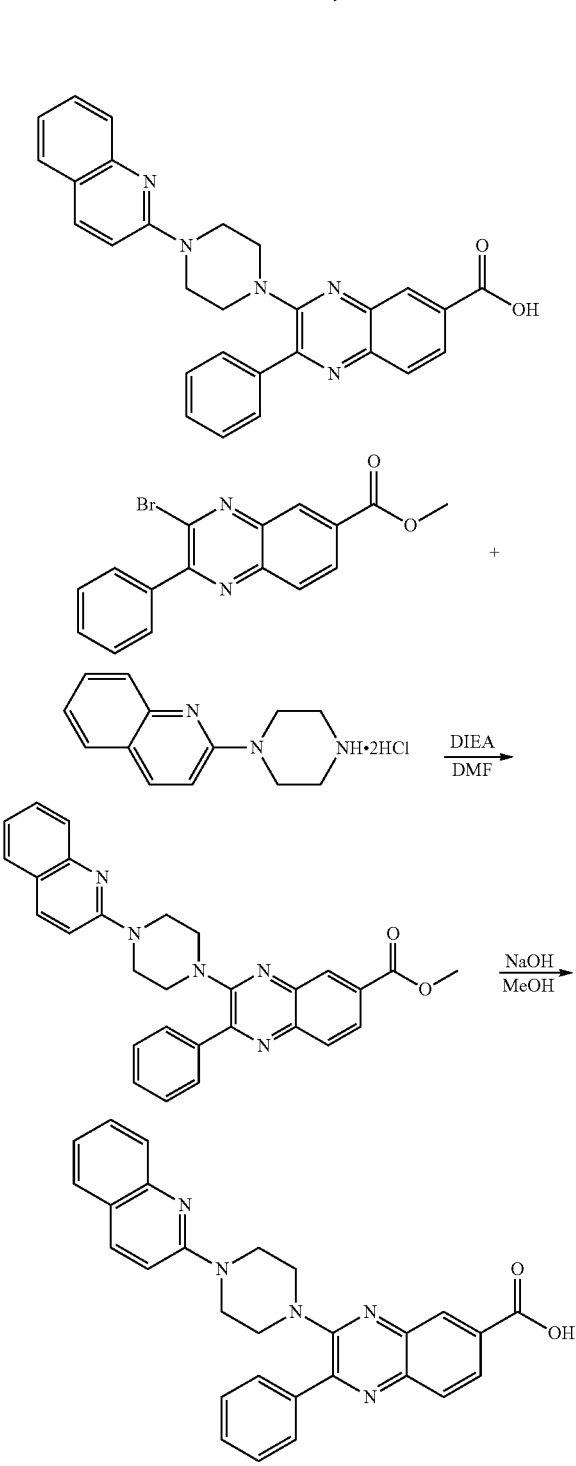

Step 1. Methyl 2-phenyl-3-(4-(quinolin-2-yl)piperazin-1-yl)quinoxaline-6-carboxylate

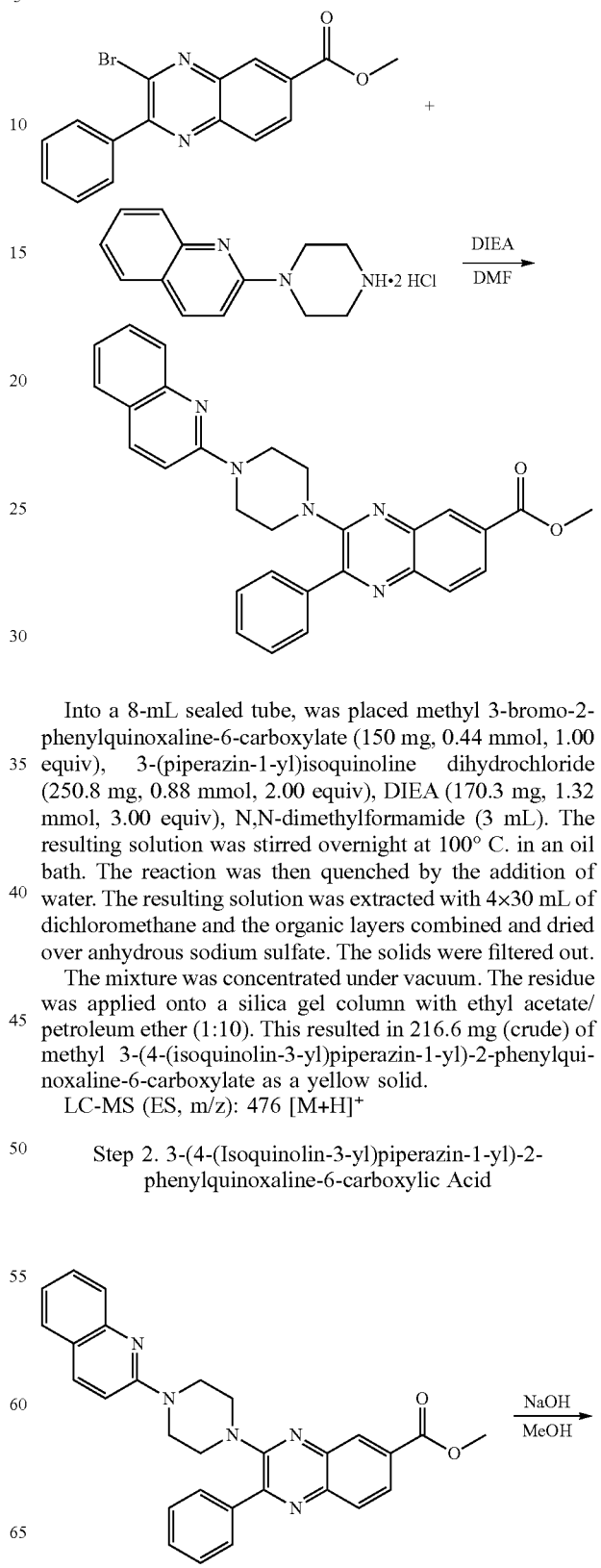

Into a 8-mL sealed tube, was placed methyl 3-bromo-2-phenylquinoxaline-6-carboxylate (150 mg, 0.44 mmol, 1.00 equiv), 3-(piperazin-1-yl)isoquinoline dihydrochloride (250.8 mg, 0.88 mmol, 2.00 equiv), DIEA (170.3 mg, 1.32 mmol, 3.00 equiv), N,N-dimethylformamide (3 mL). The resulting solution was stirred overnight at 100° C. in an oil bath. The reaction was then quenched by the addition of water. The resulting solution was extracted with 4×30 mL of dichloromethane and the organic layers combined and dried over anhydrous sodium sulfate. The solids were filtered out.

The mixture was concentrated under vacuum. The residue was applied onto a silica gel column with ethyl acetate/petroleum ether (1:10). This resulted in 216.6 mg (crude) of methyl 3-(4-(isoquinolin-3-yl)piperazin-1-yl)-2-phenylquinoxaline-6-carboxylate as a yellow solid.

LC-MS (ES, m/z): 476 [M+H]+

Step 2. 3-(4-(Isoquinolin-3-yl)piperazin-1-yl)-2-phenylquinoxaline-6-carboxylic Acid

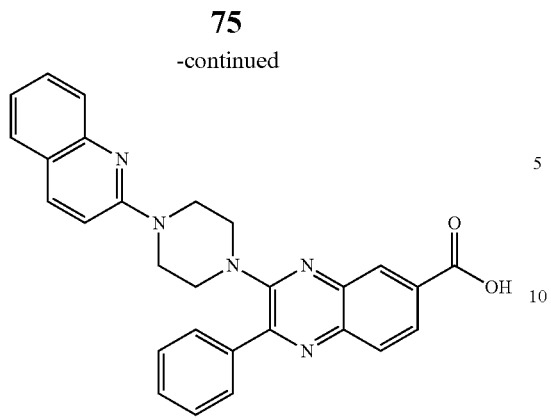

Into a 50-mL round-bottom flask, was placed a solution of methyl 3-(4-(isoquinolin-3-yl)piperazin-1-yl)-2-phenylquinoxaline-6-carboxylate (216.6 mg, 0.46 mmol, 1.00 equiv) in methanol (15 mL). This was followed by the addition of a solution of sodium hydroxide (91.2 mg, 2.28 mmol, 5.00 equiv) in water (2 mL), which was added dropwise with stirring. The resulting solution was stirred overnight at 50° C. in an oil bath. The pH value of the solution was adjusted to 3-4 with 1N hydrochloric acid. The resulting mixture was concentrated under vacuum. The resulting mixture was washed with methanol. This resulted in 56 mg (26%) of 3-(4-(isoquinolin-3-yl)piperazin-1-yl)-2-phenylquinoxaline-6-carboxylic acid as a yellow solid.

LC-MS:(ES, m/z): 462 [M+H]$^+$
$^1$H-NMR (300 MHz, DMSO, ppm): 13.290 (s, 1H), 8.351 (s, 1H), 8.073-8.031 (m, 5H), 7.729-7.703 (d, J=7.8 Hz, 1H), 7.603-7.513 (m, 5H), 7.284-7.223 (m, 2H), 3.755 (s, 4H), 3.411 (s, 4H).

EXAMPLE 22

2-(Azepan-1-yl)-3-phenylquinoxaline-6-carboxylic Acid

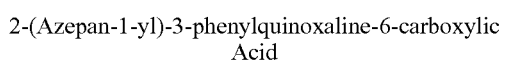

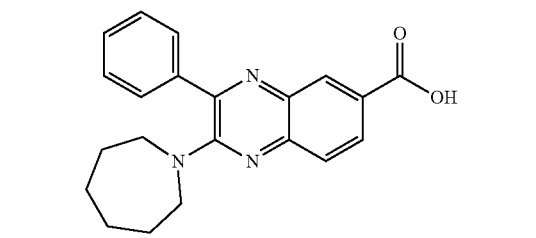

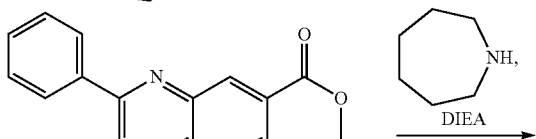

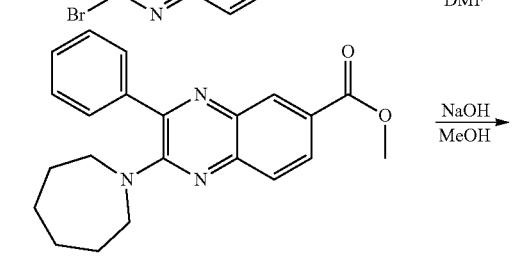

Step 1. Methyl 2-(azepan-1-yl)-3-phenylquinoxaline-6-carboxylate

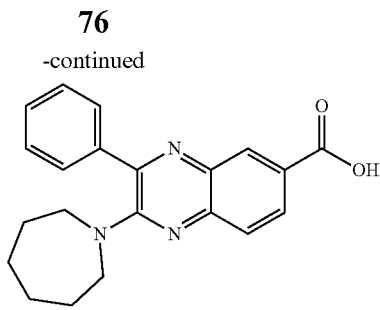

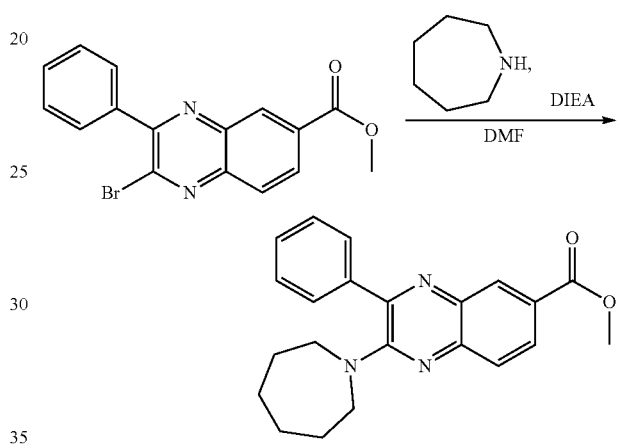

Into a 8-mL sealed tube, was placed a solution of methyl 2-bromo-3-phenylquinoxaline-6-carboxylate (150 mg, 0.44 mmol, 1.00 equiv) in N,N-dimethylformamide (4 mL), HMI (87.27 mg, 0.88 mmol, 2.00 equiv), DIEA (170.3 mg, 1.32 mmol, 3.00 equiv). The resulting solution was stirred overnight at 100° C. in an oil bath. The residue was applied onto a silica gel column with ethyl acetate/petroleum ether (1:50). This resulted in 136 mg (84%) of methyl 2-(azepan-1-yl)-3-phenylquinoxaline-6-carboxylate as a yellow solid.

LC-MS:(ES, m/z): 362 [M+H]$^+$

Step 2. 2-(Azepan-1-yl)-3-phenylquinoxaline-6-carboxylic Acid

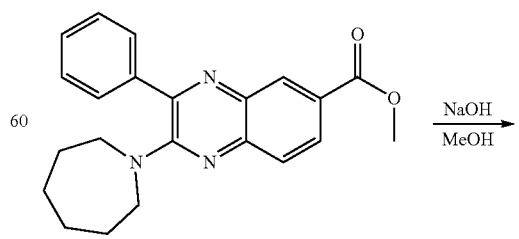

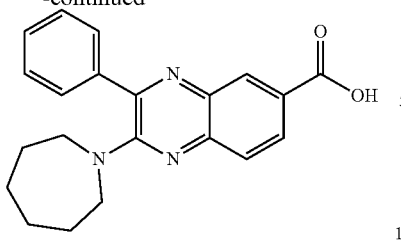

Into a 50-mL round-bottom flask, was placed a solution of methyl 2-(azepan-1-yl)-3-phenylquinoxaline-6-carboxylate (136 mg, 0.37 mmol, 1.00 equiv, 98%) in methanol (10 mL), sodium hydroxide (75.3 mg, 1.88 mmol, 5.00 equiv). The resulting solution was stirred overnight at 50° C. in an oil bath. The pH value of the solution was adjusted to 3-4 with 1N hydrogen chloride. The resulting mixture was concentrated under vacuum. The resulting mixture was washed with methanol. This resulted in 63.1 mg (47%) of 2-(azepan-1-yl)-3-phenylquinoxaline-6-carboxylic acid as a yellow solid.

LC-MS:(ES, m/z): 348 [M+H]$^+$ $^1$H-NMR (300 MHz, DMSO, ppm): 12.992 (s, 1H), 8.376-8.371 (d, J=1.5 Hz, 1H), 8.093-8.058 (m, 1H), 7.723-7.694 (t, J=8.7 Hz, 3H), 7.556-7.487 (m, 3H), 3.467-3.428 (t, J=12.7 Hz, 4H), 1.621 (s, 4H), 1.404 (s, 4H).

EXAMPLE 23

3-Phenyl-2-(piperidin-1-yl)quinoxaline-6-carboxylic Acid

Step 1. Synthesis of methyl 3-phenyl-2-(piperidin-1-yl)quinoxaline-6-carboxylate

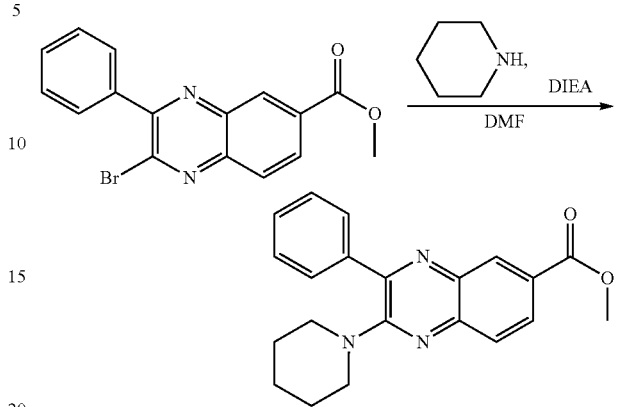

Into a 8-mL sealed tube, was placed a solution of methyl 2-bromo-3-phenylquinoxaline-6-carboxylate (150 mg, 0.44 mmol, 1.00 equiv) in N,N-dimethylformamide (4 mL), piperidine (74.8 mg, 0.88 mmol, 2.00 equiv), DIEA (170.3 mg, 1.32 mmol, 3.00 equiv). The resulting solution was stirred overnight at 100° C. in an oil bath. The residue was applied onto a silica gel column with ethyl acetate/petroleum ether (1:10). This resulted in 170.9 mg (crude) of methyl 3-phenyl-2-(piperidin-1-yl)quinoxaline-6-carboxylate as a yellow solid.

LC-MS:(ES, m/z): 348 [M+H]$^+$

Step 2. 3-Phenyl-2-(piperidin-1-yl)quinoxaline-6-carboxylic Acid

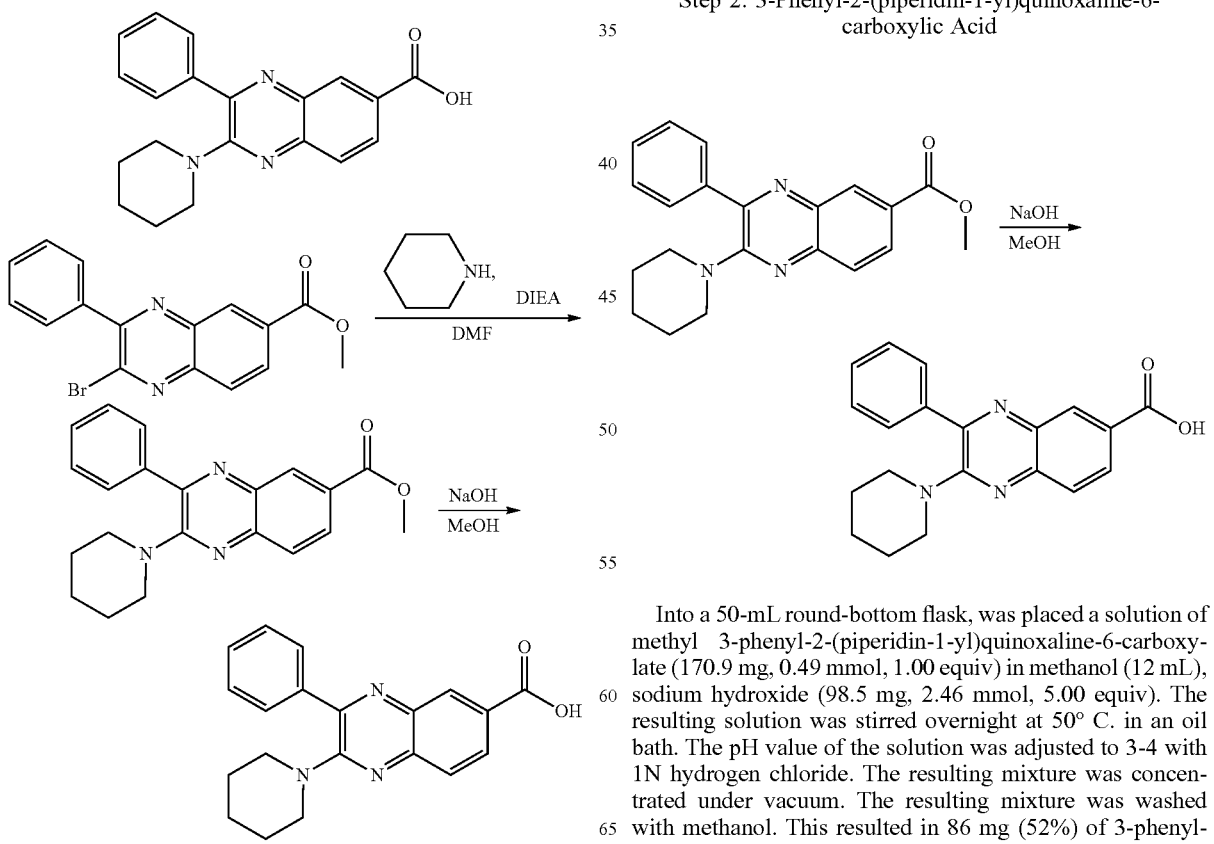

Into a 50-mL round-bottom flask, was placed a solution of methyl 3-phenyl-2-(piperidin-1-yl)quinoxaline-6-carboxylate (170.9 mg, 0.49 mmol, 1.00 equiv) in methanol (12 mL), sodium hydroxide (98.5 mg, 2.46 mmol, 5.00 equiv). The resulting solution was stirred overnight at 50° C. in an oil bath. The pH value of the solution was adjusted to 3-4 with 1N hydrogen chloride. The resulting mixture was concentrated under vacuum. The resulting mixture was washed with methanol. This resulted in 86 mg (52%) of 3-phenyl-2-(piperidin-1-yl)quinoxaline-6-carboxylic acid as a yellow solid.

LC-MS:(ES, m/z): 334 [M+H]+

¹H-NMR (300 MHz, DMSO, ppm): 13.034 (s, 1H), 8.419-8.414 (d, J=1.5 Hz, 1H), 8.131-8.096 (m, 1H), 7.955-7.934 (s, J=6.3 Hz, 1H), 7.796-7.767 (s, J=8.7 Hz, 1H), 7.585-7.490 (m, 3H), 1.530 (s, 6H).

EXAMPLE 24

2-(4-(4-Chlorophenyl)piperidin-1-yl)-3-(4-fluorophenyl)quinoxaline-6-carboxylic Acid

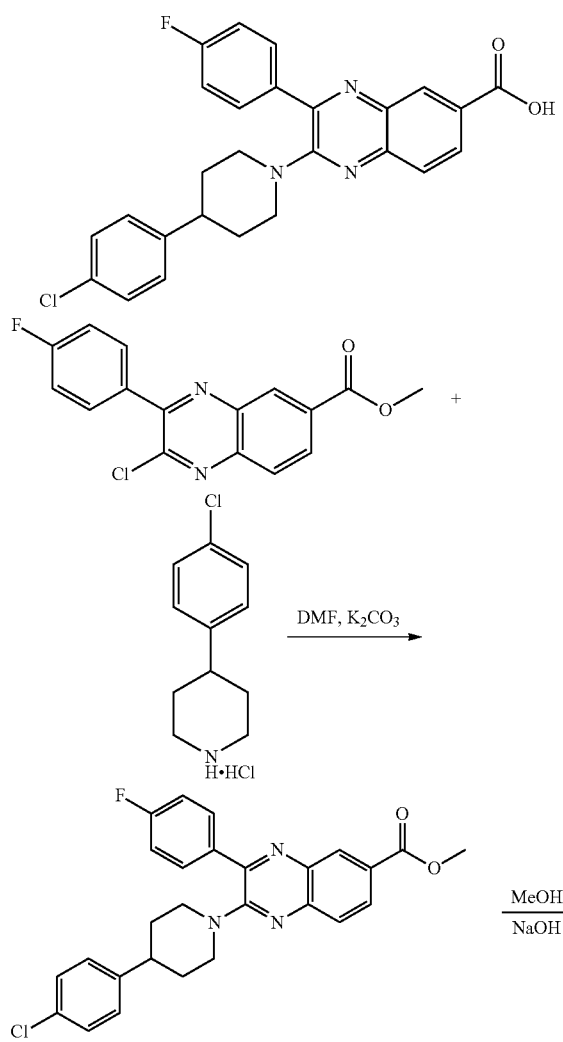

Step 1. Methyl 2-(4-(4-chlorophenyl)piperidin-1-yl)-3-(4-fluorophenyl)quinoxaline-6-carboxylate

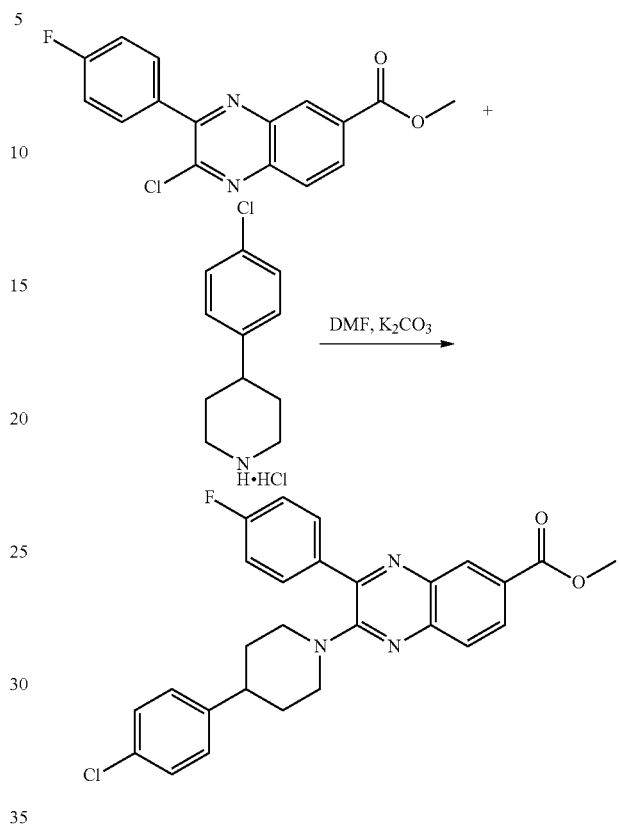

Into a 10-mL sealed tube, was placed a solution of methyl 2-chloro-3-(4-fluorophenyl)quinoxaline-6-carboxylate (150 mg, 0.47 mmol, 1.00 equiv) in N,N-dimethylformamide (5 mL), 4-(4-chlorophenyl)piperidine hydrochloride (219 mg, 0.94 mmol, 2.00 equiv), potassium carbonate (326 mg, 2.36 mmol, 5.00 equiv). The resulting solution was stirred overnight at 100° C. in an oil bath. The reaction was then quenched by the addition of 20 mL of water. The resulting solution was extracted with dichloromethane/methanol (10:1) and the organic layers were combined. The resulting mixture was concentrated under vacuum. The residue was applied onto a silica gel column with ethyl acetate/petroleum ether (1:10). This resulted in 200 mg (89%) of methyl 2-(4-(4-chlorophenyl)piperidin-1-yl)-3-(4-fluorophenyl) quinoxaline-6-carboxylate as a yellow solid.

LC-MS:(ES, m/z): 476 [M+H]+

Step 2. 2-(4-(4-Chlorophenyl)piperidin-1-yl)-3-(4-fluorophenyl)quinoxaline-6-carboxylic Acid

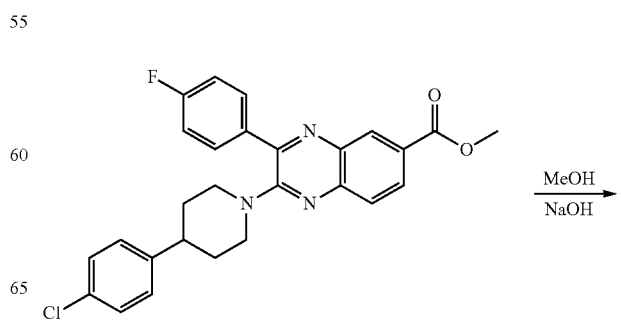

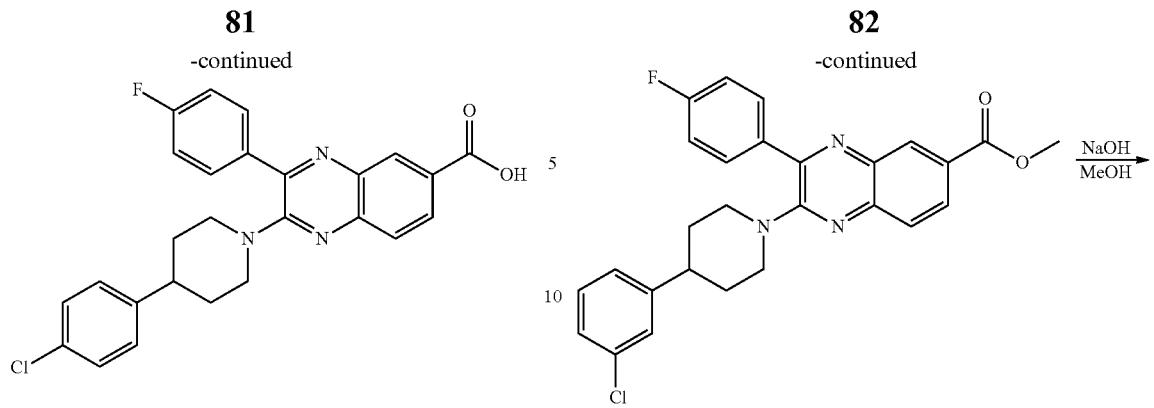

Into a 100-mL round-bottom flask, was placed a solution of methyl 2-(4-(4-chlorophenyl)piperidin-1-yl)-3-(4-fluorophenyl)quinoxaline-6-carboxylate (200 mg, 0.42 mmol, 1.00 equiv) in methanol (30 mL), sodium hydroxide (84 mg, 2.10 mmol, 5.00 equiv). The resulting solution was stirred for 130 minutes at 50° C. in an oil bath. The resulting mixture was concentrated under vacuum. The resulting solution was diluted with 30 mL of water. The pH value of the solution was adjusted to 3 with 1N hydrochloric acid. The solids were collected by filtration. The solid was dried in an oven under reduced pressure. This resulted in 110 mg (57%) of 2-(4-(4-chlorophenyl)piperidin-1-yl)-3-(4-fluorophenyl)quinoxaline-6-carboxylic acid as a yellow solid.

LC-MS:(ES, m/z): 462 [M+H]$^+$ $^1$H-NMR (300 MHz, DMSO, ppm): 13.119 (s, 1H), 8.430 (s, 1H), 8.142-8.051 (m, 3H), 7.821-7.793 (d, J=8.4 Hz, 1H), 7.437-7.281 (m, 6H), 3.923-3.88 (m, 2H), 2.934-2.742 (m, 3H), 1.732-1.645 (m, 4H).

EXAMPLE 25

2-(4-(3-Chlorophenyl)piperidin-1-yl)-3-(4-fluorophenyl)quinoxaline-6-carboxylic Acid

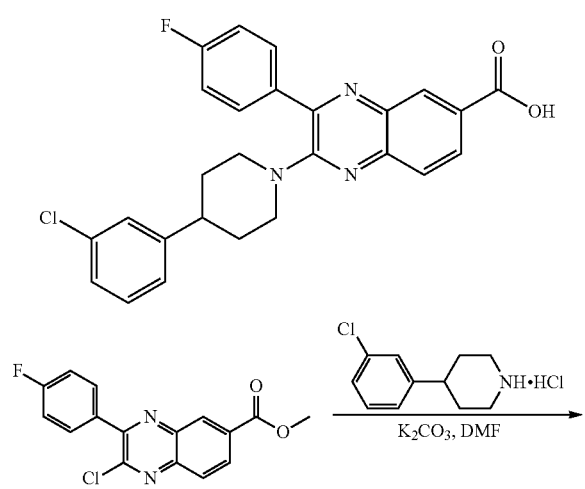

Step 1. Methyl 2-(4-(3-chlorophenyl)piperidin-1-yl)-3-(4-fluorophenyl)quinoxaline-6-carboxylate

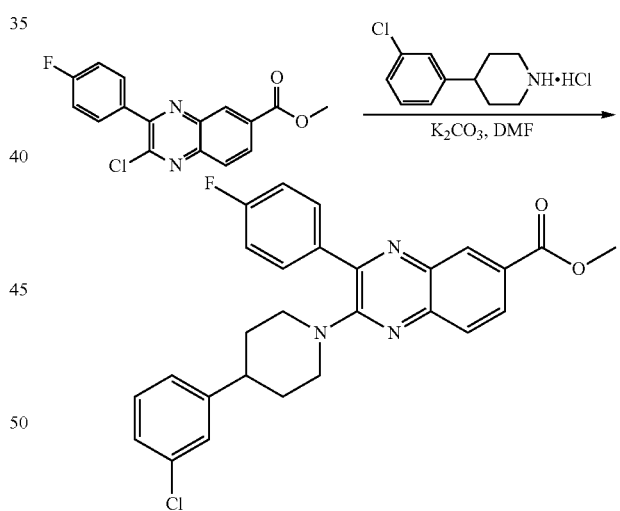

Into a 8-mL sealed tube, was placed methyl 2-chloro-3-(4-fluorophenyl)quinoxaline-6-carboxylate (200 mg, 0.63 mmol, 1.00 equiv), 4-(3-chlorophenyl)piperidine hydrochloride (292.4 mg, 1.27 mmol, 2.00 equiv), potassium carbonate (436.7 mg, 3.16 mmol, 5.00 equiv), N,N-dimethylformamide (4 mL). The resulting solution was stirred overnight at 100° C. in an oil bath. The residue was applied onto a silica gel column with ethyl acetate/petroleum ether (1:10). This resulted in 137 mg (43%) of methyl 2-(4-(3-chlorophenyl)piperidin-1-yl)-3-(4-fluorophenyl)quinoxaline-6-carboxylate as a yellow solid.

LC-MS:(ES, m/z): 476 [M+H]$^+$

Step 2. 2-(4-(3-Chlorophenyl)piperidin-1-yl)-3-(4-fluorophenyl)quinoxaline-6-carboxylic Acid

EXAMPLE 26

3-(4-Fluorophenyl)-2-(4-(4-methoxyphenyl)piperidin-1-yl)quinoxaline-6-carboxylic Acid

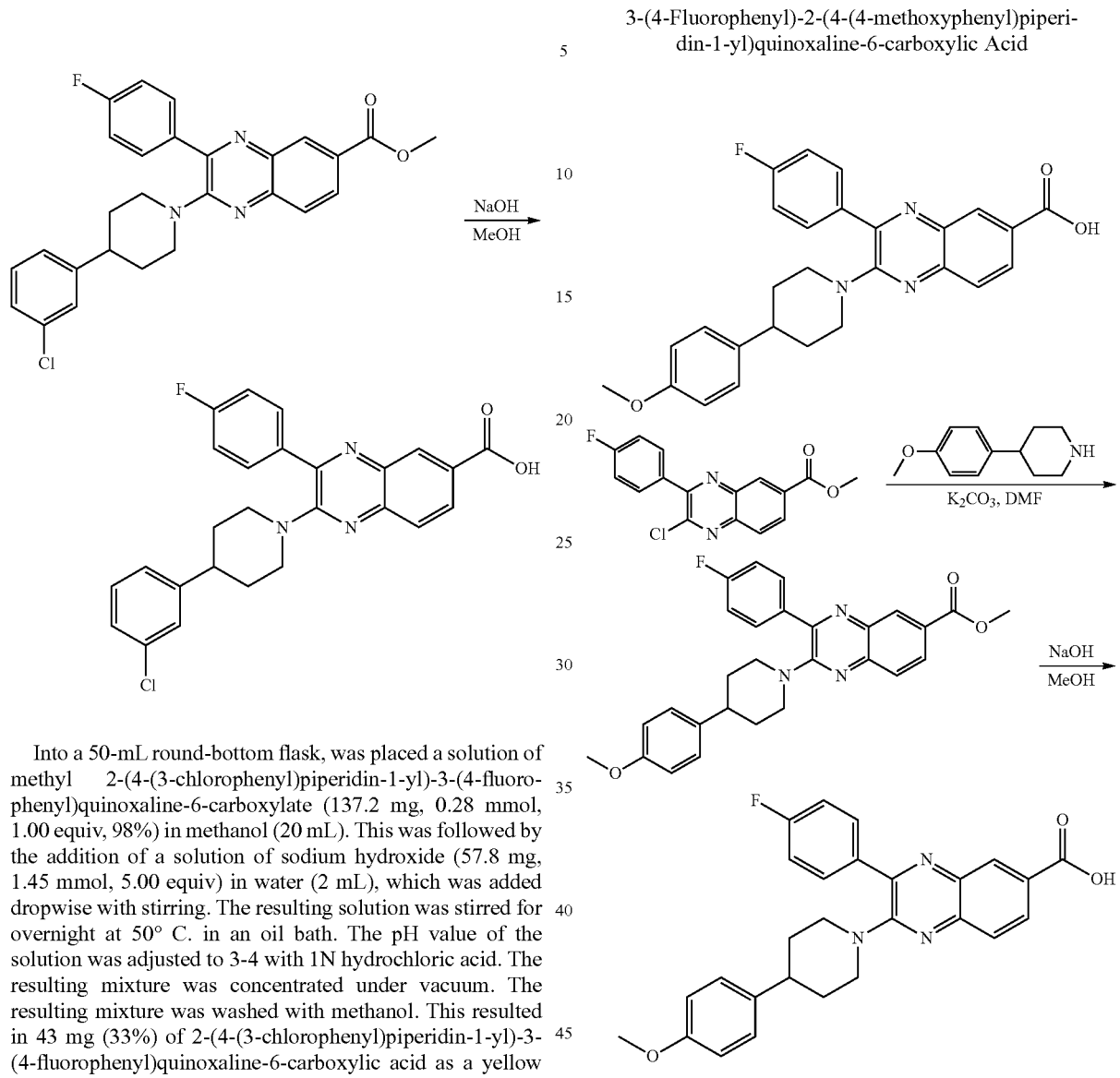

Into a 50-mL round-bottom flask, was placed a solution of methyl 2-(4-(3-chlorophenyl)piperidin-1-yl)-3-(4-fluorophenyl)quinoxaline-6-carboxylate (137.2 mg, 0.28 mmol, 1.00 equiv, 98%) in methanol (20 mL). This was followed by the addition of a solution of sodium hydroxide (57.8 mg, 1.45 mmol, 5.00 equiv) in water (2 mL), which was added dropwise with stirring. The resulting solution was stirred for overnight at 50° C. in an oil bath. The pH value of the solution was adjusted to 3-4 with 1N hydrochloric acid. The resulting mixture was concentrated under vacuum. The resulting mixture was washed with methanol. This resulted in 43 mg (33%) of 2-(4-(3-chlorophenyl)piperidin-1-yl)-3-(4-fluorophenyl)quinoxaline-6-carboxylic acid as a yellow solid.

LC-MS:(ES, m/z): 462 [M+H]$^+$ $^1$H-NMR (300 MHz, CDCl$_3$, ppm): 8.432 (s, 1H), 8.428-8.055 (m, 3H), 7.808-7.779 (d, J=8.7 Hz, 1H), 7.439-7.230 (m, 6H), 3.914-3.871 (d, J=12.9 Hz, 2H), 2.918-2.844 (m, 2H), 2.791-2.716 (t, J=22.5 Hz, 1H), 1.751-1.631 (m, 4H).

Step 1. Methyl 3-(4-fluorophenyl)-2-(4-(4-methoxyphenyl)piperidin-1-yl)quinoxaline-6-carboxylate

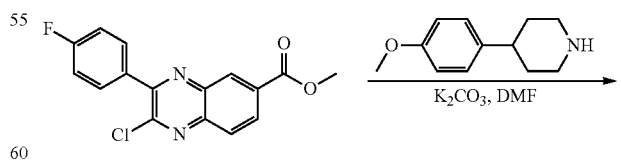

-continued

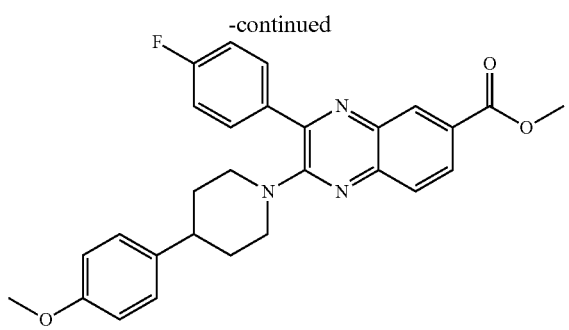

Into a 8-mL sealed tube, was placed methyl 2-chloro-3-(4-fluorophenyl)quinoxaline-6-carboxylate (200 mg, 0.63 mmol, 1.00 equiv), 4-(4-methoxyphenyl)piperidine (138 mg, 0.72 mmol, 2.00 equiv), potassium carbonate (436.7 mg, 3.16 mmol, 5.00 equiv), N,N-dimethylformamide (4 mL). The resulting solution was stirred overnight at 100° C. in an oil bath. The residue was applied onto a silica gel column with ethyl acetate/petroleum ether (1:10). This resulted in 123.9 mg (37%) of methyl 3-(4-fluorophenyl)-2-(4-(4-methoxyphenyl)piperidin-1-yl)quinoxaline-6-carboxylate as a yellow solid.

LC-MS:(ES, m/z): 472 [M+H]$^+$

Step 2. 3-(4-Fluorophenyl)-2-(4-(4-methoxyphenyl) piperidin-1-yl)quinoxaline-6-carboxylic Acid Into a 50-mL round-bottom flask, was placed a solution of methyl 3-(4-fluorophenyl)-2-(4-(4-methoxyphenyl)piperidin-1-yl)quinoxaline-6-carboxylate (123.9 mg, 0.24 mmol, 1.00 equiv, 93%) in methanol (15 mL). This was followed by the addition of a solution of sodium hydroxide (52.6 mg, 1.31 mmol, 5.00 equiv) in water (3 mL), which was added dropwise with stirring. The resulting solution was stirred for overnight at 50° C. in an oil bath. The pH value of the solution was adjusted to 3-4 with 1N hydrochloric acid. The resulting mixture was concentrated under vacuum. The resulting mixture was washed with methanol. This resulted in 60 mg (52%) of 3-(4-fluorophenyl)-2-(4-(4-methoxyphenyl)piperidin-1-yl)quinoxaline-6-carboxylic acid as a yellow solid.

LC-MS:(ES, m/z): 458 [M+H]$^+$ $^1$H-NMR (300 MHz, CDC$_3$, ppm): 8.794-8.789 (d, J=1.5 Hz, 1H), 8.309-8.274 (m, 1H), 8.085-8.038 (m, 2H), 7.900-7.871 (d, J=8.7 Hz, 1H), 7.273-7.155 (m, 4H), 6.905-6.877 (d, J=8.4 Hz, 2H), 4.079-4.035 (d, J=13.2 Hz, 2H), 2.988-2.909 (t, J=23.7 Hz, 2H), 2.733-2.656 (t, J=23.1 Hz, 1H), 1.899-1.684 (m, 4H).

EXAMPLE 27

3-(4-Fluorophenyl)-2-(4-(pyridin-2-yl)piperazin-1-yl)quinoxaline-6-carboxylic Acid

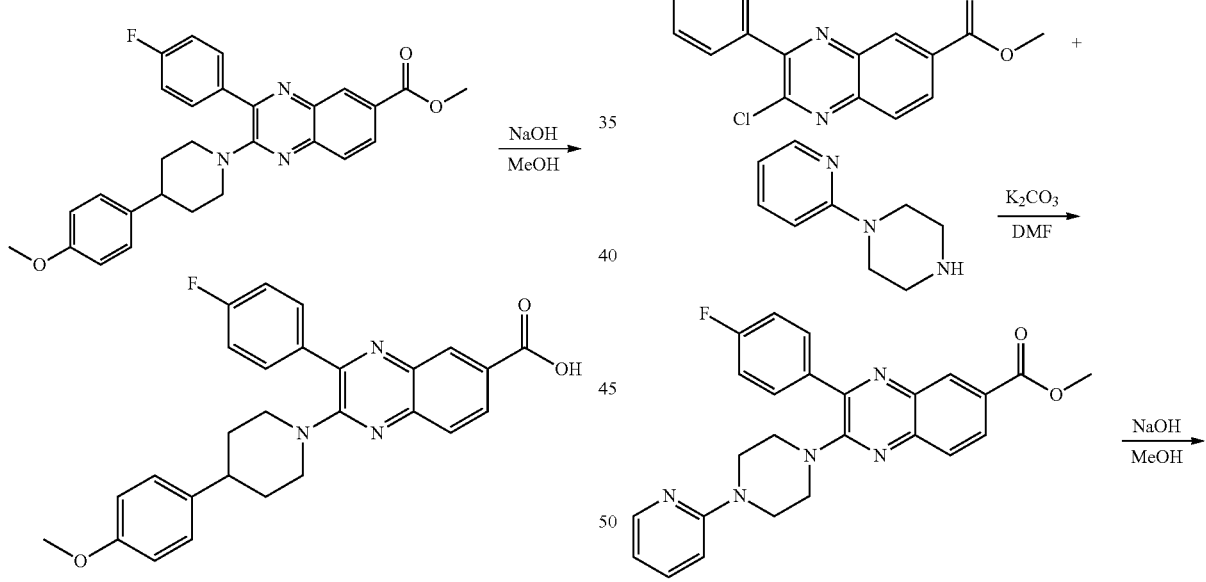

Step 1. Methyl 3-(4-fluorophenyl)-2-(4-(pyridin-2-yl)piperazin-1-yl)quinoxaline-6-carboxylate

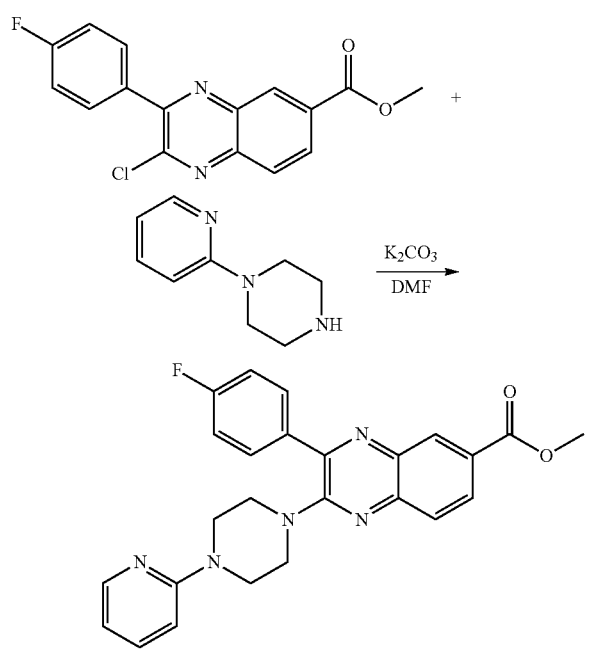

Into a 8-mL sealed tube, was placed methyl 2-chloro-3-(4-fluorophenyl)quinoxaline-6-carboxylate (200 mg, 0.63 mmol, 1.00 equiv), 1-(pyridin-2-yl)piperazine (207 mg, 1.27 mmol, 2.00 equiv), potassium carbonate (436.7 mg, 3.16 mmol, 5.00 equiv), N,N-dimethylformamide (4 mL). The resulting solution was stirred overnight at 100° C. in an oil bath. The reaction was then quenched by the addition of water. The resulting solution was extracted with 5×50 mL of dichloromethane and the organic layers combined. The mixture was concentrated under vacuum. The residue was applied onto a silica gel column with ethyl acetate/petroleum ether (1:50). This resulted in 157.4 mg (56%) of methyl 3-(4-fluorophenyl)-2-(4-(pyridin-2-yl)piperazin-1-yl)quinoxaline-6-carboxylate as a yellow solid.

LC-MS:(ES, m/z): 444 [M+H]+

Step 2. 3-(4-Fluorophenyl)-2-(4-(pyridin-2-yl)piperazin-1-yl)quinoxaline-6-carboxylic Acid

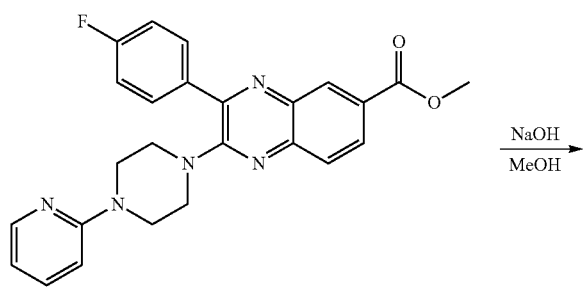

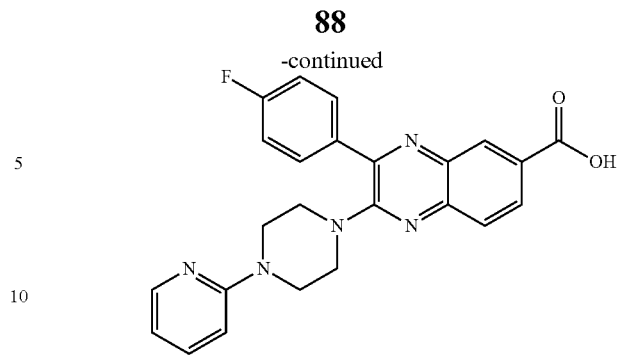

Into a 50-mL round-bottom flask, was placed a solution of methyl 3-(4-fluorophenyl)-2-(4-(pyridin-2-yl)piperazin-1-yl)quinoxaline-6-carboxylate (157.4 mg, 0.36 mmol, 1.00 equiv) in methanol (15 mL). This was followed by the addition of a solution of sodium hydroxide (71.1 mg, 1.78 mmol, 5.00 equiv) in water (2 mL) dropwise with stirring. The resulting solution was stirred overnight at 50° C. in an oil bath. The pH value of the solution was adjusted to 3-4 with 1N hydrochloric acid. The resulting mixture was concentrated under vacuum. The resulting mixture was washed with methanol. This resulted in 36 mg (23%) of 3-(4-fluorophenyl)-2-(4-(pyridin-2-yl)piperazin-1-yl)quinoxaline-6-carboxylic acid as a yellow solid.

LC-MS:(ES, m/z): 430 [M+H]+

$^1$H-NMR (300 MHz, DMSO, ppm): δ 8.468-8.463 (d, J=1.5 Hz, 1H), 8.180-8.146 (m, 3H), 8.099-8.053 (t, 1H), 7.874-7.794 (t, 1H), 7.448-7.389 (t, 2H), 7.140 (s, 1H), 6.833 (s, 1H), 3.670 (s, 4H), 3.452 (s, 4H).

EXAMPLE 28

2-Phenyl-3-(4-(3-(trifluoromethyl)pyridin-2-yl)piperazin-1-yl)quinoxaline-6-carboxylic Acid

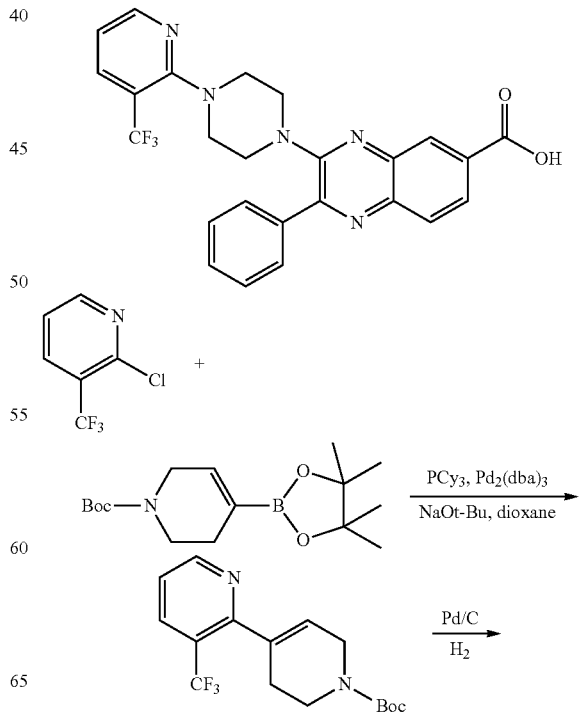

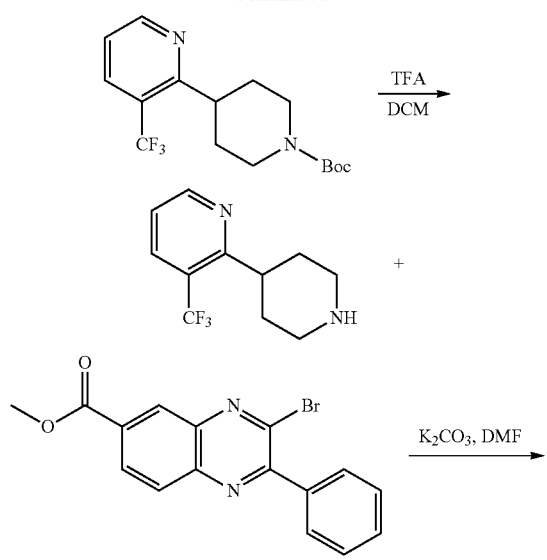

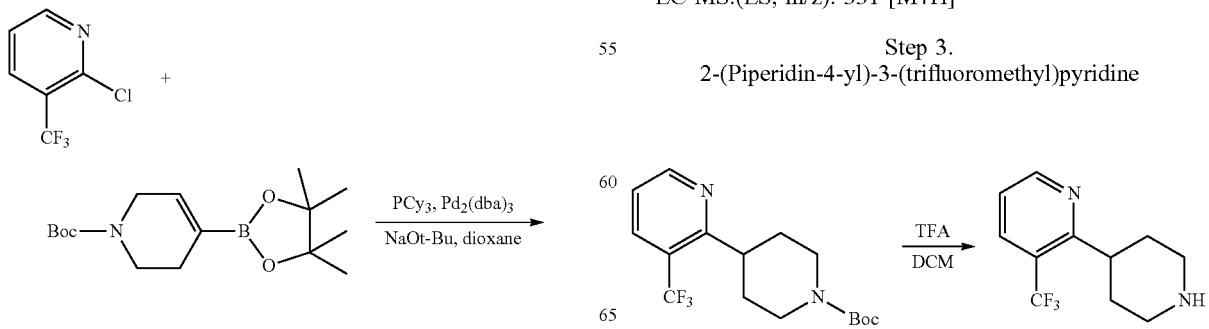

Step 1. tert-Butyl 4-(3-(trifluoromethyl)pyridin-2-yl)-5,6-dihydropyridine-1(2H)-carboxylate

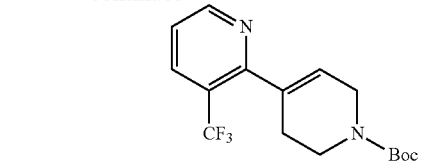

Into a 20 mL sealed tube was placed 2-chloro-3-(trifluoromethyl)pyridine (500 mg, 2.76 mmol, 1.00 equiv), tert-butyl 4-(4,4,5,5-tetramethyl-1,3,2-dioxaborolan-2-yl)-5,6-dihydropyridine-1(2H)-carboxylate (1.705 g, 5.52 mmol, 2.00 equiv), PCy$_3$ (216.4 mg, 0.77 mmol, 0.28 equiv), Pd$_2$(dba)$_3$ (304.7 mg, 0.33 mmol, 0.12 equiv), NaOt-Bu (828 mg, 8.28 mmol, 3.00 equiv), dioxane (8 mL). The resulting solution was stirred overnight at 100° C. in an oil bath. The resulting mixture was concentrated under vacuum. The residue was applied onto a silica gel column with PE/EA (10:1). This resulted in 449.3 mg (46%) of tert-butyl 4-(3-(trifluoromethyl)pyridin-2-yl)-5,6-dihydropyridine-1(2H)-carboxylate as yellow oil.

LC-MS:(ES, m/z): 329[M+H]$^+$

Step 2. tert-Butyl 4-(3-(trifluoromethyl)pyridin-2-yl)piperidine-1-carboxylate

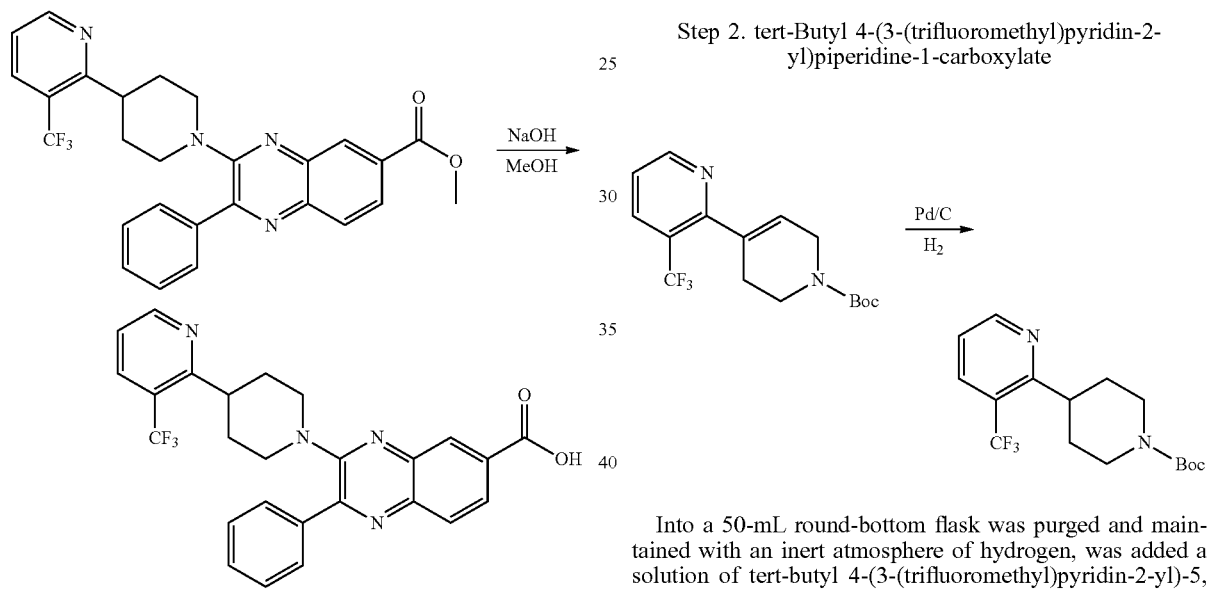

Into a 50-mL round-bottom flask was purged and maintained with an inert atmosphere of hydrogen, was added a solution of tert-butyl 4-(3-(trifluoromethyl)pyridin-2-yl)-5,6-dihydropyridine-1(2H)-carboxylate (449.3 mg, 1.27 mmol, 1.00 equiv, 93%) in methanol (20 mL) and Palladium carbon anhydrous (134.8 mg). The resulting solution was stirred overnight at room temperature. The solids were filtered out. The resulting mixture was concentrated under vacuum. This resulted in 379.8 mg (87%) of tert-butyl 4-(3-(trifluoromethyl)pyridin-2-yl)piperidine-1-carboxylate as colorless oil.

LC-MS:(ES, m/z): 331 [M+H]$^+$

Step 3. 2-(Piperidin-4-yl)-3-(trifluoromethyl)pyridine

Into a 50-mL round-bottom flask, was placed a solution of tert-butyl 4-(3-(trifluoromethyl)pyridin-2-yl)piperidine-1-carboxylate (379.8 mg, 1.10 mmol, 1.00 equiv, 96%) in dichloromethane (10 mL). This was followed by the addition of trifluoroacetic acid (5 mL) dropwise with stirring at 0° C. The resulting solution was stirred for 3 h at room temperature. The pH value of the solution was adjusted to 8-9 with sat sodium bicarbonate. The resulting solution was extracted with 6×50 mL of dichloromethane and the organic layers combined and dried over anhydrous sodium sulfate. The solids were filtered out. The resulting mixture was concentrated under vacuum. This resulted in 237.4 mg (93%) of 2-(piperidin-4-yl)-3-(trifluoromethyl)pyridine as yellow oil.

LC-MS:(ES, m/z): 231 [M+H]$^+$

Step 4. Methyl 2-phenyl-3-(4-(3-(trifluoromethyl)pyridin-2-yl)piperidin-1-yl)quinoxaline-6-carboxylate

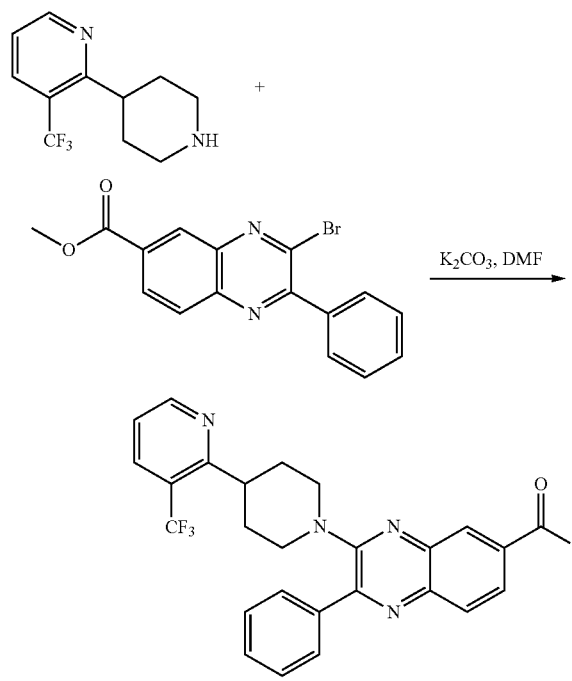

Into a 8-mL sealed tube, was placed methyl 3-bromo-2-phenylquinoxaline-6-carboxylate (176.5 mg, 0.52 mmol, 1.00 equiv), 2-(piperidin-4-yl)-3-(trifluoromethyl)pyridine (237.4 mg, 1.03 mmol, 2.00 equiv), potassium carbonate (356.1 mg, 2.58 mmol, 5.00 equiv) and N,N-dimethylformamide (4 mL). The resulting solution was stirred overnight at 100° C. in an oil bath. The residue was applied onto a silica gel column with ethyl acetate/petroleum ether (1:50). This resulted in 236.2 mg (87%) of methyl 2-phenyl-3-(4-(3-(trifluoromethyl)pyridin-2-yl)piperidin-1-yl)quinoxaline-6-carboxylate as a yellow solid.

LC-MS:(ES, m/z): 493 [M+H]$^+$

Step 5. 2-Phenyl-3-(4-(3-(trifluoromethyl)pyridin-2-yl)piperidin-1-yl)quinoxaline-6-carboxylic Acid

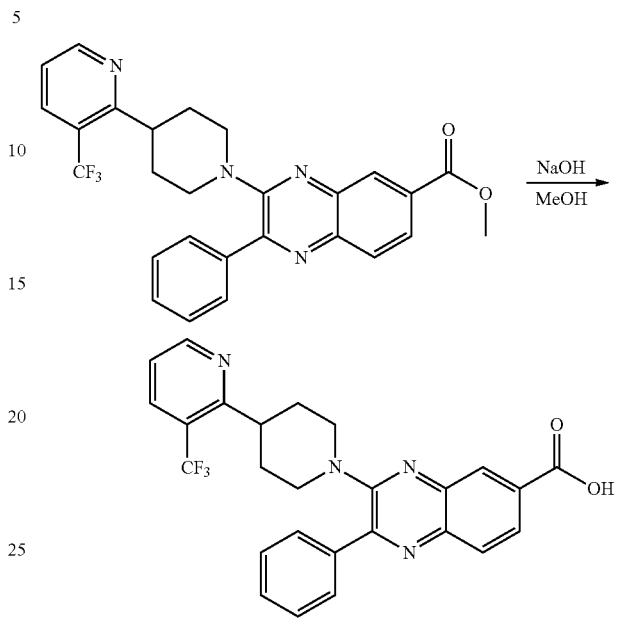

Into a 50-mL round-bottom flask, was placed a solution of methyl 2-phenyl-3-(4-(3-(trifluoromethyl) pyridin-2-yl)piperidin-1-yl)quinoxaline-6-carboxylate (236.2 mg, 0.46 mmol, 1.00 equiv, 95%) in methanol (15 mL). This was followed by the addition of a solution of sodium hydroxide (91.2 mg, 5.00 equiv) in water (2 mL), which was added dropwise with stirring. The resulting solution was stirred overnight at 50° C. in an oil bath. The pH value of the solution was adjusted to 3-4 with 1N hydrochloric acid.

The resulting mixture was concentrated under vacuum. The resulting mixture was washed with methanol. This resulted in 105.4 mg (48%) of 2-phenyl-3-(4-(3-(trifluoromethyl)pyridin-2-yl)piperidin-1-yl)quinoxaline-6-carboxylic acid as a yellow solid.

LC-MS:(ES, m/z): 479 [M+H]$^+$ $^1$H-NMR (300 MHz, DMSO, ppm): 13.201 (s, 1H), 8.848-8.834 (d, J=4.2 Hz, 1H), 8.316 (s, 1H), 8.135-8.111 (d, J=7.2 Hz, 1H), 8.028-8.010 (d, J=5.4 Hz, 4H), 7.605-7.455 (m, 4H), 3.947-3.904 (d, J=12.9 Hz, 2H), 3.186-3.147 (m, 1H), 2.946-3.881 (t, J=12.3 Hz, 2H), 2.083-1.966 (dd, J=12.6 Hz, 2H), 1.668-1.631 (d, J=11.1 Hz, 2H).

EXAMPLE 29

3-(4-Fluorophenyl)-2-(4-(4-(trifluoromethyl)phenyl)piperidin-1-yl)quinoxaline-6-carboxylic Acid

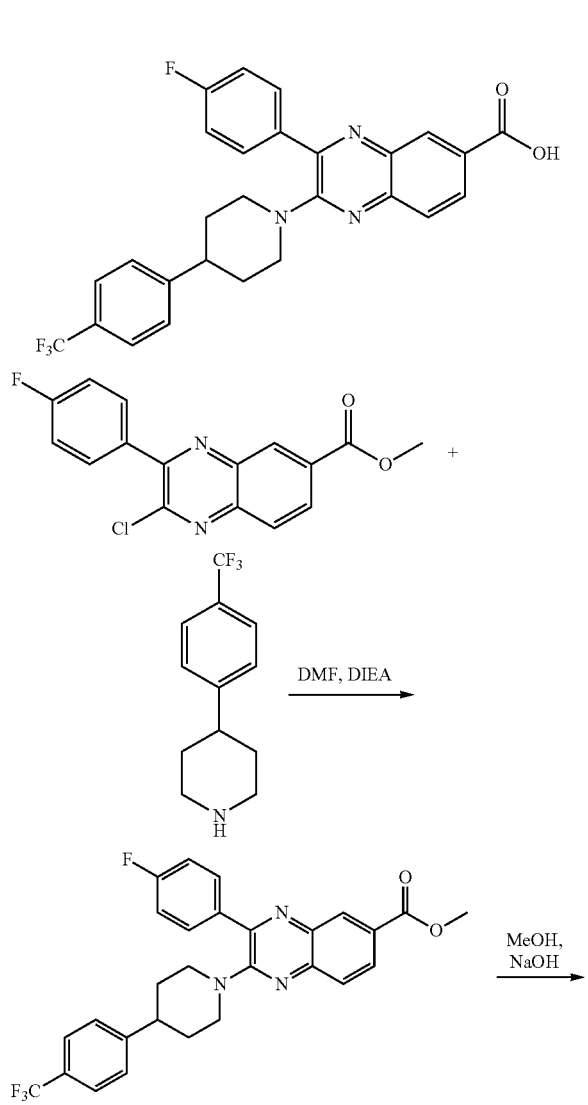

Step 1. Methyl 3-(4-fluorophenyl)-2-(4-(4-(trifluoromethyl)phenyl)piperidin-1-yl)quinoxaline-6-carboxylate

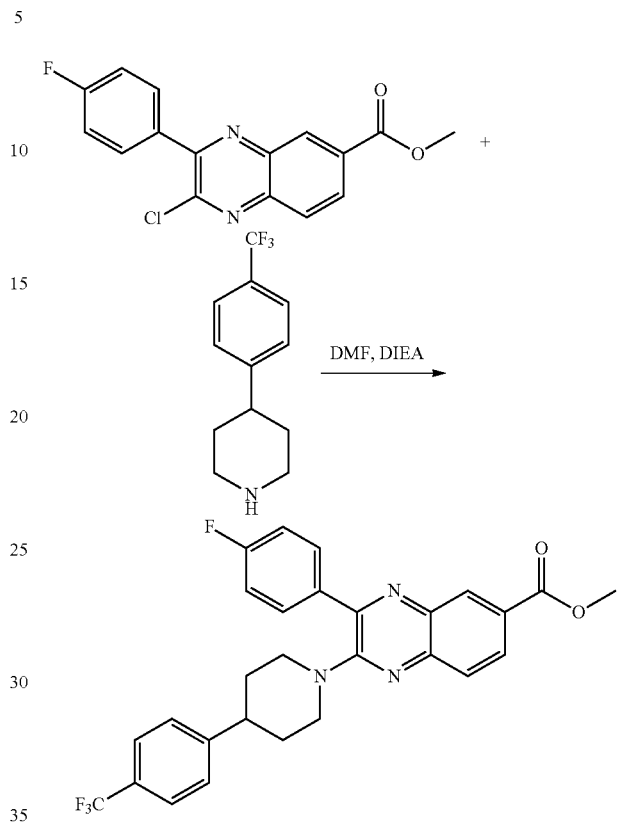

Into a 20-mL sealed tube, was placed a solution of 4-(4-(trifluoromethyl)phenyl)piperidine (420 mg, 1.83 mmol, 3.00 equiv), methyl 2-chloro-3-(4-fluorophenyl)quinoxaline-6-carboxylate (150 mg, 0.47 mmol, 1.00 equiv), DIEA (305 mg, 2.36 mmol, 5.00 equiv) in N,N-dimethylformamide (10 mL). The resulting solution was stirred overnight at 100° C. in an oil bath. The resulting mixture was concentrated under vacuum. The residue was applied onto a silica gel column with ethyl acetate/petroleum ether (1:10). This resulted in 200 mg (83%) of methyl 3-(4-fluorophenyl)-2-(4-(4-(trifluoromethyl)phenyl)piperidin-1-yl)quinoxaline-6-carboxylate as a yellow solid.

LC-MS:(ES, m/z): 510 [M+H]$^+$

Step 2. 3-(4-Fluorophenyl)-2-(4-(4-(trifluoromethyl)phenyl)piperidin-1-yl)quinoxaline-6-carboxylic Acid

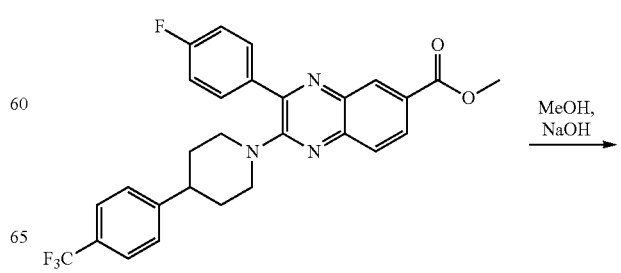

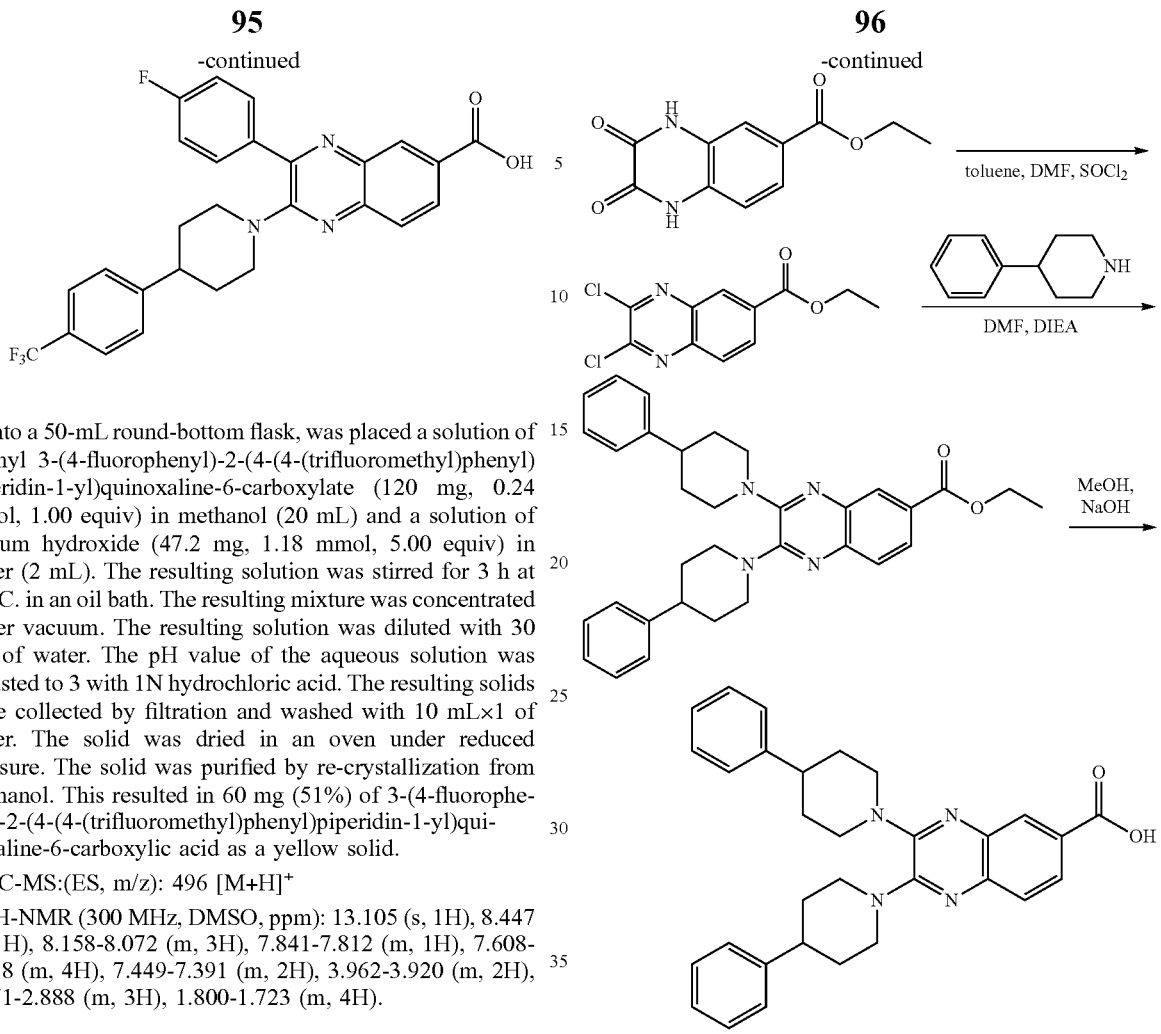

Into a 50-mL round-bottom flask, was placed a solution of methyl 3-(4-fluorophenyl)-2-(4-(4-(trifluoromethyl)phenyl)piperidin-1-yl)quinoxaline-6-carboxylate (120 mg, 0.24 mmol, 1.00 equiv) in methanol (20 mL) and a solution of sodium hydroxide (47.2 mg, 1.18 mmol, 5.00 equiv) in water (2 mL). The resulting solution was stirred for 3 h at 50° C. in an oil bath. The resulting mixture was concentrated under vacuum. The resulting solution was diluted with 30 mL of water. The pH value of the aqueous solution was adjusted to 3 with 1N hydrochloric acid. The resulting solids were collected by filtration and washed with 10 mL×1 of water. The solid was dried in an oven under reduced pressure. The solid was purified by re-crystallization from methanol. This resulted in 60 mg (51%) of 3-(4-fluorophenyl)-2-(4-(4-(trifluoromethyl)phenyl)piperidin-1-yl)quinoxaline-6-carboxylic acid as a yellow solid.

LC-MS:(ES, m/z): 496 [M+H]$^+$ $^1$H-NMR (300 MHz, DMSO, ppm): 13.105 (s, 1H), 8.447 (s, 1H), 8.158-8.072 (m, 3H), 7.841-7.812 (m, 1H), 7.608-7.558 (m, 4H), 7.449-7.391 (m, 2H), 3.962-3.920 (m, 2H), 2.971-2.888 (m, 3H), 1.800-1.723 (m, 4H).

EXAMPLE 30

2,3-Bis(4-phenylpiperidin-1-yl)quinoxaline-6-carboxylic Acid

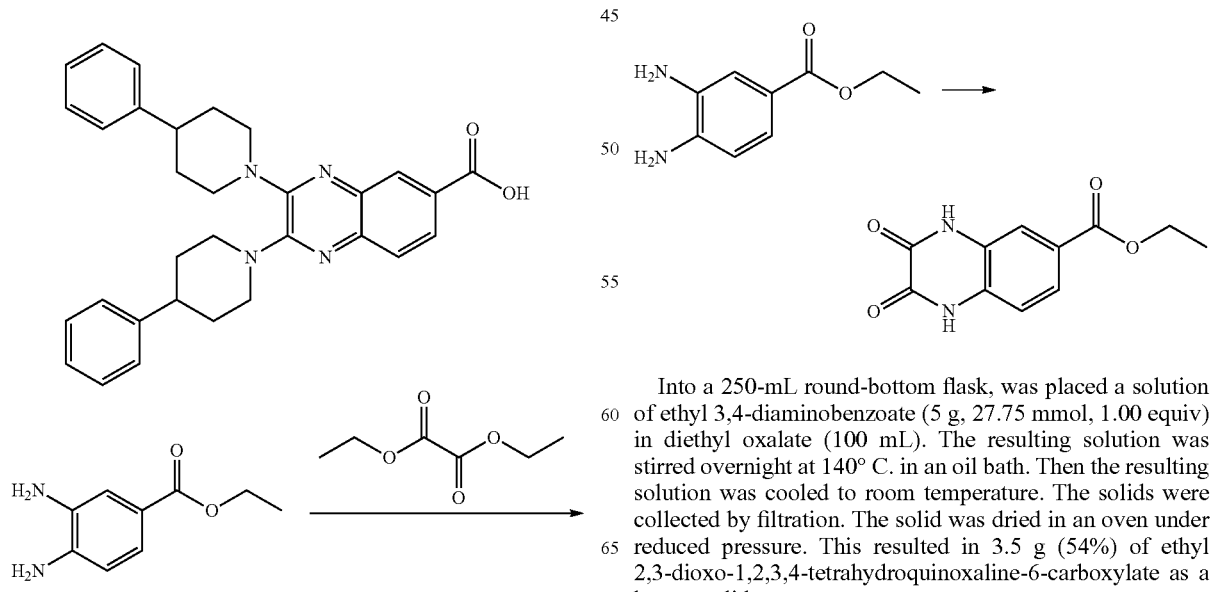

Step 1. Ethyl 2,3-dioxo-1,2,3,4-tetrahydroquinoxaline-6-carboxylate

Into a 250-mL round-bottom flask, was placed a solution of ethyl 3,4-diaminobenzoate (5 g, 27.75 mmol, 1.00 equiv) in diethyl oxalate (100 mL). The resulting solution was stirred overnight at 140° C. in an oil bath. Then the resulting solution was cooled to room temperature. The solids were collected by filtration. The solid was dried in an oven under reduced pressure. This resulted in 3.5 g (54%) of ethyl 2,3-dioxo-1,2,3,4-tetrahydroquinoxaline-6-carboxylate as a brown solid.

Step 2. Ethyl 2,3-dichloroquinoxaline-6-carboxylate

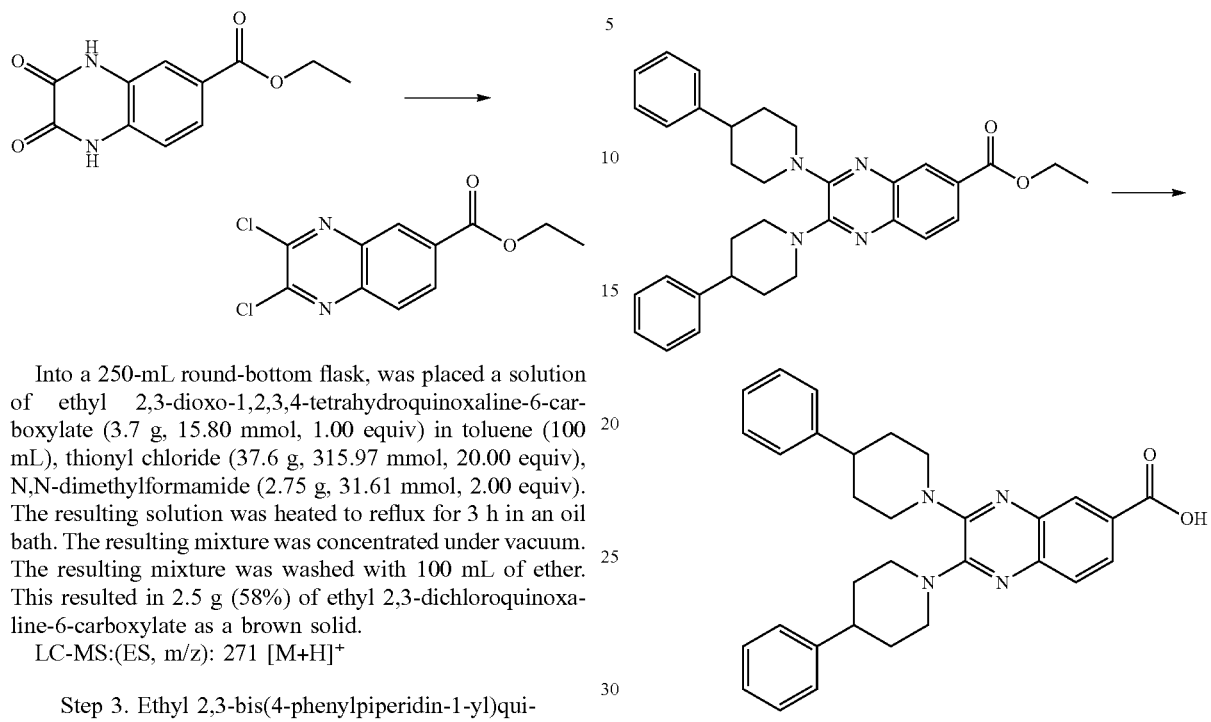

Into a 250-mL round-bottom flask, was placed a solution of ethyl 2,3-dioxo-1,2,3,4-tetrahydroquinoxaline-6-carboxylate (3.7 g, 15.80 mmol, 1.00 equiv) in toluene (100 mL), thionyl chloride (37.6 g, 315.97 mmol, 20.00 equiv), N,N-dimethylformamide (2.75 g, 31.61 mmol, 2.00 equiv). The resulting solution was heated to reflux for 3 h in an oil bath. The resulting mixture was concentrated under vacuum. The resulting mixture was washed with 100 mL of ether. This resulted in 2.5 g (58%) of ethyl 2,3-dichloroquinoxaline-6-carboxylate as a brown solid.

LC-MS:(ES, m/z): 271 [M+H]+

Step 3. Ethyl 2,3-bis(4-phenylpiperidin-1-yl)quinoxaline-6-carboxylate

Into a 20-mL sealed tube, was placed a solution of ethyl 2,3-dichloroquinoxaline-6-carboxylate (150 mg, 0.55 mmol, 1.00 equiv), 4-phenylpiperidine (298 mg, 1.85 mmol, 3.00 equiv), DIEA (398 mg, 3.09 mmol, 5.00 equiv) in N,N-dimethylformamide (10 mL). The resulting solution was stirred overnight at 100° C. in an oil bath. The resulting mixture was concentrated under vacuum. The residue was applied onto a silica gel column with ethyl acetate/petroleum ether (1:10). This resulted in 180 mg (62%) of ethyl 2,3-bis(4-phenylpiperidin-1-yl)quinoxaline-6-carboxylate as a yellow solid.

LC-MS:(ES, m/z): 521 [M+H]+

Step 4. 2,3-Bis(4-phenylpiperidin-1-yl)quinoxaline-6-carboxylic Acid

Into a 50-mL round-bottom flask, was placed a solution of ethyl 2,3-bis(4-phenylpiperidin-1-yl)quinoxaline-6-carboxylate (150 mg, 0.29 mmol, 1.00 equiv) in methanol (25 mL) and a solution of sodium hydroxide (58 mg, 1.45 mmol, 5.00 equiv) in water (2 mL). The resulting solution was stirred for 3 h at 50° C. in an oil bath. The resulting mixture was concentrated under vacuum. The resulting solution was diluted with 30 mL of water. The pH value of the aqueous solution was adjusted to 3 with 1N hydrochloric acid. The resulting solids were collected by filtration. The solid was dried in an oven under reduced pressure and purified by re-crystallization from methanol.

This resulted in 80 mg (56%) of 2,3-bis(4-phenylpiperidin-1-yl)quinoxaline-6-carboxylic acid as a yellow solid.

LC-MS:(ES, m/z): 493 [M+H]+

$^1$H-NMR (300 MHz, DMSO, ppm): 12.952 (s, 1H), 8.172 (s, 1H), 7.915-7.883 (d, J=9.6 Hz, 1H), 7.662-7.634 (d, J=8.4 Hz, 1H), 7.292-7.197 (m, 10H), 4.605-4.426 (m, 4H), 3.072-2.831 (m, 6H), 1.830-1.791 (m, 8H).

EXAMPLE 31

2,3-Bis(4-methoxyphenyl)-6-(1H-tetrazol-5-yl)quinoxaline

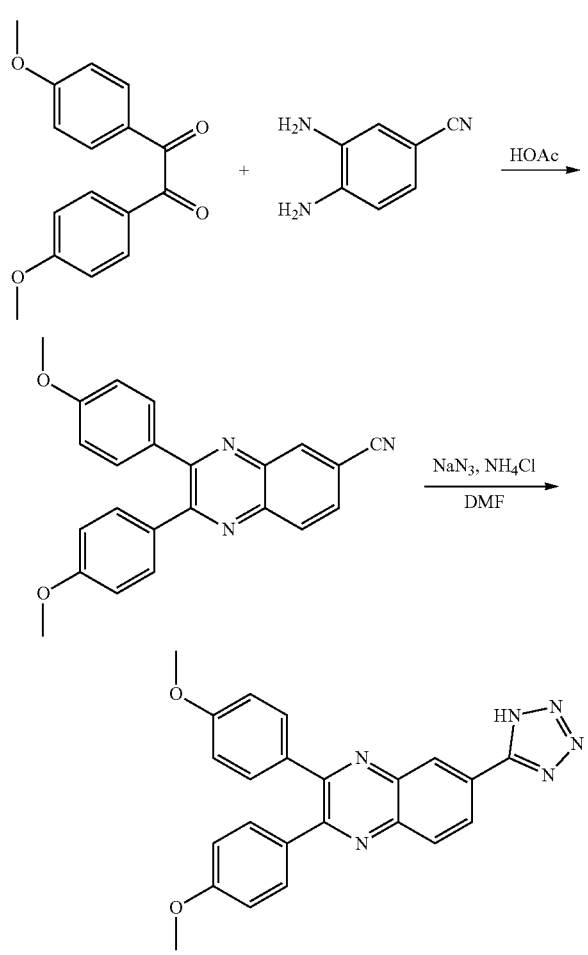

Step 1.
2,3-Bis(4-methoxyphenyl)quinoxaline-6-carbonitrile

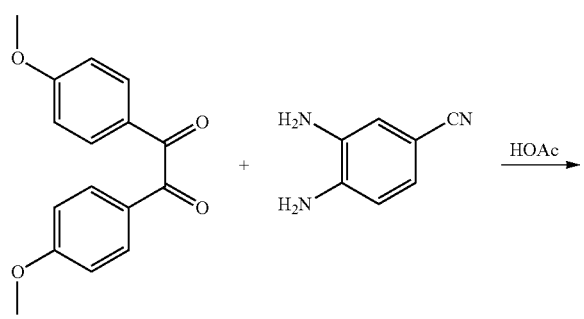

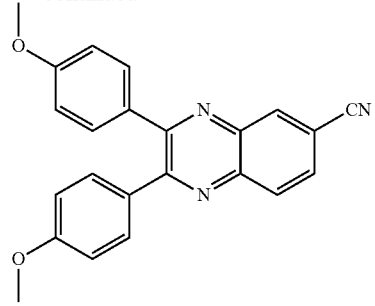

Into a 100-mL round-bottom flask, was placed a solution of 1,2-bis(4-methoxyphenyl)ethane-1,2-dione (200 mg, 0.74 mmol, 1.00 equiv) in acetic acid (20 mL), 3,4-diaminobenzonitrile (118.2 mg, 0.89 mmol, 1.20 equiv). The resulting solution was stirred for 1 h at reflux in an oil bath. The reaction was then quenched by the addition of water. The solids were collected by filtration and washed with MeOH.

This resulted in 205 mg (71%) of 2,3-bis(4-methoxyphenyl)quinoxaline-6-carbonitrile as a yellow solid.

LC-MS-PH:(ES, m/z): 368 [M+H]$^+$

Step 2. 2,3-Bis(4-methoxyphenyl)-6-(1H-tetrazol-5-yl)quinoxaline

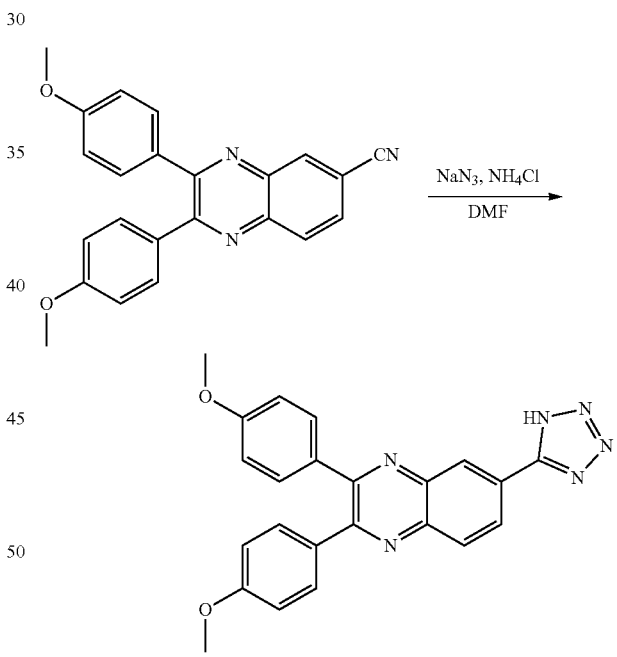

Into a 20-mL sealed tube, was placed a solution of 2,3-bis(4-methoxyphenyl)quinoxaline-6-carbonitrile (200 mg, 0.51 mmol, 1.00 equiv, 93%) in N,N-dimethylformamide (7 mL), NaN3 (500 mg, 7.69 mmol, 15.18 equiv), NH4Cl (147.9 mg, 2.79 mmol, 5.00 equiv). The resulting solution was stirred for 4 h at 100° C. in an oil bath. The reaction was then quenched by the addition of water. The resulting solution was extracted with 8×50 mL of dichloromethane/MeOH (10:1) and the organic layers combined and dried over anhydrous sodium sulfate. The solids were filtered out. The resulting mixture was concentrated under vacuum. The resulting mixture was washed with methanol.

This resulted in 47 mg (23%) of 2,3-bis(4-methoxyphenyl)-6-(1H-tetrazol-5-yl)quinoxaline as a yellow solid.

LC-MS:(ES, m/z): 411 [M+H]+

1H-NMR (300 MHz, DMSO, ppm): δ 8.760 (1H, s), 8.463-8.293 (4H, m), 7.523, 7.498 (4H, d, J=7.5 Hz), 6.995, 6.971 (4H, d, J=7.2 Hz), 3.861 (6H, s).

EXAMPLE 32

3-(4-(N-Methylmethan-3-ylsulfonamido)piperidin-1-yl)-2-phenylquinoxaline-6-carboxylic Acid

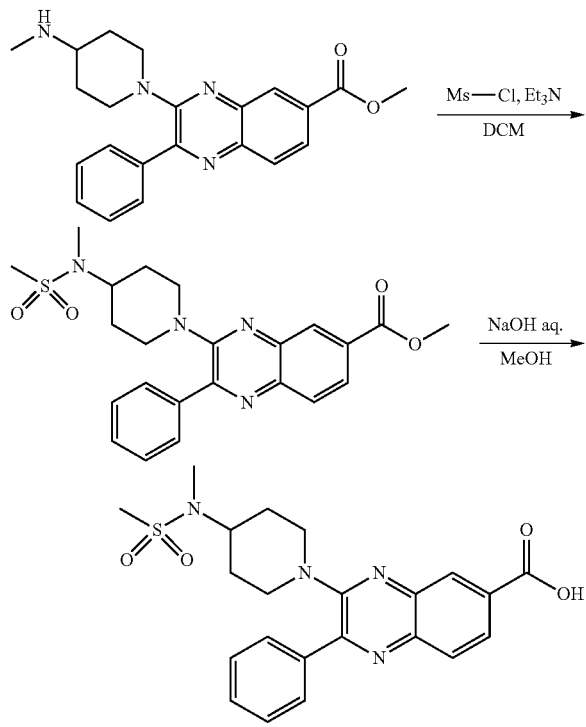

Step 1. Methyl 3-(4-(N-methylmethan-3-ylsulfonamido)piperidin-1-yl)-2-phenylquinoxaline-6-carboxylate Into a 50-mL round-bottom flask, was placed a solution of methyl 3-(4-(methylamino)piperidin-1-yl)-2-phenylquinoxaline-6-carboxylate (215 mg, 0.57 mmol, 1.00 equiv) in dichloromethane (14 mL), methanesulfonyl chloride (71.7 mg, 0.63 mmol, 1.10 equiv) and triethylamine (287.85 mg, 2.85 mmol, 5.00 equiv). The resulting solution was stirred for 3 h at room temperature. The reaction was then quenched by the addition of sat. sodium bicarbonate. The resulting solution was concentrated under vacuum. The residue was applied onto a silica gel column with ethyl acetate/petroleum ether (1:50). This resulted in 293.5 mg (crude) of methyl 3-(4-(N-methylmethan-3-ylsulfonamido)piperidin-1-yl)-2-phenylquinoxaline-6-carboxylate as a yellow solid.

LC-MS (ES, m/z): 455[M+H]+

Step 2. 3-(4-(N-methylmethan-3-ylsulfonamido)piperidin-1-yl)-2-phenylquinoxaline-6-carboxylic Acid Into a 50-mL round-bottom flask, was placed a solution of methyl 3-(4-(N-methylmethan-3-ylsulfonamido)piperidin-1-yl)-2-phenylquinoxaline-6-carboxylate (293.5 mg, 0.60 mmol, 1.00 equiv, 93%) in methanol (15 mL). This was followed by the addition of a solution of sodium hydroxide (129.3 mg, 3.23 mmol, 5.00 equiv) in water (3 mL) dropwise with stirring. The resulting solution was stirred overnight at 50° C. in an oil bath. The pH value of the solution was adjusted to 3-4 with 1N aq. hydrogen chloride. The resulting mixture was concentrated under vacuum. The resulting solid was washed with methanol and water, filtered and dried under vacuum.

This resulted in 78 mg (29%) of 3-(4-(N-methylmethan-3-ylsulfonamido)piperidin-1-yl)-2-phenylquinoxaline-6-carboxylic acid as a yellow solid.

LC-MS (ES, m/z): 441[M+H]+

1H-NMR (300 MHz, DMSO, ppm): δ 8.306 (s, 1H), 8.001-7.986 (d, J=4.5 Hz, 4H), 7.587-7.563 (d, J=7.2 Hz, 3H), 3.858-3.774 (t, J=12.6 Hz, 3H), 2.905-2.805 (m, 5H), 2.702 (s, 3H), 1.764-1.696 (t, J=10.2 Hz, 2H), 1.614-1.580 (d, J=10.2 Hz, 2H).

EXAMPLE 33

3-(4-(Methylsulfonyl)piperazin-1-yl)-2-phenylquinoxaline-6-carboxylic Acid

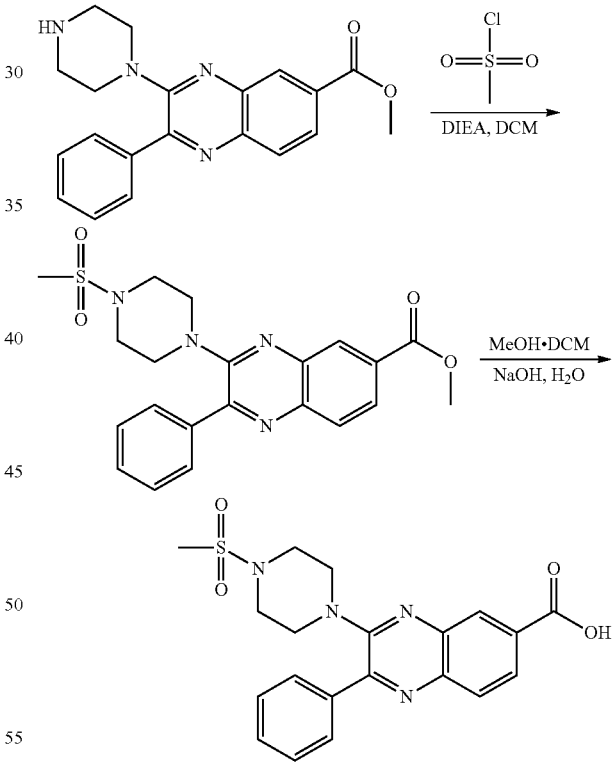

Step 1. Methyl 3-(4-(methylsulfonyl)piperazin-1-yl)-2-phenylquinoxaline-6-carboxylate Into a 100-mL round-bottom flask, was placed a solution of methyl 2-phenyl-3-(piperazin-1-yl)quinoxaline-6-carboxylate (150 mg, 0.43 mmol, 1.00 equiv), DIEA (3 mL) in DCM (15 mL). This was followed by the addition of methanesulfonyl chloride (0.5 mL) at 0° C. The resulting solution was stirred overnight at room temperature. The reaction was washed by sat. NaCl and concentrated under vacuum. This resulted in 0.17 g (93%) of methyl 3-(4-(methylsulfonyl)piperazin-1-yl)-2-phenylquinoxaline-6-carboxylate as a brown yellow oil.

Step 2. 3-(4-(Methylsulfonyl)piperazin-1-yl)-2-phenylquinoxaline-6-carboxylic Acid Into a 100-mL round-bottom flask, was placed methyl 3-(4-(methylsulfonyl)piperazin-1-yl)-2-phenylquinoxaline-6-carboxylate (170 mg, 0.40 mmol, 1.00 equiv), methanol (15 mL) in dichloromethane (5 mL). This was followed by the addition of a solution of sodium hydroxide (190 mg, 4.75 mmol, 11.90 equiv) in water (10 mL). The resulting solution was stirred for 3 h at room temperature. The resulting mixture was concentrated under vacuum and diluted by 10 ml of H$_2$O. The pH value of the aqueous solution was adjusted to 3 with hydrochloric acid. The resulting solids were collected by filtration. This resulted in 20 mg (12%) of 3-(4-(methylsulfonyl)piperazin-1-yl)-2-phenylquinoxaline-6-carboxylic acid as a brown solid.

LC-MS (ES, m/z): 413 [M+H]$^+$ $^1$H-NMR (300 MHz, DMSO, ppm): δ 13.29 (s, 1H), 8.35-7.57 (m, 8H), 3.18 (m, 4H), 2.92 (s, 3H).

EXAMPLE 34

3-(4-(N-Methylacetamido)piperidin-1-yl)-2-phenylquinoxaline-6-carboxylic Acid

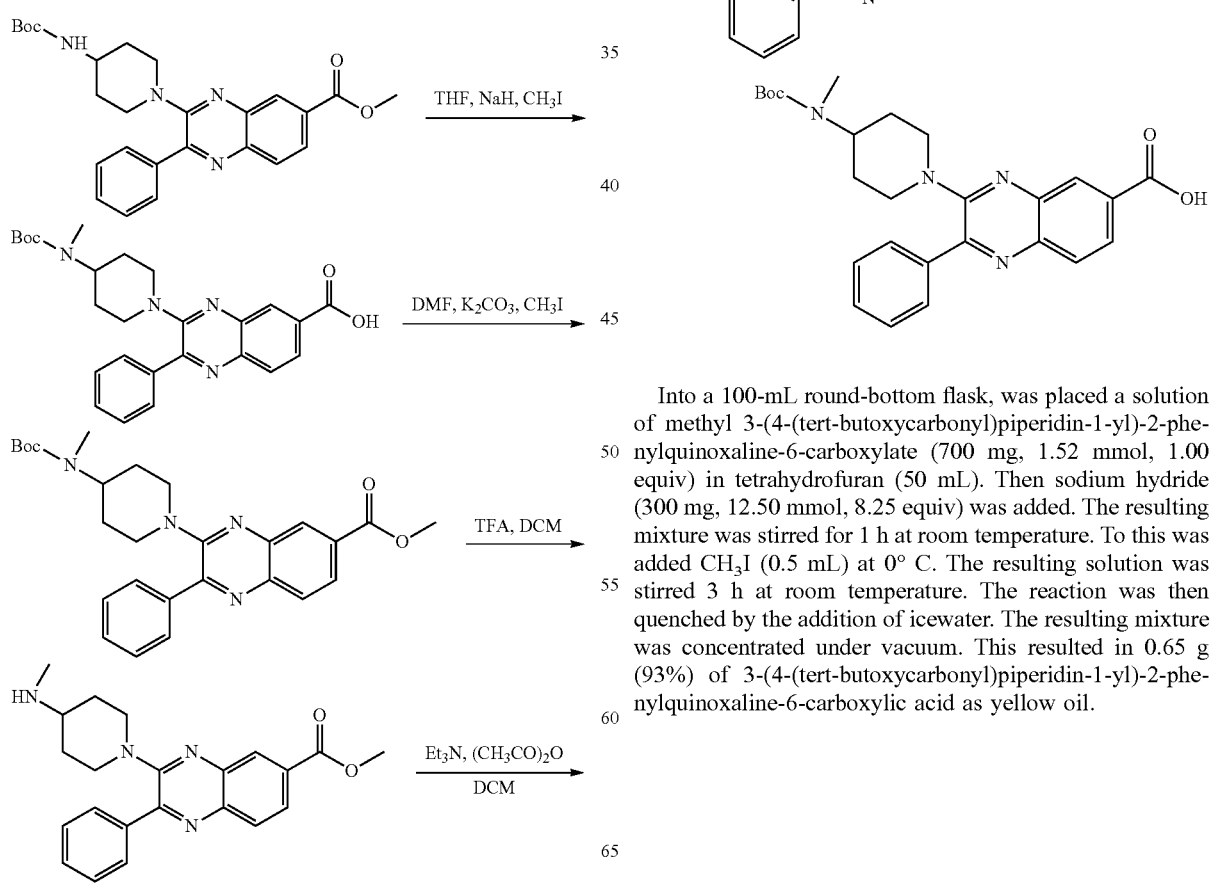

Step 1. 3-(4-(tert-Butoxycarbonyl)piperidin-1-yl)-2-phenylquinoxaline-6-carboxylic Acid:

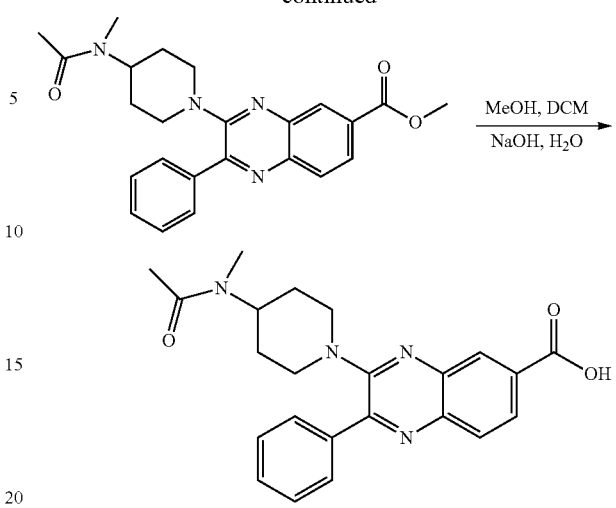

Into a 100-mL round-bottom flask, was placed a solution of methyl 3-(4-(tert-butoxycarbonyl)piperidin-1-yl)-2-phenylquinoxaline-6-carboxylate (700 mg, 1.52 mmol, 1.00 equiv) in tetrahydrofuran (50 mL). Then sodium hydride (300 mg, 12.50 mmol, 8.25 equiv) was added. The resulting mixture was stirred for 1 h at room temperature. To this was added CH$_3$I (0.5 mL) at 0° C. The resulting solution was stirred 3 h at room temperature. The reaction was then quenched by the addition of icewater. The resulting mixture was concentrated under vacuum. This resulted in 0.65 g (93%) of 3-(4-(tert-butoxycarbonyl)piperidin-1-yl)-2-phenylquinoxaline-6-carboxylic acid as yellow oil.

Step 2. Methyl 3-(4-(tert-butoxycarbonyl)piperidin-1-yl)-2-phenylquinoxaline-6-carboxylate

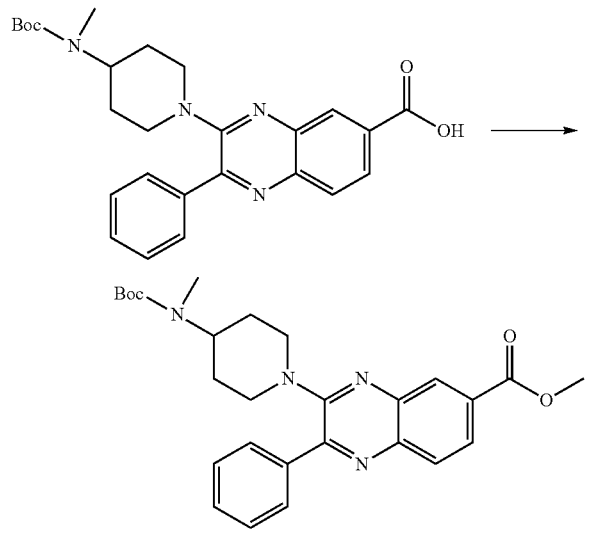

Into a 100-mL round-bottom flask purged and maintained with an inert atmosphere of nitrogen, was placed a solution of 3-(4-(tert-butoxycarbonyl)piperidin-1-yl)-2-phenylquinoxaline-6-carboxylic acid (509.7 mg, 1.10 mmol, 1.00 equiv) in N,N-dimethylformamide (15 mL), potassium carbonate (762.3 mg, 5.52 mmol, 5.00 equiv). The resulting solution was stirred 30 min at room temperature. Then CH$_3$I (783.3 mg, 5.52 mmol, 5.00 equiv) was added dropwise with stirring at 0° C. The resulting solution was stirred for 3 h at room temperature. The reaction was then quenched by the addition of water. The resulting aqueous solution was extracted with 6×20 mL of dichloromethane. The organic layers combined and dried over anhydrous sodium sulfate and concentrated under vacuum. This resulted in 285.5 mg (54%) of methyl 3-(4-(tert-butoxycarbonyl)piperidin-1-yl)-2-phenylquinoxaline-6-carboxylate as yellow oil.

LC-MS (ES, m/z): 477 [M+H]$^+$ $^1$H-NMR (300 MHz, DMSO, ppm): δ 8.67-7.51 (m, 8H), 3.99 (s, 3H), 3.95 (m, 1H), 2.74 (s, 3H), 1.45 (s, 9H).

Step 3. Methyl 3-(4-(methylamino)piperidin-1-yl)-2-phenylquinoxaline-6-carboxylate

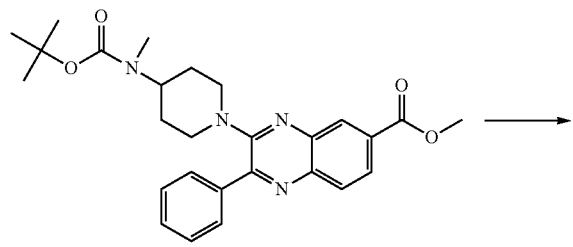

-continued

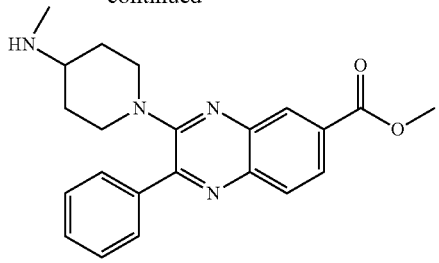

Into a 100-mL round-bottom flask, was placed a solution of methyl 3-(4-(tert-butoxycarbonyl)piperidin-1-yl)-2-phenylquinoxaline-6-carboxylate (360 mg, 0.60 mmol, 1.00 equiv, 79%) in dichloromethane (30 mL). This was followed by the addition of trifluoroacetic acid (2 mL) at 0° C. The resulting solution was stirred for 3 hr at room temperature. The resulting solution was diluted with 20 ml of H$_2$O and made pH 9 with sat. NaHCO$_3$. The aqueous solution was extracted with dichloromethane, the organic layers combined and concentrated under vacuum. This resulted in 0.20 g (89%) of methyl 3-(4-(methylamino)piperidin-1-yl)-2-phenylquinoxaline-6-carboxylate as brown red oil.

LC-MS (ES, m/z): 377 [M+H]$^+$

Step 4. Methyl 3-(4-(N-methylacetamido)piperidin-1-yl)-2-phenylquinoxaline-6-carboxylate

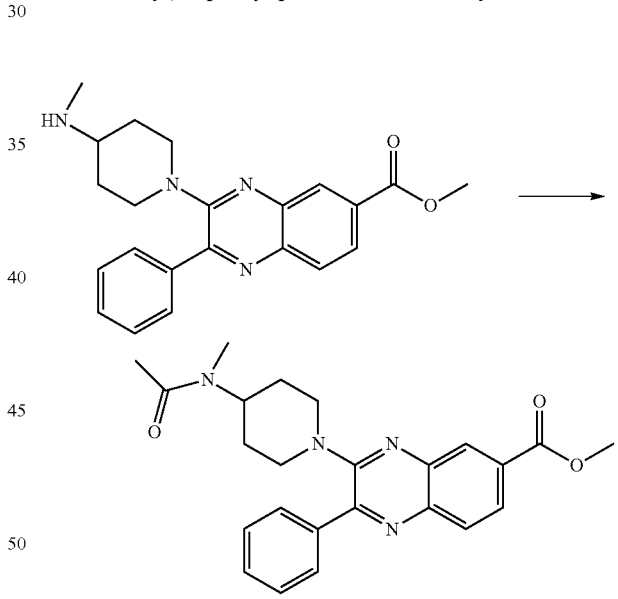

Into a 100-mL round-bottom flask, was placed a solution of methyl 3-(4-(methylamino)piperidin-1-yl)-2-phenylquinoxaline-6-carboxylate (76 mg, 0.20 mmol, 1.00 equiv) in dichloromethane (15 mL). Then Et$_3$N (1.25 mL) was added. To the above dimethylcarbonate (0.75 mL) was added at 0° C. The resulting solution was stirred for 3 hr at room temperature. The resulting mixture was concentrated under vacuum. This resulted in 0.077 g (91%) of methyl 3-(4-(N-methylacetamido)piperidin-1-yl)-2-phenylquinoxaline-6-carboxylate as light yellow oil.

LC-MS (ES, m/z): 419 [M+H]$^+$ $^1$H NMR (300 MHz, DMSO): δ 8.54-7.51 (m, 8H), 4.01 (s, 3H), 2.87 (s, 3H).

Step 5. 3-(4-(N-Methylacetamido)piperidin-1-yl)-2-phenylquinoxaline-6-carboxylic Acid

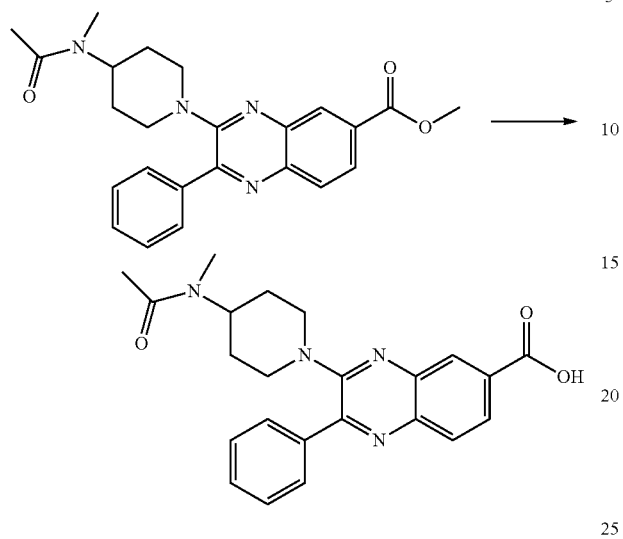

Into a 100-mL round-bottom flask, was placed a solution of methyl 3-(4-(N-methylacetamido)piperidin-1-yl)-2-phenylquinoxaline-6-carboxylate (77 mg, 0.18 mmol, 1.00 equiv) in MeOH (15 mL). Then dichloromethane (5 mL) was added. Finally to the above was added a solution of sodium hydroxide (700 mg, 17.50 mmol, 95.00 equiv) in water (3 mL). The resulting solution was stirred for 3 hr at room temperature. The resulting mixture was concentrated under vacuum, diluted with 10 ml of $H_2O$. The pH value of the aqueous solution was adjusted to 3 with aq. 3N hydrochloric acid. The resulting solids were collected by filtration. This resulted in 52 mg (70%) of 3-(4-(N-methylacetamido)piperidin-1-yl)-2-phenylquinoxaline-6-carboxylic acid as a yellow solid.

LC-MS (ES, m/z): 405 [M+H]+

$^1$H NMR (300 MHz, DMSO): δ 13.27 (s, 1H), 8.31-7.54 (m, 8H), 4.44-4.41 (m, 1H), 3.87-3.82 (m, 2H), 2.93-2.67 (m, 5H), 2.05-1.98 (m, 3H), 1.78-1.40 (m, 4H).

EXAMPLE 35

3-(4-(Methyl(phenyl)amino)piperidin-1-yl)-2-phenylquinoxaline-6-carboxylic Acid

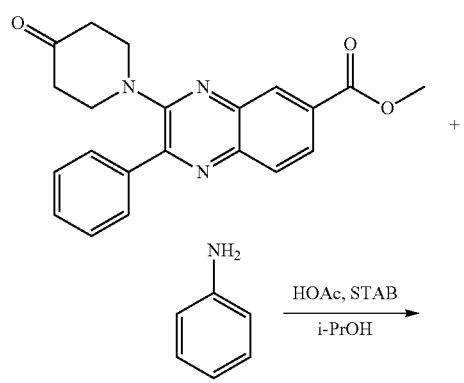

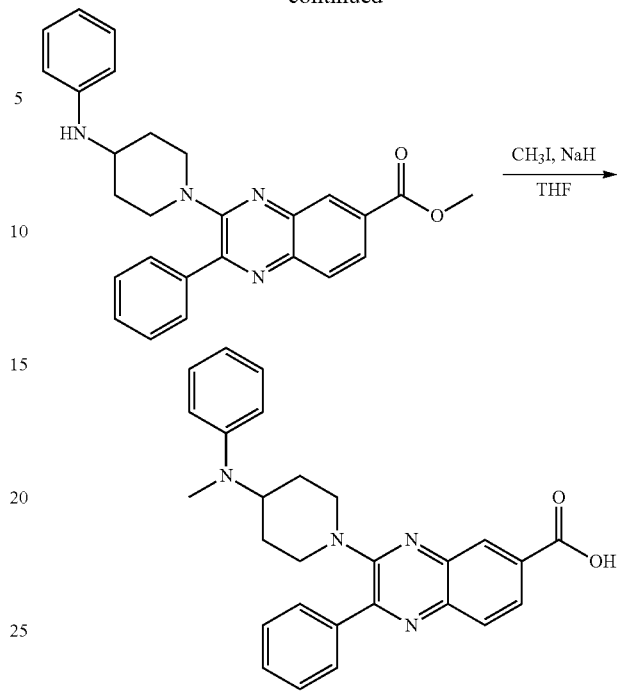

Step 1. Methyl 2-phenyl-3-(4-(phenylamino)piperidin-1-yl)quinoxaline-6-carboxylate Into a 100-mL round-bottom flask purged and maintained with an inert atmosphere of nitrogen, was placed a solution of methyl 3-(4-oxopiperidin-1-yl)-2-phenylquinoxaline-6-carboxylate (329.7 mg, 0.91 mmol, 1.00 equiv) in isopropanol (12 mL). Then aniline (255.2 mg, 2.74 mmol, 3.00 equiv) and acetic acid (221.8 mg, 3.70 mmol, 4.00 equiv) was added dropwise with stirring. The resulting solution was stirred for 1 h at 60° C. in an oil bath. To the above NaHB(OAc)$_3$ (968.1 mg, 4.57 mmol, 4.57 equiv) was added at 0° C. The resulting solution was stirred for an additional 3 h at room temperature. The reaction was then quenched by the addition of water. The resulting aqueous solution was extracted with 6×20 mL of dichloromethane. The organic layers were combined and dried over sodium sulfate and concentrated under vacuum. The residue was applied onto a silica gel column with DCM/MeOH (30:1). This resulted in 297.4 mg (74%) of methyl 2-phenyl-3-(4-(phenylamino)piperidin-1-yl)quinoxaline-6-carboxylate as a yellow solid.

LC-MS (ES, m/z): 439 [M+H]+

Step 2. 3-(4-(Methyl(phenyl)amino)piperidin-1-yl)-2-phenylquinoxaline-6-carboxylic Acid Into a 50-mL round-bottom flask, was placed a solution of methyl 2-phenyl-3-(4-(phenylamino)piperidin-1-yl)quinoxaline-6-carboxylate (297.4 mg, 0.68 mmol, 1.00 equiv) in tetrahydrofuran (16 mL). Then sodium hydride (163 mg, 6.79 mmol, 10.00 equiv) and CH$_3$I (964 mg, 6.79 mmol, 10.00 equiv) was added. The resulting solution was stirred for 2 days at room temperature. The reaction was then quenched by the addition of water. The resulting aqueous solution was extracted with 5×30 mL of dichloromethane. The organic layers were combined and concentrated under vacuum. The crude product (150 mg) was purified by Prep-HPLC with the following conditions (AGILENT Pre-HPLC(UV-Directed): Column, SunFire Prep C18, 19*150 mm 5um; mobile phase, water with 0.05% TFA and CH$_3$CN (25% CH$_3$CN up to 60% in 6 min, up to 100% in 1 min); Detector, UV 254 nm. 30 mg of product was obtained. This resulted in 30 mg (10%) of 3-(4-(methyl(phenyl)amino)piperidin-1-yl)-2-phenylquinoxaline-6-carboxylic acid as a yellow solid.

LC-MS (ES, m/z): 439[M+H]$^+$ $^1$H-NMR (300 MHz, DMSO, ppm) 8.307 (s, 1H), 8.026-8.001 (d, J=7.5 Hz, 4H), 7.591-7.539 (t, J=7.8 Hz, 3H), 7.190-7.138 (t, J=7.8 Hz, 2H), 6.827-6.800 (d, J=8.1 Hz, 2H), 6.652-6.603 (t, J=7.35 Hz, 1H), 3.885-3.845 (d, J=12 Hz, 4H), 2.965-2.885 (t, J=24 Hz, 2H), 2.713 (s, 3H), 1.769-1.736 (d, J=9.9 Hz, 2H), 1.596-1.561 (d, J=10.5 Hz, 2H).

EXAMPLE 36

3-(Diethylamino)-2-phenylquinoxaline-6-carboxylic Acid

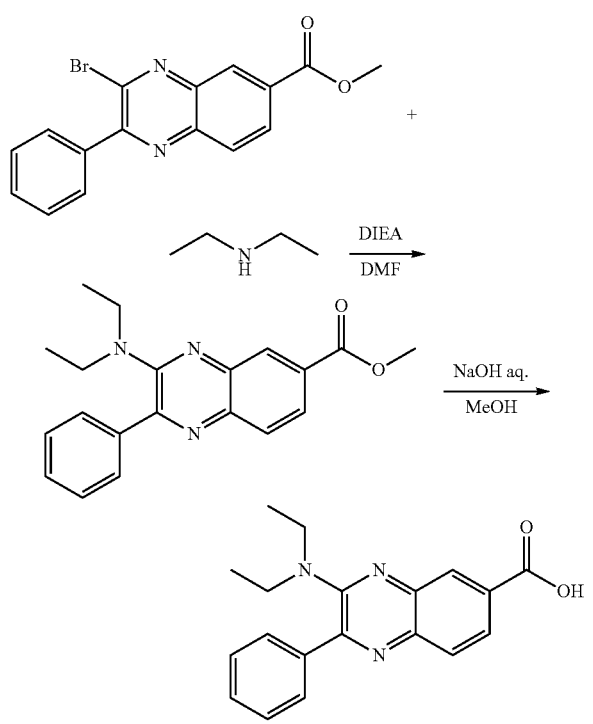

Step 1. Methyl 3-(diethylamino)-2-phenylquinoxaline-6-carboxylate

Into a 8-mL sealed tube, was placed a solution of methyl 3-bromo-2-phenylquinoxaline-6-carboxylate (150 mg, 0.44 mmol, 1.00 equiv) in N,N-dimethylformamide (3 mL), diethylamine (63.4 mg, 0.87 mmol, 2.00 equiv), and DIEA (170.3 mg, 1.32 mmol, 3.00 equiv). The resulting solution was stirred overnight at 100° C. in an oil bath. The resulting solution was concentrated under vacuum. The residue was applied onto a silica gel column and eluted with ethyl acetate/petroleum ether (1:100). This resulted in 117 mg (80%) of methyl 3-(diethylamino)-2-phenylquinoxaline-6-carboxylate as a yellow oil.

LC-MS (ES, m/z): 336 [M+H]$^+$

Step 2. 3-(Diethylamino)-2-phenylquinoxaline-6-carboxylic Acid

Into a 50-mL round-bottom flask, was placed a solution of methyl 3-(diethylamino)-2-phenylquinoxaline-6-carboxylate (117 mg, 0.35 mmol, 1.00 equiv) in methanol (15 mL). This was followed by the addition of a solution of sodium hydroxide (69.9 mg, 1.75 mmol, 5.00 equiv) in water (2 mL) dropwise with stirring. The resulting solution was stirred overnight at 50° C. in an oil bath. The pH value of the solution was adjusted to 3-4 with 1N hydrogen chloride. The resulting mixture was concentrated under vacuum. The crude product (110 mg) was purified by Prep-HPLC with the following conditions: Column, SunFire Prep C18, 5um, 19*150 mm; mobile phase, water with 0.05% TFA and methanol (70% methanol up to 90% in 10 min); Detector, UV 254 nm. This resulted in 70 mg (62%) of 3-(diethylamino)-2-phenylquinoxaline-6-carboxylic acid as a yellow solid.

LC-MS (ES, m/z): 322 [M+H]$^+$ $^1$H NMR (300 MHz, DMSO, ppm): δ 13.24 (s, 1H), 8.28 (s, 1H), 7.95 (s, 2H), 7.85-7.82 (t, J=4.5 Hz, 2H), 7.58-7.49 (m, 3H), 3.30-3.28 (d, J=6 Hz, 4H), 1.04-0.99 (t, J=7.5 Hz, 6H).

EXAMPLE 37

3-(4-Acetamidopiperidin-1-yl)-2-phenylquinoxaline-6-carboxylic Acid

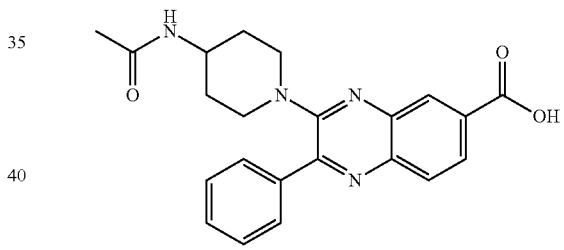

Step 1. Methyl 3-(4-(tert-Butoxycarbonyl)piperidin-1-yl)-2-phenylquinoxaline-6-carboxylate

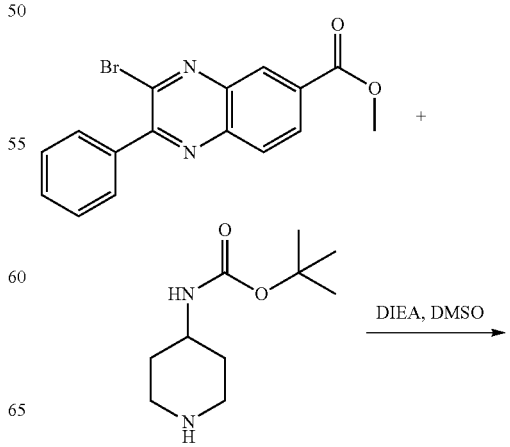

-continued

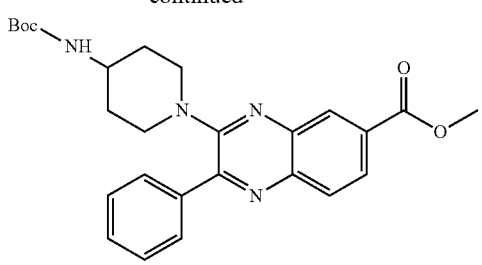

Into an 8-mL sealed tube, was placed methyl 3-bromo-2-phenylquinoxaline-6-carboxylate (200 mg, 0.58 mmol, 1.00 equiv), tert-butyl piperidin-4-yl carbamate (300 mg, 1.50 mmol, 2.58 equiv), DIEA (300 mg, 2.33 mmol, 3.98 equiv), and DMSO (2 mL). The resulting solution was stirred overnight at 100° C. The resulting solution was diluted with ethyl acetate. The resulting solution was washed with sat. sodium chloride, then concentrated under vacuum. This resulted in 0.2 g (74%) of methyl 3-(4-(tert-butoxycarbonyl)piperidin-1-yl)-2-phenylquinoxaline-6-carboxylate as a light yellow solid.

Step 2. Methyl 3-(4-aminopiperidin-1-yl)-2-phenylquinoxaline-6-carboxylate

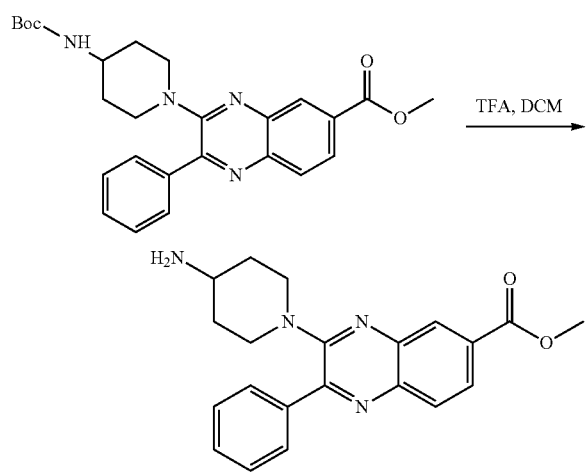

Into a 100-mL round-bottom flask, was placed a solution of methyl 3-(4-(tert-butoxycarbonyl)piperidin-1-yl)-2-phenylquinoxaline-6-carboxylate (150 mg, 0.31 mmol, 1.00 equiv, 95%) in dichloromethane (15 mL). This was followed by the addition of trifluoroacetic acid (2 mL) at 0° C. The resulting solution was stirred for 3 h at room temperature. The resulting mixture was concentrated under vacuum. The resulting solution was diluted with 10 ml of $H_2O$. The pH value of the aqueous solution was adjusted to 8 with sat. sodium bicarbonate. The resulting aqueous solution was extracted with dichloromethane. The organic layers combined and concentrated under vacuum. This resulted in 0.06 g (53%) of methyl 3-(4-aminopiperidin-1-yl)-2-phenylquinoxaline-6-carboxylate as a light yellow solid.

Step 3. Methyl 3-(4-acetamidopiperidin-1-yl)-2-phenylquinoxaline-6-carboxylate

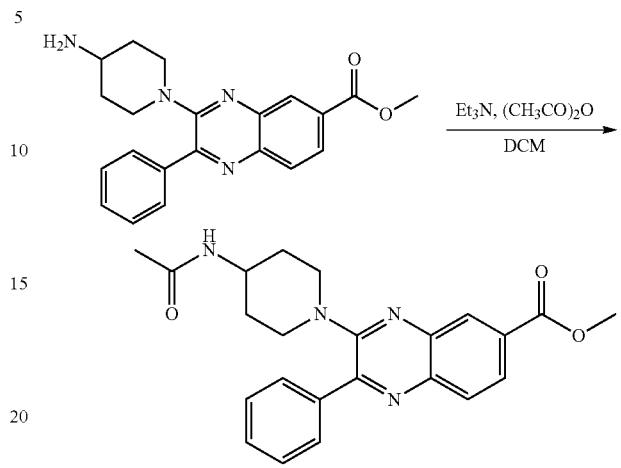

Into a 50-mL round-bottom flask, was placed a solution of methyl 3-(4-aminopiperidin-1-yl)-2-phenylquinoxaline-6-carboxylate (100 mg, 0.28 mmol, 1.00 equiv) in dichloromethane (50 mL). This was followed by the addition of triethylamine (7 mL) and acetic anhydride (1 mL) at 0° C. The resulting solution was stirred overnight at room temperature and concentrated under vacuum. This resulted in 0.1 g (90%) of methyl 3-(4-acetamidopiperidin-1-yl)-2-phenylquinoxaline-6-carboxylate as light yellow oil.

Step 4. 3-(4-Acetamidopiperidin-1-yl)-2-phenylquinoxaline-6-carboxylic Acid

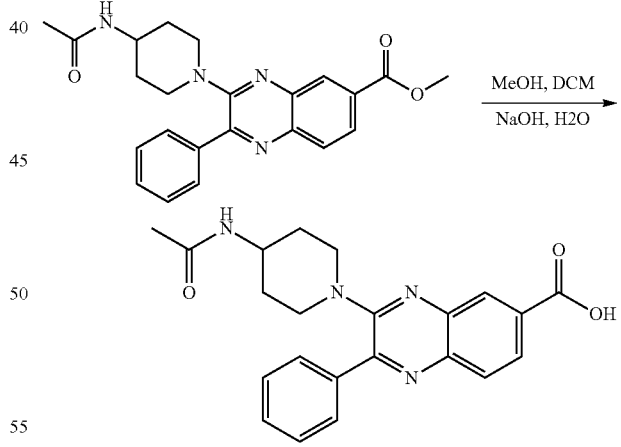

Into a 100-mL round-bottom flask was placed methyl 3-(4-acetamidopiperidin-1-yl)-2-phenylquinoxaline-6-carboxylate (100 mg, 0.25 mmol, 1.00 equiv), methanol (15 mL), dichloromethane (7 mL). To this was added a solution of sodium hydroxide (1.5 g, 37.50 mmol, 151.50 equiv) in water (7 mL). The resulting solution was stirred for 3 h at room temperature. The resulting mixture was concentrated under vacuum and diluted with 10 ml of $H_2O$. The pH of the aqueous solution was adjusted to 3 with hydrochloric acid. The resulting solids were collected by filtration. This resulted in 95 mg (94%) of 3-(4-acetamidopiperidin-1-yl)-2-phenylquinoxaline-6-carboxylic acid as a light yellow solid.

LC-MS (ES, m/z): 391 [M+H]+

1H-NMR (300 MHz, DMSO, ppm): δ 8.30 (m, 1H), 7.99-7.98 (m, 4H), 7.84-7.82 (m, 1H), 7.56-7.55 (m, 3H), 3.71-3.61 (m, 3H), 2.92-2.85 (m, 2H), 1.78 (s, 3H), 1.73-1.70 (m, 2H), 1.46-1.39 (m, 2H).

EXAMPLE 38

3-(N-Methylmethan-5-ylsulfonamido)-2-phenylquinoxaline-6-carboxylic Acid

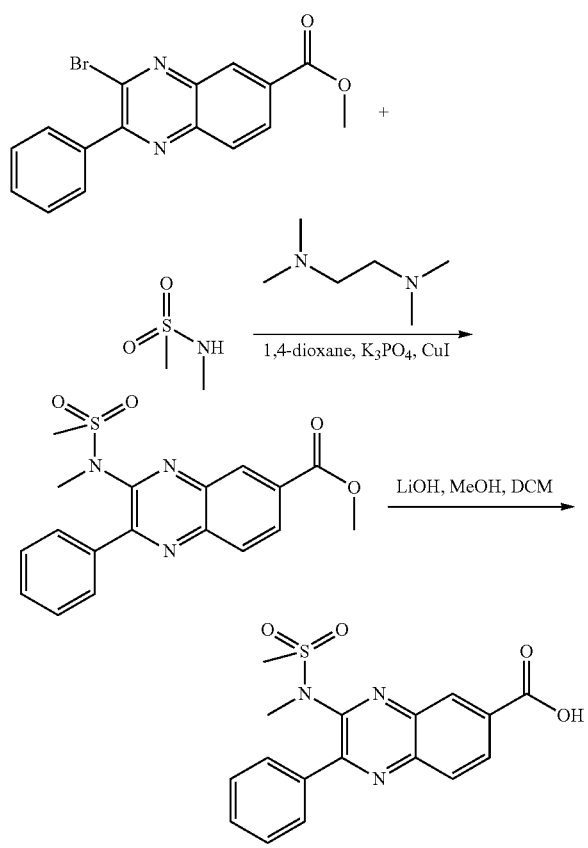

Step 1. Methyl 3-(N-methylmethan-5-ylsulfonamido)-2-phenylquinoxaline-6-carboxylate Into a 10-mL sealed tube, was placed methyl 3-bromo-2-phenylquinoxaline-6-carboxylate (200 mg, 0.58 mmol, 1.00 equiv), N-methylmethanesulfonamide (381 mg, 3.49 mmol, 3.00 equiv), K3PO4 (370 mg, 1.75 mmol, 3.00 equiv), CuI (110 mg, 0.58 mmol, 1.00 equiv), N1,N1,N2,N2-tetramethylethane-1,2-diamine (67 mg, 0.58 mmol, 1.00 equiv), 1,4-dioxane (5 mL). The resulting solution was stirred overnight at 100 degrees C. in an oil bath. The resulting mixture was concentrated under vacuum. The residue was applied onto a silica gel column with PE:EA (20:1). This resulted in 110 mg (51%) of methyl 3-(N-methylmethan-5-ylsulfonamido)-2-phenylquinoxaline-6-carboxylate as a yellow solid.

LC-MS (ES, m/z): 372 [M+H]+

Step 2. 3-(N-methylmethan-5-ylsulfonamido)-2-phenylquinoxaline-6-carboxylic Acid Into a 50-mL round-bottom flask, was placed methyl 3-(N-methylmethan-5-ylsulfonamido)-2-phenylquinoxaline-6-carboxylate (130 mg, 0.35 mmol, 1.00 equiv), LiOH (16.8 mg, 0.70 mmol, 2.00 equiv), methanol (10 mL), water (2 ml), dichloromethane (2 ml). The resulting solution was stirred for 2 hs at 50° C. in an oil bath. The resulting mixture was concentrated under vacuum. The resulting solution was diluted with 20 ml of H2O. The resulting solution was extracted with 2×20 ml of dichloromethane and the aqueous layers combined. The pH value of the solution was adjusted to 4 with aq hydrogen chloride (1 mol/L). The solids were collected by filtration. This resulted in 80 mg (63%) of 3-(N-methylmethan-5-ylsulfonamido)-2-phenylquinoxaline-6-carboxylic acid as a yellow solid.

LC-MS (ES, m/z): 358 [M+H]+

1H-NMR (300 MHz, DMSO, ppm): δ 8.645 (s, 1H), 8.366-8.338 (d, J=8.4 Hz, 1H), 8.266-8.237 (d, J=8.7 Hz, 1H), 7.944-7.913 (m, 2H), 7.612-7.577 (m, 3H), 3.269 (s, 3H), 3.141 (s, 3H).

EXAMPLE 39

3-(3,4-Dihydroisoquinolin-2(1H)-yl)-2-phenylquinoxaline-6-carboxylic Acid

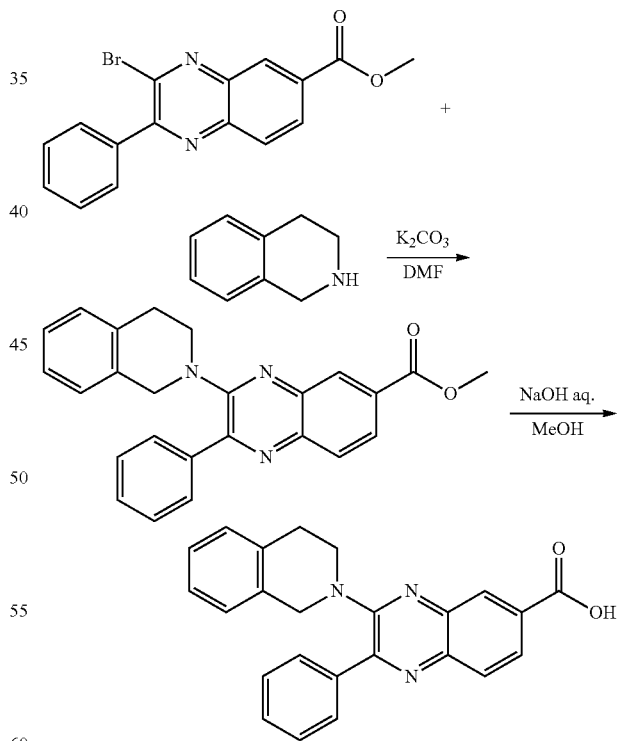

Step 1. Methyl 3-(3,4-dihydroisoquinolin-2(1H)-yl)-2-phenylquinoxaline-6-carboxylate Into a 8-mL sealed tube, was placed a solution of methyl 3-bromo-2-phenylquinoxaline-6-carboxylate (130 mg, 0.38 mmol, 1.00 equiv), N,N-dimethylformamide (5 mL), 1,2,3,4-tetrahydroisoquinoline (101.1 mg, 0.76 mmol, 2.00 equiv), potassium carbonate (157.3 mg, 1.14 mmol, 3.00 equiv). The resulting solution was stirred for overnight at 100° C. The reaction was then quenched by the addition of water. The resulting solids were collected by filtration. This resulted in 110 mg (70%) of methyl 3-(3,4-dihydroisoquinolin-2(1H)-yl)-2-phenylquinoxaline-6-carboxylate as a yellow solid.

LC-MS:(ES, m/z): 396 [M+H]⁺

Step 2. 3-(3,4-dihydroisoquinolin-2(1H)-yl)-2-phenylquinoxaline-6-carboxylic Acid

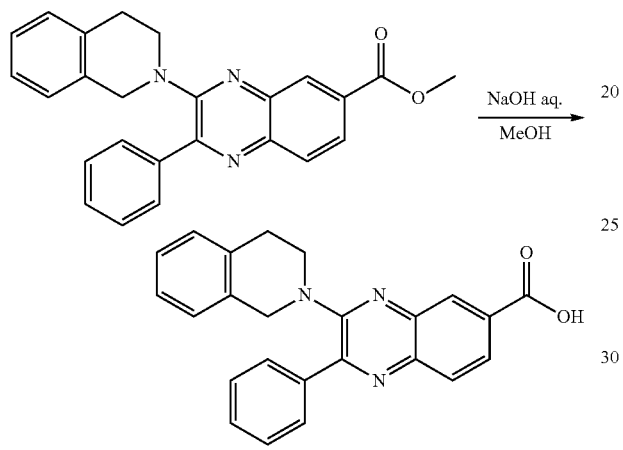

Into a 50-mL round-bottom flask, was placed a solution of methyl 3-(3,4-dihydroisoquinolin-2(1H)-yl)-2-phenylquinoxaline-6-carboxylate (110 mg, 0.26 mmol, 1.00 equiv, 95%) in methanol (15 mL). This was followed by the addition of a solution of sodium hydroxide (55.7 mg, 1.39 mmol, 5.00 equiv) in water (1.5 mL) dropwise with stirring. The resulting solution was stirred for overnight at 50° C. in an oil bath. The resulting solution was concentrated under vacuum. The residue was diluted with water. The pH value of the aqueous solution was adjusted to 3-4 with 1N hydrogen chloride. The resulting solids were collected by filtration and washed with methanol. This resulted in 68.1 mg (66%) of 3-(3,4-dihydroisoquinolin-2(1H)-yl)-2-phenylquinoxaline-6-carboxylic acid as a yellow solid.

LC-MS:(ES, m/z): 382 [M+H]⁺

¹H-NMR (300 MHz, DMSO, ppm) 8.36 (s, 1H), 8.00-7.93 (m, 4H), 7.58-7.55 (t, J=4.5 Hz, 3H), 7.18-7.14 (m, 4H), 4.57 (s, 2H), 3.39-3.36 (d, J=9 Hz, 2H), 2.72-2.70 (d, J=6 Hz, 2H).

EXAMPLE 40

3-(3,4-Dihydroquinolin-1(2H)-yl)-2-phenylquinoxaline-6-carboxylic Acid

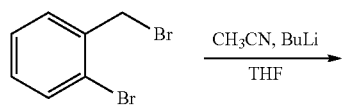

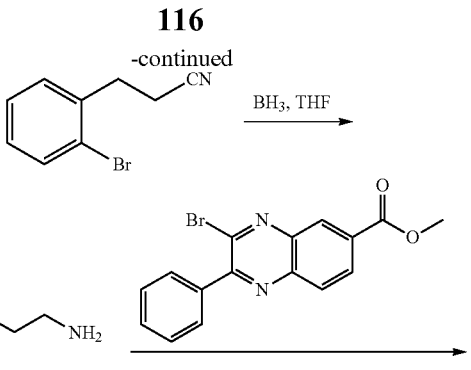

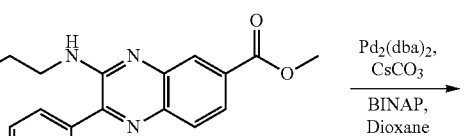

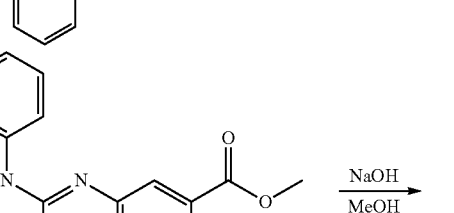

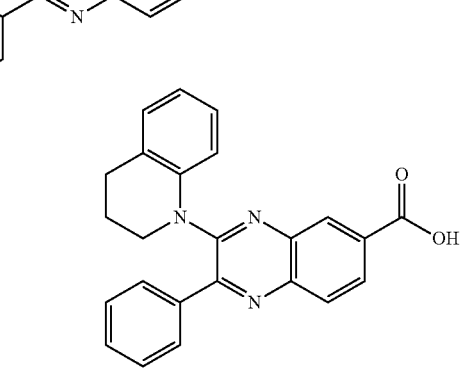

Step 1. Synthesis of 3-(2-bromophenyl)propanenitrile

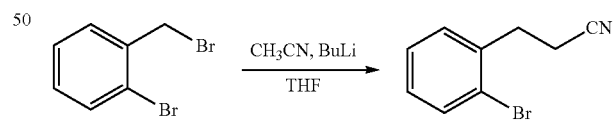

Into a 500-mL 3-necked round-bottom flask, was placed a solution of acetonitrile (49 g, 1.20 mol, 9.96 equiv) in tetrahydrofuran (150 mL). This was followed by the addition of BuLi (72 mL, 1.50 equiv) dropwise with stirring at −78° C. Stirred at −78° C. for 1 h. To this was added a solution of 1-bromo-2-(bromomethyl)benzene (30 g, 120.00 mmol, 1.00 equiv) in tetrahydrofuran (100 mL) dropwise with stirring at −78° C. The resulting solution was stirred for 1 h at −78° C. The reaction was quenched by the addition of 100 mL of water at −78° C. The resulting aqueous solution was extracted with 3×100 mL of ethyl acetate and the organic layers combined and dried over anhydrous sodium sulfate and concentrated under vacuum. The residue was applied onto a silica gel column with ethyl acetate/petroleum ether (1:20). The crude product was purified by distillation under reduced pressure (2 mm Hg) and the fraction was collected at 98-107° C. This resulted in 13.21 g (52%) of 3-(2-bromophenyl)propanenitrile as colorless oil.

GC-MS:(ES, m/z): 209 [M]+

$^1$H-NMR (300 MHz, CDC$_3$, ppm) 7.61-7.58 (d, J=7.8 Hz, 1H), 7.35-7.29 (m, 2H), 7.22-7.15 (m, 1H), 3.15-3.09 (t, J=7.5 Hz, 2H), 2.73-2.68 (t, J=7.5 Hz, 2H).

Step 2. 3-(2-Bromophenyl)propan-1-amine

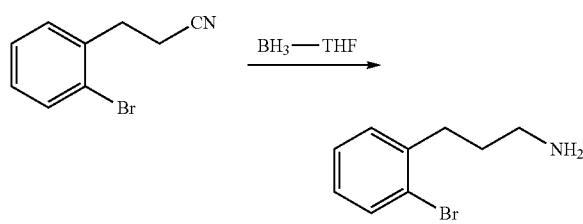

Into a 250-mL 3-necked round-bottom flask, was placed a solution of 3-(2-bromophenyl)propanenitrile (2.1 g, 10.00 mmol, 1.00 equiv) in tetrahydrofuran (20 mL). This was followed by the addition of borane (1 mol/L in THF, 50 mL, 5.00 equiv) dropwise with stirring at 0° C. The resulting solution was stirred for overnight at room temperature. The reaction was then quenched by the addition of 50 mL of water at 0° C. and extracted with 3×50 mL of ethyl acetate. The organic layers were combined and dried over anhydrous sodium sulfate and concentrated under vacuum. The residue was dissolved in 30 mL of 6N aqueous hydrogen chloride. The aqueous solution was extracted with 30 mL of ethyl acetate and the aqueous layers were combined. The pH value of the aqueous solution was adjusted to 10 with 10% aqueous sodium hydroxide. The resulting solution was extracted with 3×50 mL of ethyl acetate. The organic layers were combined and dried over anhydrous sodium sulfate, concentrated under vacuum. This resulted in 1.3 g (58%) of 3-(2-bromophenyl)propan-1-amine as colorless oil.

LC-MS:(ES, m/z): 214 [M+H]+

Step 3. Methyl 3-(3-(2-bromophenyl)propylamino)-2-phenylquinoxaline-6-carboxylate

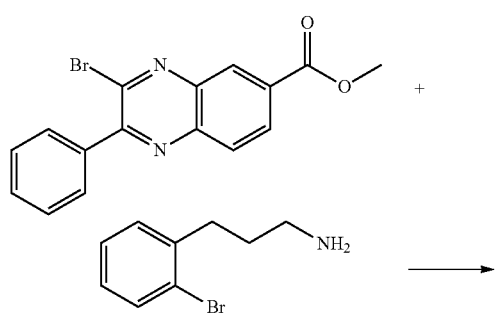

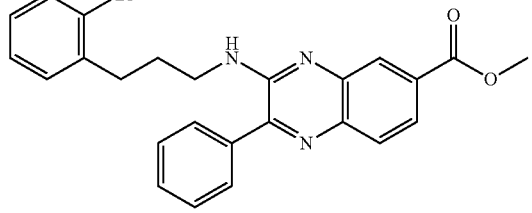

Into a 20-mL sealed tube, was placed methyl 3-chloro-2-phenylquinoxaline-6-carboxylate (180 mg, 0.60 mmol, 1.00 equiv), toluene/DMSO (5/1 mL), 3-(2-bromophenyl)propan-1-amine (385 mg, 1.80 mmol, 2.99 equiv), and potassium carbonate (414 mg, 3.00 mmol, 4.98 equiv). The resulting solution was stirred overnight at 100° C. The mixture was concentrated under vacuum. The residue was purified by silica gel chromatography with ethyl acetate/petroleum ether (1:50). This resulted in 240 mg (80%) of methyl 3-(3-(2-bromophenyl)propylamino)-2-phenylquinoxaline-6-carboxylate as a yellow solid.

LC-MS:(ES, m/z): 476 [M+H]+

$^1$H-NMR (300 MHz, DMSO, ppm): δ 1.99-1.91 (m, 2H), 2.81-2.75 (t, J=7.8 Hz, 2H), 3.54-3.47 (m, 2H), 3.92 (s, 3H), 6.97-6.93 (t, J=5.4 Hz, 1H), 7.17-7.11 (m, 1H), 7.34-7.28 (m, 1H), 7.43-7.39 (dd, J=1.5, 7.6 Hz, 4H), 7.69-7.54 (m, 2H), 7.90-7.68 (m, 2H), 7.15 (m, 1H).

Step 4. Methyl 3-(3,4-dihydroquinolin-1(2H)-yl)-2-phenylquinoxaline-6-carboxylate

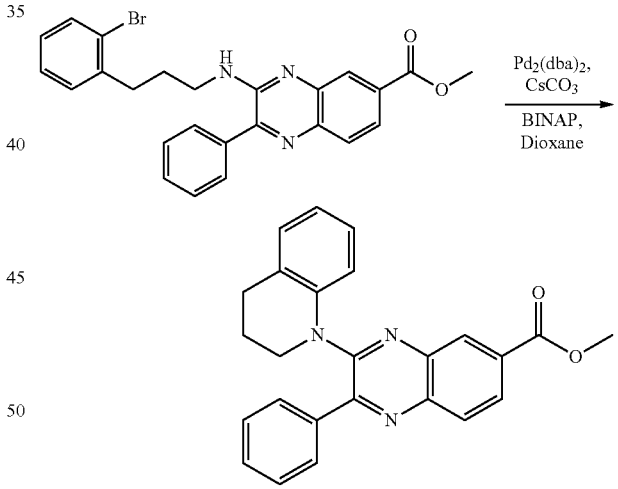

Into a 20-mL sealed tube, was placed a solution of methyl 3-(3-(2-bromophenyl)propylamino)-2-phenylquinoxaline-6-carboxylate (240 mg, 0.50 mmol, 1.00 equiv) in dioxane (10 mL), CsCO$_3$ (490 mg, 1.50 mmol, 3.00 equiv), Pd$_2$(dba)$_3$ (46 mg, 0.05 mmol, 0.10 equiv) and BINAP (125 mg, 0.20 mmol, 0.40 equiv) were added. The resulting solution was stirred overnight at 100° C. The mixture was concentrated under vacuum and purified by flash column chromatography with ethyl acetate/petroleum ether (1:50). This resulted in 180 mg (86%) of methyl 3-(3,4-dihydroquinolin-1(2H)-yl)-2-phenylquinoxaline-6-carboxylate as a yellow solid.

LC-MS:(ES, m/z): 396 [M+H]+

$^1$H-NMR (300 MHz, DMSO, ppm): δ 8.37 (s, 1H), 8.10 (d, J=0.9 Hz, 2H), 7.83-7.77 (m, 1H), 7.74-7.70 (m, 2H), 7.49-7.45 (m, 1H), 7.29-7.26 (m, 3H), 6.99-6.95 (m, 1H), 6.74-6.61 (m, 3H), 3.95 (s, 1H), 3.76-3.70 (t, J=6.6 Hz, 2H), 2.75-2.70 (t, J=6.6 Hz, 2H), 2.03-1.94 (m, 2H).

Step 5. 3-(3,4-Dihydroquinolin-1(2H)-yl)-2-phenylquinoxaline-6-carboxylic Acid

Into a 50-mL round-bottom flask, was placed a solution of methyl 3-(3,4-dihydroquinolin-1(2H)-yl)-2-phenylquinoxaline-6-carboxylate (100 mg, 0.25 mmol, 1.00 equiv), sodium hydroxide (20 mg, 0.5 mmol, 2.00 equiv), and methanol/H$_2$O (20/5 mL). The resulting solution was heated to reflux for 4 hrs and then concentrated to dryness. The residue was diluted with 15 mL water and acidified to pH=5 with 3N aq. HCl. The resulting solid was collected by filtration, washed with water, and dried to afford 65 mg (65%) of 3-(3,4-dihydroquinolin-1(2H)-yl)-2-phenylquinoxaline-6-carboxylic acid as an orange solid.

LC-MS:(ES, m/z): 382 [M+H]$^+$ $^1$H-NMR (300 MHz, DMSO, ppm): δ 8.35 (s, 1H), 8.14-8.06 (d, J=0.9 Hz, 2H), 7.74-7.70 (m, 2H), 7.29-7.26 (t, J=2.7 Hz, 3H), 6.99-6.95 (t, J=6.3 Hz, 1H), 6.74-6.60 (m, 3H), 3.80-3.75 (t, J=6.3 Hz, 2H), 2.75-2.70 (t, J=6.3 Hz, 2H), 2.02-1.93 (m, 2H).

EXAMPLE 41

3-(Phenethylamino)-2-phenylquinoxaline-6-carboxylic Acid

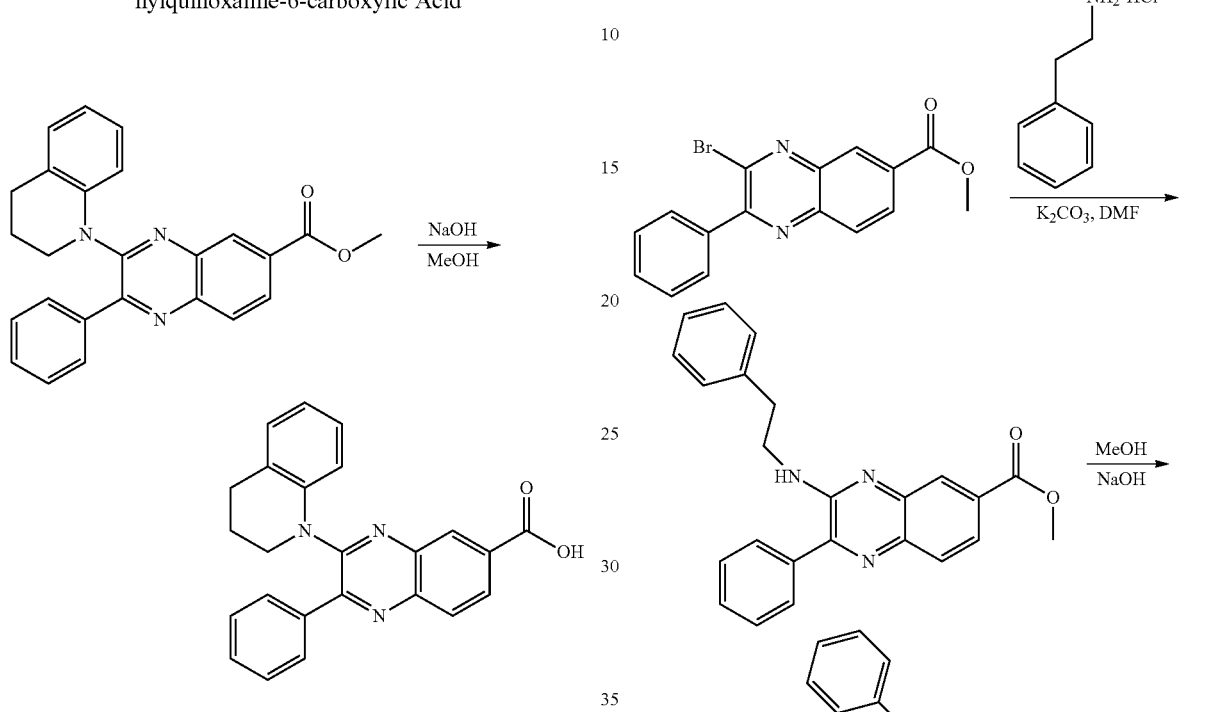

Step 1. Methyl 3-(phenethylamino)-2-phenylquinoxaline-6-carboxylate

Into a 10-mL sealed tube, was placed methyl 3-bromo-2-phenylquinoxaline-6-carboxylate (150 mg, 0.44 mmol, 1.00 equiv), 2-phenylethanamine hydrochloride (207.8 mg, 1.32 mmol, 3.00 equiv), potassium carbonate (304.4 mg, 2.21 mmol, 5.00 equiv), N,N-dimethylformamide (2 mL). The resulting solution was stirred overnight at 100° C. in an oil bath. The reaction was then quenched by the addition of 20 mL of water. The resulting solution was extracted with 3×50 mL of ethyl acetate and the organic layers combined. The organic layer was dried over anhydrous sodium sulfate and concentrated under vacuum. The residue was applied onto a silica gel column with ethyl acetate/petroleum ether (1:50). This resulted in 120 mg (71%) of methyl 3-(phenethylamino)-2-phenylquinoxaline-6-carboxylate as a yellow solid.

LC-MS:(ES, m/z): 384 [M+H]$^+$

Step 2. 3-(Phenethylamino)-2-phenylquinoxaline-6-carboxylic Acid

Into a 50-mL round-bottom flask (1 atm), was placed a solution of methyl 3-(phenethylamino)-2-phenylquinoxaline-6-carboxylate (120 mg, 0.31 mmol, 1.00 equiv) in methanol (15 mL), a solution of sodium hydroxide (50.08 g, 1.25 mol, 4.00 equiv) in water (2 mL). The resulting solution was stirred for 2 h at 50° C. in an oil bath. The resulting mixture was concentrated under vacuum. The residue was diluted in 20 mL of water. The pH value of the solution was adjusted to 4-5 with aq hydrogen chloride (1 mol/L). The resulting solids were collected by filtration. This resulted in 60 mg (52%) of 3-(phenethylamino)-2-phenylquinoxaline-6-carboxylic acid as a yellow solid.

LC-MS:(ES, m/z): 370 [M+H]+

$^1$H NMR (300 MHz, DMSO, ppm): δ 8.203-8.199 (s, 1H), 7.855 (s, 2H), 7.662-7.630 (m, 2H), 7.569-7.515 (m, 3H), 7.349-7.194 (m, 5H), 6.809-6.773 (m, 1H), 3.706-3.639 (m, 2H), 2.982-2.933 (m, 2H).

EXAMPLE 42

3-(Methyl(phenethyl)amino)-2-phenylquinoxaline-6-carboxylic Acid

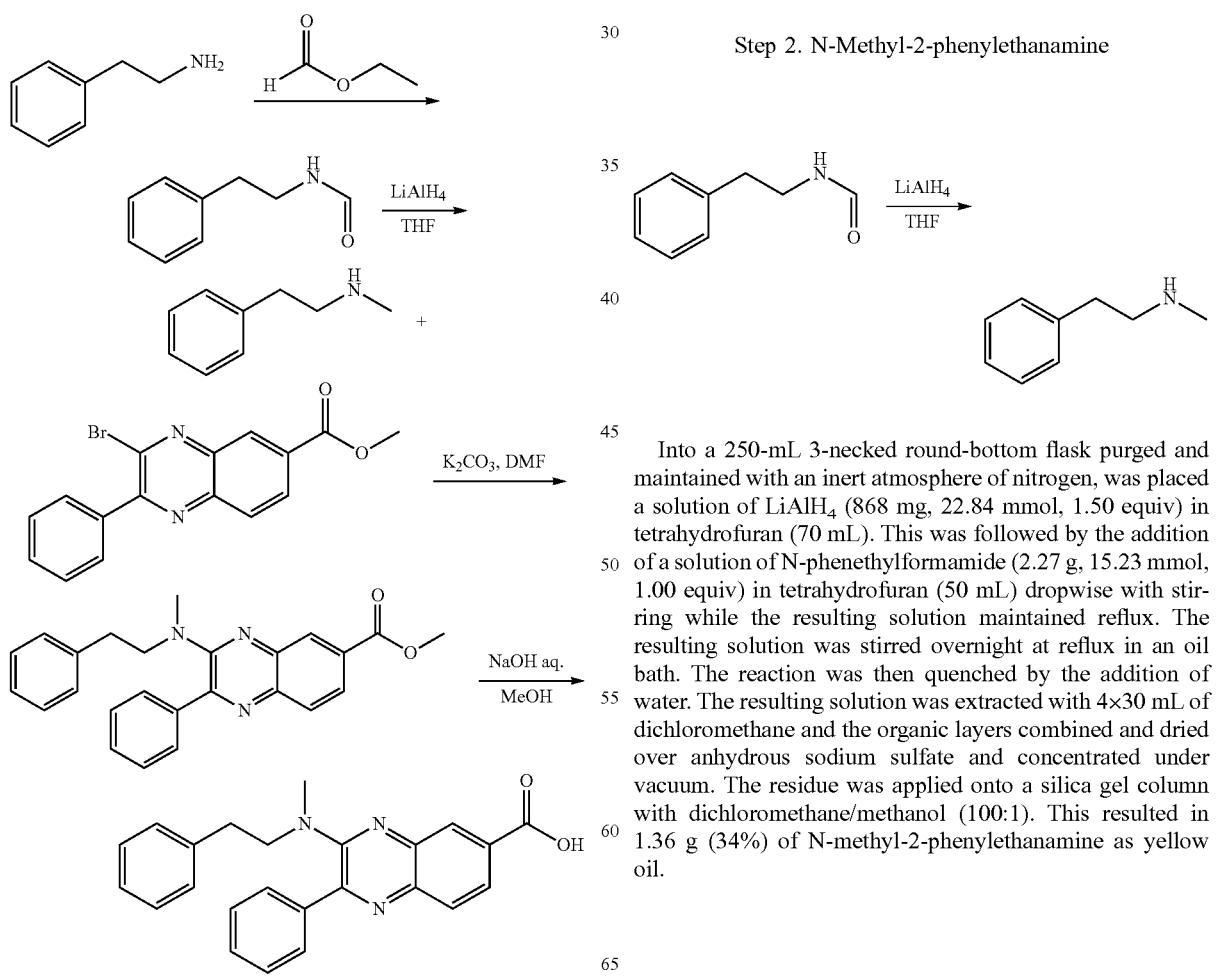

Step 1. N-Phenethylformamide

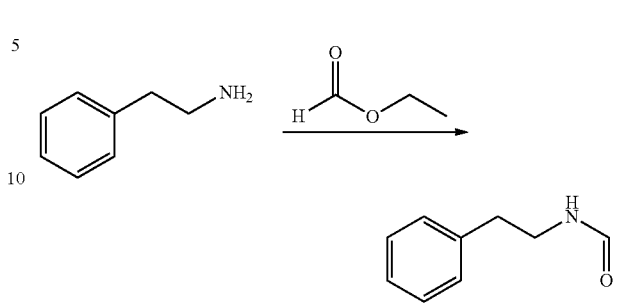

Into a 100-mL 3-necked round-bottom flask purged and maintained with an inert atmosphere of nitrogen, was placed 2-phenylethanamine (1.9 g, 15.70 mmol, 1.00 equiv). This was followed by the addition of ethyl formate (5 g, 67.57 mmol, 4.30 equiv) dropwise with stirring. The resulting solution was stirred overnight at 50° C. The resulting solution was concentrated under vacuum. The residue was applied onto a silica gel column with dichloromethane/methanol (70:1). This resulted in 2.27 g (97%) of N-phenethylformamide as yellow oil.

LC-MS:(ES, m/z): 150 [M+H]+

Step 2. N-Methyl-2-phenylethanamine

Into a 250-mL 3-necked round-bottom flask purged and maintained with an inert atmosphere of nitrogen, was placed a solution of LiAlH$_4$ (868 mg, 22.84 mmol, 1.50 equiv) in tetrahydrofuran (70 mL). This was followed by the addition of a solution of N-phenethylformamide (2.27 g, 15.23 mmol, 1.00 equiv) in tetrahydrofuran (50 mL) dropwise with stirring while the resulting solution maintained reflux. The resulting solution was stirred overnight at reflux in an oil bath. The reaction was then quenched by the addition of water. The resulting solution was extracted with 4×30 mL of dichloromethane and the organic layers combined and dried over anhydrous sodium sulfate and concentrated under vacuum. The residue was applied onto a silica gel column with dichloromethane/methanol (100:1). This resulted in 1.36 g (34%) of N-methyl-2-phenylethanamine as yellow oil.

123

Step 3. Methyl 3-(methyl(phenethyl)amino)-2-phenylquinoxaline-6-carboxylate

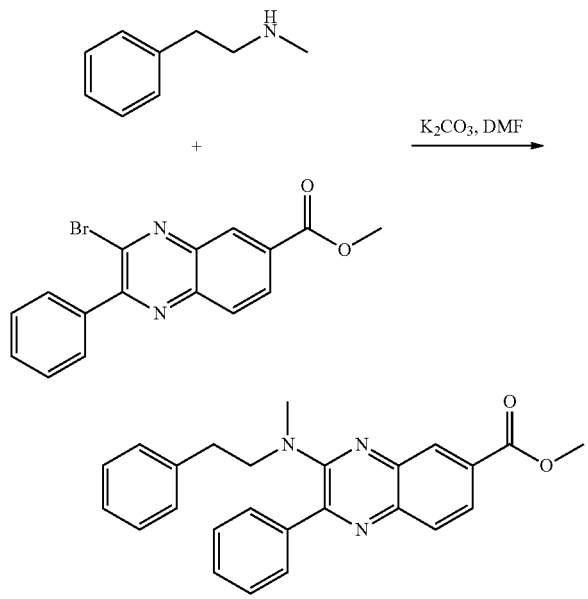

Into a 8-mL sealed tube, was placed a solution of methyl 3-bromo-2-phenylquinoxaline-6-carboxylate (150 mg, 0.44 mmol, 1.00 equiv) in N,N-dimethylformamide (5 mL), N-methyl-2-phenylethanamine (177.6 mg, 1.32 mmol, 3.00 equiv), potassium carbonate (181.6 mg, 1.32 mmol, 3.00 equiv). The resulting solution was stirred overnight at 100° C. in an oil bath. The reaction was then quenched by the addition of water. The resulting solution was extracted with 3×20 mL of dichloromethane and the organic layers combined and dried over anhydrous sodium sulfate and concentrated under vacuum. The residue was applied onto a silica gel column with ethyl acetate/petroleum ether (100:1). This resulted in 153.3 mg (85%) of methyl 3-(methyl(phenethyl)amino)-2-phenylquinoxaline-6-carboxylate as a yellow solid.

LC-MS:(ES, m/z): 398 [M+H]$^+$ $^1$H-NMR (300 MHz, CDC$_3$, ppm): δ 8.52-8.51 (d, J=3 Hz, 1H), 8.06-8.05 (d, J=3 Hz, 1H), 8.03-8.02 (d, J=3 Hz, 1H), 8.00-7.65 (m, 2H), 7.48-7.42 (m, 3H), 7.24-7.05 (m, 3H), 7.04-7.02 (d, J=6 Hz, 2H), 3.99 (s, 3H), 3.63-3.58 (t, J=7.5 Hz, 2H), 2.90-2.74 (m, 5H).

Step 4. 3-(Methyl(phenethyl)amino)-2-phenylquinoxaline-6-carboxylic Acid

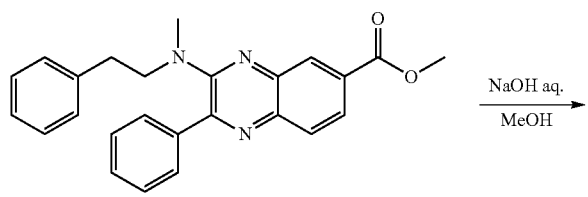

124

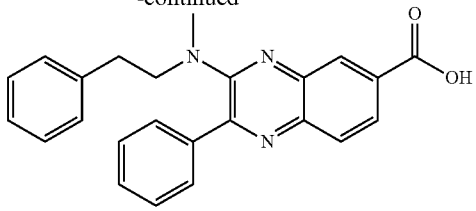

Into a 50-mL round-bottom flask, was placed a solution of methyl 3-(methyl(phenethyl)amino)-2-phenylquinoxaline-6-carboxylate (144.7 mg, 0.35 mmol, 1.00 equiv, 96%) in methanol (20 mL). This was followed by the dropwise addition of a solution of sodium hydroxide (72.9 mg, 1.82 mmol, 5.00 equiv) in water (2 mL) with stirring. The resulting solution was stirred overnight at 50° C. in an oil bath. Then it was concentrated under vacuum and diluted with 10 ml of water. The pH value of the aqueous solution was adjusted to 3-4 with 1N aq. hydrogen chloride. The resulting solid was collected by filtration and washed with methanol. This resulted in 52.6 mg (38%) of 3-(methyl(phenethyl)amino)-2-phenylquinoxaline-6-carboxylic acid as a yellow solid.

LC-MS:(ES, m/z): 384 [M+H]$^+$ $^1$H-NMR (300 MHz, DMSO, ppm): δ 8.28 (s, 1H), 7.96-7.89 (m, 2H), 7.65-7.62 (m, 2H), 7.50-7.48 (t, J=3 Hz, 3H), 7.22-7.03 (m, 5H), 3.57-3.52 (t, J=7.5 Hz, 2H), 2.89-2.79 (m, 5H).

EXAMPLE 43

3-(Isopropyl(methyl)amino)-2-phenylquinoxaline-6-carboxylic Acid

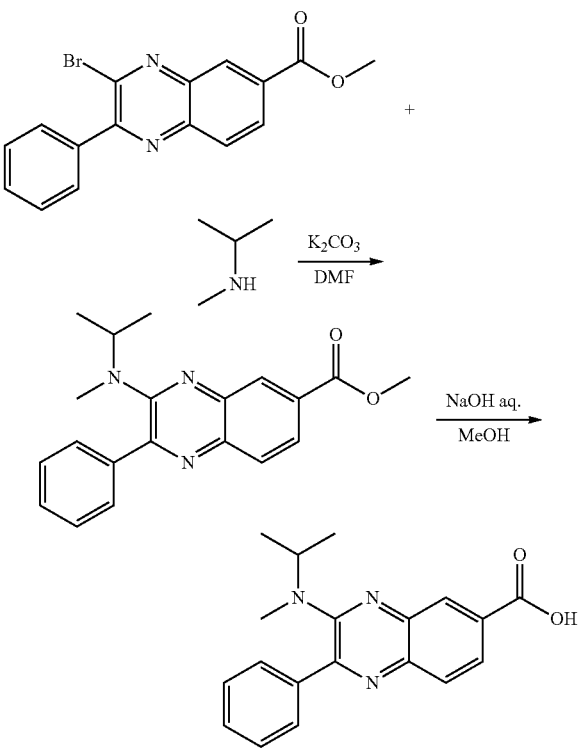

Step 1. Methyl 3-(isopropyl(methyl)amino)-2-phenylquinoxaline-6-carboxylate

Into a 8-mL sealed tube, was placed a solution of methyl 3-bromo-2-phenylquinoxaline-6-carboxylate (170 mg, 0.50 mmol, 1.00 equiv) in N,N-dimethylformamide (5 mL), N-methylpropan-2-amine (73 mg, 1.00 mmol, 2.00 equiv), and potassium carbonate (207 mg, 1.50 mmol, 3.00 equiv). The resulting solution was stirred overnight at 100° C. The reaction was then quenched by the addition of water. The resulting solids were collected by filtration. This resulted in 109.8 mg (59%) of methyl 3-(isopropyl(methyl)amino)-2-phenylquinoxaline-6-carboxylate as a yellow solid.

LC-MS:(ES, m/z): 336 [M+H]$^+$

Step 2. 3-(Isopropyl(methyl)amino)-2-phenylquinoxaline-6-carboxylic Acid

Into a 50-mL round-bottom flask, was placed a solution of methyl 3-(isopropyl(methyl)amino)-2-phenylquinoxaline-6-carboxylate (109.8 mg, 0.29 mmol, 1.00 equiv, 90%) in methanol (20 mL). This was followed by the dropwise addition of a solution of sodium hydroxide (65.6 mg, 1.64 mmol, 5.00 equiv) in water (3 mL) with stirring. The resulting solution was stirred overnight at 50° C. in an oil bath. The pH value of the solution was adjusted to 3-4 with 1N hydrogen chloride. The filtrate was concentrated under vacuum. The resulting solids were collected by filtration and washed with methanol and water. This resulted in 58 mg (59%) of 3-(isopropyl(methyl)amino)-2-phenylquinoxaline-6-carboxylic acid as a yellow solid.

LC-MS:(ES, m/z): 322 [M+H]$^+$ $^1$H-NMR (300 MHz, DMSO, ppm): δ 8.26 (s, 1H), 7.94 (s, 2H), 7.86-7.83 (m 2H), 7.58-7.50 (m, 3H), 4.25-4.16 (m, 1H), 2.67 (s, 3H), 1.05-1.02 (d, J=9 Hz, 6H).

EXAMPLE 44

3-(Cyclohexylamino)-2-phenylquinoxaline-6-carboxylic Acid

Step 1. Methyl 3-(cyclohexylamino)-2-phenylquinoxaline-6-carboxylate

Into a 10-mL sealed tube, was placed methyl 3-bromo-2-phenylquinoxaline-6-carboxylate (150 mg, 0.44 mmol, 1.00 equiv), cyclohexanamine (131.03 mg, 1.32 mmol, 3.00 equiv), potassium carbonate (304.41 mg, 2.21 mmol, 5.00 equiv), and N,N-dimethylformamide (2 mL). The resulting solution was stirred overnight at 100° C. in an oil bath. The reaction was then quenched by the addition of 20 mL of water. The resulting aqueous solution was extracted with 3×50 mL of ethyl acetate. The organic layers were combined and washed with 5×30 mL of aq. sodium chloride. The organic layers were dried over anhydrous sodium sulfate and concentrated in vacuo. The residue was purified by silica gel chromatography with ethyl acetate/petroleum ether (1:50). This resulted in 80 mg (46%) of methyl 3-(cyclohexylamino)-2-phenylquinoxaline-6-carboxylate as a yellow solid.

LC-MS:(ES, m/z): 362 [M+H]$^+$

Step 2. 3-(Cyclohexylamino)-2-phenylquinoxaline-6-carboxylic Acid

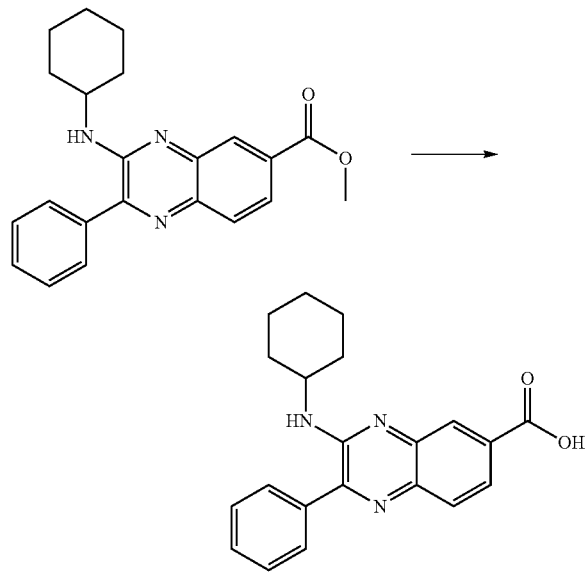

Into a 50-mL round-bottom flask, was placed a solution of methyl 3-(cyclohexylamino)-2-phenylquinoxaline-6-carboxylate (80 mg, 0.22 mmol, 1.00 equiv) in methanol (15 mL), a solution of sodium hydroxide (44.32 mg, 1.11 mmol, 5.00 equiv) in water (2 mL). The resulting solution was stirred for 2 hrs at 50° C. in an oil bath. The resulting mixture was concentrated under vacuum. The residue was diluted in 20 mL of water. The pH value of the solution was adjusted to 4-5 with aq hydrogen chloride (1 mol/L). The resulting solids were collected by filtration. This resulted in 60 mg (76%) of 3-(cyclohexylamino)-2-phenylquinoxaline-6-carboxylic acid as a yellow solid.

LC-MS (ES, m/z): 334 [M+H]$^+$ $^1$H-NMR (300 MHz, DMSO, ppm): δ 8.155 (s, 1H), 7.879-7.850 (d, J=8.7 Hz, 2H), 7.815-7.772 (m, 2H), 7.597-7.578 (m, 3H), 6.248-6.222 (d, J=8.4 Hz, 1H), 4.091 (s, 1H), 1.966 (m, 2H), 1.694-1.598 (m, 3H), 1.370 (m, 4H), 1.239-1.181 (m, 1H).

EXAMPLE 45

3-(2-Methylpiperidin-1-yl)-2-phenylquinoxaline-6-carboxylic Acid

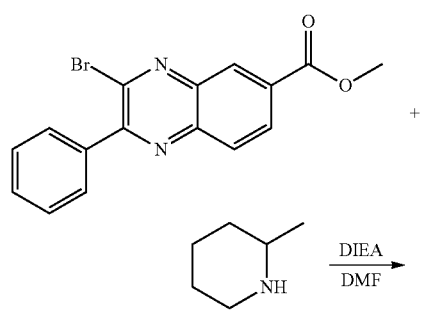

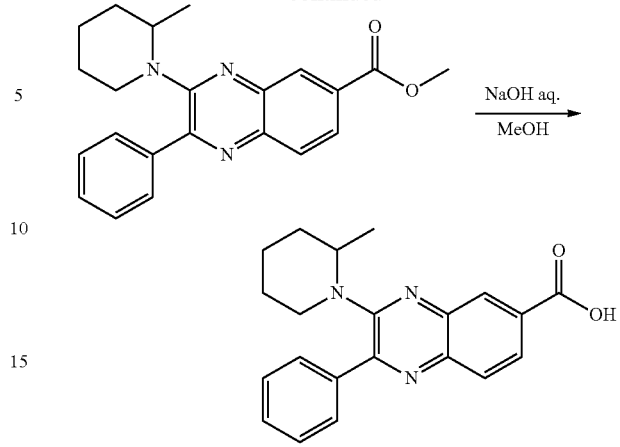

Step 1. Methyl 3-(2-methylpiperidin-1-yl)-2-phenylquinoxaline-6-carboxylate

Into a 8-mL sealed tube, was placed methyl 3-bromo-2-phenylquinoxaline-6-carboxylate (150 mg, 0.44 mmol, 1.00 equiv), 2-methylpiperidine (130.86 mg, 1.32 mmol, 3.00 equiv), DIEA (170.28 mg, 1.32 mmol, 3.00 equiv), N,N-dimethylformamide (4 mL). The resulting solution was stirred overnight at 100° C. in an oil bath. The reaction was then quenched by the addition of water. The resulting solution was extracted with 4×20 mL of dichloromethane and the organic layers combined and dried over anhydrous sodium sulfate. The resulting mixture was concentrated under vacuum. The residue was applied onto a silica gel column with ethyl acetate/petroleum ether (1:7). This resulted in 60 mg (36%) of methyl 3-(2-methylpiperidin-1-yl)-2-phenylquinoxaline-6-carboxylate as yellow oil.

LC-MS:(ES, m/z): 362 [M+H]$^+$ $^1$H-NMR (300 MHz, CDC$_3$, ppm): δ 8.580-8.575 (s, 1H), (d, J=1.5 Hz, 1H), 8.10-7.98 (m, 4H), 7.56-7.48 (m, 3H), 4.18-4.14 (t, J=6 Hz, 1H), 4.01 (s, 3H), 3.20-3.12 (m, 1H), 1.76-1.61 (m, 6H), 1.14-1.12 (d, J=6.9 Hz, 3H).

Step 2. 3-(2-Methylpiperidin-1-yl)-2-phenylquinoxaline-6-carboxylic Acid

Into a 50-mL round-bottom flask, was placed a solution of methyl 3-(2-methylpiperidin-1-yl)-2-phenylquinoxaline-6-carboxylate (107.9 mg, 0.30 mmol, 1.00 equiv) in methanol (20 mL). This was followed by the dropwise addition of a solution of sodium hydroxide (60 mg, 1.50 mmol, 5.00 equiv) in water (3 mL) with stirring. The resulting solution was stirred overnight at 50° C. in an oil bath and concentrated under vacuum and diluted by 10 ml of water. The pH value of the aqueous solution was adjusted to 3-4 with 1N hydrogen chloride. The resulting solid was collected by filtration and washed with methanol. This resulted in 54 mg (50%) of 3-(2-methylpiperidin-1-yl)-2-phenylquinoxaline-6-carboxylic acid as a yellow solid.

LC-MS:(ES, m/z): 348 [M+H]$^+$ $^1$H-NMR (300 MHz, DMSO, ppm): δ 8.26 (s, 1H), 7.99-7.92 (m, 4H), 7.57-7.51 (m, 3H), 4.07-4.05 (d, J=5.7 Hz, 1H), 3.10-3.03 (m, 1H), 1.62-1.34 (m, 6H), 1.08-1.04 (t, J=6.6 Hz, 3H).

EXAMPLE 46

3-(Cyclopropyl(methyl)amino)-2-phenylquinoxaline-6-carboxylic Acid

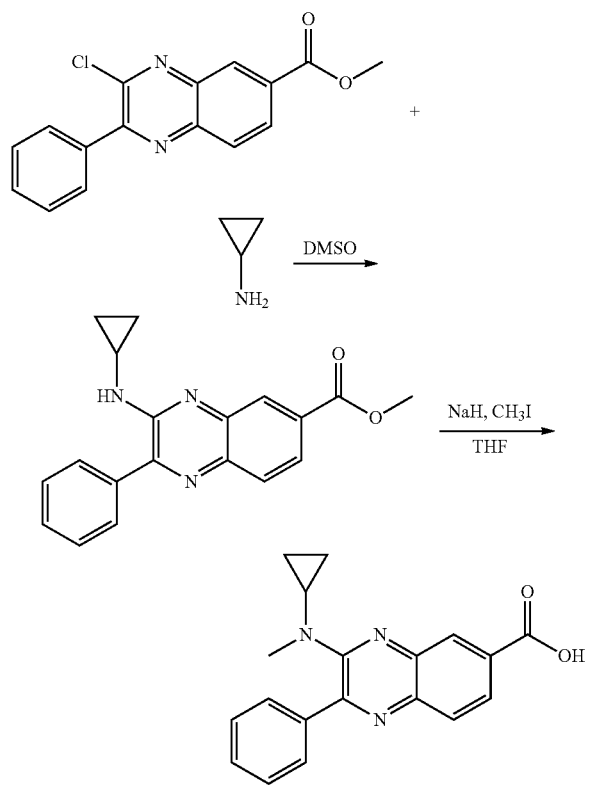

Step 1. Methyl 3-(cyclopropylamino)-2-phenylquinoxaline-6-carboxylate

Into a 20-mL sealed tube, was placed methyl 3-chloro-2-phenylquinoxaline-6-carboxylate (200 mg, 0.67 mmol, 1.00 equiv), cyclopropanamine (10 mL), DMSO (1 mL). The resulting solution was stirred overnight at 50° C. in an oil bath. The resulting mixture was concentrated under vacuum. The resulting solution was diluted with $H_2O$. The resulting solids were collected by filtration and applied onto a silica gel column with PE/EA (50:1). This resulted in 182.4 mg (83%) of methyl 3-(cyclopropylamino)-2-phenylquinoxaline-6-carboxylate as a yellow solid.

LC-MS:(ES, m/z): 320 [M+H]$^+$

Step 2. 3-(Cyclopropyl(methyl)amino)-2-phenylquinoxaline-6-carboxylic Acid

Into a 50-mL round-bottom flask purged and maintained with an inert atmosphere of nitrogen, was placed a solution of methyl 3-(cyclopropylamino)-2-phenylquinoxaline-6-carboxylate (182.4 mg, 0.56 mmol, 1.00 equiv, 98%) in tetrahydrofuran (17 mL). Sodium hydride (274.5 mg, 11.44 mmol, 20.00 equiv) was added. The resulting solution was stirred for 1 h at room temperature. This was followed by the dropwise addition of $CH_3I$ (809.4 mg, 5.70 mmol, 10.00 equiv) with stirring at 0° C. The resulting solution was allowed to react, with stirring, overnight at room temperature. The resulting mixture was concentrated under vacuum and diluted with 10 ml of water. The pH value of the aqueous solution was adjusted to 3-4 with 1N hydrogen chloride. The resulting solid was collected by filtration and washed with water and methanol. This resulted in 66.5 mg (36%) of 3-(cyclopropyl(methyl)amino)-2-phenylquinoxaline-6-carboxylic acid as a yellow solid.

LC-MS:(ES, m/z): 320 [M+H]$^+$ $^1$H-NMR (300 MHz, DMSO, ppm): δ 8.26 (s, 1H), 7.95 (s, 2H), 7.80-7.78 (d, J=6 Hz, 2H), 7.51-7.50 (d, J=6.9 Hz, 3H), 3.00 (s, 3H), 2.45 (s, 1H), 0.43 (s, 4H).

EXAMPLE 47

3-(2-Methylpyrrolidin-1-yl)-2-phenylquinoxaline-6-carboxylic Acid

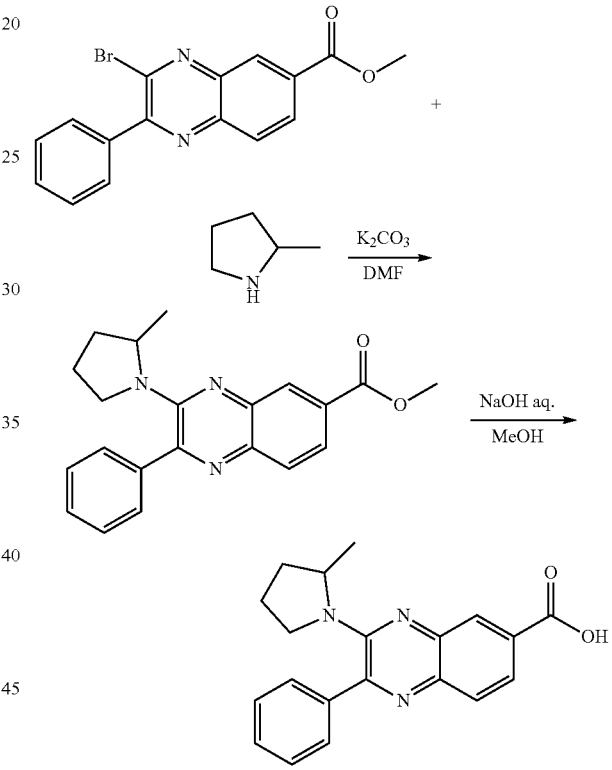

Step 1. Methyl 3-(2-methylpyrrolidin-1-yl)-2-phenylquinoxaline-6-carboxylate Into a 8-mL sealed tube, was placed methyl 3-bromo-2-phenylquinoxaline-6-carboxylate (150 mg, 0.44 mmol, 1.00 equiv), 2-methylpyrrolidine (74.8 mg, 0.88 mmol, 2.00 equiv), potassium carbonate (181.6 mg, 1.32 mmol, 3.00 equiv), and N,N-dimethylformamide (4 mL). The resulting solution was stirred overnight at 100° C. in an oil bath. The reaction was t quenched by the addition of water and the resulting solution was extracted with 5×20 mL of dichloromethane and the organic layers were combined and dried over anhydrous sodium sulfate and concentrated in vacuo. The residue was purified by silica gel chromatography with ethyl acetate/petroleum ether (1:100). This resulted in 110.3 mg (72%) of methyl 3-(2-methylpyrrolidin-1-yl)-2-phenylquinoxaline-6-carboxylate as yellow oil.

LC-MS:(ES, m/z): 348 [M+H]+

Step 2. 3-(2-methylpyrrolidin-1-yl)-2-phenylquinoxaline-6-carboxylic Acid

Into a 50-mL round-bottom flask, was placed a solution of methyl 3-(2-methylpyrrolidin-1-yl)-2-phenylquinoxaline-6-carboxylate (110 mg, 0.32 mmol, 1.00 equiv) in methanol (20 mL). Then a solution of sodium hydroxide (63.4 mg, 1.58 mmol, 5.00 equiv) in water (2.5 mL) was added dropwise with stirring. The resulting solution was stirred for 8 h at 50° C. in an oil bath. The resulting mixture was concentrated under vacuum and diluted with 10 ml of water. The pH value of the aqueous solution was adjusted to 3-4 with 1N hydrogen chloride. The resulting solid was collected by filtration and washed with hexane. This resulted in 40 mg (38%) of 3-(2-methylpyrrolidin-1-yl)-2-phenylquinoxaline-6-carboxylic acid as a yellow solid.

LC-MS:(ES, m/z): 334 [M+H]+

1H-NMR (300 MHz, DMSO, ppm): δ 8.25 (s, 1H), 7.91 (s, 2H), 7.74-7.72 (d, J=6 Hz, 2H), 7.54-7.51 (d, J=9 Hz, 3H), 4.24-4.22 (d, J=6 Hz, 1H), 3.02-2.93 (m, 2H), 2.12 (s, 1H), 1.75 (s, 1H), 1.53 (s, 2H), 1.33-1.31 (d, J=6 Hz, 3H).

EXAMPLE 48

3-(sec-Butyl(methyl)amino)-2-phenylquinoxaline-6-carboxylic Acid

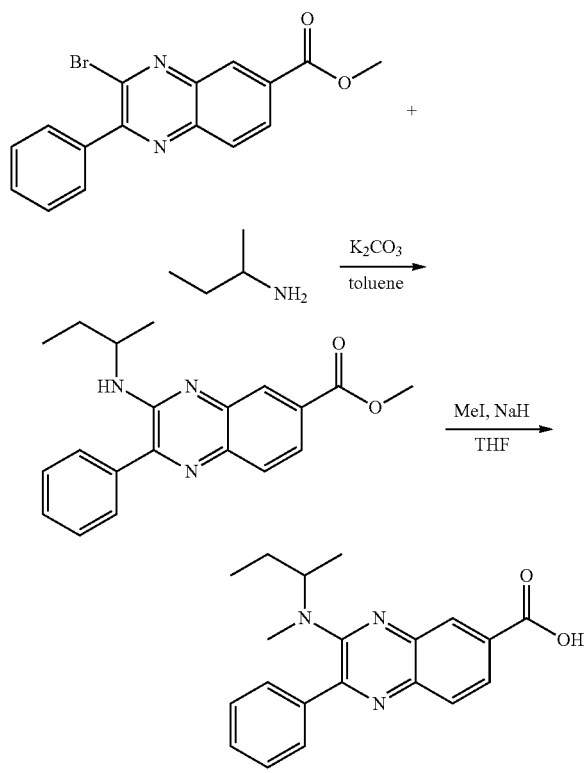

Step 1. Methyl 3-(sec-butylamino)-2-phenylquinoxaline-6-carboxylate

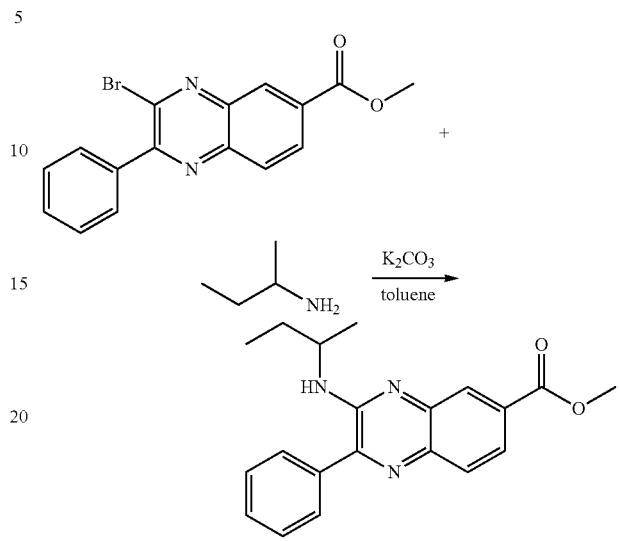

Into a 8-mL sealed tube, was placed methyl 3-bromo-2-phenylquinoxaline-6-carboxylate (150 mg, 0.44 mmol, 1.00 equiv), butan-2-amine (193 mg, 2.64 mmol, 6.00 equiv), potassium carbonate (181.6 mg, 1.32 mmol, 3.00 equiv), toluene (3 mL). The resulting solution was stirred overnight at 100° C. in an oil bath. The resulting solution was concentrated under vacuum. The residue was applied onto a silica gel column with ethyl acetate/petroleum ether (1:10). This resulted in 109 mg (crude) of methyl 3-(sec-butylamino)-2-phenylquinoxaline-6-carboxylate as yellow oil.

LC-MS:(ES, m/z): 336 [M+H]+

Step 2. 3-(sec-Butyl(methyl)amino)-2-phenylquinoxaline-6-carboxylic Acid

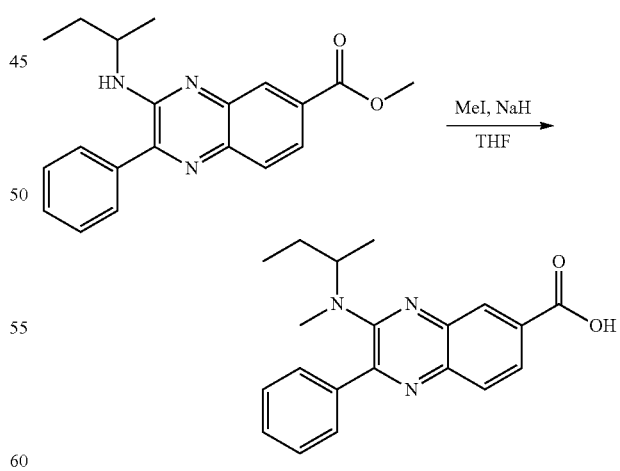

Into a 50-mL round-bottom flask, was placed a solution of methyl 3-(sec-butylamino)-2-phenylquinoxaline-6-carboxylate (133.6 mg, 0.40 mmol, 1.00 equiv) in tetrahydrofuran (12 mL), and sodium hydride (96 mg, 4.00 mmol, 10.03 equiv). The resulting solution was stirred 1 h at room temperature. Then a solution of methyl iodide (284 mg, 2.00 mmol, 5.01 equiv) in tetrahydrofuran (1 mL) was added dropwise with stirring. The resulting solution was stirred overnight at room temperature. The pH value of the solution was adjusted to 3-4 with 1N hydrogen chloride. The resulting solution was concentrated under vacuum. The residue was purified by silica gel chromatography with dichloromethane/petroleum ether (10:1). The crude product (130 mg) was purified by Prep-HPLC under the following conditions (1 #-Waters 2767-1): Column, SunFire Prep C18, Sum, 19*100 mm; mobile phase, water with 0.05% TFA and CH$_3$CN (60% CH$_3$CN up to 80% in 6 min, up to 100% in 1 min, down to 60% in 1 min); Detector, UV 220 254 nm. This resulted in 52 mg (39%) of 3-(sec-butyl(methyl) amino)-2-phenylquinoxaline-6-carboxylic acid as a yellow solid.

LC-MS:(ES, m/z): 336 [M+H]$^+$ $^1$H-NMR (300 MHz, DMSO, ppm): δ 8.26 (s, 1H), 7.94 (s, 2H), 7.81-7.78 (t, J=9 Hz, 2H), 7.57-7.51 (m, 3H), 3.99-3.92 (q, J=9 Hz, 1H), 2.67 (s, 3H), 1.56-1.37 (m, 2H), 1.02-1.00 (d, J=4 Hz, 3H), 0.65-0.60 (t, J=6 Hz, 3H).

EXAMPLE 49

(R)-3-(3-Hydroxypyrrolidin-1-yl)-2-phenylquinoxaline-6-carboxylic Acid

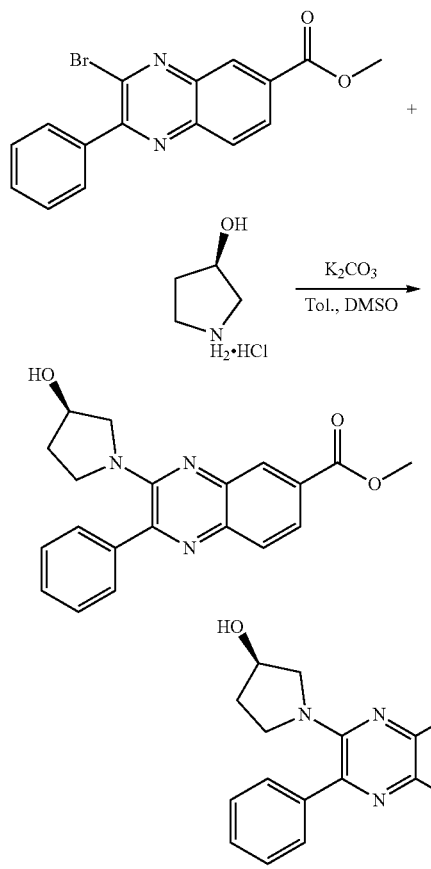

Step 1. (R)-methyl 3-(3-hydroxypyrrolidin-1-yl)-2-phenylquinoxaline-6-carboxylate Into an 8-mL sealed tube, was placed methyl 3-bromo-2-phenylquinoxaline-6-carboxylate (150 mg, 0.44 mmol, 1.00 equiv), (R)-pyrrolidin-3-ol hydrochloride (212 mg, 1.72 mmol, 4.00 equiv), potassium carbonate (200 mg, 1.55 mmol, 3.00 equiv), toluene (5 mL), DMSO (1.7 mL). The resulting solution was stirred overnight at 100° C. in an oil bath. The reaction was then quenched by the addition of 20 ml of water. The resulting solution was extracted with 5×10 mL of dichloromethane and the organic layers combined and concentrated under vacuum. The residue was applied onto a silica gel column with dichloromethane/methanol (70:1). This resulted in 147.4 mg (95%) of (R)-methyl 3-(3-hydroxypyrrolidin-1-yl)-2-phenylquinoxaline-6-carboxylate as a yellow solid.

LC-MS (ES, m/z): 350 [M+H]$^+$

Step 2. (R)-3-(3-hydroxypyrrolidin-1-yl)-2-phenylquinoxaline-6-carboxylic Acid

Into a 50-mL round-bottom flask, was placed a solution of (R)-methyl 3-(3-hydroxypyrrolidin-1-yl)-2-phenylquinoxaline-6-carboxylate (147.4 mg, 0.42 mmol, 1.00 equiv) in methanol (15 mL). This was followed by the dropwise addition of a solution of sodium hydroxide (84.5 mg, 2.11 mmol, 5.00 equiv) in water (2 mL) with stirring. The resulting solution was stirred overnight at 50° C. in an oil bath. The pH value of the solution was adjusted to 3-4 with 1N hydrogen chloride. The resulting mixture was concentrated under vacuum. The crude product (120 mg) was purified by Prep-HPLC with the following conditions (1 #-Waters 2767-1): Column, SunFire Prep C18, Sum, 19*100 mm; mobile phase, water with 0.05% TFA and CH$_3$CN (20% CH$_3$CN up to 50% in 6 min, up to 100% in 1 min, down to 20% in 1 min); Detector, UV 220 254 nm. This resulted in 35 mg (24%) of (R)-3-(3-hydroxypyrrolidin-1-yl)-2-phenylquinoxaline-6-carboxylic acid as a yellow solid.

LC-MS:(ES, m/z): 336 [M+H]$^+$ $^1$H-NMR (300 MHz, DMSO, ppm): δ 8.34 (s, 1H), 8.24-7.49 (m, 7H), 4.21 (s, 1H), 3.53-3.27 (m, 3H), 3.00-2.96 (d, J=16 Hz, 1H), 1.89-1.52 (m, 2H).

EXAMPLE 50

(S)-3-(3-Hydroxypyrrolidin-1-yl)-2-phenylquinoxaline-6-carboxylic Acid

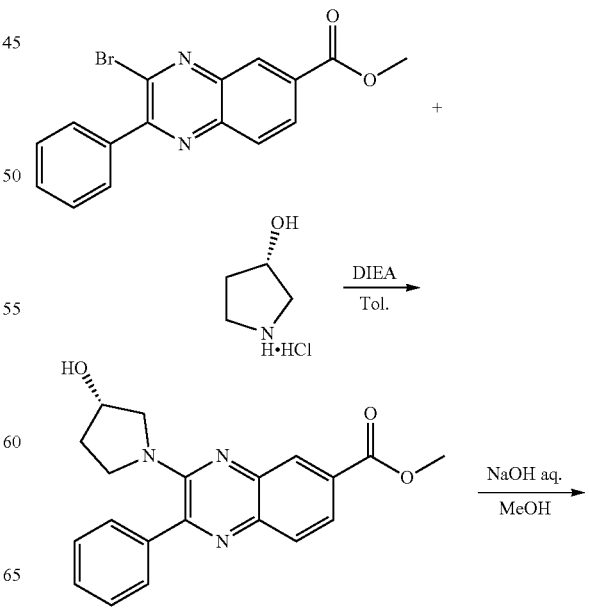

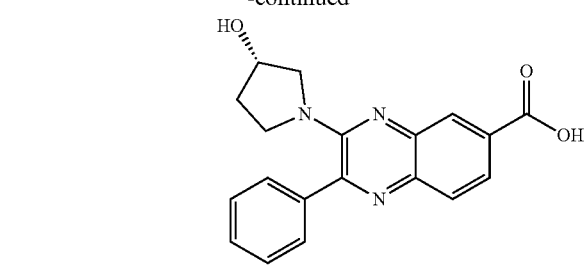

Step 1. (S)-Methyl 3-(3-hydroxypyrrolidin-1-yl)-2-phenylquinoxaline-6-carboxylate

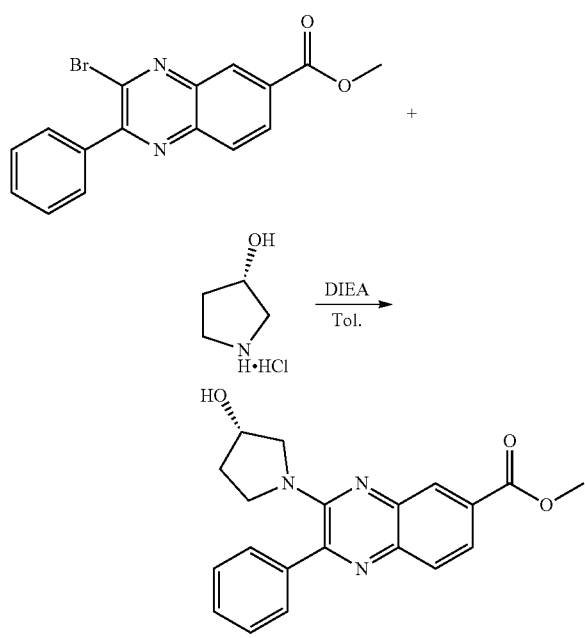

Into an 8-mL sealed tube, was placed methyl 3-bromo-2-phenylquinoxaline-6-carboxylate (150 mg, 0.44 mmol, 1.00 equiv), (S)-pyrrolidin-3-ol hydrochloride (163 mg, 1.32 mmol, 3.00 equiv), DIEA (227 mg, 1.76 mmol, 4.00 equiv), toluene (4 mL), in DMSO (2 ml). The resulting solution was stirred at 100° C. for 7 hrs. Then the reaction was quenched by the addition of water. The resulting solution was extracted with 5×15 mL of dichloromethane and the organic layers were combined and concentrated in vacuo. The residue was purified by silica gel chromatography with dichloromethane/methanol (70:1). This resulted in 176 mg (crude) of (S)-methyl 3-(3-hydroxypyrrolidin-1-yl)-2-phenylquinoxaline-6-carboxylate as a yellow solid.

LC-MS:(ES, m/z): 350 [M+H]$^+$ $^1$H-NMR (300 MHz, CDC$_3$, ppm): δ 8.56 (s, 1H), 8.04-7.96 (m, 2H), 7.75-7.73 (t, J=1.5 Hz, 2H), 7.54-7.46 (m, 3H), 4.50 (s, 1H), 4.00 (s, 3H), 3.70-3.30 (m, 4H), 2.00 (s, 2H).

Step 2. (S)-3-(3-Hydroxypyrrolidin-1-yl)-2-phenylquinoxaline-6-carboxylic Acid

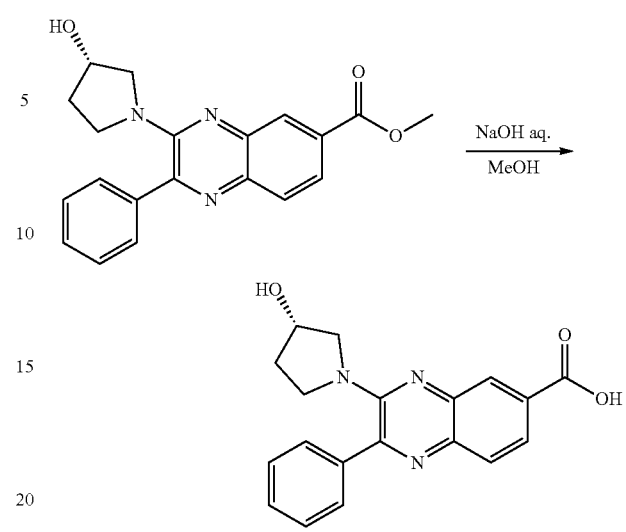

Into a 50-mL round-bottom flask, was placed a solution of (S)-methyl 3-(3-hydroxypyrrolidin-1-yl)-2-phenylquinoxaline-6-carboxylate (170 mg, 0.49 mmol, 1.00 equiv) in methanol (20 mL). This was followed by the dropwise addition of a solution of sodium hydroxide (97.4 mg, 2.44 mmol, 5.00 equiv) in water (2.5 mL) with stirring. The resulting solution was stirred overnight at 50° C. in an oil bath. The pH value of the solution was adjusted to 3-4 with 1N hydrogen chloride. The resulting solid was collected by filtration and washed with water and methanol. The solid was dried in an oven. This resulted in 40 mg (25%) of (S)-3-(3-hydroxypyrrolidin-1-yl)-2-phenylquinoxaline-6-carboxylic acid as a yellow solid.

LC-MS:(ES, m/z): 336 [M+H]$^+$ $^1$H-NMR (300 MHz, DMSO, ppm): δ 8.32-8.24 (d, J=24 Hz, 1H), 7.94-7.86 (m, 2H), 7.70-7.68 (m, J=2.1 Hz, 2H), 7.54-7.52 (d, J=6 Hz, 3H), 4.89 (s, 1H), 4.22 (s, 1H), 3.55-3.49 (m, 2H), 3.00-2.96 (d, J=12 Hz, 1H), 1.89-1.79 (m, 2H).

EXAMPLE 51

(R)-3-(2-(Methoxymethyl)pyrrolidin-1-yl)-2-phenylquinoxaline-6-carboxylic Acid

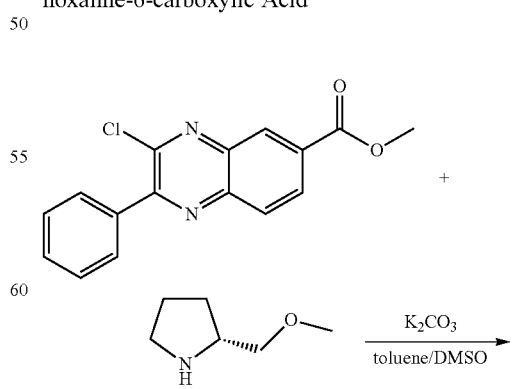

-continued

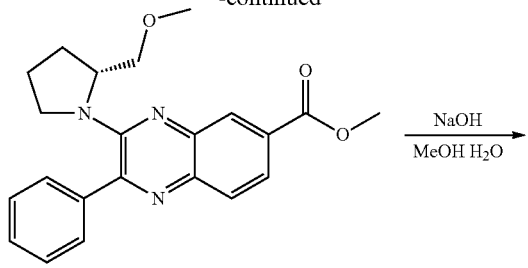

Step 1. (S)-methyl 3-(2-(methoxymethyl)pyrrolidin-1-yl)-2-phenylquinoxaline-6-carboxylate

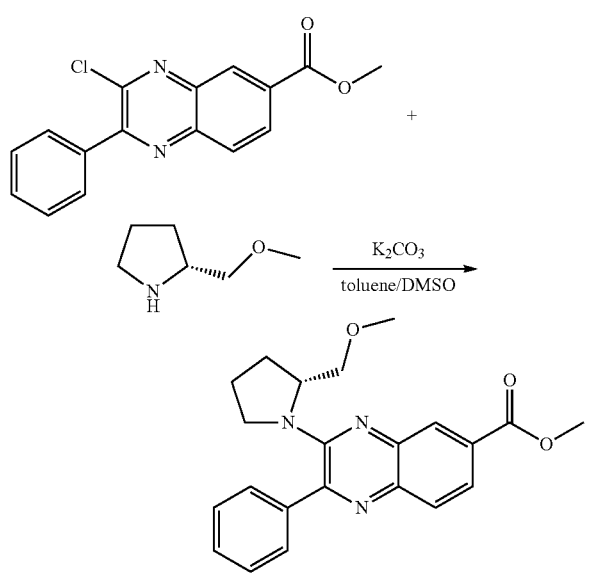

Into a 10-mL pressure tank reactor, was placed (S)-2-(methoxymethyl)pyrrolidine (96.45 mg, 0.85 mmol, 5.00 equiv), methyl 3-chloro-2-phenylquinoxaline-6-carboxylate (50 mg, 0.17 mmol, 1.00 equiv), potassium carbonate (46.7 mg, 0.34 mmol, 2.00 equiv), toluene/DMSO (2/0.4 mL). The resulting solution was stirred overnight at 100° C. in an oil bath. The resulting mixture was concentrated under vacuum. The reaction was then quenched by the addition of 10 mL of water. The resulting solution was extracted with 3×30 mL of ethyl acetate and the organic layers combined. The residue was applied onto a silica gel column with ethyl acetate/petroleum ether (1:50). This resulted in 17 mg (27%) of (S)-methyl 3-(2-(methoxymethyl)pyrrolidin-1-yl)-2-phenylquinoxaline-6-carboxylate as a yellow solid.

LC-MS (ES, m/z): 378 [M+H]$^+$

Step 2. (R)-3-(2-(methoxymethyl)pyrrolidin-1-yl)-2-phenylquinoxaline-6-carboxylic Acid

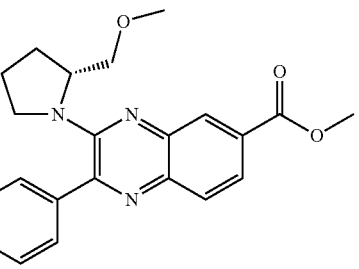

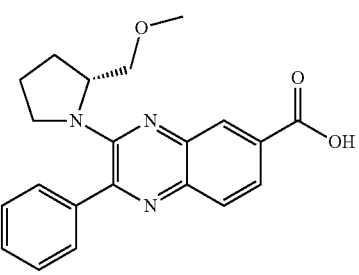

Into a 50-mL round-bottom flask, was placed a solution of (R)-methyl 3-(2-(methoxymethyl)pyrrolidin-1-yl)-2-phenylquinoxaline-6-carboxylate (66 mg, 0.18 mmol, 1.00 equiv) in methanol (15 mL). A solution of sodium hydroxide (35 mg, 0.88 mmol, 5.00 equiv) in water (2 mL) was added. The resulting solution was stirred for 2 hrs at 50° C. in an oil bath. The resulting mixture was concentrated under vacuum and diluted in 20 mL of water. The pH value of the aqueous solution was adjusted to 4-5 with hydrogen chloride (1 mol/L). The resulting solids were collected by filtration. The residue was applied onto a silica gel column with dichloromethane/methanol (10:1). This resulted in 25 mg (39%) of (R)-3-(2-(methoxymethyl)pyrrolidin-1-yl)-2-phenylquinoxaline-6-carboxylic acid as a yellow solid.

LC-MS (ES, m/z): 364 [M+H]$^+$ $^1$H-NMR (300 MHz, DMSO, ppm): δ 13.12 (s, 1H), 8.243-8.239 (d, J=1.2 Hz, 1H), 7.95-7.88 (m, 2H), 7.75-7.72 (m, 2H), 7.56-7.49 (m, 3H), 4.51-4.47 (m, 1H), 3.70-3.65 (m, 1H), 3.52-3.47 (m, 1H), 3.32-3.30 (d, J=5.1 Hz 1H), 2.96-2.93 (m, 2H), 2.06-2.03 (m, 1H), 1.82-1.74 (m, 2H), 1.58-1.55 (m, 1H).

EXAMPLE 52

(R)-3-(2-(Hydroxymethyl)pyrrolidin-1-yl)-2-phenylquinoxaline-6-carboxylic Acid

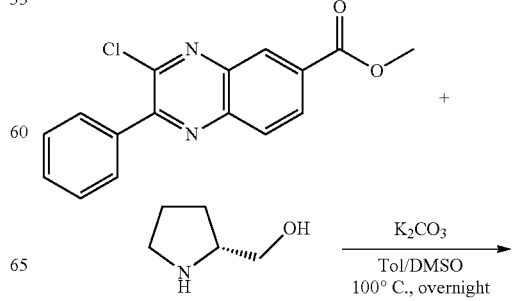

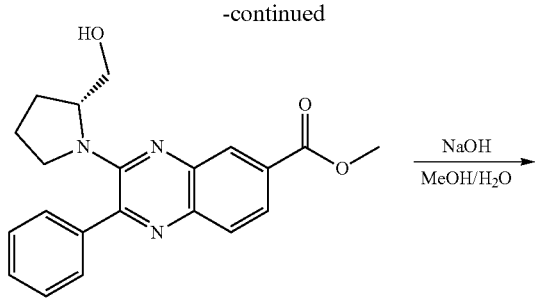

Step 1. (R)-methyl 3-(2-(hydroxymethyl)pyrrolidin-1-yl)-2-phenylquinoxaline-6-carboxylate

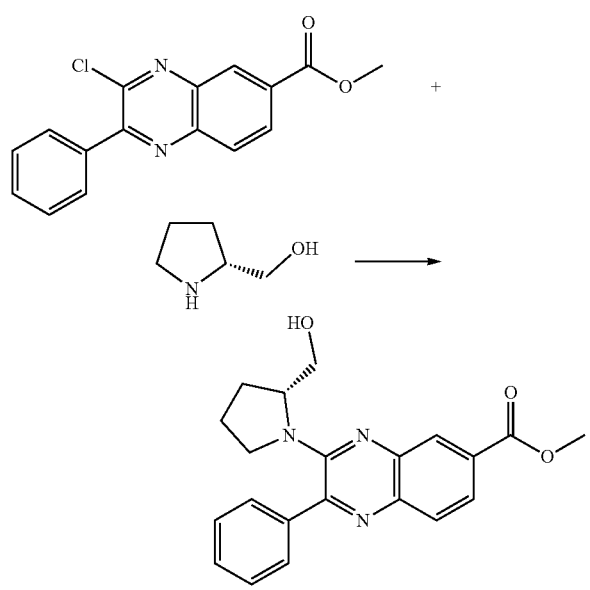

Into an 8-mL sealed tube, was placed a solution of methyl 3-chloro-2-phenylquinoxaline-6-carboxylate (150 mg, 0.50 mmol, 1.00 equiv), (R)-pyrrolidin-2-ylmethanol (150 mg, 1.49 mmol, 3.00 equiv), and potassium carbonate (345 mg, 2.50 mmol, 5.00 equiv) in Tol/DMSO (2.5/0.5 mL). The resulting mixture was stirred overnight at 100° C. The residue was purified by silica gel chromatography with ethyl acetate/petroleum ether (1:50). This resulted in 120 mg (63%) of (R)-methyl 3-(2-(hydroxymethyl)pyrrolidin-1-yl)-2-phenylquinoxaline-6-carboxylate as a yellow solid.

LC-MS:(ES, m/z): 364 [M+H]$^+$ $^1$H-NMR (300 MHz, DMSO, ppm): δ 8.26 (d, J=1.5 Hz, 1H), 7.97-7.87 (m, 2H), 7.80-7.77 (dd, J=1.8, 7.6 Hz, 2H), 7.56-7.46 (m, 3H), 4.78-4.74 (t, J=5.7 Hz, 1H), 4.36-4.32 (t, J=4.5 Hz, 1H), 3.93 (s, 3H), 3.72-3.67 (q, J=5.4 Hz, 2H), 2.97-2.92 (m, 2H), 2.04-1.75 (m, 4H).

Step 2. (R)-3-(2-(hydroxymethyl)pyrrolidin-1-yl)-2-phenylquinoxaline-6-carboxylic Acid

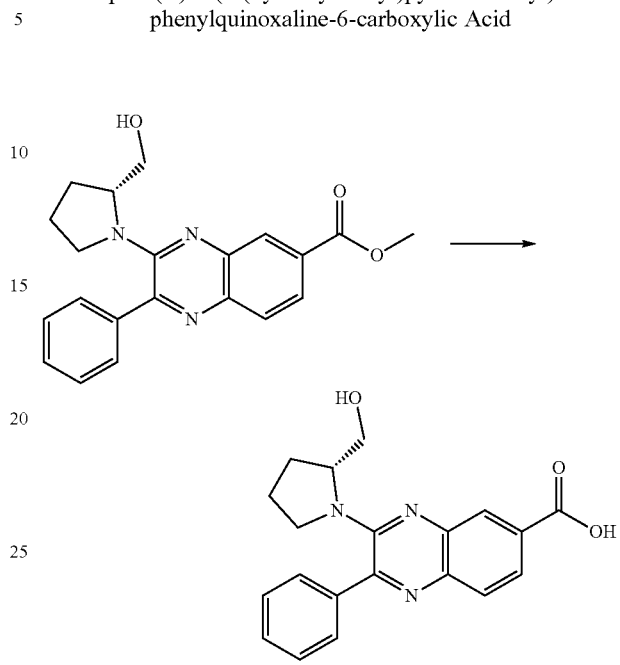

Into a 100-mL round-bottom flask, was placed a solution of (R)-methyl 3-(2-(hydroxymethyl)pyrrolidin-1-yl)-2-phenylquinoxaline-6-carboxylate (120 mg, 0.33 mmol, 1.00 equiv) and sodium hydroxide (66 mg, 1.65 mmol, 4.99 equiv) in methanol/H$_2$O (20/5 mL). The reaction was stirred for 5 h at 70° C. and concentrated to dryness. The residue was dissolved in 20 mL H$_2$O and washed with 10 mL EtOAc. The pH of the aqueous layer was adjusted to 7 with 1N HCl and extracted with DCM/MeOH (10/1, 20 mL×5). The organic layers were combined and dried over Na$_2$SO$_4$ and concentrated to dryness. This resulted in 80 mg (66%) of (R)-3-(2-(hydroxymethyl)pyrrolidin-1-yl)-2-phenylquinoxaline-6-carboxylic acid as a yellow solid.

LC-MS (ES, m/z): 350 [M+H]$^+$ $^1$H-NMR (300 MHz, DMSO, ppm): δ 8.21 (s, 1H), 7.94-7.90 (d, J=8.1 Hz, 1H), 7.82-7.76 (m, 3H), 7.53-7.45 (m, 3H), 4.35 (s, 1H), 3.69-3.67 (d, J=3.9 Hz, 2H), 3.00-2.89 (m, 2H), 2.02-1.97 (m, 1H), 1.91-1.74 (m, 2H), 1.58-1.49 (m, 1H).

EXAMPLE 53

(S)-3-(2-(Hydroxymethyl)pyrrolidin-1-yl)-2-phenylquinoxaline-6-carboxylic Acid

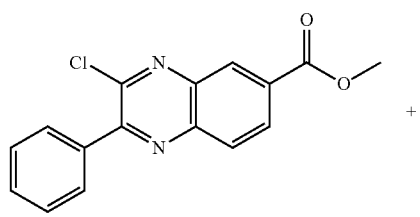

Step 1. (S)-methyl 3-(2-(hydroxymethyl)pyrrolidin-1-yl)-2-phenylquinoxaline-6-carboxylate

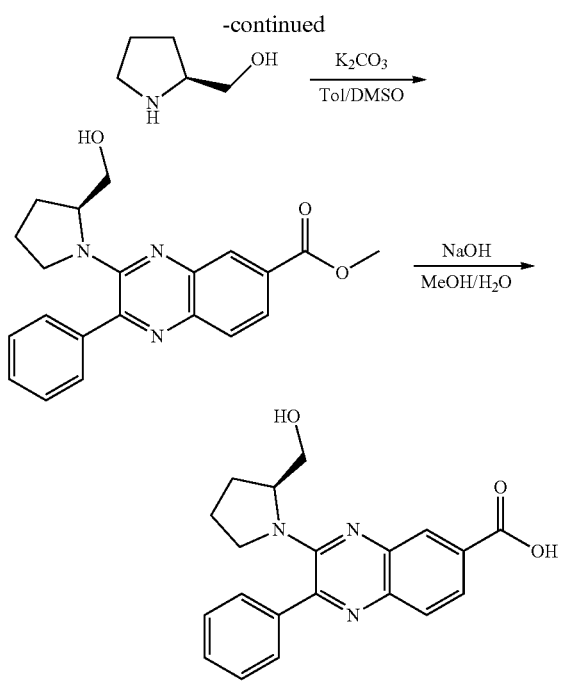

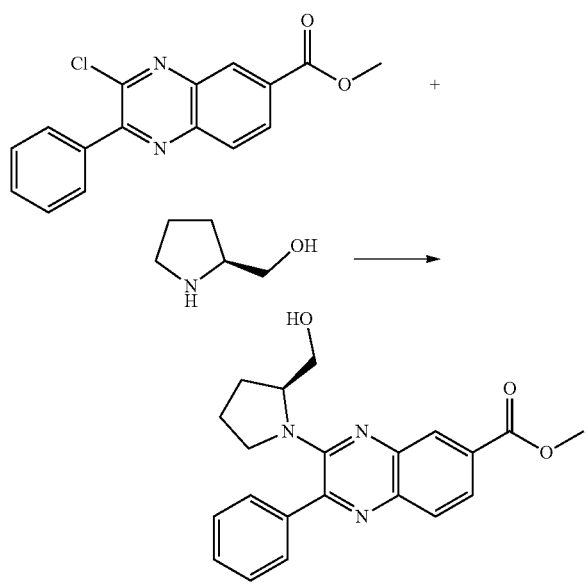

Into an 8-mL sealed tube, was placed a solution of methyl 3-chloro-2-phenylquinoxaline-6-carboxylate (150 mg, 0.50 mmol, 1.00 equiv), (S)-pyrrolidin-2-ylmethanol (150 mg, 1.49 mmol, 3.00 equiv), potassium carbonate (345 mg, 2.50 mmol, 5.00 equiv) in Tol/DMSO (2.5/0.5 mL). The resulting mixture was stirred for overnight at 100° C. The residue was applied onto a silica gel column with ethyl acetate/petroleum ether (1:50). This resulted in 104 mg (54%) of (S)-methyl 3-(2-(hydroxymethyl)pyrrolidin-1-yl)-2-phenylquinoxaline-6-carboxylate as a yellow solid.

LC-MS:(ES, m/z): 364 [M+H]⁺

$^1$H-NMR (300 MHz, DMSO, ppm): δ 8.26 (d, J=1.5 Hz, 1H), 7.97-7.87 (m, 2H), 7.80-7.77 (m, 2H), 7.55-7.47 (m, 3H), 4.78-4.73 (t, J=5.7 Hz, 1H), 4.35-4.32 (d, J=4.5 Hz, 1H), 3.93 (s, 3H), 3.76-3.67 (m, 2H), 3.00-2.92 (m, 2H), 1.99-1.49 (m, 4H).

Step 2. (S)-3-(2-(hydroxymethyl)pyrrolidin-1-yl)-2-phenylquinoxaline-6-carboxylic Acid

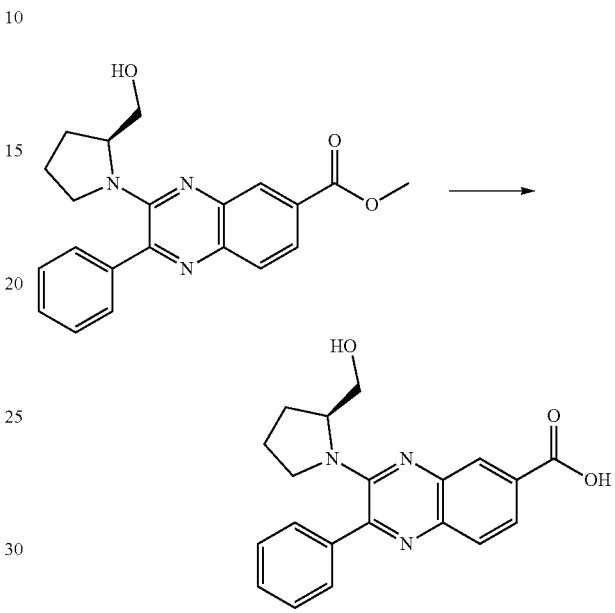

Into a 100-mL round-bottom flask, was placed a solution of (S)-methyl 3-(2-(hydroxymethyl)pyrrolidin-1-yl)-2-phenylquinoxaline-6-carboxylate (104 mg, 0.29 mmol, 1.00 equiv) and sodium hydroxide (57.3 mg, 1.43 mmol, 5.00 equiv) in methanol/H₂O (20/5 mL). The reaction was stirred for 5 h at 70° C., concentrated to dryness, dissolved in 20 mL of H₂O and washed with 10 mL EtOAc. The aqueous layer was adjusted pH to 7 with 1N HCl and extracted with DCM/MeOH (10/1, 20 mL×5). The organic layer was combined, dried over Na₂SO₄, and concentrated in vacuo. This resulted 45 mg (43%) of (S)-3-(2-(hydroxymethyl)pyrrolidin-1-yl)-2-phenylquinoxaline-6-carboxylic acid as a yellow solid.

LC-MS:(ES, m/z): 350 [M+H]⁺

$^1$H-NMR (300 MHz, DMSO, ppm): δ 8.23 (d, J=0.6 Hz, 1H), 7.93-7.86 (m, 2H), 7.80-7.77 (m, 2H), 7.55-7.48 (m, 3H), 4.75 (s, 1H), 4.34 (t, J=3 Hz, 1H), 3.73-3.64 (m, 2H), 2.97-2.91 (m, 2H), 2.01-1.96 (m, 1H), 1.89-1.75 (m, 2H), 1.58-1.53 (m, 1H).

EXAMPLE 54

3-(3-Methylmorpholino)-2-phenylquinoxaline-6-carboxylic Acid

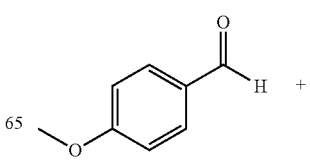

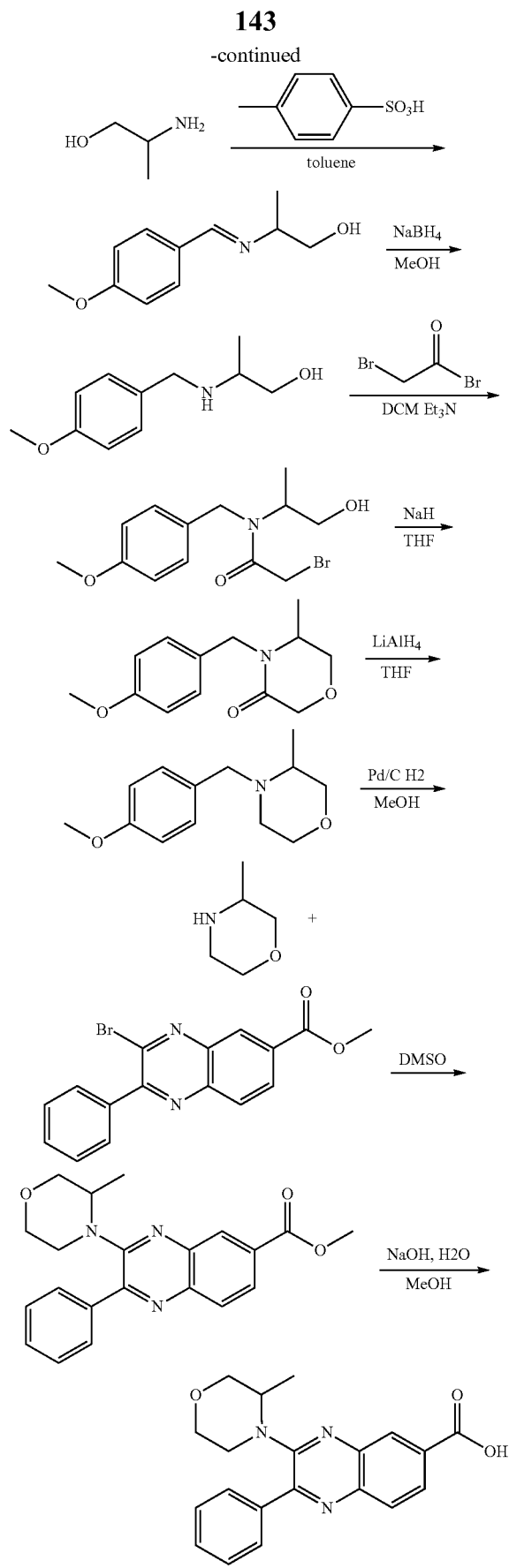

Step 1.
(E)-2-(4-methoxybenzylideneamino)propan-1-ol

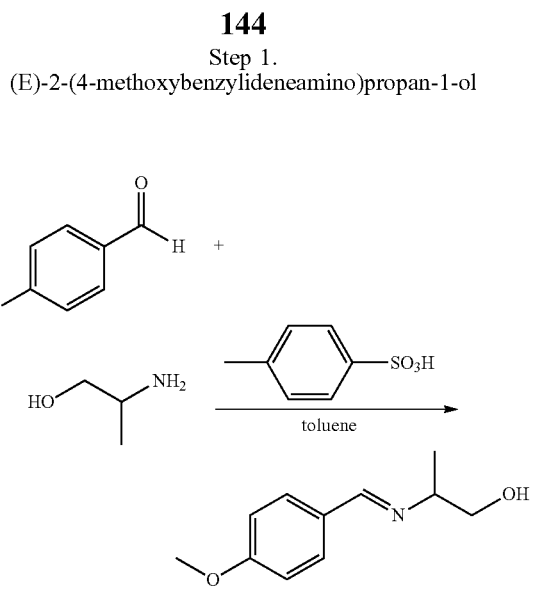

Into a 500-mL 3-necked round-bottom flask purged and maintained with an inert atmosphere of nitrogen, was placed 4-methoxybenzaldehyde (54.4 g, 400.00 mmol, 1.00 equiv), 2-aminopropan-1-ol (30 g, 400.00 mmol, 1.00 equiv), 4-methylbenzenesulfonic acid (3.84 g, 20.21 mmol, 0.05 equiv), toluene (300 mL). The resulting solution was heated to reflux for overnight in an oil bath. The resulting mixture was concentrated under vacuum. The resulting mixture was washed with 3×50 mL of hexane. The resulting solids were collected by filtration. This resulted in 63 g (82%) of (E)-2-(4-methoxybenzylideneamino)propan-1-ol as a white solid.

$^1$H-NMR (300 MHz, CDCl$_3$, ppm): δ 8.289 (s, 1H), 7.713-7.666 (m, 2H), 6.960-6.913 (m, 2H), 3.861 (s, 3H), 3.712-3.693 (d, J=5.7 Hz, 2H), 3.522-3.460 (m, 1H), 1.255-1.240 (t, J=4.5 Hz, 3H).

Step 2. 2-(4-Methoxybenzylamino)propan-1-ol

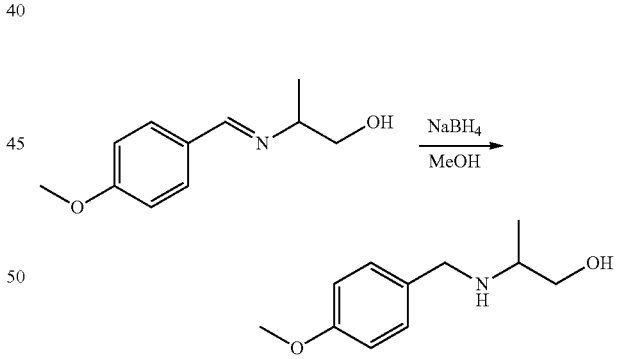

Into a 250-mL 3-necked round-bottom flask, was placed a solution of (E)-2-(4-methoxybenzylideneamino)propan-1-ol (15 g, 77.72 mmol, 1.00 equiv) in methanol (150 mL). This was followed by the addition of NaBH$_4$ (5.88 g, 155.56 mmol, 2.00 equiv) in several batches at −10-0° C. The resulting solution was stirred for 2 hs at −10-0° C. in an ice/salt bath. The resulting mixture was concentrated under vacuum and diluted with 200 mL of water. The resulting aqueous solution was extracted with 3×100 mL of ethyl acetate and the organic layers was combined and dried over anhydrous magnesium sulfate, concentrated under vacuum. This resulted in 11.1 g (73%) of 2-(4-methoxybenzylamino)propan-1-ol as a white solid.

LC-MS:(ES, m/z): 196 [M+H]+

$^1$H NMR (300 MHz, CDCl$_3$, ppm): δ 7.281-7.251 (d, J=6 Hz, 2H), 6.907-6.860 (m, 2H), 3.817 (s, 3H), 3.722-3.592 (m, 2H), 3.323-3.264 (m, 1H), 2.887-2.830 (m, 1H), 1.120-1.098 (d, J=6.6 Hz, 3H)

Step 3. N-(4-Methoxybenzyl)-2-bromo-N-(1-hydroxypropan-2-yl)acetamide

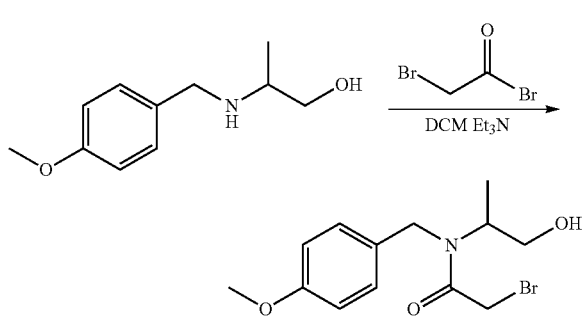

Into a 250-mL 3-necked round-bottom flask purged and maintained with an inert atmosphere of nitrogen, was placed a solution of 2-(4-methoxybenzylamino)propan-1-ol (11 g, 56.41 mmol, 1.00 equiv) in dichloromethane (100 mL). This was followed by the addition of triethylamine (5.7 g, 56.44 mmol, 1.00 equiv). To this was added a solution of 2-bromoacetyl bromide (11.4 g, 56.44 mmol, 1.00 equiv) in dichloromethane (50 mL) dropwise with stirring at −17~−25° C. The resulting solution was stirred for 1 h at −17~−25° C. in a liquid nitrogen bath. The resulting mixture was washed with 3×100 mL of water. The organic layer was dried over anhydrous magnesium sulfate and concentrated under vacuum. This resulted in 16 g (90%) of N-(4-methoxybenzyl)-2-bromo-N-(1-hydroxypropan-2-yl)acetamide as yellow oil.

LC-MS:(ES, m/z): 316 [M+H]+

Step 4. 4-(4-Methoxybenzyl)-5-methylmorpholin-3-one

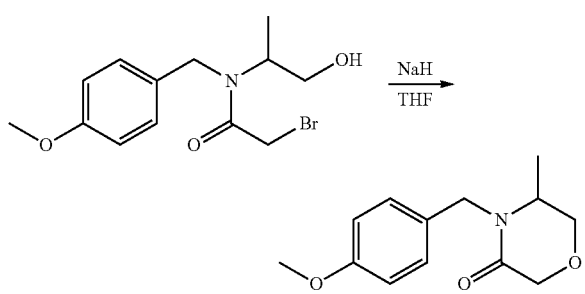

Into a 500-mL 3-necked round-bottom flask purged and maintained with an inert atmosphere of nitrogen, was placed a solution of sodium hydride (3.46 g, 100.92 mmol, 2.00 equiv, 70%) in tetrahydrofuran (200 mL). This was followed by the dropwise addition of a solution of N-(4-methoxybenzyl)-2-bromo-N-(1-hydroxypropan-2-yl)acetamide (16 g, 50.47 mmol, 1.00 equiv) in tetrahydrofuran (100 mL) with stirring at 25° C. The resulting solution was stirred overnight at 25° C. in an oil bath. The reaction was then quenched by the addition of 200 g of water/ice. The resulting solution was extracted with 5×200 mL of dichloromethane and the organic layers combined. The organic layers were washed with 3×50 mL of H$_2$O. Dried over anhydrous magnesium sulfate and concentrated under vacuum. This resulted in 11.9 g (crude) of 4-(4-methoxybenzyl)-5-methylmorpholin-3-one as yellow oil.

LC-MS:(ES, m/z): 236 [M+H]+

Step 5. 4-(4-Methoxybenzyl)-3-methylmorpholine

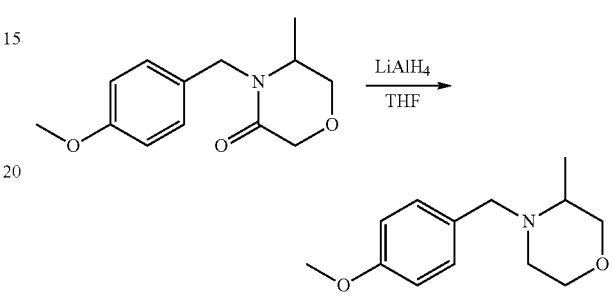

Into a 250-mL 3-necked round-bottom flask purged and maintained with an inert atmosphere of nitrogen, was placed a solution of LiAlH$_4$ (3.83 g, 100.79 mmol, 2.00 equiv) in tetrahydrofuran (100 mL). This was followed by the addition of a solution of 4-(4-methoxybenzyl)-5-methylmorpholin-3-one (11.9 g, 50.42 mmol, 1.00 equiv) in tetrahydrofuran (50 mL) dropwise with stirring at 0° C. The resulting solution was heated to reflux for 1 h in an oil bath and cooled to room temperature. The resulting solution was diluted with 100 mL of H$_2$O. The resulting solution was extracted with 3×200 mL of ethyl acetate and the organic layers combined and dried over anhydrous magnesium sulfate and concentrated under vacuum. The residue was applied onto a silica gel column with ethyl acetate/petroleum ether (1:30). This resulted in 7 g (58%) of 4-(4-methoxybenzyl)-3-methylmorpholine as yellow oil.

LC-MS:(ES, m/z): 222 [M+H]+

Step 6. 3-Methylmorpholine

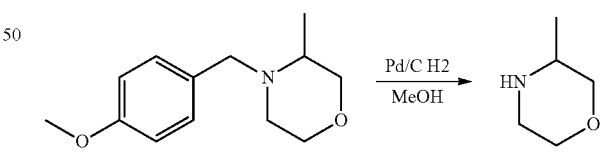

Into a 250-mL round-bottom flask purged and maintained with an inert atmosphere of nitrogen, was placed a solution of 4-(4-methoxybenzyl)-3-methylmorpholine (7 g, 31.53 mmol, 1.00 equiv) in methanol (70 mL). This was followed by the addition of Palladium carbon (10%) (2 g). Then H$_2$ (g) was introduced in. The resulting solution was stirred for overnight at 50° C. in an oil bath. The solids were filtered out. The resulting solution was concentrated under vacuum. This resulted in 2.1 g (66%) of 3-methylmorpholine as yellow oil.

LC-MS:(ES, m/z): 102 [M+H]+

Step 7. Methyl 3-(3-methylmorpholino)-2-phenylquinoxaline-6-carboxylate

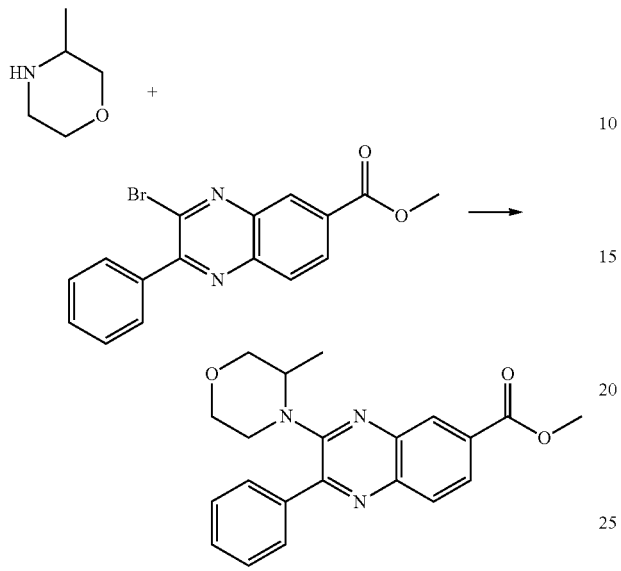

Into a 10-mL sealed tube, was placed methyl 3-bromo-2-phenylquinoxaline-6-carboxylate (150 mg, 0.44 mmol, 1.00 equiv), and 3-methylmorpholine (443 mg, 4.39 mmol, 10.00 equiv) in DMSO (1 mL). The resulting solution was stirred overnight at 100° C. in an oil bath. The resulting mixture was concentrated in vacuo. The residue was applied onto a silica gel column with ethyl acetate/petroleum ether (1:50). This resulted in 46 mg (29%) of methyl 3-(3-methylmorpholino)-2-phenylquinoxaline-6-carboxylate as a yellow solid.

LC-MS:(ES, m/z): 364 [M+H]$^+$ $^1$H-NMR (300 MHz, CDC$_3$, ppm): δ 8.615-8.609 (d, J=1.8 Hz, 1H), 8.158-7.984 (m, 4H), 7.574-7.502 (m, 3H), 4.053-3.403 (m, 10H), 1.218-1.196 (d, J=6.6 Hz, 3H).

Step 8. 3-(3-Methylmorpholino)-2-phenylquinoxaline-6-carboxylic Acid

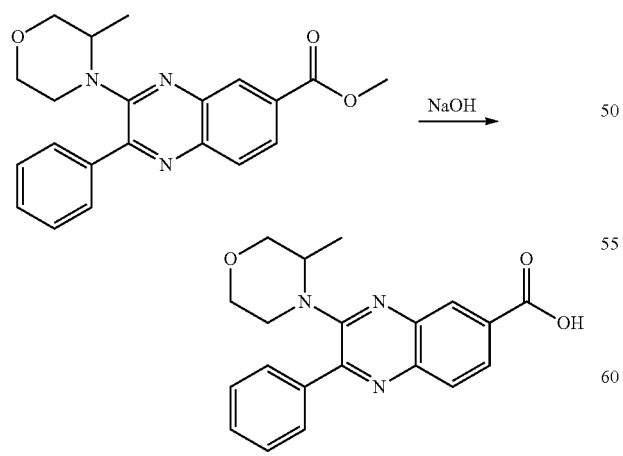

Into a 50-mL round-bottom flask, was placed a solution of methyl 3-(3-methylmorpholino)-2-phenylquinoxaline-6-carboxylate (45 mg, 0.12 mmol, 1.00 equiv) in methanol (10 mL). Then a solution of sodium hydroxide (25 mg, 0.62 mmol, 5.00 equiv) in water (2 mL) was added. The resulting solution was stirred for 2 hrs at 50° C. in an oil bath. The resulting mixture was concentrated in vacuo. The residue was diluted by 20 mL of water. The pH value of the aqueous solution was adjusted to 4-5 with aq. hydrogen chloride (1 mol/L). The resulting solids were collected by filtration.

This resulted in 40 mg (90%) of 3-(3-methylmorpholino)-2-phenylquinoxaline-6-carboxylic acid as a yellow solid.

LC-MS:(ES, m/z): 350 [M+H]$^+$ $^1$H-NMR (300 MHz, DMSO, ppm): δ 13.257 (s, 1H), 8.310 (s, 1H), 8.037-7.963 (m, 4H), 7.585-7.504 (m, 3H), 3.818-3.770 (m, 2H), 3.732-3.437 (m, 3H), 3.312-3.171 (m, 2H), 1.074-1.096 (d, J=6.6 Hz, 3H).

EXAMPLE 55

(S)-3-(2-Methylpyrrolidin-1-yl)-2-phenylquinoxaline-6-carboxylic Acid

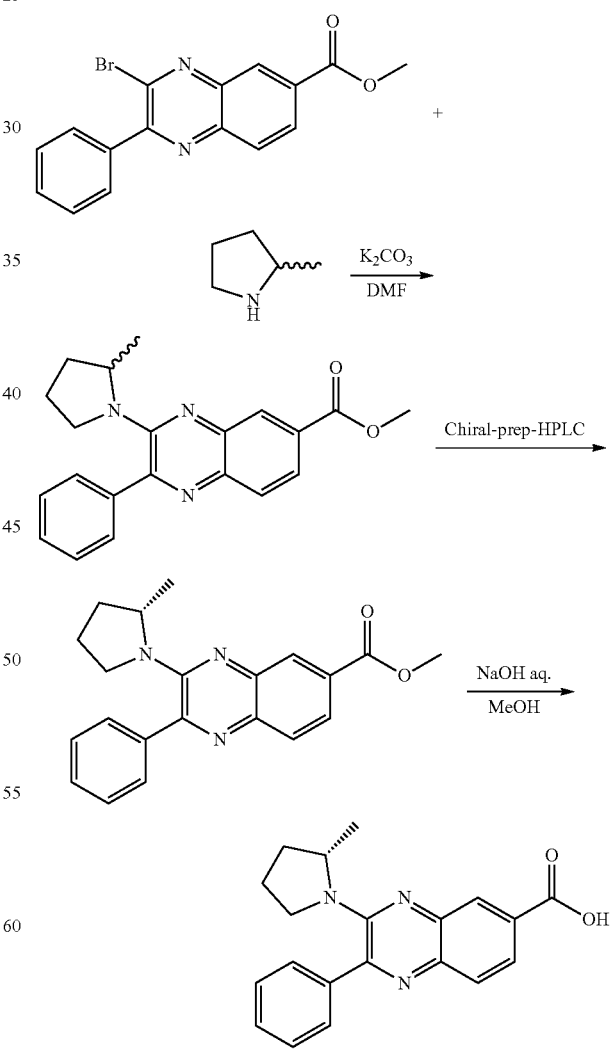

Step 1. (S)-methyl 3-(2-methylpyrrolidin-1-yl)-2-phenylquinoxaline-6-carboxylate

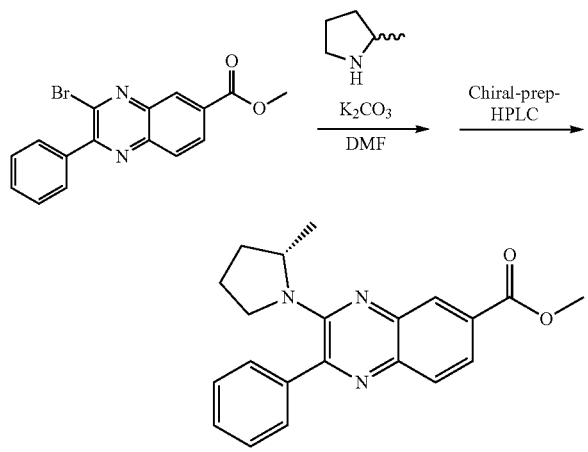

Into a 20-mL sealed tube, was placed methyl 3-bromo-2-phenylquinoxaline-6-carboxylate (500 mg, 1.67 mmol, 1.00 equiv), 2-methylpyrrolidine (285 mg, 2.92 mmol, 2.00 equiv), potassium carbonate (693.8 mg, 4.01 mmol, 3.00 equiv), N,N-dimethylformamide (6 mL). The resulting solution was stirred overnight at 100° C. in an oil bath. The reaction was then quenched by the addition of water. The resulting solution was extracted with 12×20 mL of dichloromethane and the organic layers combined and dried over anhydrous sodium sulfate and concentrated under vacuum. The residue was applied onto a silica gel column with ethyl acetate/petroleum ether (1:100). This resulted in 590.7 mg (92%) of methyl 3-(2-methylpyrrolidin-1-yl)-2-phenylquinoxaline-6-carboxylate as yellow oil. Then the isomer was sent for chiral-prep-HPLC to get the product of (S)-methyl 3-(2-methylpyrrolidin-1-yl)-2-phenylquinoxaline-6-carboxylate (193.6 mg).

LC-MS:(ES, m/z): 348 [M+H]+

$^1$H-NMR (300 MHz, CDC$_3$, ppm): δ 8.26-8.25 (d, J=1.5 Hz, 1H), 7.96-7.87 (m, 2H), 7.75-7.71 (m, 2H), 7.57-7.47 (m, 3H), 4.27-4.20 (m, 1H), 3.93 (s, 3H), 3.01-2.93 (m, 2H), 2.11 (s, 1H), 1.76-1.75 (d, J=3 Hz, 1H), 1.56-1.50 (m, 2H), 1.34-1.32 (d, J=6 Hz, 3H).

Step 2. (S)-3-(2-methylpyrrolidin-1-yl)-2-phenylquinoxaline-6-carboxylic Acid

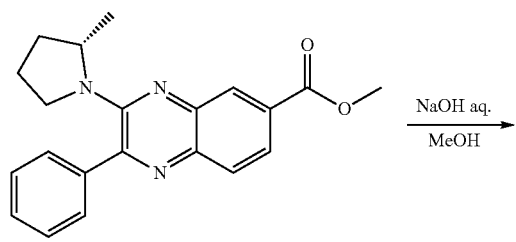

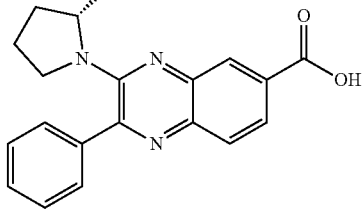

Into a 50-mL round-bottom flask, was placed a solution of (S)-methyl 3-(2-methylpyrrolidin-1-yl)-2-phenylquinoxaline-6-carboxylate (193.6 mg, 0.56 mmol, 1.00 equiv) in methanol (15 mL). A solution of sodium hydroxide (111.6 mg, 2.79 mmol, 5.00 equiv) in water (1.5 mL) was added. The resulting solution was stirred overnight at 50° C. in an oil bath and concentrated to dryness. The residue was diluted by 10 mL of water and adjusted to PH=3-4 with 1N hydrogen chloride. The resulting solid was collected by filtration. This resulted in 130 mg (69%) of (S)-3-(2-methylpyrrolidin-1-yl)-2-phenylquinoxaline-6-carboxylic acid as a yellow solid.

LC-MS (ES, m/z): 334 [M+H]+

$^1$H-NMR (300 MHz, DMSO, ppm): δ 8.25 (s, 1H), 7.94-7.87 (m, 2H), 7.75-7.73 (d, J=6 Hz, 2H), 7.56-7.49 (m, 3H), 4.27-4.21 (m, 1H), 3.02-2.94 (m, 2H), 2.12 (s, 1H), 1.75 (s, 1H), 1.56-1.51 (m, 2H), 1.34-1.32 (d, J=6 Hz, 3H).

EXAMPLE 56

(S)-3-(2-Methylpyrrolidin-1-yl)-2-phenylquinoxaline-6-carboxylic Acid

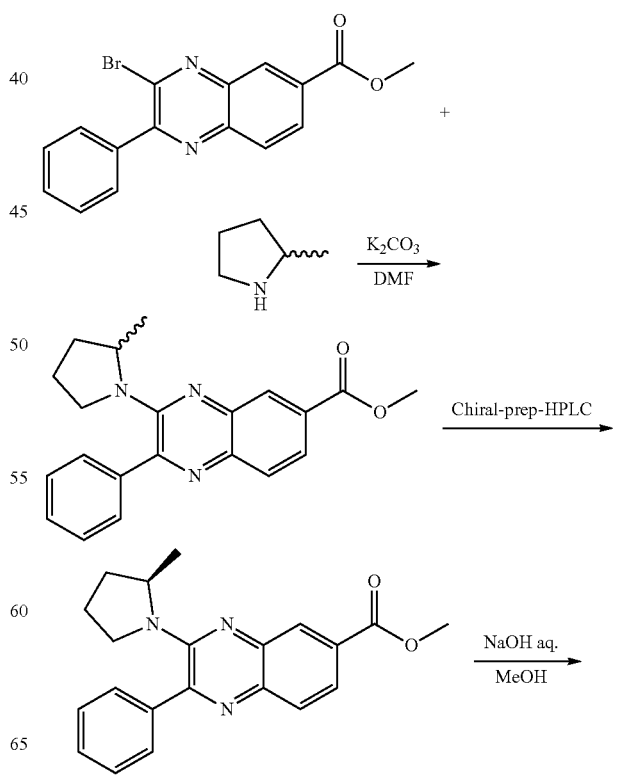

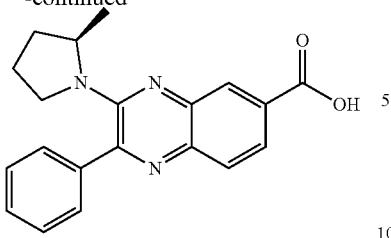

Step 1. (R)-methyl 3-(2-methylpyrrolidin-1-yl)-2-phenylquinoxaline-6-carboxylate

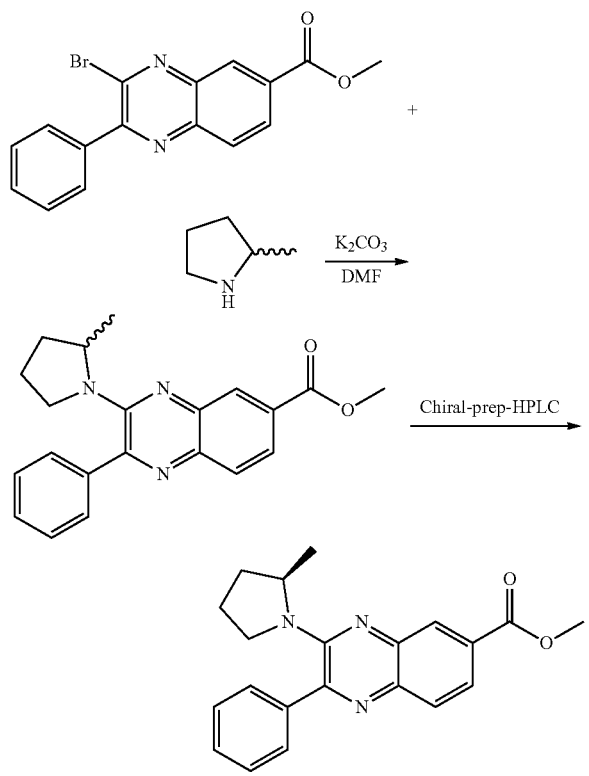

Into a 20-mL sealed tube, was placed methyl 3-bromo-2-phenylquinoxaline-6-carboxylate (500 mg, 1.67 mmol, 1.00 equiv), 2-methylpyrrolidine (285 mg, 2.92 mmol, 2.00 equiv), potassium carbonate (693.8 mg, 4.01 mmol, 3.00 equiv), N,N-dimethylformamide (6 mL). The resulting solution was stirred overnight at 100° C. in an oil bath. The reaction was then quenched by the addition of water. The resulting aqueous solution was extracted with 12×20 mL of dichloromethane and the organic layers combined and dried over anhydrous sodium sulfate and concentrated under vacuum. The residue was applied onto a silica gel column with ethyl acetate/petroleum ether (1:100). This resulted in 590.7 mg (92%) of methyl 3-(2-methylpyrrolidin-1-yl)-2-phenylquinoxaline-6-carboxylate as yellow oil. Then the isomer was sent for chiral-prep-HPLC to get the product of (R)-methyl 3-(2-methylpyrrolidin-1-yl)-2-phenylquinoxaline-6-carboxylate (178 mg).

LC-MS:(ES, m/z): 348 [M+H]+

1H-NMR (300 MHz, DMSO, ppm): δ 8.26-8.25 (d, J=3 Hz, 1H), 7.96-7.88 (m, 2H), 7.74-7.71 (m, 2H), 7.55-7.47 (m, 3H), 4.22 (s, 1H), 3.92 (s, 3H), 2.98 (m, 2H), 2.11 (s, 1H), 1.75 (s, 1H), 1.53 (m, 2H), 1.33-1.31 (d, J=6 Hz, 3H).

Step 2. (R)-3-(2-methylpyrrolidin-1-yl)-2-phenylquinoxaline-6-carboxylic Acid

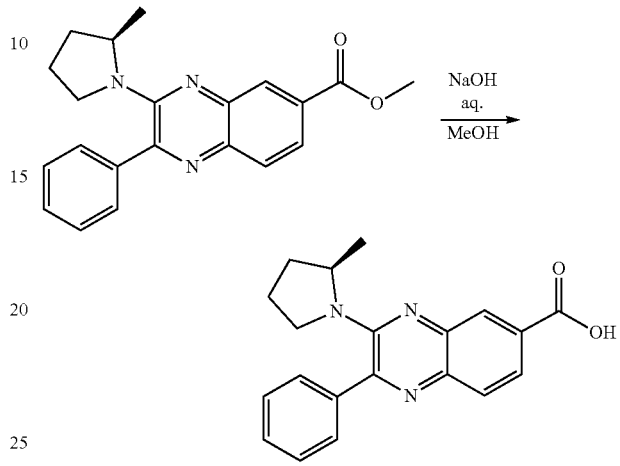

Into a 50-mL round-bottom flask, was placed a solution of (R)-methyl 3-(2-methylpyrrolidin-1-yl)-2-phenylquinoxaline-6-carboxylate (178 mg, 0.51 mmol, 1.00 equiv) in methanol (15 mL). A solution of sodium hydroxide (102.6 mg, 2.56 mmol, 5.00 equiv) in water (1.5 mL) was added. The resulting solution was stirred overnight at 50° C. in an oil bath and concentrated to dryness. The residue and diluted by 10 ml of water and pH value of the aqueous solution was adjusted to pH=3-4 with 1N hydrogen chloride. The resulting solid was collected by filtration as product. This resulted in 130 mg (75%) of (R)-3-(2-methylpyrrolidin-1-yl)-2-phenylquinoxaline-6-carboxylic acid as a yellow solid.

LC-MS:(ES, m/z): 334 [M+H]+

1H-NMR (300 MHz, DMSO, ppm): δ 8.25 (s, 1H), 7.94-7.87 (m, 2H), 7.75-7.73 (d, J=6 Hz, 2H), 7.56-7.49 (m, 3H), 4.25-4.23 (d, J=6 Hz, 1H), 3.02-2.94 (m, 2H), 2.12 (s, 1H), 1.75 (s, 1H), 1.54 (s, 2H), 1.34-1.32 (d, J=6 Hz, 3H).

EXAMPLE 57

2-(4-Fluorophenyl)-3-(isopropyl(methyl)amino)quinoxaline-6-carboxylic Acid

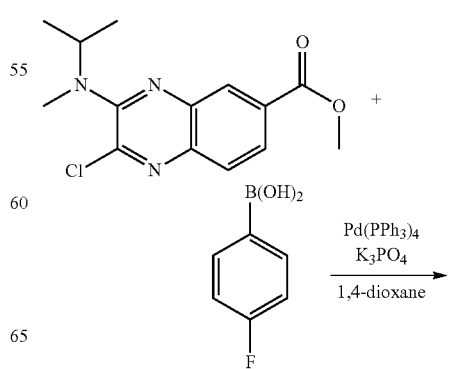

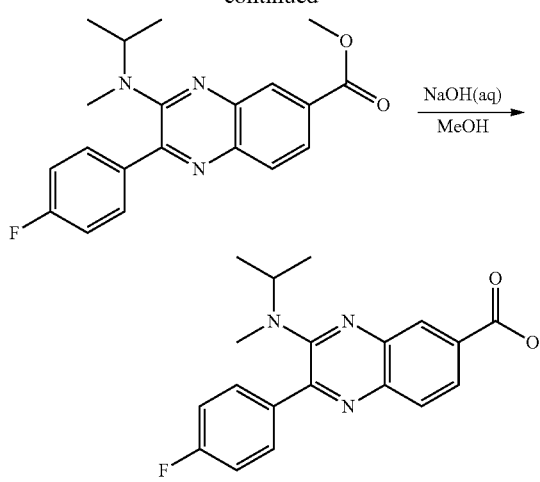

Step 1. Methyl 2-(4-fluorophenyl)-3-(isopropyl(methyl) amino)quinoxaline-6-carboxylate Into a 10-mL sealed tube, was placed methyl 2-chloro-3-(isopropyl(methyl)amino)quinoxaline-6-carboxylate (40 mg, 0.14 mmol, 1.00 equiv), 4-fluorophenylboronic acid (57.4 mg, 0.41 mmol, 3.00 equiv), Pd(PPh$_3$)$_4$ (31.4 mg, 0.03 mmol, 0.20 equiv), K$_3$PO$_4$ (116 mg, 0.55 mmol, 4.00 equiv), 1,4-dioxane (3 mL). The resulting solution was stirred for overnight at 110° C. in an oil bath. The solids were filtered out. The filtrate was concentrated under vacuum. The residue was purified by prep-TLC with ethyl acetate/petroleum ether (1:8). This resulted in 42 mg (87%) of methyl 2-(4-fluorophenyl)-3-(isopropyl(methyl)amino)quinoxaline-6-carboxylate as a yellow solid.

LC-MS:(ES, m/z): 354 [M+H]$^+$ $^1$H-NMR (300 MHz, CDC$_3$, ppm): δ 8.600-8.595 (d, J=1.5 Hz, 1H), 8.094-7.903 (m, 4H), 7.281-7.180 (m, 2H), 4.295-4.251 (m, 1H), 4.006 (s, 3H), 2.779 (s, 3H), 1.127-1.105 (d, J=6.6 Hz, 6H).

Step 2. 2-(4-fluorophenyl)-3-(isopropyl(methyl) amino)quinoxaline-6-carboxylic Acid Into a 50-mL round-bottom flask, was placed a solution of methyl 2-(4-fluorophenyl)-3-(isopropyl(methyl)amino)quinoxaline-6-carboxylate (40 mg, 0.11 mmol, 1.00 equiv) in methanol (10 mL). Then a solution of sodium hydroxide (22.67 mg, 0.57 mmol, 5.00 equiv) in water (1 mL) was added. The resulting solution was stirred for 5 h at 50° C. in an oil bath. The resulting mixture was concentrated under vacuum. The reaction was then quenched by the addition of 20 mL of water. The pH value of the aqueous solution was adjusted to 4-5 with aq. hydrogen chloride (1 mol/L). The resulting solids were collected by filtration. This resulted in 30 mg (76%) of 2-(4-fluorophenyl)-3-(isopropyl(methyl) amino)quinoxaline-6-carboxylic acid as a yellow solid.

LC-MS:(ES, m/z): 340 [M+H]$^+$ $^1$H-NMR (300 MHz, DMSO, ppm): δ 13.192 (s, 1H), 8.264 (s, 1H), 7.946-7.897 (m, 4H), 7.404-7.346 (m, 2H), 4.189-4.146 (m, 1H), 2.671 (s, 3H), 1.053-1.032 (d, J=6.3 Hz, 6H).

EXAMPLE 58

3-(Isopropyl(methyl)amino)-2-(4-methoxyphenyl) quinoxaline-6-carboxylic Acid

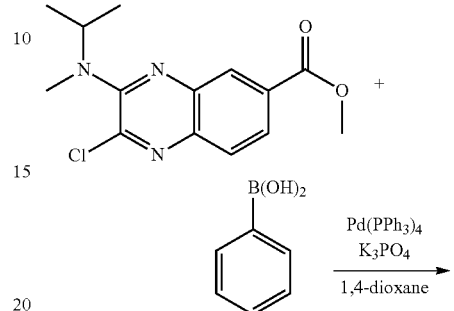

Step 1. Methyl 3-(isopropyl(methyl)amino)-2-(4-methoxyphenyl)quinoxaline-6-carboxylate

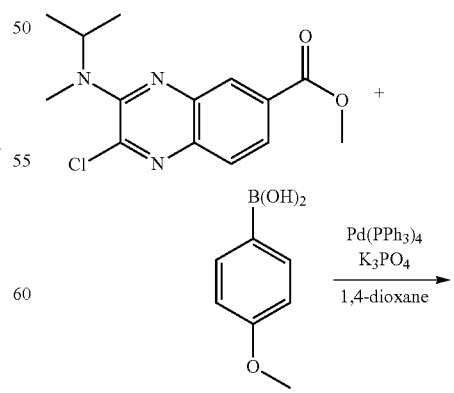

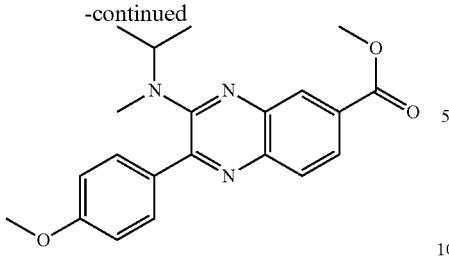

Into a 10-mL sealed tube, was placed methyl 2-chloro-3-(isopropyl(methyl)amino)quinoxaline-6-carboxylate (40 mg, 0.14 mmol, 1.00 equiv), 4-methoxyphenylboronic acid (62.6 mg, 0.41 mmol, 3.00 equiv), Pd(PPh₃)₄ (31.4 mg, 0.03 mmol, 0.20 equiv), K₃PO₄ (116 mg, 0.55 mmol, 4.00 equiv), 1,4-dioxane (3 mL). The resulting solution was stirred for overnight at 110° C. in an oil bath. The solids were filtered out. The filtrate was concentrated under vacuum. The residue was purified by prep-TLC with ethyl acetate/petroleum ether (1:8). This resulted in 40 mg (80%) of methyl 3-(isopropyl(methyl)amino)-2-(4-methoxyphenyl)quinoxaline-6-carboxylate as a yellow solid.

LC-MS:(ES, m/z): 366 [M+H]⁺

Step 2. 3-(isopropyl(methyl)amino)-2-(4-methoxyphenyl)quinoxaline-6-carboxylic Acid

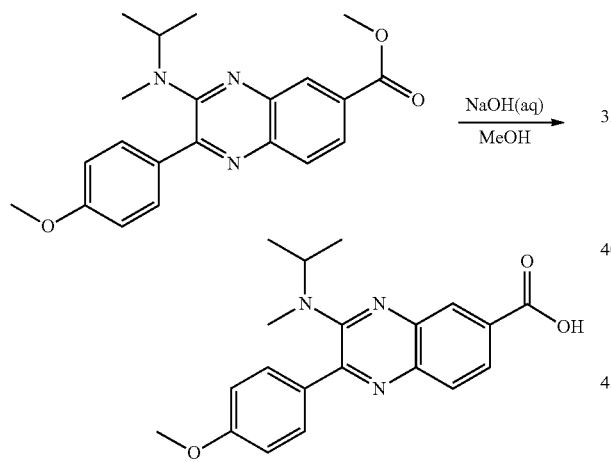

Into a 50-mL round-bottom flask, was placed a solution of methyl 3-(isopropyl(methyl)amino)-2-(4-methoxyphenyl)quinoxaline-6-carboxylate (40 mg, 0.11 mmol, 1.00 equiv) in methanol (10 mL). Then a solution of sodium hydroxide (21.9 mg, 0.55 mmol, 5.00 equiv) in water (1 mL) was added. The resulting solution was stirred for 5 hrs at 50° C. in an oil bath. The resulting mixture was concentrated under vacuum. The reaction was then quenched by the addition of 20 mL of water. The pH value of the aqueous solution was adjusted to 4-5 with aq. 1N hydrogen chloride. The resulting solids were collected by filtration. This resulted in 25 mg (65%) of 3-(isopropyl(methyl)amino)-2-(4-methoxyphenyl)quinoxaline-6-carboxylic acid as a yellow solid.

LC-MS:(ES, m/z): 352 [M+H]⁺

¹H-NMR (300 MHz, DMSO, ppm): δ 13.141 (s, 1H), 8.243 (s, 1H), 7.955-7.840 (m, 4H), 7.105-7.076 (d, J=8.7 Hz, 2H), 4.237-4.194 (m, 1H), 3.842 (s, 3H), 2.683 (s, 3H), 1.059-1.037 (d, J=6.6 Hz, 6H).

EXAMPLE 59

(R)-3-(Methyl(1-phenylethyl)amino)-2-phenylquinoxaline-6-carboxylic Acid

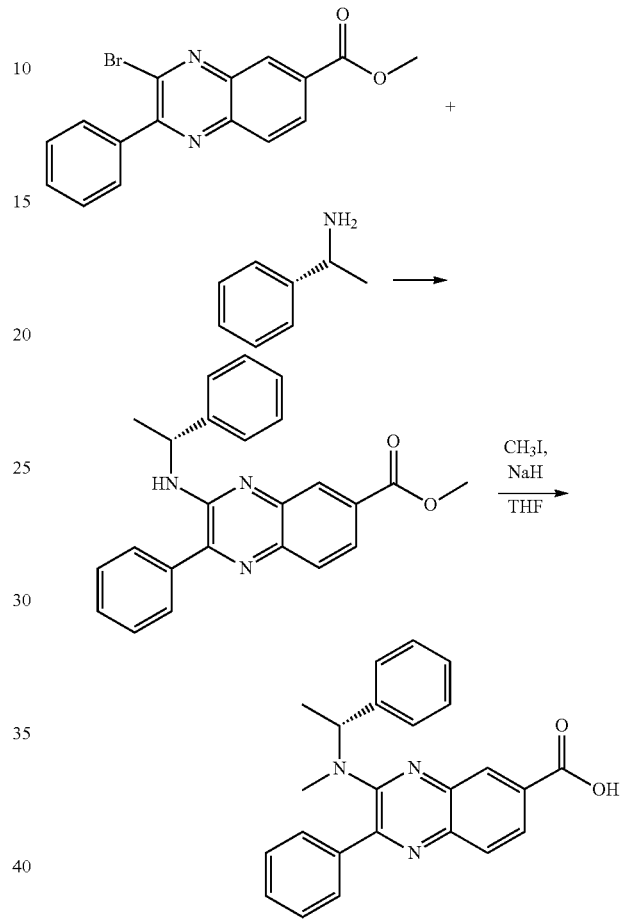

Step 1. (R)-methyl 2-phenyl-3-(1-phenylethylamino)quinoxaline-6-carboxylate

Into a 8-mL pressure tank reactor, was placed methyl 3-bromo-2-phenylquinoxaline-6-carboxylate (150 mg, 0.44 mmol, 1.00 equiv), (R)-1-phenylethanamine (4 mL). The resulting solution was stirred overnight at 100° C. in an oil bath. The residue was applied onto a silica gel column with ethyl acetate/petroleum ether (1:5). This resulted in 144 mg (81%) of (R)-methyl 2-phenyl-3-(1-phenylethylamino)quinoxaline-6-carboxylate as a yellow solid.

LC-MS:(ES, m/z): 384 [M+H]⁺

¹H-NMR (300 MHz, CDC₃, ppm): δ 8.56 (s, 1H), 8.51 (s, 1H), 8.50-4.25 (m, 12H), 5.60-5.59 (d, J=3 Hz, 2H), 4.00 (s, 3H), 1.62-1.60 (t, J=3 Hz, 3H).

Step 2. (R)-3-(methyl(1-phenylethyl)amino)-2-phenylquinoxaline-6-carboxylic Acid Into a 50-mL round-bottom flask purged and maintained with an inert atmosphere of nitrogen, was placed a solution of (R)-methyl 2-phenyl-3-(1-phenylethylamino)quinoxaline-6-carboxylate (141 mg, 0.37 mmol, 1.00 equiv) in THF (20 mL), sodium hydride (294.5 mg, 7.36 mmol, 20.00 equiv, 60%). The resulting solution was stirred for 1 h at room temperature in an ice/salt bath. This was followed by the addition of a solution of CH$_3$I (522.8 mg, 3.68 mmol, 10.00 equiv) in THF (1 mL) dropwise with stirring at 0° C. The resulting solution was stirred overnight at 20° C. The pH value of the solution was adjusted to 3-4 with 1N aqueous hydrogen chloride. The resulting mixture was concentrated under vacuum. The residue was applied onto a silica gel column with dichloromethane/methanol (10:1). This resulted in 57 mg (39%) of (R)-3-(methyl(1-phenylethyl)amino)-2-phenylquinoxaline-6-carboxylic acid as a yellow solid.

LC-MS:(ES, m/z): 384 [M+H]$^+$ $^1$H-NMR (300 MHz, DMSO, ppm): δ 8.24 (s, 1H), 8.01-7.99 (d, J=3 Hz, 1H), 7.91-7.83 (m, 3H), 7.54-7.47 (m, 3H), 7.36-7.22 (m, 5H), 5.45-5.42 (d, J=9 Hz, 1H), 2.50-2.46 (d, J=12 Hz, 3H), 1.48-1.46 (d, J=6 Hz, 3H).

EXAMPLE 60

(S)-3-(Methyl(1-phenylethyl)amino)-2-phenylquinoxaline-6-carboxylic Acid

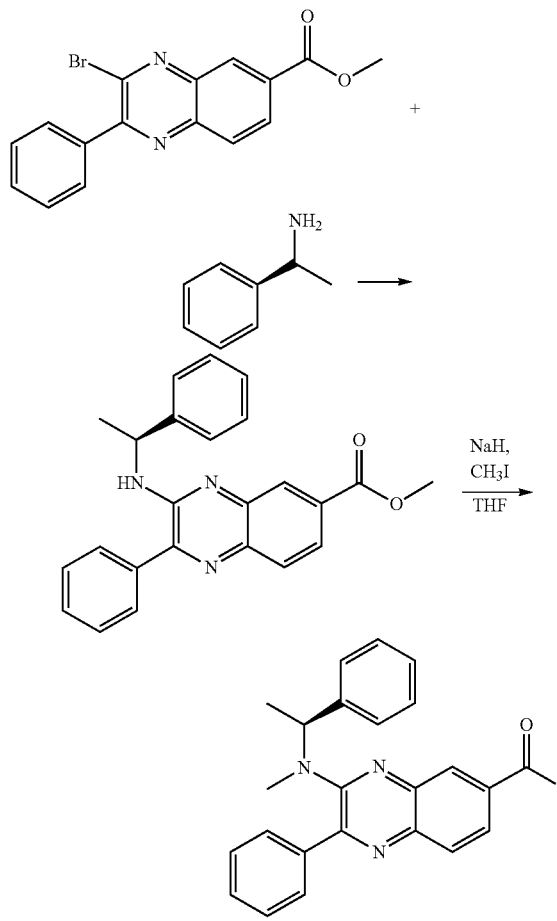

Step 1. (S)-methyl 2-phenyl-3-(1-phenylethylamino)quinoxaline-6-carboxylate

Into a 8-mL pressure tank reactor, was placed methyl 3-bromo-2-phenylquinoxaline-6-carboxylate (150 mg, 0.44 mmol, 1.00 equiv), (S)-1-phenylethanamine (4 mL). The resulting solution was stirred overnight at 100° C. in an oil bath. The residue was applied onto a silica gel column with ethyl acetate/petroleum ether (1:50). This resulted in 78 mg (46%) of (S)-methyl 2-phenyl-3-(1-phenylethylamino)quinoxaline-6-carboxylate as a yellow oil.

LC-MS:(ES, m/z): 384 [M+H]$^+$ $^1$H-NMR (300 MHz, CDC$_3$, ppm): δ 8.43-8.42 (d, J=3 Hz, 1H), 8.02-7.92 (m, 2H), 7.78-7.75 (m, 2H), 7.63-7.56 (m, 3H), 7.43-7.25 (m, 6H), 5.52-5.51 (t, J=3 Hz, 2H), 4.00 (s, 3H), 1.62-1.56 (m, 4H).

Step 2. (S)-3-(methyl(1-phenylethyl)amino)-2-phenylquinoxaline-6-carboxylic Acid Into a 50-mL round-bottom flask purged and maintained with an inert atmosphere of nitrogen, was placed a solution of (S)-methyl 2-phenyl-3-(1-phenylethylamino)quinoxaline-6-carboxylate (110 mg, 0.29 mmol, 1.00 equiv) in THF (9 mL), sodium hydride (137.9 mg, 5.74 mmol, 20.00 equiv, 60%). The resulting solution was stirred for 1 h at room temperature in an ice/salt bath. This was followed by the addition of a solution of CH$_3$I (407.8 mg, 2.87 mmol, 10.00 equiv) THF (1 mL) dropwise with stirring at 0° C. The resulting solution was stirred for overnight at 20° C. in an ice/salt bath. The pH value of the solution was adjusted to 3-4 with 1N hydrogen chloride. The resulting mixture was concentrated under vacuum. The residue was applied onto a silica gel column with dichloromethane/methanol (10:1). This resulted in 40 mg (36%) of (S)-3-(methyl(1-phenylethyl)amino)-2-phenylquinoxaline-6-carboxylic acid as a yellow solid.

LC-MS:(ES, m/z): 384 [M+H]$^+$ $^1$H-NMR (300 MHz, DMSO, ppm): δ 8.26 (s, 1H), 8.02-7.95 (m, 2H), 7.89-7.85 (m, 2H), 7.57-7.50 (m, 3H), 7.34-7.25 (m, 5H), 5.55-5.48 (m, 1H), 2.51-2.48 (d, J=6 Hz, 3H), 1.51-1.49 (d, J=6 Hz, 3H).

EXAMPLE 61

(R)-3-(sec-Butyl(methyl)amino)-2-phenylquinoxaline-6-carboxylic Acid

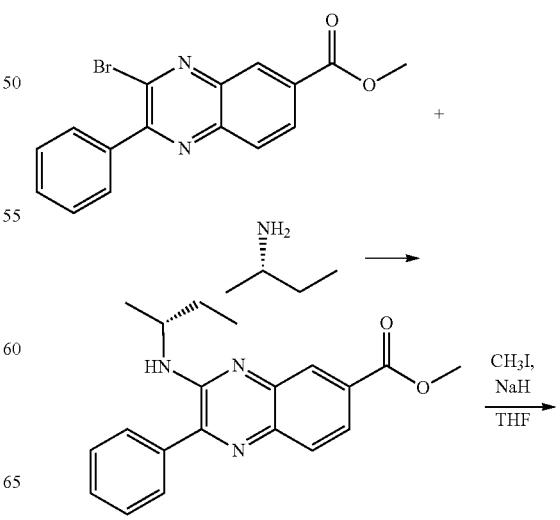

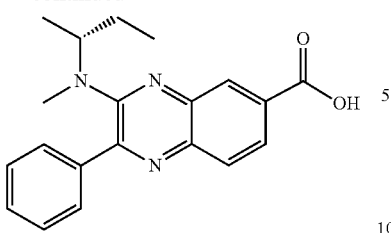

Step 1. (R)-methyl 3-(sec-butylamino)-2-phenylquinoxaline-6-carboxylate

Into a 8-mL sealed tube, was placed methyl 3-bromo-2-phenylquinoxaline-6-carboxylate (150 mg, 0.439 mmol, 1.00 equiv), (S)-butan-2-amine (2 mL), DMSO (1 mL). The resulting solution was stirred overnight at 60° C. in an oil bath. The resulting mixture was concentrated under vacuum and diluted with H$_2$O. The resulting solids were collected by filtration. The residue was applied onto a silica gel column with PE/EA (50:1). This resulted in 114 mg of (R)-methyl 3-(sec-butylamino)-2-phenylquinoxaline-6-carboxylate as yellow oil.

LC-MS:(ES, m/z): 336 [M+H]$^+$ $^1$H-NMR (300 MHz, CDC$_3$, ppm): δ 8.49 (s, 1H), 8.01-7.95 (m, 2H), 7.75-7.72 (m, 2H), 7.63-7.54 (m, 3H), 5.09-5.07 (d, J=6 Hz, 1H), 4.40-4.31 (m, 1H), 4.00 (s, 3H), 1.66-1.57 (m, 2H), 1.26-1.24 (d, J=6 Hz, 3H), 1.00-0.95 (t, J=7.2 Hz, 3H).

Step 2. (R)-3-(sec-butyl(methyl)amino)-2-phenylquinoxaline-6-carboxylic Acid

Into a 50-mL round-bottom flask purged and maintained with an inert atmosphere of nitrogen, was placed a solution of (R)-methyl 3-(sec-butylamino)-2-phenylquinoxaline-6-carboxylate (110 mg, 0.33 mmol, 1.00 equiv) in tetrahydrofuran (9 mL). sodium hydride (132 mg, 3.3 mmol, 10.00 equiv, 60%) was added. The resulting solution was stirred for 1 h at room temperature. This was followed by the dropwise addition of a solution of CH$_3$I (922.5 mg, 6.50 mmol, 20.00 equiv) in tetrahydrofuran (2 mL) with stirring at 0° C. The resulting solution was stirred for overnight at 20° C. The resulting mixture was concentrated under vacuum and diluted by 10 ml of H$_2$O. The pH value of the aqueous solution was adjusted to 3-4 with 1N hydrogen chloride. The resulting solid was collected by filtration. This resulted solid in 67 mg (59%) of (R)-3-(sec-butyl(methyl)amino)-2-phenylquinoxaline-6-carboxylic acid as a yellow solid.

LC-MS:(ES, m/z): 336 [M+H]$^+$ $^1$H-NMR (300 MHz, DMSO, ppm): δ 8.26 (s, 1H), 7.94 (s, 2H), 7.82-7.80 (t, J=1.8 Hz, 2H), 7.59-7.49 (m, 3H), 3.99-3.92 (m, 1H), 2.68 (s, 3H), 2.59-1.35 (m, 2H), 1.03-1.01 (d, J=6 Hz, 3H), 0.66-0.61 (t, J=6 Hz, 3H).

EXAMPLE 62

3-(1H-Indol-1-yl)-2-phenylquinoxaline-6-carboxylic Acid

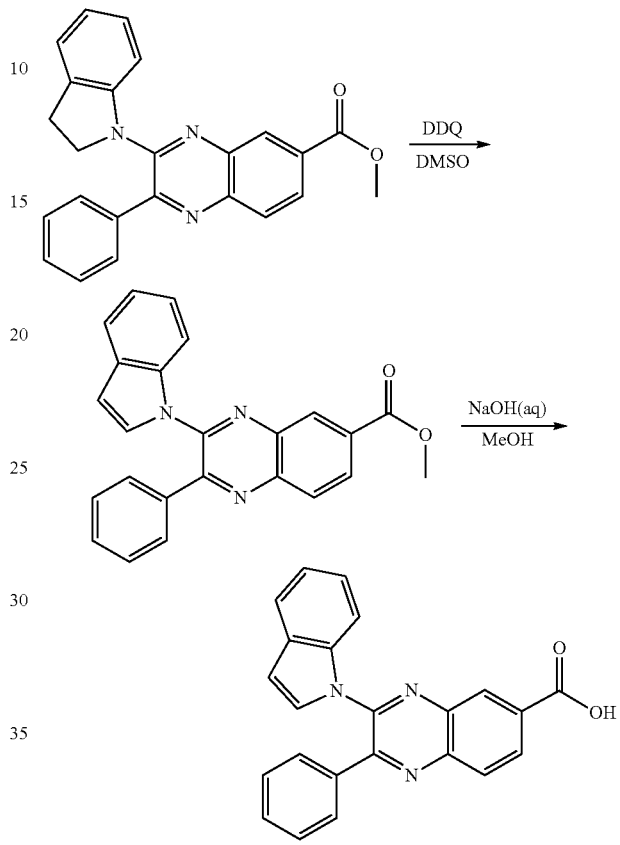

Step 1. Methyl 3-(1H-indol-1-yl)-2-phenylquinoxaline-6-carboxylate

Into a 10-mL sealed tube, was placed methyl 3-(indolin-1-yl)-2-phenylquinoxaline-6-carboxylate (150 mg, 0.39 mmol, 1.00 equiv), DDQ (447 mg, 1.97 mmol, 4.00 equiv), DMSO (3 mL). The resulting solution was stirred for overnight at 30° C. in an oil bath. The resulting solution was diluted with 20 mL of H$_2$O. The resulting solids were collected by filtration and applied onto a silica gel column with ethyl acetate/petroleum ether (1:50). This resulted in 30 mg (20%) of methyl 3-(1H-indol-1-yl)-2-phenylquinoxaline-6-carboxylate as a yellow solid.

LC-MS:(ES, m/z): 380 [M+H]$^+$

Step 2. 3-(1H-Indol-1-yl)-2-phenylquinoxaline-6-carboxylic Acid

Into a 50-mL round-bottom flask, was placed a solution of methyl 3-(1H-indol-1-yl)-2-phenylquinoxaline-6-carboxylate (40 mg, 0.11 mmol, 1.00 equiv) in methanol (10 mL). A solution of sodium hydroxide (21.1 mg, 0.53 mmol, 5.00 equiv) in H$_2$O (2 mL) was added. The resulting solution was stirred for 2 hrs at 50° C. in an oil bath. The resulting mixture was concentrated in vacuo. The resulting solution was diluted with 20 mL of H₂O. The pH value of the aqueous solution was adjusted to 4-5 with aq. 1N hydrogen chloride. The resulting solids were collected by filtration. The crude product (50 mL) was further purified by Flash-Prep-HPLC with the following conditions (IntelFlash-1): Column, silica gel; mobile phase, H₂O/CH₃CN=100:1 increasing to H₂O/CH₃CN=100:60 within 40 min; Detector, UV 254 nm. This resulted in 15 mg (38%) of 3-(1H-indol-1-yl)-2-phenylquinoxaline-6-carboxylic acid as a yellow solid.

LC-MS:(ES, m/z): 366 [M+H]⁺

¹H-NMR (300 MHz, DMSO, ppm): δ 8.442-8.351 (m, 2H), 8.088-8.059 (m, 1H), 7.658-7.599 (m, 2H), 7.429-7.272 (m, 8H), 7.176-7.102 (m, 2H), 6.601-6.591 (d, J=3 Hz, 1H).

EXAMPLE 63

2-(3,4-Difluorophenyl)-3-(isopropyl(methyl)amino)quinoxaline-6-carboxylic Acid

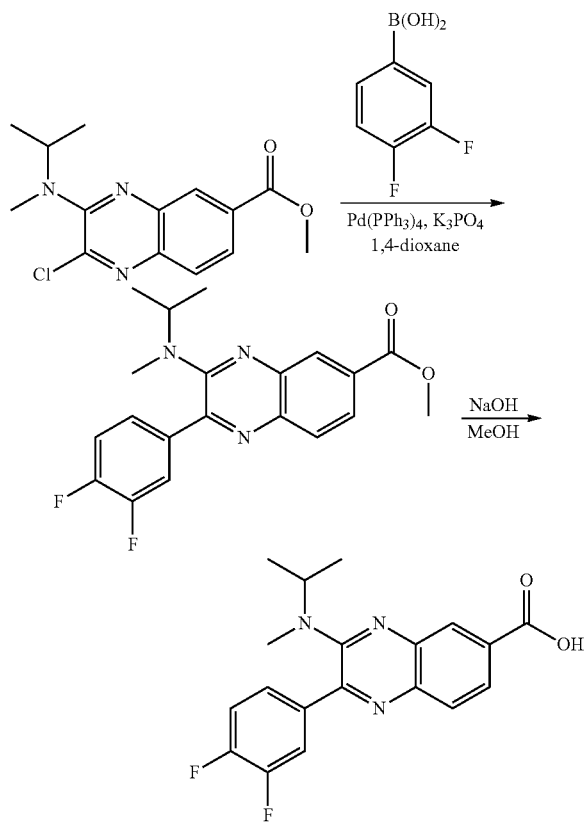

Step 1. Methyl 2-(3,4-difluorophenyl)-3-(isopropyl(methyl)amino)quinoxaline-6-carboxylate Into a 10-mL sealed tube, was placed methyl 2-chloro-3-(isopropyl(methyl)amino)quinoxaline-6-carboxylate (150 mg, 0.51 mmol, 1.00 equiv), 3,4-difluorophenylboronic acid (241 mg, 1.54 mmol, 3.00 equiv), Pd(PPh₃)₄ (118 mg, 0.10 mmol, 0.20 equiv), K₃PO₄ (433 mg, 2.05 mmol, 4.00 equiv), 1,4-dioxane (5 mL). The resulting solution was stirred for overnight at 100° C. in an oil bath. The resulting mixture was concentrated under vacuum. The residue was applied onto a silica gel column with ethyl acetate/petroleum ether (1:30). This resulted in 100 mg (53%) of methyl 2-(3,4-difluorophenyl)-3-(isopropyl(methyl)amino)quinoxaline-6-carboxylate as a yellow solid.

LC-MS:(ES, m/z): 372 [M+H]⁺

Step 2. 2-(3,4-Difluorophenyl)-3-(isopropyl(methyl)amino)quinoxaline-6-carboxylic Acid Into a 50-mL round-bottom flask, was placed a solution of methyl 2-(3,4-difluorophenyl)-3-(isopropyl(methyl)amino)quinoxaline-6-carboxylate (90 mg, 0.24 mmol, 1.00 equiv) in methanol (15 mL). A solution of sodium hydroxide (49 mg, 1.23 mmol, 5.05 equiv) in H₂O (2 mL) was added. The resulting solution was stirred for 2 hrs at 50° C. in an oil bath. The resulting mixture was concentrated under vacuum. The resulting solution was diluted with 20 mL of H₂O. The pH value of the solution was adjusted to 4-5 with aq. hydrogen chloride (1 mol/L). The resulting solids were collected by filtration. The crude product (90 mg) was purified by Prep-HPLC with the following conditions (1 #-Waters 2767-1): Column, SunFire Prep C18, Sum, 19*150 mm; mobile phase, water with 0.05% TFA and CH₃CN (60% CH3CN up to 90% in 8 min, up to 100% in 1.5 min); Detector, UV 220 254 nm. This resulted in 25 mg (28%) of 2-(3,4-difluorophenyl)-3-(isopropyl(methyl)amino)quinoxaline-6-carboxylic acid as a yellow solid.

LC-MS:(ES, m/z): 358 [M+H]⁺

¹H-NMR (300 MHz, DMSO, ppm): δ 13.194 (s, 1H), 8.266 (s, 1H), 7.960-7.918 (m, 3H), 7.717-7.704 (d, J=3.9 Hz, 1H), 7.630-7.595 (m, 1H), 4.173-4.129 (m, 1H), 2.677 (s, 3H), 1.064-1.042 (d, J=6.6 Hz, 6H).

EXAMPLE 64

2-(4-Chlorophenyl)-3-(isopropyl(methyl)amino)quinoxaline-6-carboxylic Acid

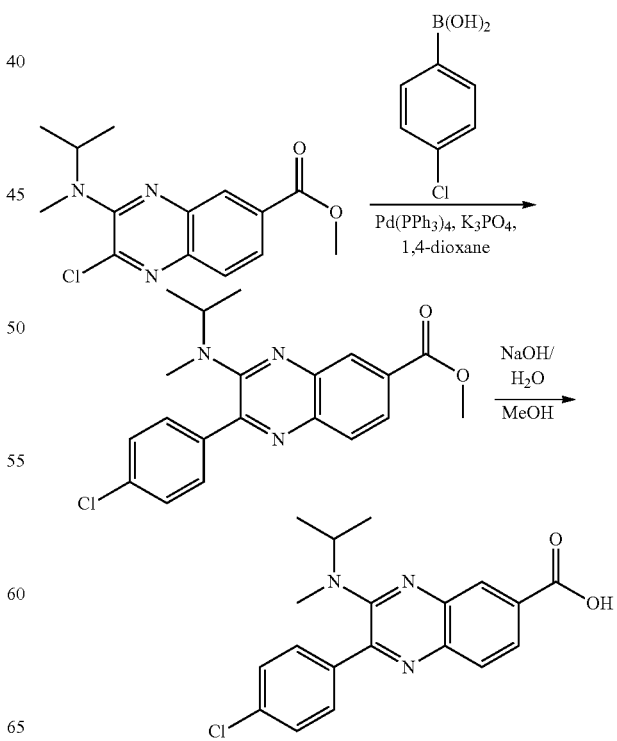

Step 1. Methyl 2-(4-chlorophenyl)-3-(isopropyl (methyl)amino)quinoxaline-6-carboxylate Into a 10-mL sealed tube, was placed methyl 2-chloro-3-(isopropyl(methyl)amino)quinoxaline-6-carboxylate (200 mg, 0.68 mmol, 1.00 equiv), 4-chlorophenylboronic acid (162 mg, 1.03 mmol, 3.00 equiv), Pd(PPh$_3$)$_4$ (157 mg, 0.14 mmol, 0.20 equiv), K$_3$PO$_4$ (578 mg, 2.74 mmol, 4.00 equiv), 1,4-dioxane (5 mL). The resulting solution was stirred for overnight at 100° C. in an oil bath. The resulting mixture was concentrated under vacuum. The residue was applied onto a silica gel column with ethyl acetate/petroleum ether (1:30). This resulted in 50 mg (20%) of methyl 2-(4-chlorophenyl)-3-(isopropyl(methyl)amino)quinoxaline-6-carboxylate as a yellow solid.

LC-MS:(ES, m/z): 370 [M+H]$^+$

Step 2. 2-(4-Chlorophenyl)-3-(isopropyl(methyl) amino)quinoxaline-6-carboxylic Acid

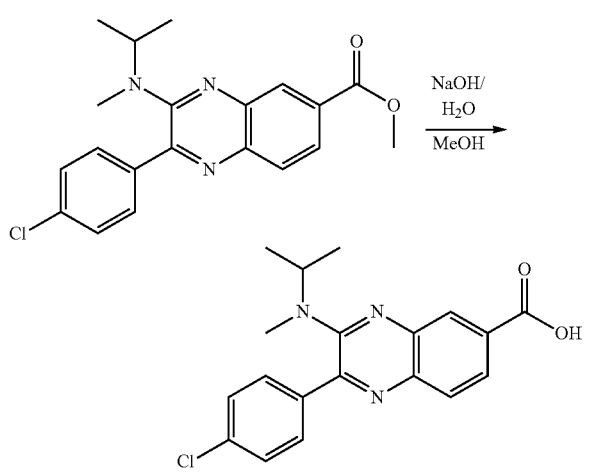

Into a 50-mL round-bottom flask, was placed a solution of methyl 2-(4-chlorophenyl)-3-(isopropyl(methyl)amino)quinoxaline-6-carboxylate (98 mg, 0.27 mmol, 1.00 equiv) in methanol (15 mL), a solution of sodium hydroxide (53 mg, 1.32 mmol, 5.00 equiv) in water (2 mL). The resulting solution was stirred for 2 h at 50° C. in an oil bath. The resulting mixture was concentrated under vacuum. The resulting solution was diluted with 20 mL of water. The pH value of the aqueous solution was adjusted to 4-5 with aq. hydrogen chloride (1 mol/L). The resulting solids were collected by filtration. The crude product (80 mg) was purified by Prep-HPLC with the following conditions (1#-Waters 2767-1): Column, SunFire Prep C18, 5um, 19*150 mm; mobile phase, water with 0.05% TFA and CH$_3$CN (60% CH$_3$CN up to 90% in 8 min, up to 100% in 1.5 min); Detector, UV 220 254 nm. This resulted in 25 mg (25%) of 2-(4-chlorophenyl)-3-(isopropyl(methyl)amino)quinoxaline-6-carboxylic acid as a yellow solid.

LC-MS:(ES, m/z): 356 [M+H]$^+$ $^1$H NMR (300 MHz, DMSO, ppm): δ 8.265 (s, 1H), 7.953-7.950 (d, J=0.9 Hz, 2H), 7.907-7.878 (m, 2H), 7.626-7.597 (m, 2H), 4.220-4.134 (m, 1H), 2.671 (s, 3H), 1.062-1.040 (d, J=6.6 Hz, 6H).

EXAMPLE 65

(R)-2-Phenyl-3-(2-(trifluoromethyl)pyrrolidin-1-yl) quinoxaline-6-carboxylic Acid

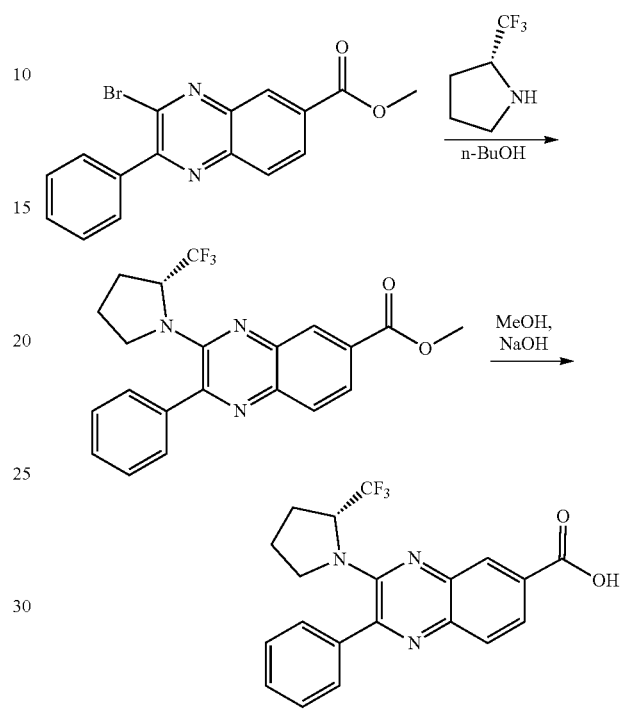

Step 1. (R)-methyl 2-phenyl-3-(2-(trifluoromethyl) pyrrolidin-1-yl)quinoxaline-6-carboxylate Into a 8-mL sealed tube, was placed methyl 3-bromo-2-phenylquinoxaline-6-carboxylate (100 mg, 0.29 mmol, 1.00 equiv), (R)-2-(trifluoromethyl)pyrrolidine (95 mg, 0.68 mmol, 2.36 equiv), n-BuOH (1.5 mL). The resulting solution was stirred for 3 days at 110° C. The resulting mixture was concentrated under vacuum. The residue was applied onto a silica gel column with ethyl acetate/petroleum ether (1:10). This resulted in 30 mg (26%) of (R)-methyl 2-phenyl-3-(2-(trifluoromethyl)pyrrolidin-1-yl)quinoxaline-6-carboxylate as a yellow solid.

LC-MS:(ES, m/z): 402 [M+H]$^+$

Step 2. (R)-2-phenyl-3-(2-(trifluoromethyl)pyrrolidin-1-yl)quinoxaline-6-carboxylic Acid Into a 25-mL round-bottom flask, was placed (R)-methyl 2-phenyl-3-(2-(trifluoromethyl)pyrrolidin-1-yl)quinoxaline-6-carboxylate (40 mg, 0.10 mmol, 1.00 equiv), sodium hydroxide (20 mg, 0.50 mmol, 5.00 equiv), methanol (5 mL), water (1 mL). The resulting solution was stirred for 5 hs at 50° C. in an oil bath. The resulting mixture was concentrated under vacuum. The residue was diluted in 5 mL of water.

The PH value was aqueous solution was adjusted to 4 with aq hydrochloric acid (1N). The resulting solids were collected by filtration. The crude product (50 mg) was purified by Prep-HPLC with the following conditions (1 #-Waters 2767-1): Column, SunFire Prep C18, 5um, 19*150 mm;

mobile phase, water with 0.05% TFA and CH₃CN (60% CH3CN up to 90% in 8 min, up to 100% in 1.5 min); Detector, UV 220 254 nm. This resulted in 12 mg (30%) of (R)-2-phenyl-3-(2-(trifluoromethyl)pyrrolidin-1-yl)quinoxaline-6-carboxylic acid as a yellow solid.

LC-MS:(ES, m/z): 388 [M+H]$^+$ $^1$H-NMR (300 MHz, DMSO, ppm): δ 13.178 (s, 1H), 8.334 (s, 1H), 8.034-8.031 (d, J=0.9 Hz, 2H), 7.804-7.777 (m, 2H), 7.612-7.507 (m, 3H), 5.710-5.635 (m, 1H), 3.017-2.928 (m, 2H), 2.293-2.250 (m, 1H), 2.018-1.950 (m, 1H), 1.837-1.800 (m, 1H), 1.712-1.658 (m, 1H).

EXAMPLE 66

3-(6-Methoxy-3,4-dihydroquinolin-1(2H)-yl)-2-phenylquinoxaline-6-carboxylic Acid

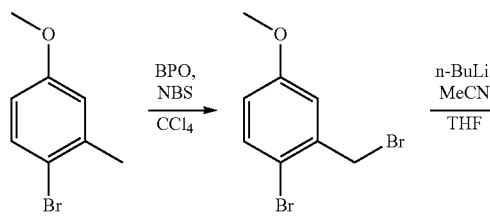

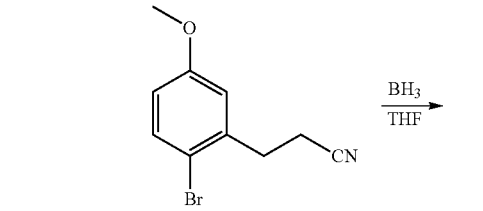

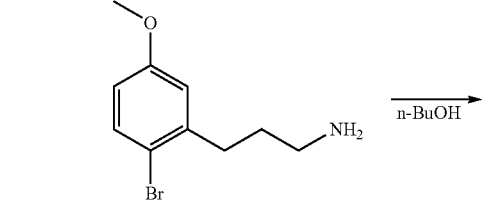

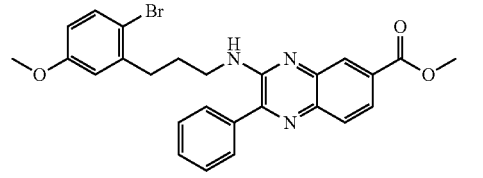

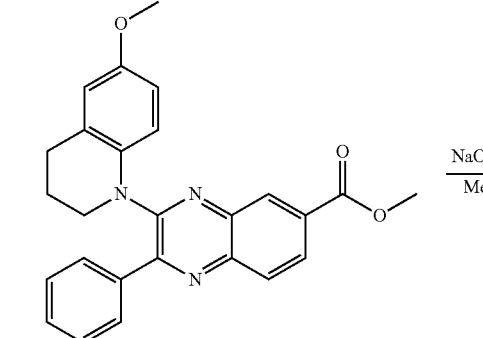

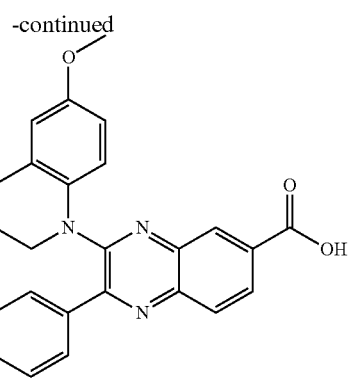

Step 1.
1-Bromo-2-(bromomethyl)-4-methoxybenzene

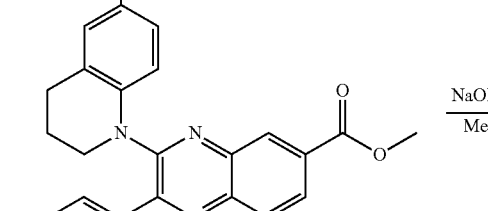

Into a 1000-mL round-bottom flask, was placed a solution of 1-bromo-4-methoxy-2-methylbenzene (20 g, 100.00 mmol, 1.00 equiv) in CCl₄ (200 mL). Then NBS (19.58 g, 110.00 mmol, 1.10 equiv) and BPO (1.21 g, 5.00 mmol, 0.05 equiv) were added. The resulting solution was heated to reflux for 7 hs in an oil bath. The resulting solids were filtered out. The filtrate was concentrated under vacuum and applied onto a silica gel column with ethyl acetate/petroleum ether (1:500). This resulted in 5.9 g (21%) of 1-bromo-2-(bromomethyl)-4-methoxybenzene as a light yellow solid.

Step 2. 3-(2-Bromo-5-methoxyphenyl)propanenitrile

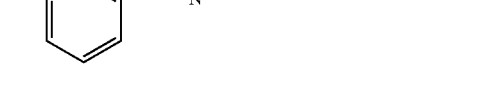

Into a 100-mL 3-necked round-bottom flask purged and maintained with an inert atmosphere of nitrogen, was placed a solution of MeCN (6.2 g, 151.22 mmol, 10.00 equiv) in tetrahydrofuran (20 mL). This was followed by the addition of n-BuLi (15.1 mL, 2.50 equiv, 2.5 M in hexane) dropwise with stirring at −78° C. The resulting solution was stirred for 1 h at −78° C. in a liquid nitrogen bath. To this was added a solution of 1-bromo-2-(bromomethyl)-4-methoxybenzene (4.2 g, 15.11 mmol, 1.00 equiv) in tetrahydrofuran (10 mL) dropwise with stirring at −78° C. The resulting solution was allowed to react, with stirring, for an additional 1 h while the temperature was maintained at −78° C. in a liquid nitrogen bath. The reaction mixture was then quenched by the addition of aqNH₄Cl and extracted by EA (100 ml*3). The organic layers was concentrated and applied onto a silica gel column with PE/EA (10:1). This resulted in 2.29 g (63%) of 3-(2-bromo-5-methoxyphenyl)propanenitrile as a yellow semi-solid.

¹H-NMR (300 MHz, CDC₃, ppm): δ 7.43-7.40 (m, 1H), 6.84-6.83 (d, J=3 Hz, 1H), 6.71-6.68 (m, 1H), 3.78-3.75 (d, J=9 Hz, 1H), 3.04-2.93 (m, 2H), 2.67-2.62 (t, J=6 Hz, 2H).

Step 3.
3-(2-Bromo-5-methoxyphenyl)propan-1-amine

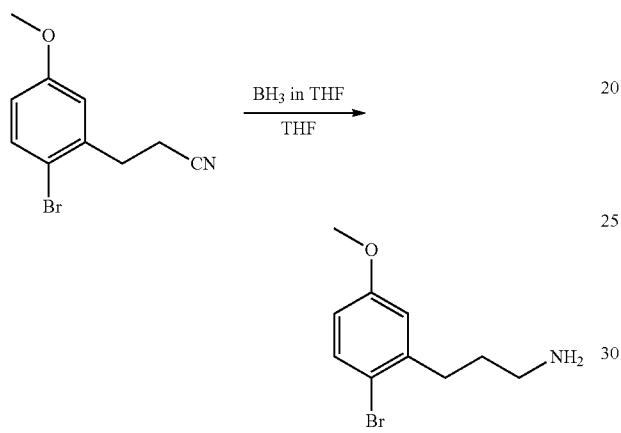

Into a 250-mL round-bottom flask, was placed a solution of 3-(2-bromo-5-methoxyphenyl)propanenitrile (2.39 g, 10.00 mmol, 1.00 equiv) in tetrahydrofuran (40 mL). This was followed by the addition of BH₃ solution in tetrahydrofuran (30 mL, 3.00 equiv) dropwise with stirring at 0° C. The resulting solution was stirred for 6 hs at 20° C. in an oil bath. The reaction was then quenched by the addition of water. The resulting solution was concentrated under vacuum. The residue was diluted in water. The pH value of the aqueous solution was adjusted to 8-9 with 1N sodium hydroxide. The resulting aqueous solution was extracted with 10×50 mL of dichloromethane. The organic layers was combined and dried over anhydrous sodium sulfate and concentrated under vacuum. This resulted in 2.23 g (crude) of 3-(2-bromo-5-methoxyphenyl)propan-1-amine as yellow oil.

LC-MS:(ES, m/z): 244 [M+H]⁺

Step 4. Methyl 3-(3-(2-bromo-5-methoxyphenyl) propylamino)-2-phenylquinoxaline-6-carboxylate

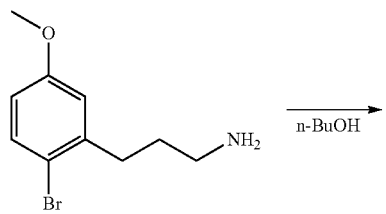

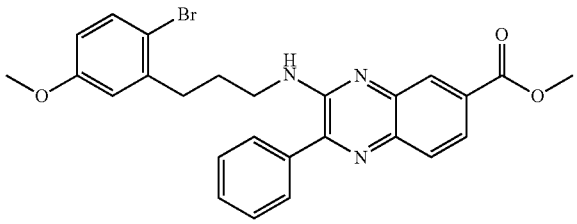

Into a 8-mL sealed tube, was placed methyl 3-bromo-2-phenylquinoxaline-6-carboxylate (200 mg, 0.58 mmol, 1.00 equiv), 3-(2-bromo-5-methoxyphenyl)propan-1-amine (1.14 g, 2.35 mmol, 4.00 equiv, 50%), n-BuOH (3 mL). The resulting solution was stirred overnight at 100° C. in an oil bath. The resulting mixture was concentrated under vacuum. The residue was applied onto a silica gel column with ethyl acetate/petroleum ether (1:50). This resulted in 245 mg (83%) of methyl 3-(3-(2-bromo-5-methoxyphenyl)propylamino)-2-phenylquinoxaline-6-carboxylate as a yellow semi-solid.

LC-MS:(ES, m/z): 506 [M+H]⁺

Step 5. Methyl 3-(6-methoxy-3,4-dihydroquinolin-1 (2H)-yl)-2-phenylquinoxaline-6-carboxylate

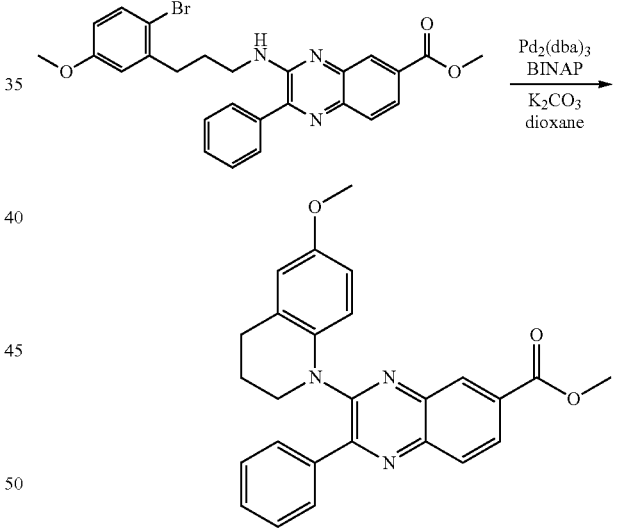

Into a 8-mL sealed tube, was placed methyl 3-(3-(2-bromo-5-methoxyphenyl)propylamino)-2-phenylquinoxaline-6-carboxylate (245 mg, 0.49 mmol, 1.00 equiv), Pd₂(dba)₃ (44.6 mg, 0.05 mmol, 0.10 equiv), BINAP (60.4 mg, 0.10 mmol, 0.20 equiv), Cs₂CO₃ (479.2 mg, 1.47 mmol, 3.03 equiv), dioxane (4 mL). The resulting solution was stirred overnight at 100° C. in an oil bath. The residue was applied onto a silica gel column with ethyl acetate/petroleum ether (1:70). This resulted in 118 mg (57%) of methyl 3-(6-methoxy-3,4-dihydroquinolin-1(2H)-yl)-2-phenylquinoxaline-6-carboxylate as a yellow solid. LC-MS:(ES, m/z): 426 [M+H]⁺

Step 6. 3-(6-Methoxy-3,4-dihydroquinolin-1(2H)-yl)-2-phenylquinoxaline-6-carboxylic Acid

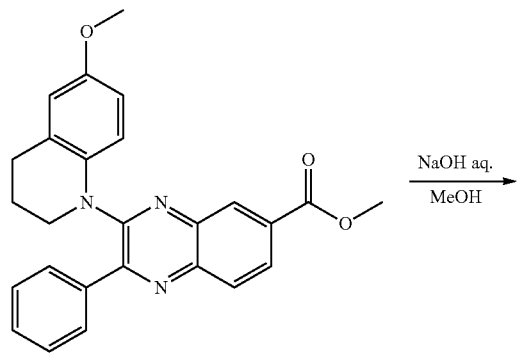

Into a 50-mL round-bottom flask, was placed a solution of methyl 3-(6-methoxy-3,4-dihydroquinolin-1(2H)-yl)-2-phenylquinoxaline-6-carboxylate (118 mg, 0.28 mmol, 1.00 equiv) in methanol (15 mL). This was followed by the addition of a solution of sodium hydroxide (55.6 mg, 1.39 mmol, 5.00 equiv) in water (2 mL) dropwise with stirring. The resulting solution was stirred overnight at 50° C. in an oil bath. The resulting mixture was concentrated under vacuum. The resulting solution was diluted with of $H_2O$. The pH value of the aqueous solution was adjusted to 3-4 with 1N hydrogen chloride. The resulting solids were collected by filtration. The crude product (100 mg) was purified by Prep-HPLC with the following conditions (1 #-Waters 2767-1): Column, SunFire Prep C18, 19*150 mm Sum; mobile phase, water with 0.05% TFA and $CH_3CN$ (60% $CH_3CN$ up to 75% in 8 min, up to 100% in 1.5 min); Detector, UV 220 254 nm. This resulted in 57 mg (40%) of 3-(6-methoxy-3,4-dihydroquinolin-1(2H)-yl)-2-phenylquinoxaline-6-carboxylic acid as a orange solid.

LC-MS:(ES, m/z): 412 [M+H]$^+$ $^1$H-NMR (300 MHz, CDC$_3$, ppm): δ 8.30 (s, 1H), 8.04 (d, J=0.6 Hz, 2H), 7.71-7.68 (m, 2H), 7.29-7.27 (t, J=3 Hz, 3H), 6.64-6.59 (m, 2H), 6.34-6.30 (t, J=3 Hz, 1H), 3.74-3.70 (t, J=6 Hz, 2H), 3.60 (s, 3H), 2.72-2.67 (t, J=6 Hz, 2H), 1.96-1.92 (t, J=6 Hz, 2H).

EXAMPLE 67

3-(Indolin-1-yl)-2-phenylquinoxaline-6-carboxylic Acid

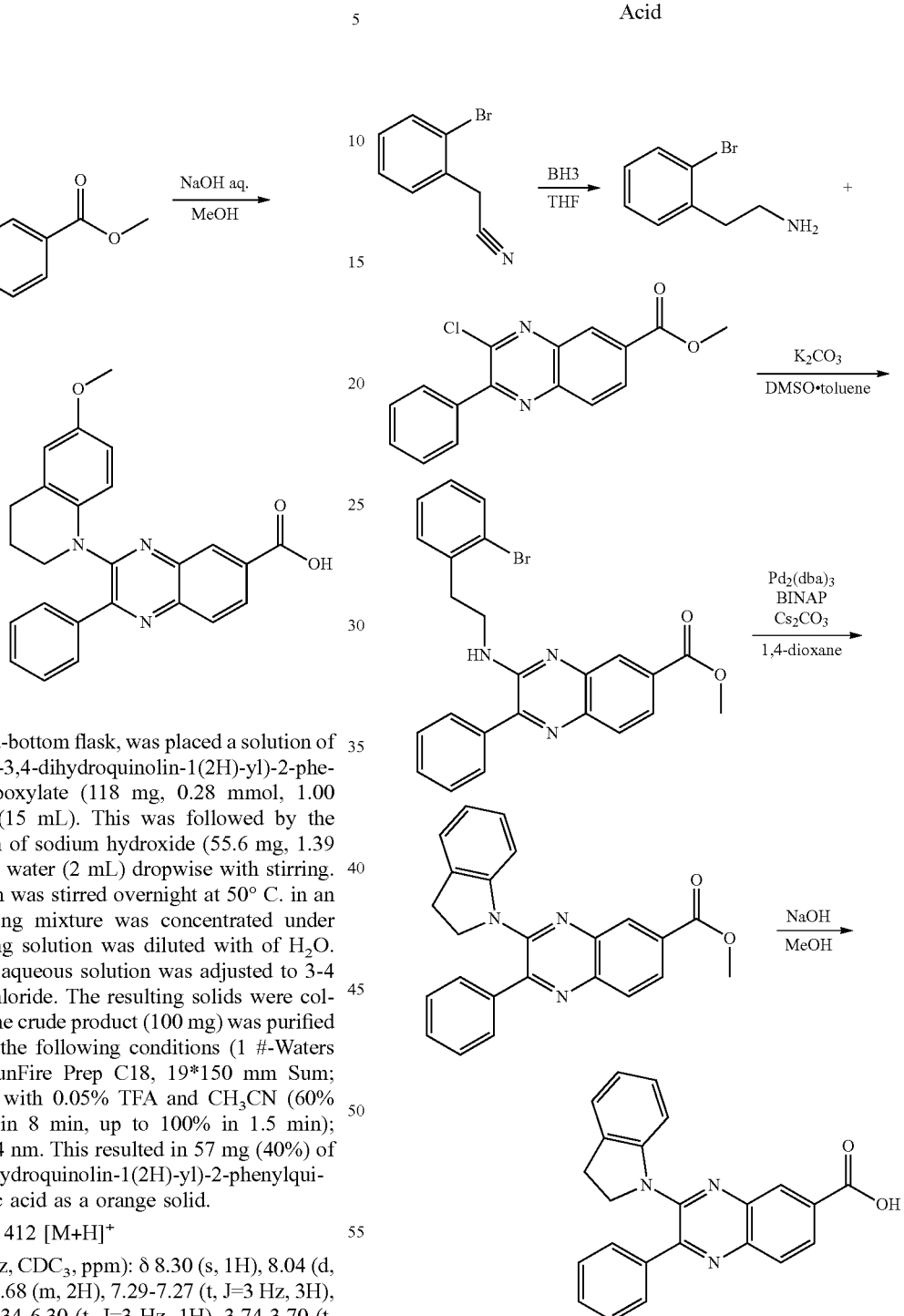

Step 1. 2-(2-Bromophenyl)ethanamine

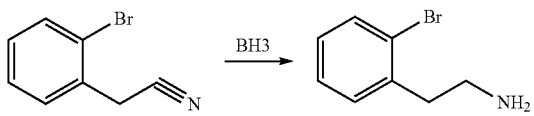

Into a 500-mL 3-necked round-bottom flask, was placed 2-(2-bromophenyl)acetonitrile (9.8 g, 49.99 mmol, 1.00 equiv), tetrahydrofuran (50 mL). This was followed by the addition of BH$_3$ solution (250 mL, 1N in tetrahydrofuran) dropwise with stirring at 0° C. The resulting solution was stirred overnight at room temperature. The reaction was then quenched by the addition of 50 mL of water. The resulting mixture was concentrated under vacuum. The resulting solution was diluted with 50 mL of H$_2$O.

The pH value of the aqueous solution was adjusted to 2 with aq. hydrogen chloride (5 N). The aqueous solution was washed with 3×20 mL of EA and adjusted to pH to 11 with sodium hydroxide. The resulting aqueous solution was extracted with 3×50 mL of ethyl acetate and the organic layers combined and concentrated under vacuum. This resulted in 5 g (50%) of 2-(2-bromophenyl)ethanamine as brown oil.

LC-MS:(ES, m/z): 200 [M+H]$^+$

Step 2. Methyl 3-(2-bromophenethylamino)-2-phenylquinoxaline-6-carboxylate

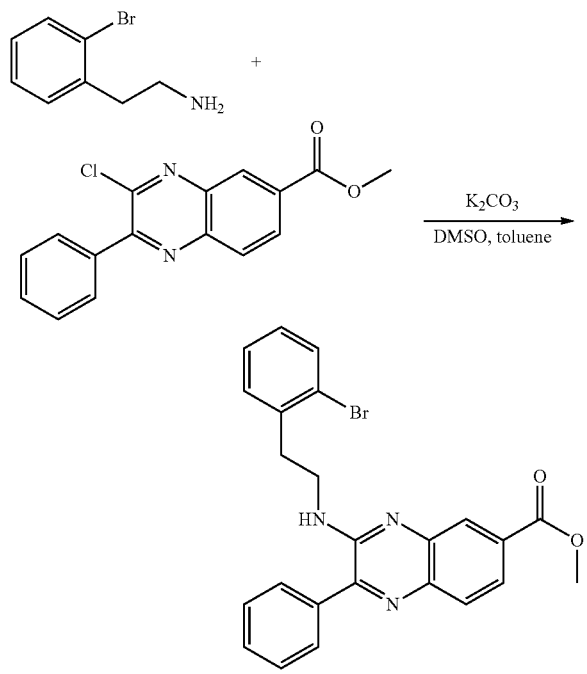

Into a 10-mL sealed tube, was placed methyl 3-chloro-2-phenylquinoxaline-6-carboxylate (150 mg, 0.50 mmol, 1.00 equiv), 2-(2-bromophenyl)ethanamine (300.5 mg, 1.51 mmol, 3.00 equiv), potassium carbonate (347.3 mg, 2.52 mmol, 5.00 equiv), toluene/DMSO (5/1 mL). The resulting solution was stirred for overnight at 100° C. in an oil bath. The resulting mixture was concentrated under vacuum and applied onto a silica gel column with ethyl acetate/petroleum ether (1:50). This resulted in 110 mg (47%) of methyl 3-(2-bromophenethylamino)-2-phenylquinoxaline-6-carboxylate as a yellow solid.

LC-MS:(ES, m/z): 462 [M+H]$^+$ $^1$H-NMR (300 MHz, CDC$_3$, ppm): δ 8.508-8.503 (d, J=1.5 Hz, 1H), 8.037-7.936 (m, 2H), 7.633-7.513 (m, 6H), 7.281-7.152 (m, 2H), 7.140-7.083 (m, 1H), 5.312-5.278 (m, 1H), 3.912-3.848 (m, 2H), 3.203-3.157 (t, J=6.9 Hz, 2H).

Step 3. Methyl 3-(indolin-1-yl)-2-phenylquinoxaline-6-carboxylate

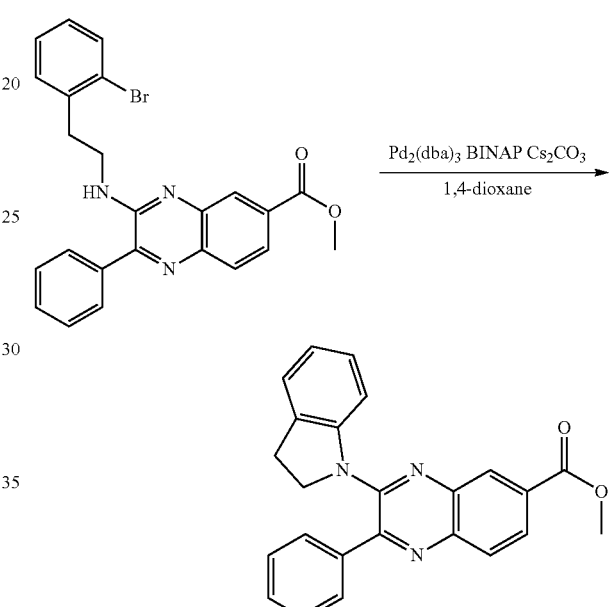

Into a 10-mL sealed tube, was placed methyl 3-(2-bromophenethylamino)-2-phenylquinoxaline-6-carboxylate (110 mg, 0.24 mmol, 1.00 equiv), Pd$_2$(dba)$_3$ (22 mg, 0.02 mmol, 0.10 equiv), BINAP (59.37 mg, 0.10 mmol, 0.40 equiv), Cs$_2$CO$_3$ (233 mg, 0.71 mmol, 3.00 equiv), 1,4-dioxane (5 mL). The resulting solution was stirred for overnight at 100° C. in an oil bath. The resulting solids were filtered out. The filtrate was concentrated under vacuum and applied onto a silica gel column with ethyl acetate/petroleum ether (1:50). This resulted in 90 mg (99%) of methyl 3-(indolin-1-yl)-2-phenylquinoxaline-6-carboxylate as a orange solid.

LC-MS:(ES, m/z): 382 [M+H]$^+$ $^1$H-NMR (300 MHz, CDCl$_3$, ppm): δ 8.654 (s, 1H), 8.194-8.119 (m, 2H), 7.916-7.884 (m, 2H), 7.779-7.457 (m, 4H), 7.281-7.228 (m, 1H), 7.136-7.085 (t, J=7.65 Hz, 1H), 6.960-6.912 (t, J=7.2 Hz, 1H), 4.020 (s, 3H), 3.853-3.798 (t, J=8.25 Hz, 2H), 3.122-3.068 (t, J=8.1 Hz, 2H).

Step 4.
3-(Indolin-1-yl)-2-phenylquinoxaline-6-carboxylic Acid

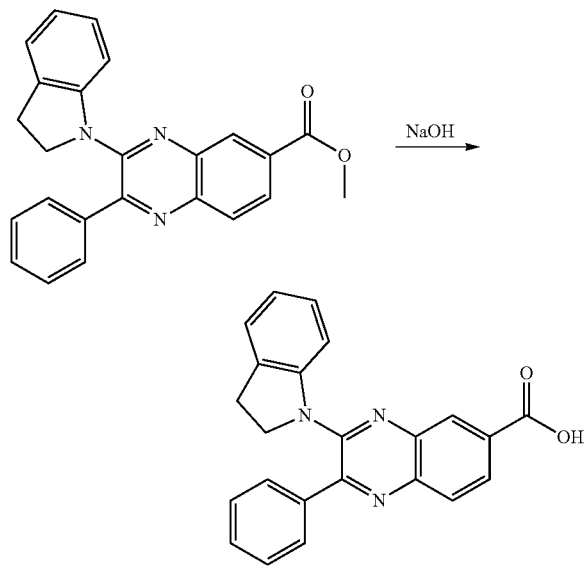

Into a 50-mL round-bottom flask, was placed a solution of methyl 3-(indolin-1-yl)-2-phenylquinoxaline-6-carboxylate (90 mg, 0.24 mmol, 1.00 equiv) in methanol (15 mL). Then a solution of sodium hydroxide (47.2 mg, 1.18 mmol, 5.00 equiv) in water (2 mL) was added. The resulting solution was stirred for 2 hrs at 50° C. in an oil bath. The resulting mixture was concentrated under vacuum. The residue was diluted in 20 mL of water. The pH value of the aqueous solution was adjusted to 4-5 with aqueous hydrogen chloride (1 mol/L). The resulting solids were collected by filtration. This resulted in 80 mg (92%) of 3-(indolin-1-yl)-2-phenylquinoxaline-6-carboxylic acid as an orange solid.

LC-MS:(ES, m/z): 368 [M+H]$^+$ $^1$H-NMR (300 MHz, DMSO, ppm): δ 8.362 (s, 1H), 8.127-7.983 (m, 2H), 7.868-7.855 (d, J=3.9 Hz, 2H), 7.454 (s, 3H), 7.261-7.175 (m, 2H), 7.010-6.961 (t, J=7.35 Hz, 1H), 6.849-6.801 (t, J=7.2 Hz, 1H), 3.781-3.730 (t, J=7.65 Hz, 2H), 3.043-2.992 (t, J=7.65 Hz, 2H).

EXAMPLE 68

3-(2,3-Dihydrobenzo[b][1,4]oxazin-4-yl)-2-phenylquinoxaline-6-carboxylic Acid

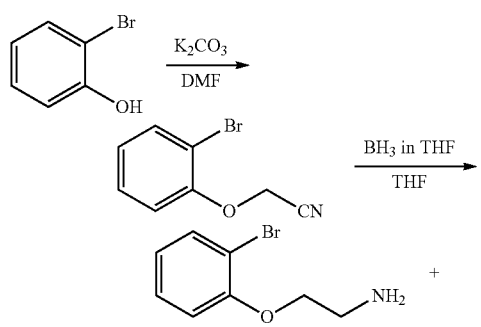

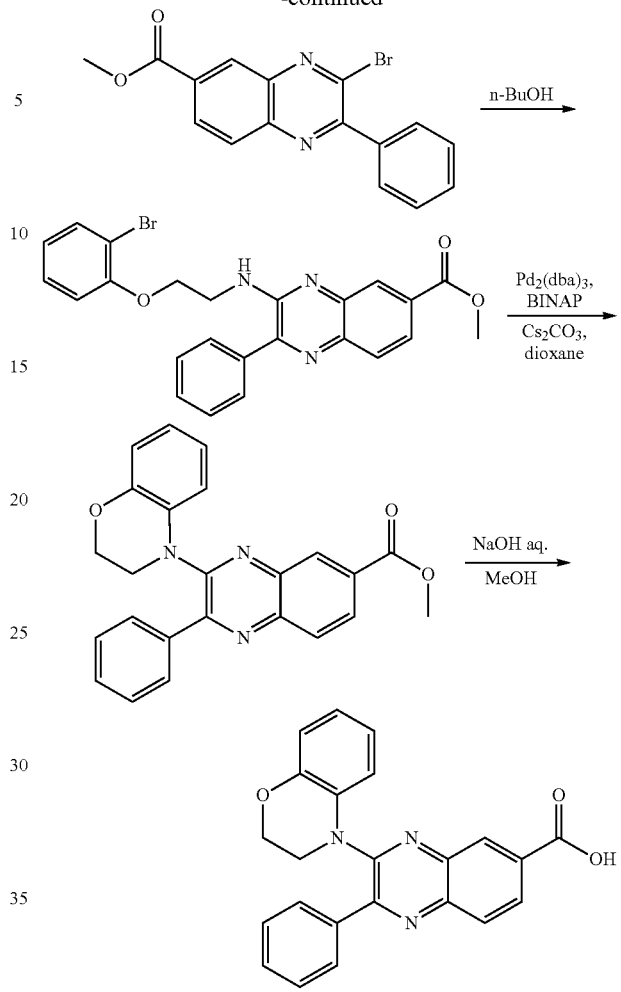

Step 1. 2-(2-Bromophenoxy)acetonitrile

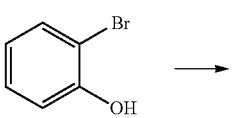

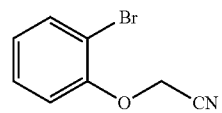

Into a 50-mL round-bottom flask, was placed 2-bromophenol (5.1 g, 29.48 mmol, 1.00 equiv), 2-bromoacetonitrile (5.3 g, 44.19 mmol, 1.50 equiv), potassium carbonate (8 g, 57.97 mmol, 2.00 equiv), N,N-dimethylformamide (20 mL). The resulting solution was stirred overnight at 60° C. in an oil bath. The resulting solution was diluted with 5×50 mL of EA. The organic layer was washed with 50 mL of H$_2$O. Organic layers were collected and concentrated under vacuum. The residue was applied onto a silica gel column with ethyl acetate/petroleum ether (1:100). This resulted in 6 g (96%) of 2-(2-bromophenoxy)acetonitrile as a brown solid.

LC-MS (ES, m/z): 212 [M+H]$^+$

Step 2. 2-(2-Bromophenoxy)ethanamine

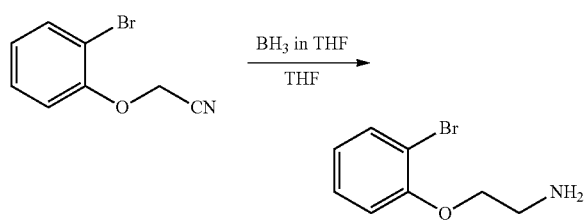

Into a 500-mL 3-necked round-bottom flask purged and maintained with an inert atmosphere of nitrogen, was placed a solution of 2-(2-bromophenoxy)acetonitrile (5.63 g, 26.68 mmol, 1.00 equiv) in tetrahydrofuran (20 mL). This was followed by the addition of $BH_3$ in tetrahydrofuran (143 mL, 5.30 equiv) dropwise with stirring at 0° C. The resulting solution was stirred overnight at 20° C. in an oil bath and quenched by the addition of water (10 ml). The resulting mixture was concentrated under vacuum and diluted with water. The pH value of the aqueous solution was adjusted to 10 with 1N sodium hydroxide and extracted with 6×50 mL of dichloromethane. The organic layers was combined and concentrated under vacuum. This resulted in 5.67 g (crude) of 2-(2-bromophenoxy)ethanamine as pale brown oil.

LC-MS:(ES, m/z): 216 [M+H]+

Step 3. Methyl 3-(2-(2-bromophenoxy)ethylamino)-2-phenylquinoxaline-6-carboxylate

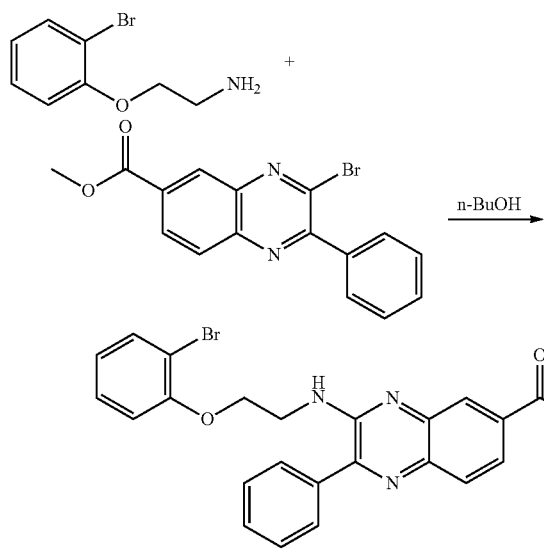

Into a 8-mL pressure tank reactor, was placed methyl 3-bromo-2-phenylquinoxaline-6-carboxylate (150 mg, 0.44 mmol, 1.00 equiv), 2-(2-bromophenoxy)ethanamine (750 mg, 1.74 mmol, 3.98 equiv, 50%), n-BuOH (2 mL). The resulting solution was stirred overnight at 100° C. in an oil bath. The resulting mixture was concentrated under vacuum. The residue was applied onto a silica gel column with PE/EA (10:1). This resulted in 163.9 mg (crude) of methyl 3-(2-(2-bromophenoxy)ethylamino)-2-phenylquinoxaline-6-carboxylate as a yellow solid.

Step 4. Methyl 3-(2,3-dihydrobenzo[b][1,4]oxazin-4-yl)-2-phenylquinoxaline-6-carboxylate

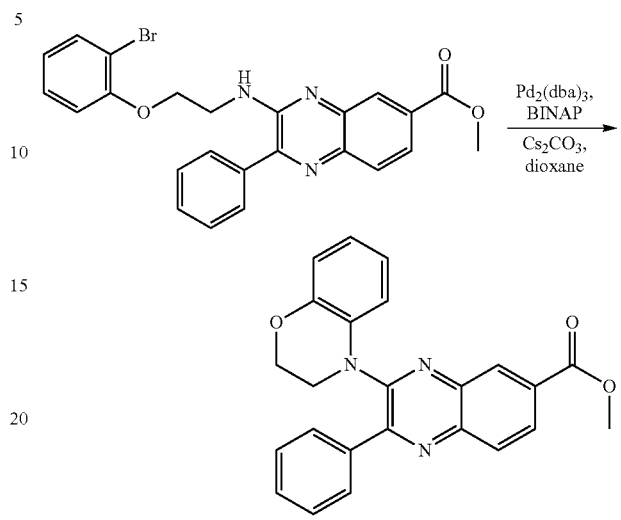

Into a 20-mL sealed tube purged and maintained with an inert atmosphere of nitrogen, was placed methyl 3-(2-(2-bromophenoxy)ethylamino)-2-phenylquinoxaline-6-carboxylate (363.9 mg, 0.76 mmol, 1.00 equiv), $Pd_2(dba)_3$ (70.2 mg, 0.08 mmol, 0.10 equiv), BINAP (189.8 mg, 0.31 mmol, 0.40 equiv), $Cs_2CO_3$ (746.1 mg, 2.29 mmol, 3.00 equiv), 1,4-dioxane (5 mL). The resulting solution was stirred overnight at 100° C. in an oil bath and concentrated under vacuum. The residue was applied onto a silica gel column with ethyl acetate/petroleum ether (1:50). This resulted in 166.8 mg (44%) of methyl 3-(2,3-dihydrobenzo[b][1,4]oxazin-4-yl)-2-phenylquinoxaline-6-carboxylate as yellow oil.

LC-MS:(ES, m/z): 398 [M+H]+

Step 5. 3-(2,3-Dihydrobenzo[b][1,4]oxazin-4-yl)-2-phenylquinoxaline-6-carboxylic Acid

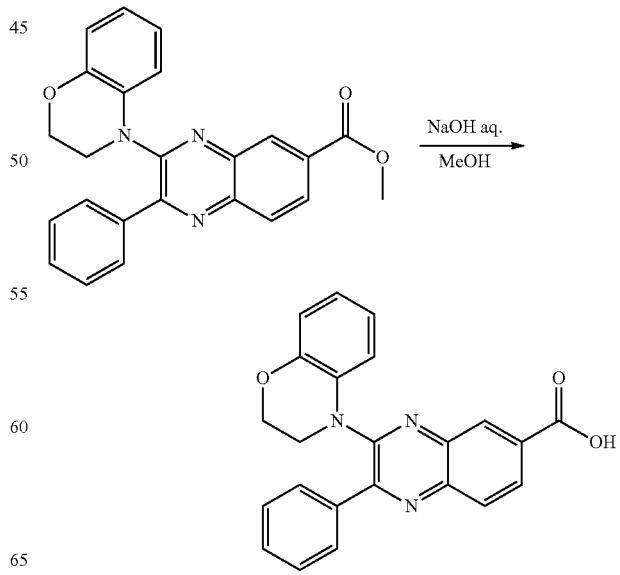

Into a 50-mL round-bottom flask, was placed a solution of methyl 3-(2,3-dihydrobenzo[b][1,4]oxazin-4-yl)-2-phenylquinoxaline-6-carboxylate (166.8 mg, 0.34 mmol, 1.00 equiv, 80%) in methanol (15 mL). This was followed by the addition of a solution of sodium hydroxide (84 mg, 2.10 mmol, 5.00 equiv) in water (1.5 mL) dropwise with stirring. The resulting solution was stirred overnight at 50° C. in an oil bath. The pH value of the aqueous solution was adjusted to 3-4 with 1N aqueous hydrogen chloride and concentrated under vacuum. The crude product (100 mg) was purified by Prep-HPLC with the following conditions (1 #-Waters 2767-2): Column, SunFire Prep C18, 5um, 19*150 mm; mobile phase, water with 0.05% TFA and CH$_3$CN (20% CH$_3$CN up to 35% in 8 min, up to 70% in 8 min, up to 100% in 1.5 min); Detector, uv 220&254 nm. This resulted in 40 mg (31%) of 3-(2,3-dihydrobenzo[b][1,4]oxazin-4-yl)-2-phenylquinoxaline-6-carboxylic acid as a orange solid.

LC-MS:(ES, m/z): 384 [M+H]$^+$ $^1$H-NMR (300 MHz, DMSO, ppm): δ 13.21 (s, 1H), 8.34 (s, 1H), 8.16-8.09 (m, 2H), 7.91-7.88 (m, 2H), 7.42-7.40 (t, J=6 Hz, 3H), 6.91-6.88 (d, J=9 Hz, 1H), 6.77-6.73 (t, J=6 Hz, 2H), 6.59-6.53 (m, 1H), 4.29-4.28 (d, J=3 Hz, 2H), 3.67 (s, 2H).

EXAMPLE 69

3-(Isopropyl(methyl)amino)-2-(3-methoxyphenyl)quinoxaline-6-carboxylic Acid

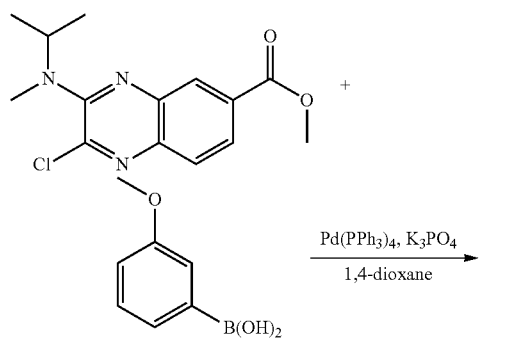

Step 1. Methyl 3-(isopropyl(methyl)amino)-2-(3-methoxyphenyl)quinoxaline-6-carboxylate

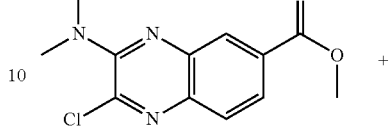

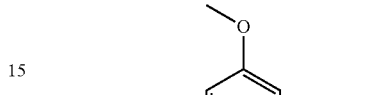

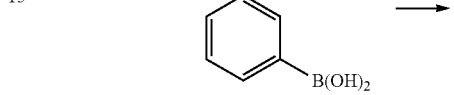

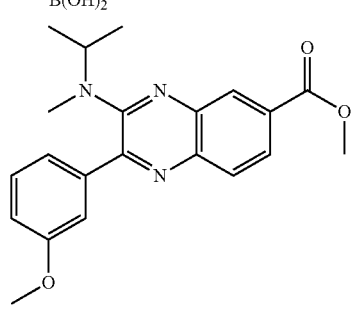

Into a 10-mL sealed tube, was placed methyl 2-chloro-3-(isopropyl(methyl)amino)quinoxaline-6-carboxylate (120 mg, 0.41 mmol, 1.00 equiv), 3-methoxyphenylboronic acid (188 mg, 1.23 mmol, 3.00 equiv), Pd(PPh$_3$)$_4$ (94 mg, 0.08 mmol, 0.20 equiv), K$_3$PO$_4$ (346 mg, 1.64 mmol, 4.00 equiv), 1,4-dioxane (4 mL). The resulting solution was stirred for overnight at 100° C. in an oil bath. The resulting mixture was concentrated under vacuum. The residue was applied onto a silica gel column with ethyl acetate/petroleum ether (1:30). This resulted in 50 mg (33%) of methyl 3-(isopropyl(methyl)amino)-2-(3-methoxyphenyl)quinoxaline-6-carboxylate as a yellow solid.

LC-MS:(ES, m/z): 366 [M+H]$^+$

Step 2. 3-(Isopropyl(methyl)amino)-2-(3-methoxyphenyl)quinoxaline-6-carboxylic Acid

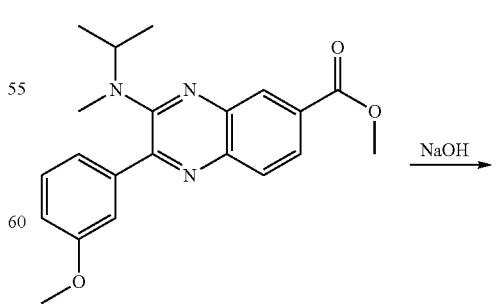

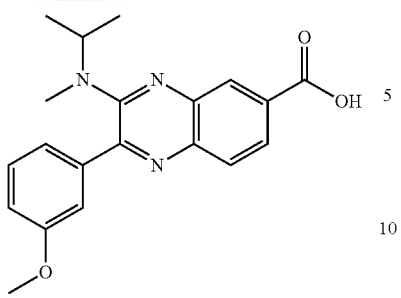

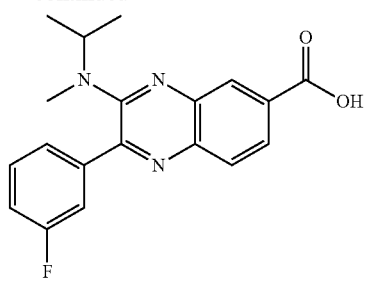

Into a 50-mL round-bottom flask, was placed methyl 3-(isopropyl(methyl)amino)-2-(3-methoxyphenyl)quinoxaline-6-carboxylate (50 mg, 0.14 mmol, 1.00 equiv), methanol (10 mL), sodium hydroxide (27.4 mg, 0.69 mmol, 5.00 equiv), water (2 mL). The resulting solution was stirred for 2 hs at 50° C. in an oil bath. The resulting mixture was concentrated under vacuum. The resulting solution was diluted with 20 mL of H2O. The pH value of the aqueous solution was adjusted to 4-5 with hydrogen chloride (1 mol/L). The resulting solids were collected by filtration. This resulted in 20 mg (41%) of 3-(isopropyl(methyl)amino)-2-(3-methoxyphenyl)quinoxaline-6-carboxylic acid as a yellow solid.

LC-MS:(ES, m/z): 352 [M+H]$^+$ $^1$H-NMR (300 MHz, DMSO, ppm): δ 8.250 (s, 1H), 7.931 (s, 2H), 7.382-7.250 (m, 3H), 7.076 (s, 1H), 4.218 (s, 1H), 3.827 (s, 3H), 2.699 (s, 3H), 1.030-1.048 (d, J=5.4 Hz, 6H).

EXAMPLE 70

2-(3-Fluorophenyl)-3-(isopropyl(methyl)amino)quinoxaline-6-carboxylic Acid

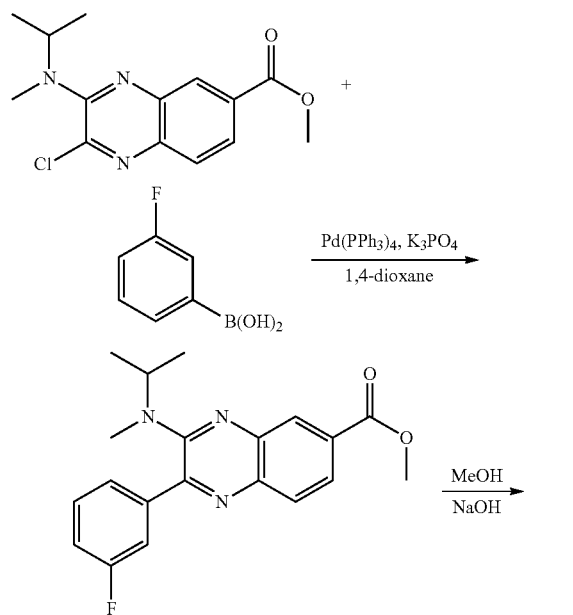

Step 1. Methyl 2-(3-fluorophenyl)-3-(isopropyl (methyl)amino)quinoxaline-6-carboxylate

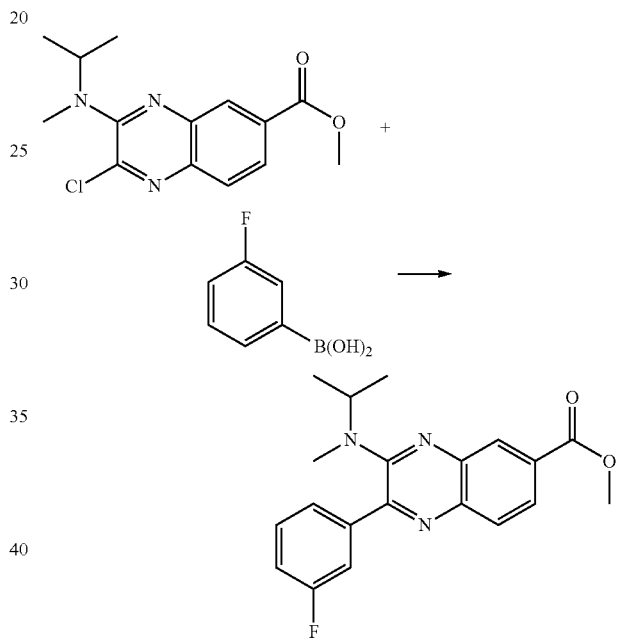

Into a 10-mL sealed tube, was placed methyl 2-chloro-3-(isopropyl(methyl)amino)quinoxaline-6-carboxylate (110 mg, 0.38 mmol, 1.00 equiv), 3-fluorophenylboronic acid (157.4 mg, 1.12 mmol, 3.00 equiv), Pd(PPh$_3$)$_4$ (86.5 mg, 0.07 mmol, 0.20 equiv), K$_3$PO$_4$ (318 mg, 1.51 mmol, 4.00 equiv), 1,4-dioxane (4 mL). The resulting solution was stirred for overnight at 100° C. in an oil bath. The resulting mixture was concentrated under vacuum. The residue was applied onto a silica gel column with ethyl acetate/petroleum ether (1:30). This resulted in 75 mg (57%) of methyl 2-(3-fluorophenyl)-3-(isopropyl(methyl)amino)quinoxaline-6-carboxylate as a yellow solid.

LC-MS:(ES, m/z): 354 [M+H]$^+$

Step 2. 2-(3-Fluorophenyl)-3-(isopropyl(methyl)amino)quinoxaline-6-carboxylic Acid

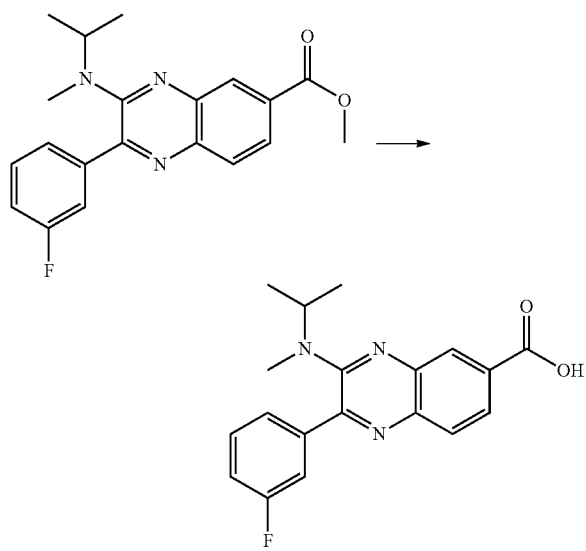

Into a 50-mL round-bottom flask, was placed methyl 2-(3-fluorophenyl)-3-(isopropyl(methyl)amino)quinoxaline-6-carboxylate (75 mg, 0.21 mmol, 1.00 equiv), methanol (15 mL), sodium hydroxide (42 mg, 1.05 mmol, 4.94 equiv), water (2 mL). The resulting solution was stirred for 2 hs at 50° C. in an oil bath. The resulting mixture was concentrated under vacuum. The resulting solution was diluted with 20 mL of H₂O. The pH value of the aqueous solution was adjusted to 4-5 with aqueous hydrogen chloride (1 mol/L). The resulting solids were collected by filtration. The crude product (70 mg) was purified by Prep-HPLC with the following conditions (1 #-Waters 2767-2): Column, SunFire Prep C18, Sum, 19*150 mm; mobile phase, water with 0.05% TFA and CH₃CN (50% CH₃CN up to 80% in 8 min, up to 100% in 1.5 min); Detector, uv 220&254 nm. This resulted in 20 mg (27%) of 2-(3-fluorophenyl)-3-(isopropyl(methyl)amino)quinoxaline-6-carboxylic acid as a yellow solid.

LC-MS:(ES, m/z): 340 [M+H]⁺

¹H-NMR (300 MHz, DMSO, ppm): δ 8.266 (s, 1H), 7.984-7.924 (m, 2H), 7.689-7.623 (m, 2H), 7.596-7.550 (m, 1H), 7.378-7.316 (m, 1H), 4.216-4.130 (m, 1H), 2.676 (s, 3H), 1.053-1.031 (d, J=6.6 Hz, 6H).

EXAMPLE 71

2-(2-Fluorophenyl)-3-(isopropyl(methyl)amino)quinoxaline-6-carboxylic Acid

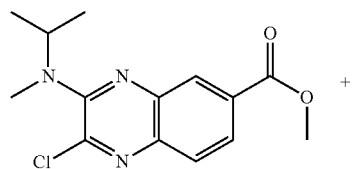

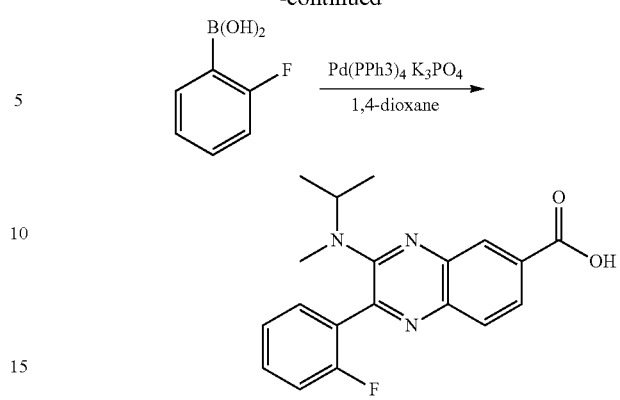

Into a 10-mL round-bottom flask, was placed methyl 2-chloro-3-(isopropyl methyl) amino)quinoxaline carboxylate (80 mg, 0.27 mmol, 1.00 equiv), 2-fluorophenylboronic acid (115 mg, 0.82 mmol, 3.00 equiv), Pd(PPh₃)₄ (62.9 mg, 0.05 mmol, 0.20 equiv), 1,4-dioxane (3 mL), K₃PO₄ (231 mg, 1.09 mmol, 4.00 equiv). The resulting solution was stirred for overnight at 100° C. in an oil bath. The resulting mixture was concentrated under vacuum. The resulting solution was diluted with 40 mL of DCM:MeOH=10:1. The solids were filtered out. The filtrate was concentrated in vacuo. The crude product (100 mg) was purified by Prep-HPLC with the following conditions (1 #-Waters 2767-1): Column, SunFire Prep C18, 19*150 mm Sum; mobile phase, water with 0.05% TFA and CH₃CN (50% CH₃CN up to 80% in 8 min, up to 100% in 1.5 min); Detector, UV 220&254 nm. This resulted in 40 mg (43%) of 2-(2-fluorophenyl)-3-(isopropyl(methyl)amino)quinoxaline-6-carboxylic acid as a yellow solid.

LC-MS:(ES, m/z): 340 [M+H]⁺

¹H-NMR (300 MHz, CDC₃, ppm): δ 13.250 (s, 1H), 8.268 (s, 1H), 7.945 (s, 1H), 7.776-7.731 (m, 1H), 7.602-7.538 (m, 1H), 7.424-7.342 (m, 2H), 4.299-4.212 (m, 1H), 2.636 (s, 3H), 1.017-0.995 (d, J=6.6 Hz, 6H).

EXAMPLE 72

3-(Cyclopentyl(methyl)amino)-2-phenylquinoxaline-6-carboxylic Acid

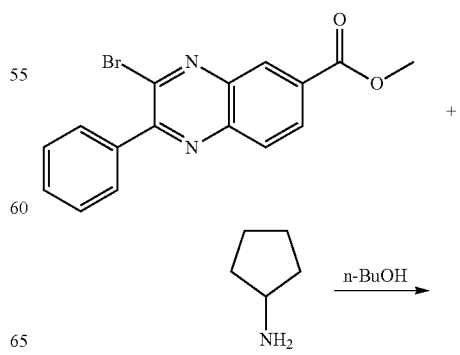

183
-continued

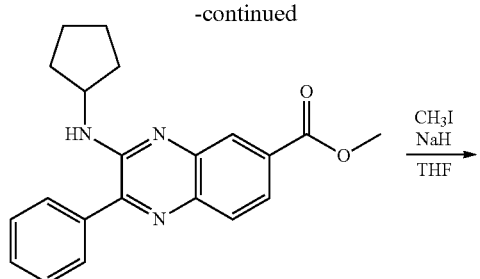

ether (1:50) resulting in 214.1 mg (crude) of methyl 3-(cyclopentylamino)-2-phenylquinoxaline-6-carboxylate as a yellow oil.

LC-MS (ES, m/z): 348 [M+H]$^+$

Step 2. Methyl 3-(cyclopentyl(methyl)amino)-2-phenylquinoxaline-6-carboxylate

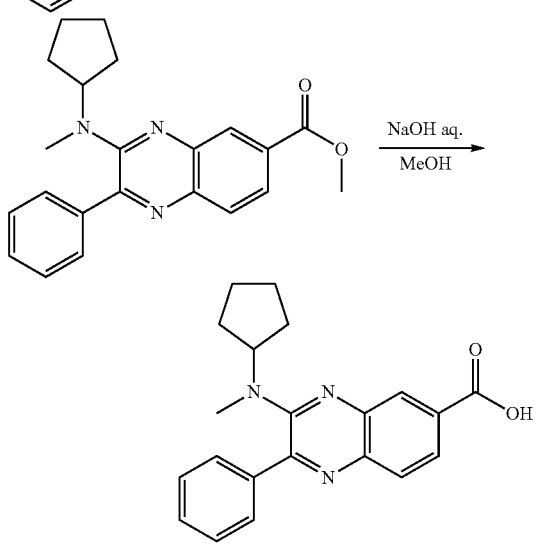

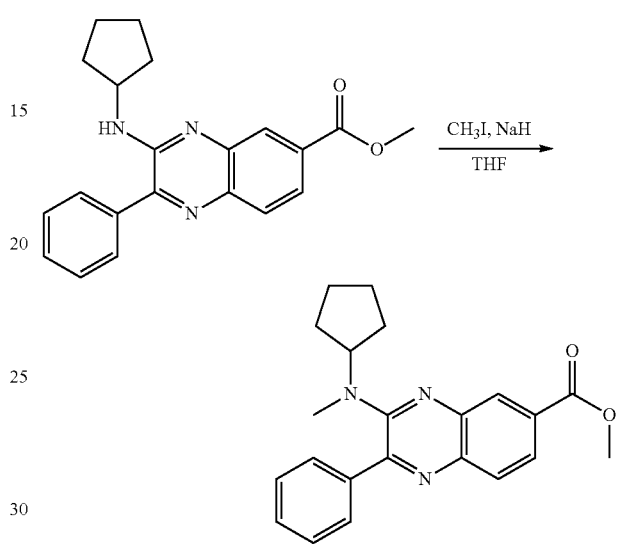

Step 1. Methyl 3-(cyclopentylamino)-2-phenylquinoxaline-6-carboxylate

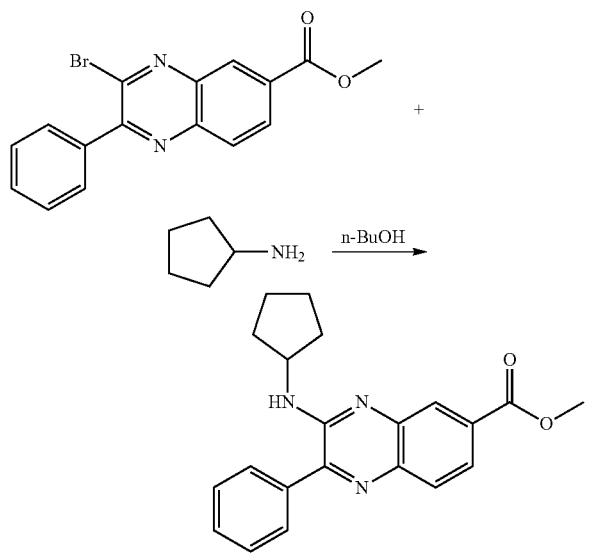

Into a 50-mL round-bottom flask purged and maintained with an inert atmosphere of nitrogen, was placed a solution of methyl 3-(cyclopentylamino)-2-phenylquinoxaline-6-carboxylate (214.1 mg, 0.62 mmol, 1.00 equiv) in tetrahydrofuran (10 mL). This was followed by the addition of sodium hydride (246.8 mg, 6.17 mmol, 10.00 equiv, 60%) dropwise with stirring at 0° C. The resulting solution was stirred for 1 h at room temperature. To this was added a solution of CH$_3$I (1.75 g, 12.32 mmol, 20.00 equiv) in tetrahydrofuran (2 mL) dropwise with stirring at 0° C. The resulting solution was stirred overnight at room temperature. The reaction was then quenched by the addition of water. The resulting mixture was concentrated under vacuum. This resulted in 200 mg (crude) of methyl 3-(cyclopentyl(methyl)amino)-2-phenylquinoxaline-6-carboxylate as yellow oil.

LC-MS:(ES, m/z): 362 [M+H]$^+$

Step 3. 3-(Cyclopentyl(methyl)amino)-2-phenylquinoxaline-6-carboxylic Acid

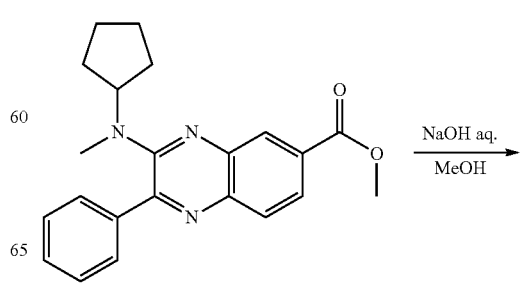

Into an 8-mL scaled tube, was placed methyl 3-bromo-2-phenylquinoxaline-6-carboxylate (200 mg, 0.58 mmol, 1.00 equiv), cyclopentanamine (246.8 mg, 2.90 mmol, 5.00 equiv), and n-BuOH (2 mL). The resulting solution was stirred for 4 hrs at 100° C. in an oil bath. The resulting mixture was concentrated in vacuo. The residue was purified by silica gel chromatography with ethyl acetate/petroleum

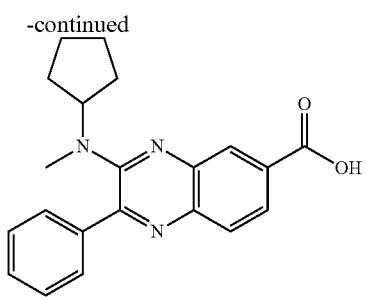

Into a 50-mL round-bottom flask, was placed a solution of methyl 3-(cyclopentyl(methyl)amino)-2-phenylquinoxaline-6-carboxylate (200 mg, 0.55 mmol, 1.00 equiv) in methanol (15 mL). This was followed by the addition of a solution of sodium hydroxide (110.8 mg, 2.77 mmol, 5.00 equiv) in water (3 mL) dropwise with stirring. The resulting solution was stirred for 3 hs at 50° C. in an oil bath. The pH value of the aqueous solution was adjusted to 3-4 with 1N hydrogen chloride. The resulting solids were collected by filtration and washed with ether. This resulted in 56 mg (29%) of 3-(cyclopentyl(methyl)amino)-2-phenylquinoxaline-6-carboxylic acid as a yellow solid.

LC-MS:(ES, m/z): 348 [M+H]$^+$ $^1$H-NMR (300 MHz, DMSO, ppm): δ 13.15-13.12 (t, J=3 Hz, 1H), 8.26 (s, 1H), 7.94 (d, J=0.3 Hz, 2H), 7.85-7.83 (d, J=6 Hz, 2H), 7.56-7.48 (m, 3H), 4.31-4.27 (t, J=6 Hz, 1H), 2.69 (s, 3H), 1.67-1.54 (m, 6H), 1.40-1.38 (d, J=6 Hz, 2H).

EXAMPLE 73

3-(Isopropyl(methyl)amino)-2-(4-methoxyphenyl)quinoxaline-6-carboxylic Acid

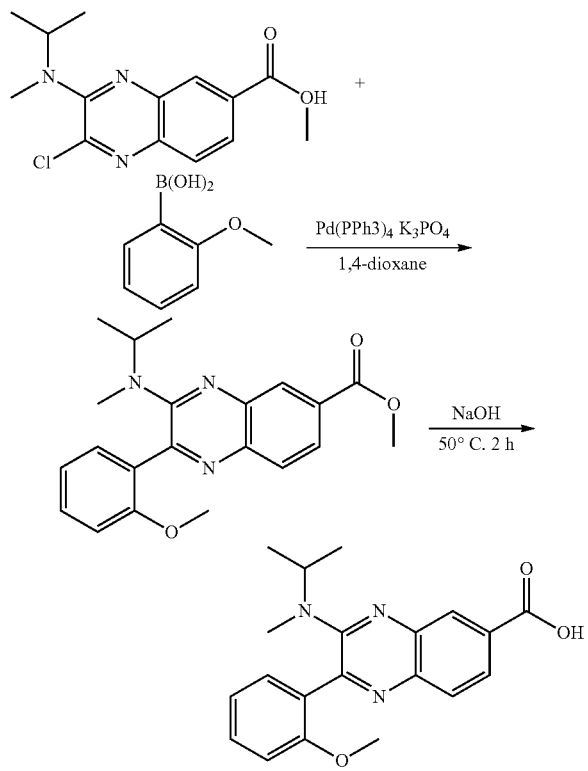

Step 1. Methyl 3-(isopropyl(methyl)amino)-2-(2-methoxyphenyl)quinoxaline-6-carboxylate Into a 10-mL sealed tube, was placed methyl 2-chloro-3-(isopropyl(methyl)amino)quinoxaline-6-carboxylate (290 mg, 0.99 mmol, 1.00 equiv), 2-methoxyphenylboronic acid (453.5 mg, 2.96 mmol, 3.00 equiv), Pd(PPh$_3$)$_4$ (228 mg, 0.20 mmol, 0.20 equiv), K$_3$PO$_4$ (837 mg, 3.97 mmol, 4.00 equiv), 1,4-dioxane (4 mL). The resulting solution was stirred for overnight at 100° C. in an oil bath. The resulting mixture was concentrated under vacuum and applied onto a silica gel column with ethyl acetate/petroleum ether (1:40). This resulted in 100 mg (28%) of methyl 3-(isopropyl(methyl)amino)-2-(2-methoxyphenyl)quinoxaline-6-carboxylate as a yellow solid.

LC-MS:(ES, m/z): 366 [M+H]$^+$

Step 2. 3-(Isopropyl(methyl)amino)-2-(4-methoxyphenyl)quinoxaline-6-carboxylic Acid

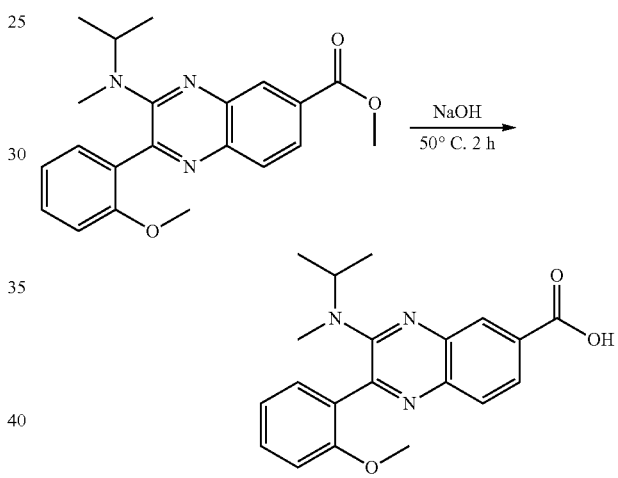

Into a 50-mL round-bottom flask, was placed methyl 3-(isopropyl(methyl)amino)-2-(4-methoxyphenyl)quinoxaline-6-carboxylate (110 mg, 0.30 mmol, 1.00 equiv), methanol (15 mL), sodium hydroxide (60 mg, 1.50 mmol, 5.00 equiv), and water (2 mL). The resulting solution was stirred for 5 hr at 50° C. in an oil bath. The resulting mixture was concentrated in vacuo and diluted with 20 mL of water. The pH value of the aqueous solution was adjusted to 4-5 with aq. hydrogen chloride (1 mol/L). The resulting solids were collected by filtration. This resulted in 50 mg (46%) of 3-(isopropyl(methyl)amino)-2-(4-methoxyphenyl)quinoxaline-6-carboxylic acid as a yellow solid.

LC-MS:(ES, m/z): 352 [M+H]$^+$ $^1$H-NMR (300 MHz, DMSO, ppm): δ 13.099 (s, 1H), 8.218 (s, 1H), 7.882-7.879 (d, J=0.9 Hz, 2H), 7.532-7.447 (m, 2H), 7.161-7.090 (m, 2H), 4.449-4.405 (m, 1H), 3.744 (s, 3H), 2.565 (s, 3H), 1.002-0.980 (d, J=6.6 Hz, 6H).

EXAMPLE 74

(S)-2-(4-Fluorophenyl)-3-(2-methylpyrrolidin-1-yl)quinoxaline-6-carboxylic Acid

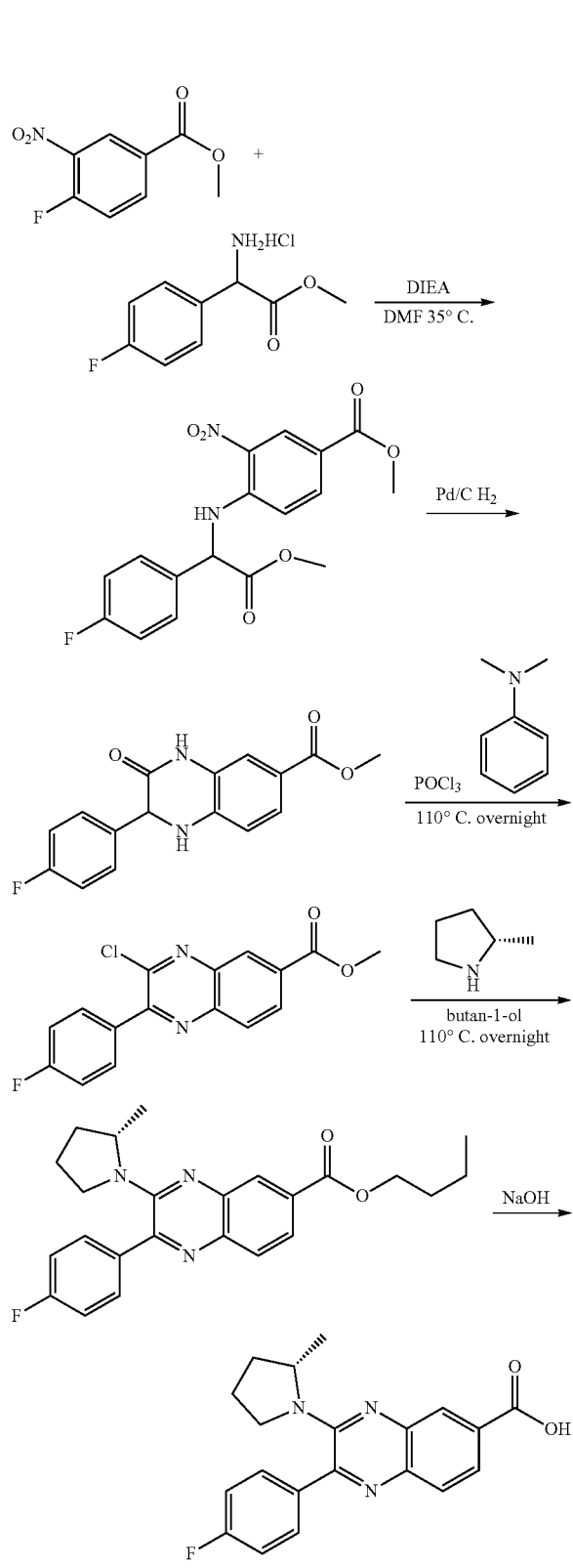

Step 1. Methyl 4-(1-(4-fluorophenyl)-2-methoxy-2-oxoethylamino)-3-nitrobenzoate

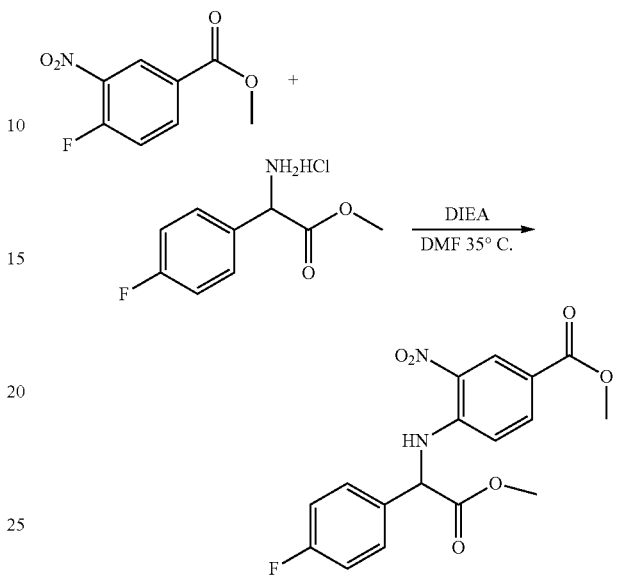

Into a 250-mL round-bottom flask, was placed methyl 4-fluoro-3-nitrobenzoate (15.4 g, 77.78 mmol, 1.00 equiv), N,N-dimethylformamide (100 mL), methyl 2-amino-2-(4-fluorophenyl)acetate hydrochloride (20.4 g, 93.15 mmol, 1.20 equiv), and DIEA (50.2 g, 389.15 mmol, 5.00 equiv). The reaction was stirred overnight at 35° C. in an oil bath.

The resulting solution was diluted with 500 ml of $H_2O$ and the resulting solids were collected by filtration. This resulted in 15 g (53%) of methyl 4-(1-(4-fluorophenyl)-2-methoxy-2-oxoethylamino)-3-nitrobenzoate as a yellow solid.

Step 2. Methyl 2-(4-fluorophenyl)-3-oxo-1,2,3,4-tetrahydroquinoxaline-6-carboxylate

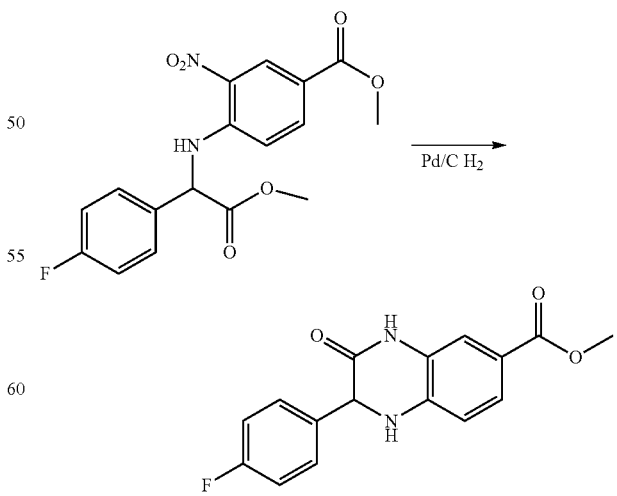

Into a 100-mL round-bottom flask, was placed methyl 4-(1-(4-fluorophenyl)-2-methoxy-2-oxoethylamino)-3-nitrobenzoate (3.5 g, 9.67 mmol, 1.00 equiv), methanol (50 mL), and palladium on carbon (10%) (500 mg). Hydrogen gas was introduced to the reaction and it. was stirred overnight at 30° C. in an oil bath. Then the solids were filtered off and the filtrate was concentrated in vacuo. This resulted in 2.6 g (90%) of methyl 2-(4-fluorophenyl)-3-oxo-1,2,3,4-tetrahydroquinoxaline-6-carboxylate as a light yellow solid.

LC-MS:(ES, m/z): 301[M+H]+

Step 3. Methyl 3-chloro-2-(4-fluorophenyl)quinoxaline-6-carboxylate

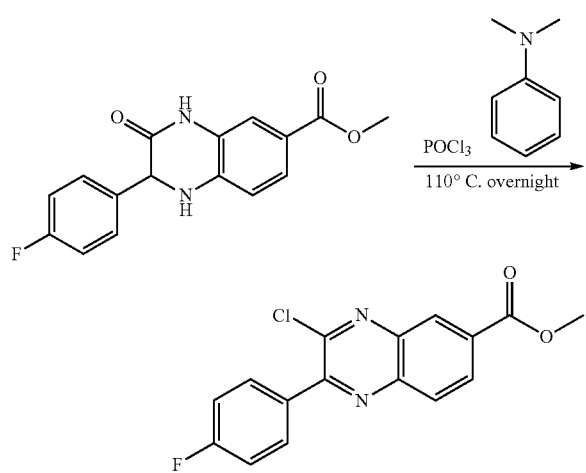

Into a 100-mL round-bottom flask, was placed methyl 2-(4-fluorophenyl)-3-oxo-1,2,3,4-tetrahydroquinoxaline-6-carboxylate (1.2 g, 4.00 mmol, 1.00 equiv), POCl₃ (12.2 g, 80.26 mmol, 20.00 equiv), N,N-dimethylbenzenamine (4.9 g, 40.50 mmol, 10.00 equiv). The resulting solution was stirred for overnight at 110° C. in an oil bath. The resulting mixture was concentrated under vacuum and diluted with 50 mL of water. The pH value of the aqueous solution was adjusted to 7 with sodium bicarbonate (4 mol/L). The resulting mixture was concentrated under vacuum and purified by silica gel chromatography with ethyl acetate/petroleum ether (1:40). This resulted in 0.5 g (40%) of methyl 3-chloro-2-(4-fluorophenyl)quinoxaline-6-carboxylate as a white solid.

LC-MS:(ES, m/z): 317 [M+H]+

¹H-NMR (300 MHz, CDC₃, ppm): δ 8.785-8.779 (d, J=1.8 Hz, 1H), 8.433-8.398 (m, 1H), 8.214-8.185 (d, J=8.7 Hz, 1H), 7.973-7.926 (m, 2H), 7.265 (d, 1H), 4.052 (s, 3H).

Step 4. (S)-Butyl 2-(4-fluorophenyl)-3-(2-methylpyrrolidin-1-yl)quinoxaline-6-carboxylate

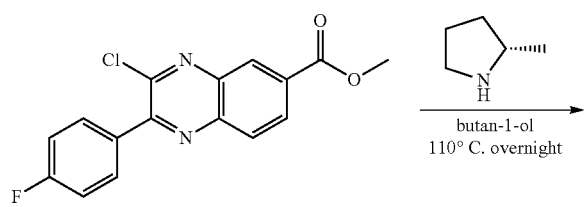

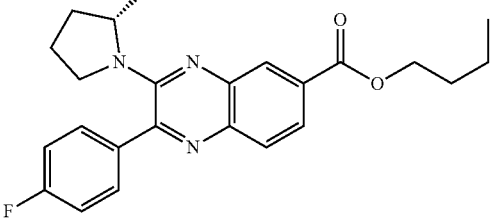

Into a 10-mL sealed tube, was placed methyl 3-chloro-2-(4-fluorophenyl)quinoxaline-6-carboxylate (150 mg, 0.47 mmol, 1.00 equiv), (S)-2-methylpyrrolidine (403 mg, 4.74 mmol, 9.99 equiv), butan-1-ol (2 mL). The resulting solution was stirred overnight at 110° C. in an oil bath. The resulting mixture was concentrated under vacuum. This resulted in 150 mg (crude) of (S)-butyl 2-(4-fluorophenyl)-3-(2-methylpyrrolidin-1-yl)quinoxaline-6-carboxylate as a yellow solid.

LC-MS:(ES, m/z): 408 [M+H]+

Step 5. (S)-2-(4-Fluorophenyl)-3-(2-methylpyrrolidin-1-yl)quinoxaline-6-carboxylic Acid

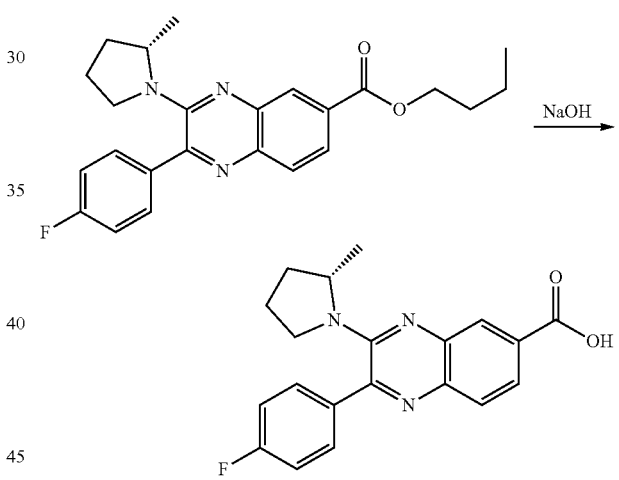

Into a 10-mL sealed tube, was placed (S)-butyl 2-(4-fluorophenyl)-3-(2-methylpyrrolidin-1-yl)quinoxaline-6-carboxylate (150 mg, 0.37 mmol, 1.00 equiv), methanol (15 mL), sodium hydroxide (74 mg, 1.85 mmol, 5.02 equiv), water (2 mL). The resulting solution was stirred for 2 hrs at 50° C. in an oil bath. The resulting mixture was concentrated under vacuum and diluted with 20 mL of H₂O. The pH value of the aqueous solution was adjusted to 4-5 with aq. hydrogen chloride (1 mol/L). The resulting solids were collected by filtration. The crude product (150 mg) was purified by Prep-HPLC with the following conditions (1 #-Waters 2767-1): Column, SunFire Prep C18, 19*150 mm Sum; mobile phase, water with 0.05% TFA and CH₃CN (60% CH₃CN up to 75% in 8 min, up to 100% in 1.5 min); Detector, UV 220 254 nm. This resulted in 60 mg (46%) of (S)-2-(4-fluorophenyl)-3-(2-methylpyrrolidin-1-yl)quinoxaline-6-carboxylic acid as a yellow solid.

LC-MS:(ES, m/z): 352 [M+H]+

¹H-NMR (300 MHz, DMSO, ppm): δ 13.161 (s, 1H), 8.243-8.240 (d, J=0.9 Hz, 1H), 7.941-7.770 (m, 4H), 7.395-

7.336 (t, J=8.85 Hz, 2H), 4.242-4.221 (m, 1H), 3.018-2.936 (m, 2H), 2.126 (s, 1H), 1.767 (s, 1H), 1.336-1.316 (d, J=6.0 Hz, 3H).

EXAMPLE 75

Butyl 2-(4-fluorophenyl)-3-(piperidin-1-yl)quinoxaline-6-carboxylate

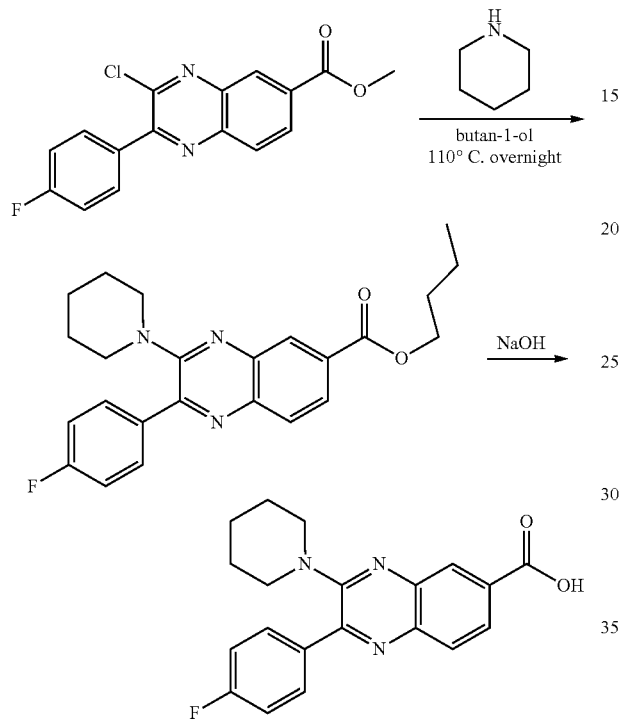

Step 1. Butyl 2-(4-fluorophenyl)-3-(piperidin-1-yl)quinoxaline-6-carboxylate Into a 10-mL sealed tube, was placed methyl 3-chloro-2-(4-fluorophenyl)quinoxaline-6-carboxylate (150 mg, 0.47 mmol, 1.00 equiv), piperidine (403 mg, 4.74 mmol, 10.00 equiv), butan-1-ol (2 mL). The resulting solution was stirred for overnight at 110° C. in an oil bath. The resulting mixture was concentrated under vacuum. This resulted in 150 mg (crude) of butyl 2-(4-fluorophenyl)-3-(piperidin-1-yl)quinoxaline-6-carboxylate as a yellow solid.

LC-MS (ES, m/z): 408 [M+H]+

Step 2. 2-(4-Fluorophenyl)-3-(piperidin-1-yl)quinoxaline-6-carboxylic Acid

Into a 50-mL round-bottom flask, was placed butyl 2-(4-fluorophenyl)-3-(piperidin-1-yl)quinoxaline-6-carboxylate (150 mg, 0.37 mmol, 1.00 equiv), methanol (15 mL), sodium hydroxide (74 mg, 1.85 mmol, 5.02 equiv), water (2 mL). The resulting solution was stirred for 2 hs at 50° C. in an oil bath. The resulting mixture was concentrated under vacuum and diluted with 20 mL of H2O. The pH value of the aqueous solution was adjusted to 4-5 with aq hydrogen chloride (1 mol/L). The resulting solids were collected by filtration. The crude product (150 mg) was purified by Prep-HPLC with the following conditions (Gilson Pre-HPLC (Max. pressure: 8 MPa)): Column, SunFire Prep C18, 19*150 mm Sum; mobile phase, water with 0.05% TFA and CH3CN (70% CH3CN up to 77.5% in 6 min, up to 100% in 0.1 min, hold 100% in 1.9 min); Detector, UV 220NMnm. This resulted in 70 mg (52%) of 2-(4-fluorophenyl)-3-(piperidin-1-yl)quinoxaline-6-carboxylic acid as a yellow solid.

LC-MS:(ES, m/z): 352 [M+H]+

1H-NMR (300 MHz, DMSO, ppm) δ 13.206 (s, 1H), 8.275 (s, 1H), 8.085-7.943 (m, 4H), 7.416-7.357 (t, J=5.9 Hz, 2H), 3.198 (s, 4H), 1.533 (s, 6H).

EXAMPLE 76

3-(Azepan-1-yl)-2-(4-fluorophenyl)quinoxaline-6-carboxylic Acid

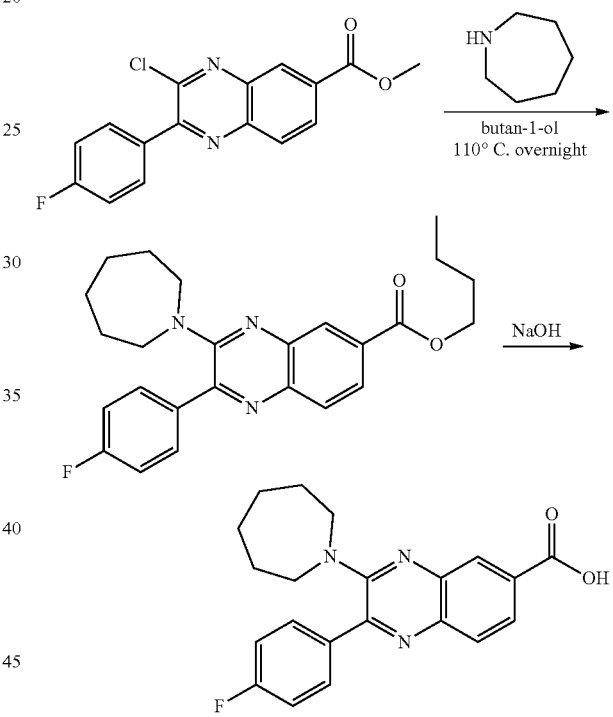

Step 1. Butyl 3-(azepan-1-yl)-2-(4-fluorophenyl)quinoxaline-6-carboxylate

Into a 10-mL sealed tube, was placed methyl 3-chloro-2-(4-fluorophenyl)quinoxaline-6-carboxylate (150 mg, 0.47 mmol, 1.00 equiv), azepane (470 mg, 4.75 mmol, 10.00 equiv), butan-1-ol (2 mL). The resulting solution was stirred for overnight at 110° C. in an oil bath. The resulting mixture was concentrated under vacuum. This resulted in 150 mg (crude) of butyl 3-(azepan-1-yl)-2-(4-fluorophenyl)quinoxaline-6-carboxylate as a yellow solid.

LC-MS (ES, m/z): 422 [M+H]+

Step 2. 3-(Azepan-1-yl)-2-(4-fluorophenyl)quinoxaline-6-carboxylic Acid

Into a 50-mL round-bottom flask, was placed butyl 3-(azepan-1-yl)-2-(4-fluorophenyl)quinoxaline-6-carboxylate (150 mg, 0.36 mmol, 1.00 equiv), methanol (15 mL), sodium hydroxide (71 mg, 1.77 mmol, 4.98 equiv), water (2 mL). The resulting solution was stirred for 2 hrs at 50° C. in an oil bath. The resulting mixture was concentrated under vacuum. The resulting solution was diluted with 20 mL of H₂O. The pH value of the aqueous solution was adjusted to 4-5 with aq hydrogen chloride (1 mol/L). The resulting solids were collected by filtration. The crude product (150 mg) was purified by Prep-HPLC with the following conditions (1 #-Waters 2767-1): Column, XbridgePrep Shield RP 18, Sum, 19*150 mm; mobile phase, water with 0.05% TFA and CH₃CN (60% CH₃CN up to 90% in 8 min, up to 100% in 1.5 min); Detector, UV 220 254 nm. This resulted in 80 mg (61%) of 3-(azepan-1-yl)-2-(4-fluorophenyl)quinoxaline-6-carboxylic acid as a yellow solid.

LC-MS:(ES, m/z): 366 [M+H]⁺

¹H-NMR (300 MHz, DMSO, ppm): δ 13.188 (s, 1H), 8.225 (s, 1H), 7.932-7.709 (m, 4H), 7.388-7.329 (t, J=8.85 Hz, 2H), 3.343-3.334 (m, 4H), 1.630 (s, 4H), 1.415 (s, 4H).

EXAMPLE 77

2-(Benzo[d][1,3]dioxol-5-yl)-3-(isopropyl(methyl) amino)quinoxaline-6-carboxylic Acid

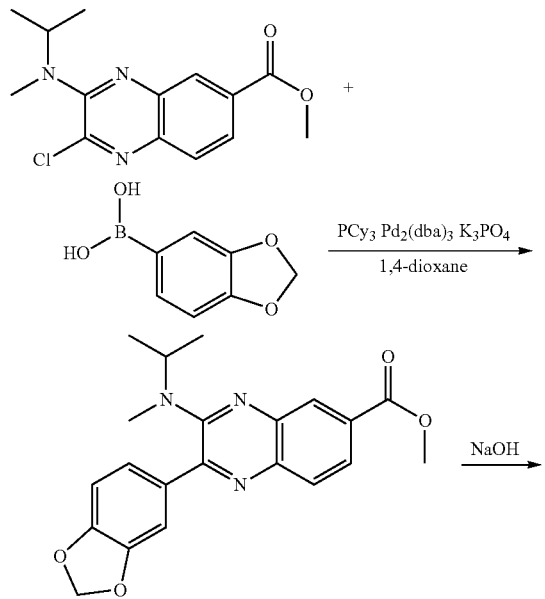

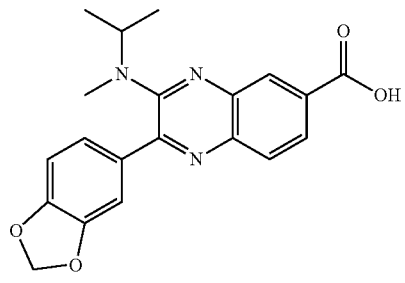

Step 1. Methyl 2-(benzo[d][1,3]dioxol-5-yl)-3-(isopropyl(methyl)amino)quinoxaline-6-carboxylate

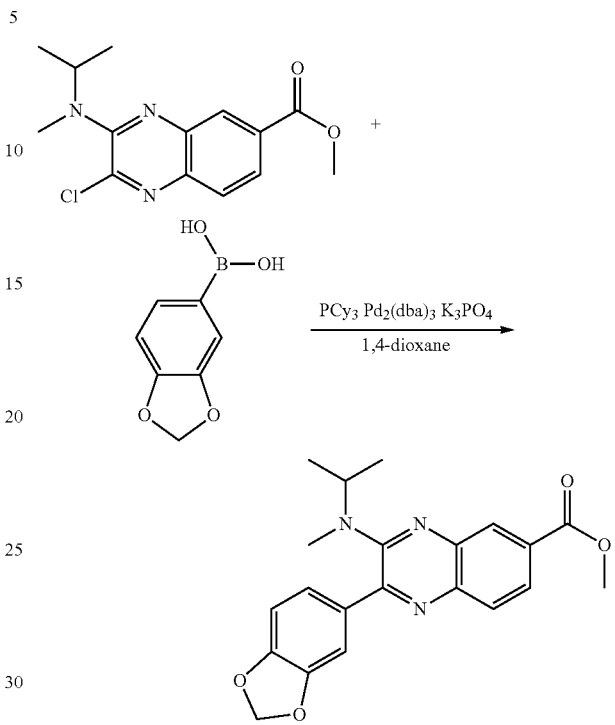

Into a 10-mL sealed tube, was placed methyl 2-chloro-3-(isopropyl(methyl)amino)quinoxaline-6-carboxylate (160 mg, 0.55 mmol, 1.00 equiv), benzo[d][1,3]dioxol-5-ylboronic acid (271 mg, 1.63 mmol, 3.00 equiv), PCy₃ (76 mg, 0.27 mmol, 0.40 equiv), Pd₂(dba)₃ (130 mg, 0.14 mmol, 0.20 equiv), K₃PO₄ (462 mg, 2.18 mmol, 4.00 equiv), and 1,4-dioxane (3 mL). The resulting solution was stirred for overnight at 100° C. in an oil bath. The resulting mixture was concentrated under vacuum. The residue was applied onto a silica gel column with ethyl acetate/petroleum ether (1:4). This resulted in 150 mg (72%) of methyl 2-(benzo[d][1,3]dioxol-5-yl)-3-(isopropyl(methyl)amino)quinoxaline-6-carboxylate as a yellow solid.

LC-MS-PH:(ES, m/z): 380 [M+H]⁺

Step 2. 2-(Benzo[d][1,3]dioxol-5-yl)-3-(isopropyl (methyl)amino)quinoxaline-6-carboxylic Acid

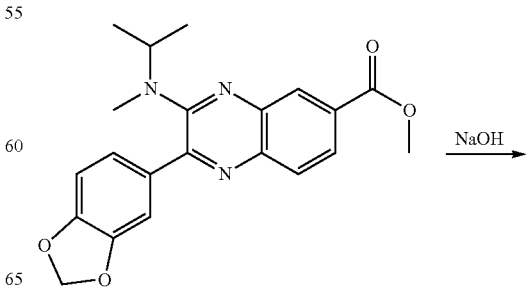

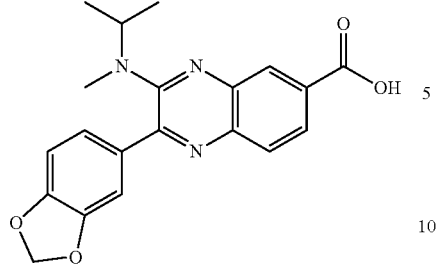

Into a 50-mL round-bottom flask, was placed a solution of methyl 2-(benzo[d][1,3]dioxol-5-yl)-3-(isopropyl(methyl)amino)quinoxaline-6-carboxylate (150 mg, 0.40 mmol, 1.00 equiv), methanol (15 mL), sodium hydroxide (79 mg, 1.98 mmol, 4.99 equiv), and water (2 mL). The resulting solution was stirred for 2 h at 50° C. in an oil bath. The resulting mixture was concentrated under vacuum. The resulting solution was diluted with 20 mL of H₂O. The pH value of the aqueous solution was adjusted to 4-5 with hydrogen chloride (1 mol/L). The resulting solids were collected by filtration. This resulted in 60 mg (40%) of 2-(benzo[d][1,3]dioxol-5-yl)-3-(isopropyl(methyl)amino)quinoxaline-6-carboxylic acid as a yellow solid.

LC-MS:(ES, m/z): 366 [M+H]⁺

¹H NMR (300 MHz, DMSO, ppm) δ 13.035 (s, 1H), 8.238 (s, 1H), 7.946-7.895 (m, 2H), 7.412-7.388 (m, 2H), 7.075-7.055 (d, J=6.0 Hz, 1H), 6.123 (s, 2H), 4.233-4.183 (m, 1H), 2.693 (s, 3H), 1.060-1.043 (d, J=5.1 Hz, 6H).

EXAMPLE 78

2-(4-Fluorophenyl)-3-(3-(methoxymethyl)piperidin-1-yl)quinoxaline-6-carboxylic Acid

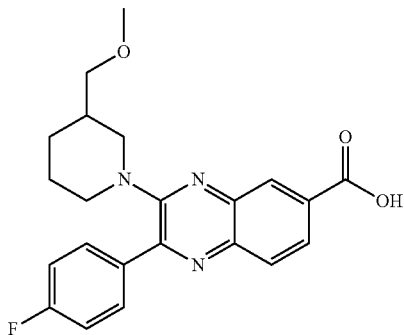 [SMILES: COCC1CCCN(c2nc3cc(C(=O)O)ccc3nc2-c2ccc(F)cc2)C1]

Step 1. Methyl 2-(4-fluorophenyl)-3-(3-(methoxymethyl)piperidin-1-yl)quinoxaline-6-carboxylate

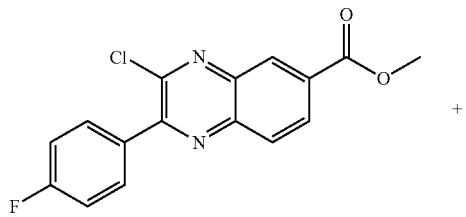

+

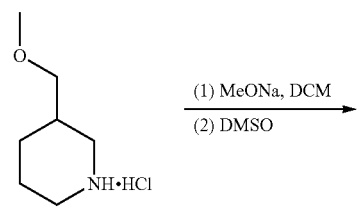

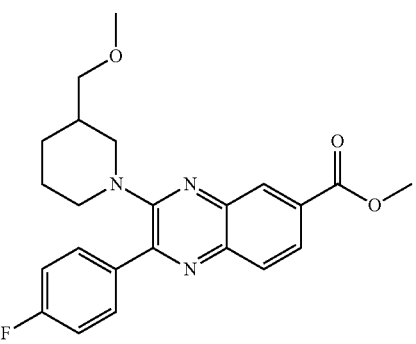

Into a 50-mL sealed tube, was placed a solution of 3-(methoxymethyl)piperidine hydrochloride (170 mg, 1.03 mmol, 2.00 equiv) in dichloromethane (7 mL), and sodium methoxide (128 mg, 2.37 mmol, 5.00 equiv). The resulting solution was stirred for 3 h at room temperature. The solids were filtered out. The resulting mixture was concentrated under vacuum and was added into a 8-mL sealed tube with methyl 3-chloro-2-(4-fluorophenyl)quinoxaline-6-carboxylate (150 mg, 0.47 mmol, 1.00 equiv) and DMSO (4 mL). The mixture was stirred overnight at 100° C. Water was added to quench the reaction and the resulting solids were collected by filtration. The residue was purified by silica gel column chromatography with PE/EA (50:1). This resulted in 179.9 mg (88%) of methyl 2-(4-fluorophenyl)-3-(3-(methoxymethyl)piperidin-1-yl)quinoxaline-6-carboxylate as a yellow solid.

LC-MS:(ES, m/z): 410 [M+H]⁺

Step 2. 2-(4-Fluorophenyl)-3-(3-(methoxymethyl)piperidin-1-yl)quinoxaline-6-carboxylic Acid

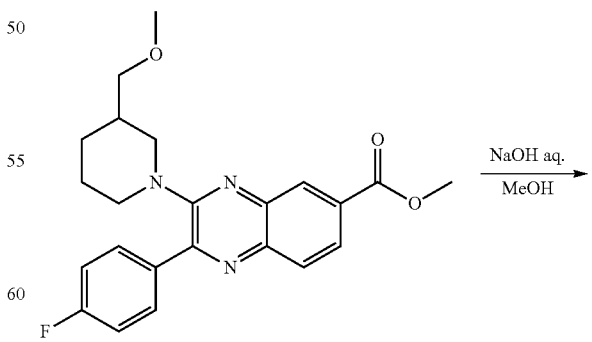

-continued

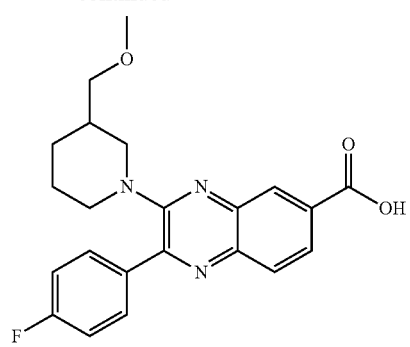

Into a 50-mL round-bottom flask, was placed a solution of methyl 2-(4-fluorophenyl)-3-(3-(methoxymethyl)piperidin-1-yl)quinoxaline-6-carboxylate (152.3 mg, 0.37 mmol, 1.00 equiv) in methanol (15 mL). This was followed by the addition of a solution of sodium hydroxide (44.7 mg, 1.12 mmol, 3.00 equiv) in water (1.5 mL) dropwise with stirring. The resulting solution was stirred for 4 h at 50° C. in an oil bath. The resulting mixture was concentrated under vacuum. The resulting solution was diluted with water. The pH value of the aqueous solution was adjusted to 3-4 with 1N hydrogen chloride. The resulting solids were collected by filtration and the crude product (240 mg) was purified by Prep-HPLC under the following conditions (AGILENT Pre-HPLC(UV-Directed)): Column, SunFire Prep C18, 19*150 mm 5um; mobile phase, water with 0.05% TFA and CH$_3$CN (45% CH$_3$CN up to 60% in 8 min, hold 60% in 5 min, up to 100% in 0.1 min, hold 100% in 1.4 min); Detector, uv 220&254 nm. This resulted in 89 mg (61%) of 2-(4-fluorophenyl)-3-(3-(methoxymethyl)piperidin-1-yl)quinoxaline-6-carboxylic acid as a yellow solid.

LC-MS:(ES, m/z): 396 [M+H]$^+$ $^1$H-NMR (300 MHz, DMSO, ppm) 13.22 (s, 1H), 8.29-8.28 (d, J=3 Hz, 1H), 8.05-7.95 (m, 4H), 7.41-7.35 (t, J=9H, 2H), 3.77-3.73 (d, J=12 Hz, 1H), 3.59-3.55 (d, J=12 Hz, 1H), 3.19-3.07 (m, 5H), 2.77-2.70 (t, J=10.5 Hz, 1H), 2.60-2.57 (d, J=9 Hz, 1H), 1.72 (s, 1H), 1.67-1.57 (m, 3H), 1.50-1.49 (m, 1H).

EXAMPLE 79

3-(3,3-Dimethylpiperidin-1-yl)-2-(4-fluorophenyl)quinoxaline-6-carboxylic Acid

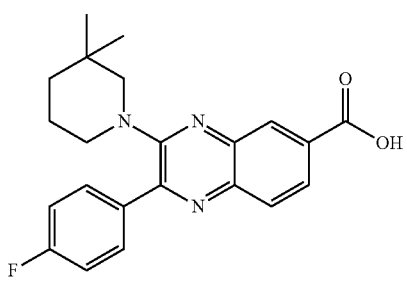 [SMILES: CC1(C)CCCN(c2nc3cc(C(=O)O)ccc3nc2-c2ccc(F)cc2)C1]

Step 1. Methyl 3-(3,3-dimethylpiperidin-1-yl)-2-(4-fluorophenyl)quinoxaline-6-carboxylate

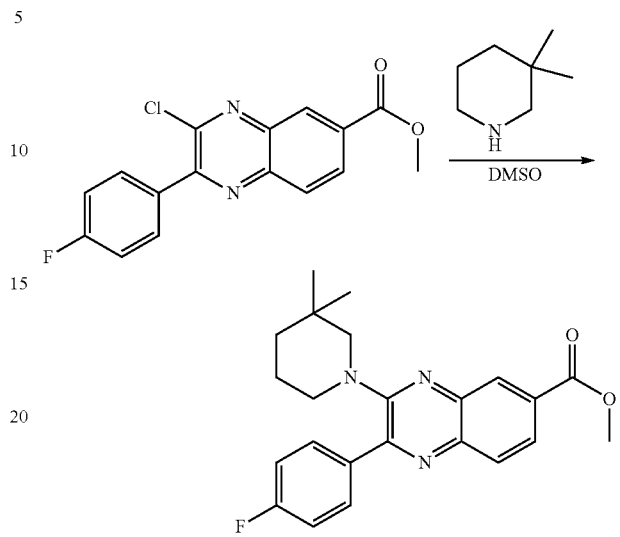

Into a 10-mL sealed tube, was placed methyl 3-chloro-2-(4-fluorophenyl)quinoxaline-6-carboxylate (150 mg, 0.47 mmol, 1.00 equiv), 3,3-dimethylpiperidine (107 mg, 0.95 mmol, 2.00 equiv), DMSO (2 mL). The resulting solution was stirred overnight at 100° C. in an oil bath. The resulting solution was diluted with 20 mL of H$_2$O. The resulting solids were collected by filtration. The residue was purified by silica gel column chromatography with ethyl acetate/petroleum ether (1:40). This resulted in 120 mg (64%) of methyl 3-(3,3-dimethylpiperidin-1-yl)-2-(4-fluorophenyl)quinoxaline-6-carboxylate as a yellow solid.

LC-MS:(ES, m/z): 394 [M+H]$^+$

Step 2. 3-(3,3-Dimethylpiperidin-1-yl)-2-(4-fluorophenyl)quinoxaline-6-carboxylic Acid

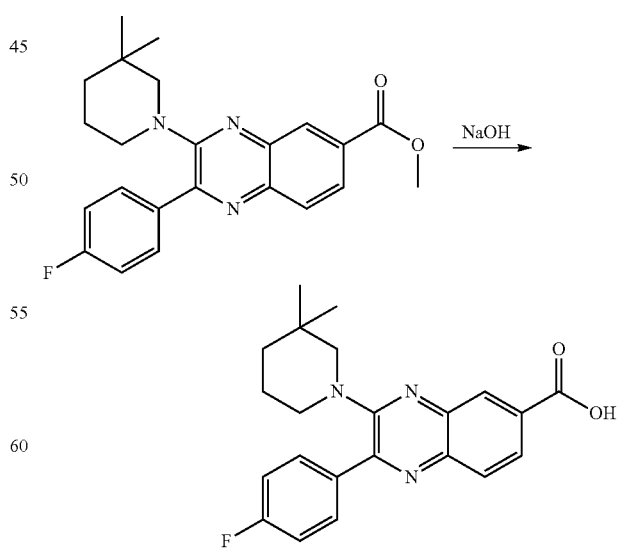

Into a 50-mL round-bottom flask, was placed a solution of methyl 3-(3,3-dimethylpiperidin-1-yl)-2-(4-fluorophenyl)

quinoxaline-6-carboxylate (120 mg, 0.31 mmol, 1.00 equiv), methanol (15 mL), sodium hydroxide (61 mg, 1.52 mmol, 4.99 equiv), and water (2 mL). The resulting solution was stirred for 2 h at 50° C. in an oil bath. The resulting mixture was concentrated under vacuum. The resulting solution was diluted with 20 mL of H₂O. The pH value of the aqueous solution was adjusted to 4-5 with hydrogen chloride (1 mol/L). The resulting solids were collected by filtration. This resulted in 60 mg (52%) of 3-(3,3-dimethylpiperidin-1-yl)-2-(4-fluorophenyl)quinoxaline-6-carboxylic acid as a yellow solid.

LC-MS:(ES, m/z): 380 [M+H]⁺

¹H-NMR (300 MHz, DMSO, ppm) δ 8.291-8.290 (d, J=0.3 Hz, 1H), 7.992-7.957 (m, 4H), 7.435-7.391 (t, J=6.6 Hz, 2H), 3.067-3.039 (m, 4H), 1.466 (s, 2H), 1.357-1.329 (m, 2H), 0.905 (s, 6H).

EXAMPLE 80

2-(4-Fluorophenyl)-3-(3-methylpiperidin-1-yl)quinoxaline-6-carboxylic Acid

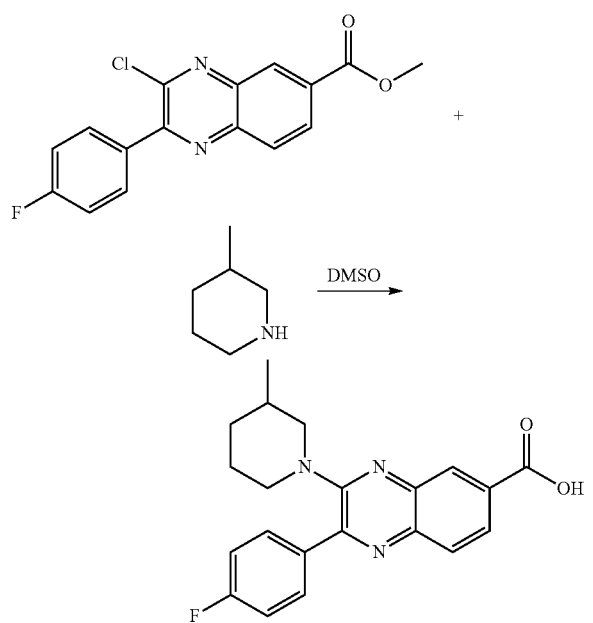

Into a 8-mL sealed tube, was placed methyl 3-chloro-2-(4-fluorophenyl)quinoxaline-6-carboxylate (200 mg, 0.63 mmol, 1.00 equiv), 3-methylpiperidine (313 mg, 3.16 mmol, 5.00 equiv), DMSO (3 mL). The resulting solution was stirred for overnight at 110° C. in an oil bath. The reaction was then quenched by the addition of water. The pH value of the aqueous solution was adjusted to 3-4 with 1N hydrogen chloride. The resulting solids were collected by filtration. The crude product (240 mg) was purified by Prep-HPLC under the following conditions (1 #-UV1-SHIMADZU-SPD-20A): Column, SunFire Prep C18, 5 um, 19*150 mm; mobile phase, water with 0.05% TFA and CH₃CN (30% CH₃CN up to 100% in 8 min, hold 100% in 1.5 min, down to 30% in 1 min); Detector, Gilson UV Detector 220 nm. This resulted in 75 mg (32%) of 2-(4-fluorophenyl)-3-(3-methylpiperidin-1-yl)quinoxaline-6-carboxylic acid as a yellow solid.

LC-MS:(ES, m/z): 366 [M+H]⁺

¹H NMR (300 MHz, DMSO, ppm) 13.24 (s, 1H), 8.28 (s, 1H), 8.05-7.94 (m, 4H), 7.41-7.35 (t, J=9 Hz, 2H), 3.64-3.60 (d, J=12 Hz, 2H), 2.70-2.51 (m, 1H), 2.50-2.37 (m, 1H), 1.75-1.46 (m, 5H), 1.06-1.05 (d, J=3 Hz, 3H).

EXAMPLE 81

2-(2,3-Dihydrobenzo[b][1,4]dioxin-6-yl)-3-(isopropyl(methyl)amino)quinoxaline-6-carboxylic Acid

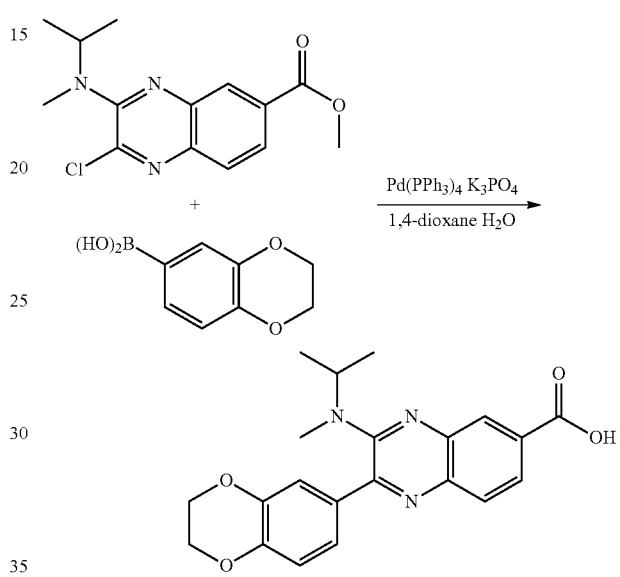

Into a 10-mL sealed tube, was placed methyl 2-chloro-3-(isopropyl(methyl)amino)quinoxaline-6-carboxylate (150 mg, 0.51 mmol, 1.00 equiv), 2,3-dihydrobenzo[b][1,4]dioxin-6-ylboronic acid (184 mg, 1.02 mmol, 2.00 equiv), Pd(PPh₃)₂Cl₂ (36 mg, 0.05 mmol, 0.10 equiv), K₃PO₄ (433 mg, 2.04 mmol, 3.99 equiv), 1,4-dioxane/H₂O (4/1 mL). The resulting solution was stirred overnight at 100° C. in an oil bath. The resulting mixture was concentrated under vacuum. The residue was purified by silica gel column chromatography with dichloromethane/methanol (10:1). The crude product (70 mg) was purified by Prep-HPLC under the following conditions (1 #-Waters 2767-1): Column, SunFire Prep C18, 19*150 mm 5 um; mobile phase, water with 0.05% TFA and CH₃CN (48% CH₃CN up to 68% in 8 min, up to 100% in 2 min); Detector, UV 220 254 nm. This resulted in 20 mg (10%) of 2-(2,3-dihydrobenzo[b][1,4]dioxin-6-yl)-3-(isopropyl(methyl)amino)quinoxaline-6-carboxylic acid as a yellow solid.

LC-MS:(ES, m/z): 380 [M+H]⁺

¹H NMR (300 MHz, DMSO, ppm) 813.109 (s, 1H), 8.233 (s, 1H), 7.949-7.885 (m, 2H), 7.402-7.356 (m, 2H), 7.008-6.980 (d, J=8.4 Hz, 1H), 4.315 (s, 4H), 4.251-4.163 (m, 1H), 2.729-2.693 (d, J=10.8 Hz, 3H), 1.061-1.039 (d, J=6.6 Hz, 6H).

EXAMPLE 82

3-(Isopropyl(methyl)amino)-2-(4-(methylsulfonyl)phenyl)quinoxaline-6-carboxylic Acid

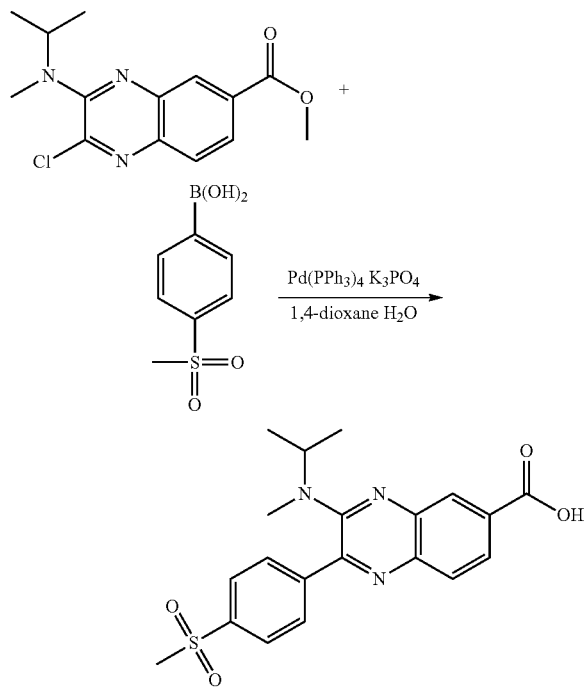

Into a 10-mL round-bottom flask, was placed methyl 2-chloro-3-(isopropyl(methyl) amino) quinoxaline-6-carboxylate (150 mg, 0.51 mmol, 1.00 equiv), 4-(methylsulfonyl)phenylboronic acid (205 mg, 1.02 mmol, 2.00 equiv), $Pd(PPh_3)_4$ (59 mg, 0.05 mmol, 0.10 equiv), $K_3PO_4$ (433 mg, 2.04 mmol, 3.99 equiv), and 1,4-dioxane/$H_2O$ (4/2 mL). The resulting solution was stirred overnight at 100° C. in an oil bath. The resulting mixture was concentrated under vacuum. The residue was purified by silica gel column chromatography with dichloromethane/methanol (1:30). The crude product (60 mg) was purified by Prep-HPLC under the following conditions (1#-Waters 2767-2): Column, SunFire Prep C18, 19*150 mm 5 um; mobile phase, water with 0.05% TFA and $CH_3CN$ (35% $CH_3CN$ up to 57% in 9 min, up to 100% in 0.1 min, hold 100% in 0.9 min); Detector, uV 220&254 nm. This resulted in 25 mg (12%) of 3-(isopropyl(methyl)amino)-2-(4-(methylsulfonyl)phenyl)quinoxaline-6-carboxylic acid as a yellow solid.

LC-MS:(ES, m/z): 400 [M+H]$^+$ $^1$H-NMR (300 MHz, DMSO, ppm) δ 13.198 (s, 1H), 8.280 (s, 1H), 8.091 (s, 4H), 7.997-7.968 (d, J=8.7 Hz, 2H), 4.232-4.189 (m, 1H), 3.329-3.292 (d, J=11.1 Hz, 3H), 2.653 (s, 3H), 1.077-1.055 (d, J=6.6 Hz, 6H).

EXAMPLE 83

2-(Benzo[d][1,3]dioxol-5-yl)-3-((S)-2-methylpyrrolidin-1-yl)quinoxaline-6-carboxylic Acid

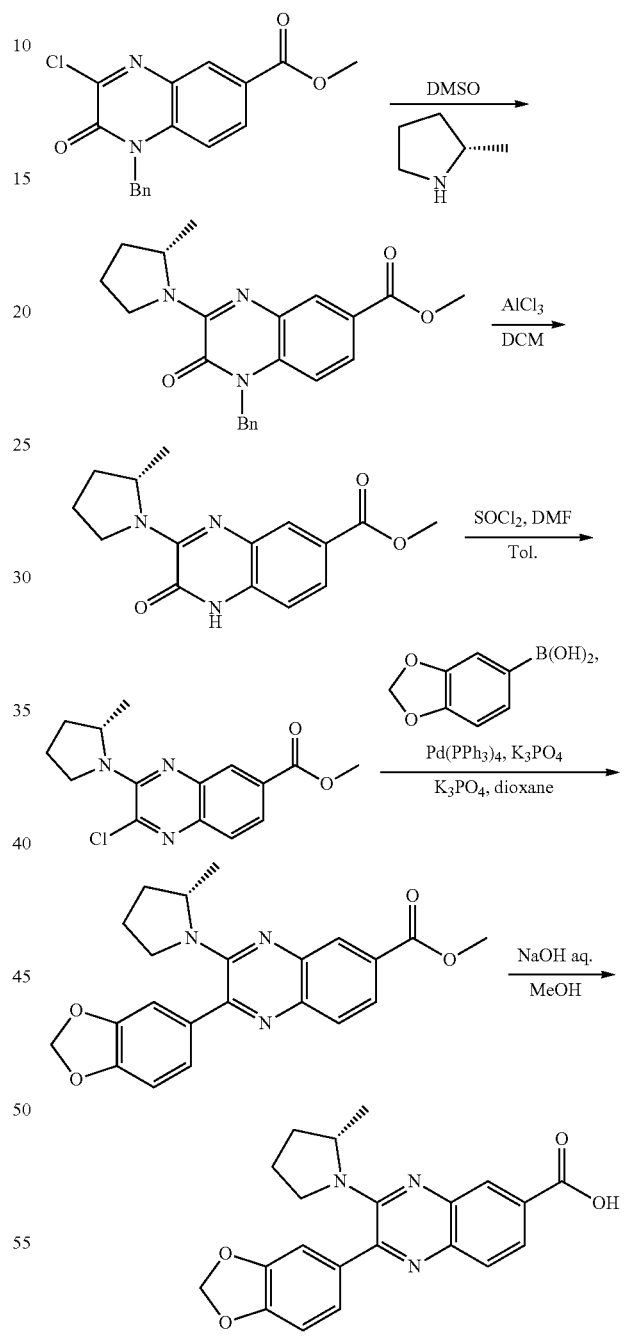

Step 1. (S)-methyl 1-benzyl-3-(2-methylpyrrolidin-1-yl)-2-oxo-1,2-dihydroquinoxaline-6-carboxylate

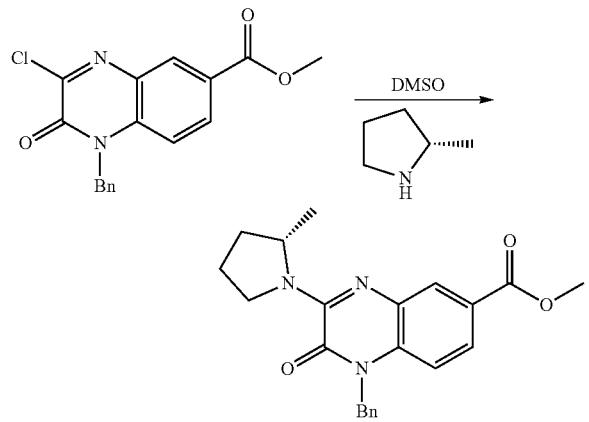

Into a 50-mL round-bottom flask, was placed methyl 1-benzyl-3-chloro-2-oxo-1,2-dihydroquinoxaline-6-carboxylate (3 g, 9.15 mmol, 1.00 equiv), (S)-2-methylpyrrolidine (1.55 g, 18.24 mmol, 2.00 equiv), DMSO (16 mL). The resulting solution was stirred overnight at 80° C. in an oil bath. The resulting solution was concentrated under vacuum. The residue was purified by silica gel column chromatography with ethyl acetate/petroleum ether (1:20). This resulted in 2.2 g (64%) of (S)-methyl 1-benzyl-3-(2-methylpyrrolidin-1-yl)-2-oxo-1,2-dihydroquinoxaline-6-carboxylate as a light yellow solid.

LC-MS:(ES, m/z): 378 [M+H]+

Step 2. (S)-methyl 3-(2-methylpyrrolidin-1-yl)-2-oxo-1,2-dihydroquinoxaline-6-carboxylate

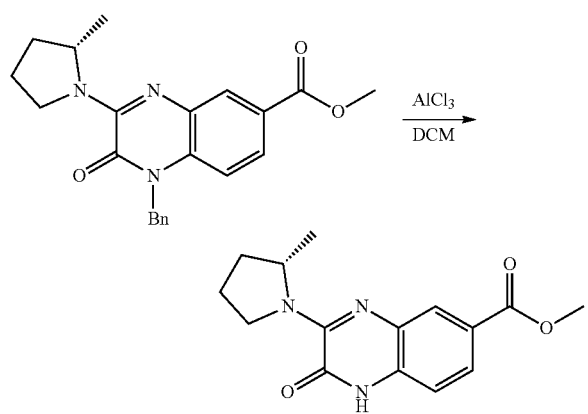

Into a 250-mL round-bottom flask, was placed a solution of (S)-methyl 1-benzyl-3-(2-methylpyrrolidin-1-yl)-2-oxo-1,2-dihydroquinoxaline-6-carboxylate (2.2 g, 5.84 mmol, 1.00 equiv) in dichloromethane (100 mL). This was followed by the addition of AlCl3 (7.7 g, 58.33 mmol, 10.00 equiv) in several batches. The resulting solution was stirred overnight at 30° C. in an oil bath. The resulting solution was concentrated under vacuum. The residue was applied onto a silica gel column with dichloromethane/methanol (1:100). This resulted in 900 mg (53%) of (S)-methyl 3-(2-methylpyrrolidin-1-yl)-2-oxo-1,2-dihydroquinoxaline-6-carboxylate as a brown solid.

LC-MS:(ES, m/z): 288 [M+H]+

Step 3. (S)-methyl 2-chloro-3-(2-methylpyrrolidin-1-yl)quinoxaline-6-carboxylate

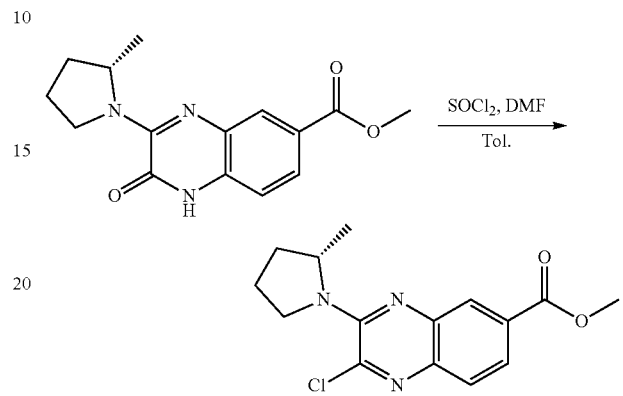

Into a 100-mL round-bottom flask, was placed a solution of (S)-methyl 3-(2-methylpyrrolidin-1-yl)-2-oxo-1,2-dihydroquinoxaline-6-carboxylate (900 mg, 3.14 mmol, 1.00 equiv), toluene (20 mL), thionyl chloride (11.2 g, 94.12 mmol, 30.00 equiv), N,N-dimethylformamide (4 mL). The resulting solution was heated to reflux for 3 hr in an oil bath. The resulting mixture was concentrated under vacuum. The residue was purified by silica gel column chromatography with ethyl acetate/petroleum ether (1:50). This resulted in 143 mg (13%) of (S)-methyl 2-chloro-3-(2-methylpyrrolidin-1-yl)quinoxaline-6-carboxylate as yellow oil.

LC-MS:(ES, m/z): 306 [M+H]+

Step 4. Methyl 2-(benzo[d][1,3]dioxol-5-yl)-3-((S)-2-methylpyrrolidin-1-yl)quinoxaline-6-carboxylate

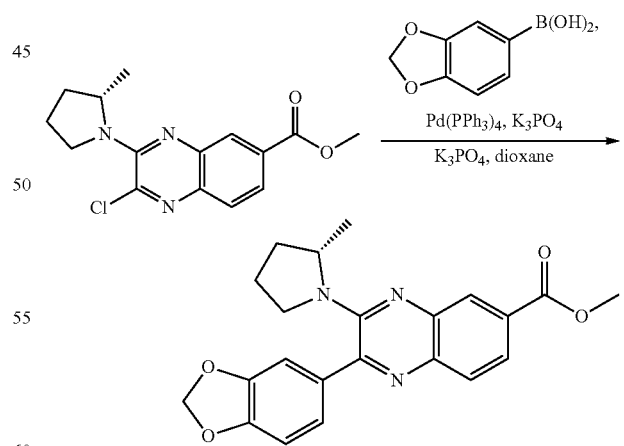

Into a 8-mL sealed tube purged and maintained with an inert atmosphere of nitrogen, was placed (S)-methyl 2-chloro-3-(2-methylpyrrolidin-1-yl)quinoxaline-6-carboxylate (89.2 mg, 0.29 mmol, 1.00 equiv), benzo[d][1,3]dioxol-5-ylboronic acid (97.1 mg, 0.58 mmol, 2.00 equiv), Pd(PPh3)4 (33.7 mg, 0.03 mmol, 0.10 equiv), K3PO4 (248 mg, 1.17 mmol, 4.00 equiv), dioxane (4 mL). The resulting solution was stirred overnight at 100° C. in an oil bath. The resulting solution was concentrated under vacuum. The residue was purified by silica gel column chromatography with PE/EA (50:1). This resulted in 94 mg (82%) of methyl 2-(benzo[d][1,3]dioxol-5-yl)-3-((S)-2-methylpyrrolidin-1-yl)quinoxaline-6-carboxylate as yellow oil.

LC-MS:(ES, m/z): 392 [M+H]$^+$

Step 5. 2-(benzo[d][1,3]dioxol-5-yl)-3-((S)-2-methylpyrrolidin-1-yl)quinoxaline-6-carboxylic Acid

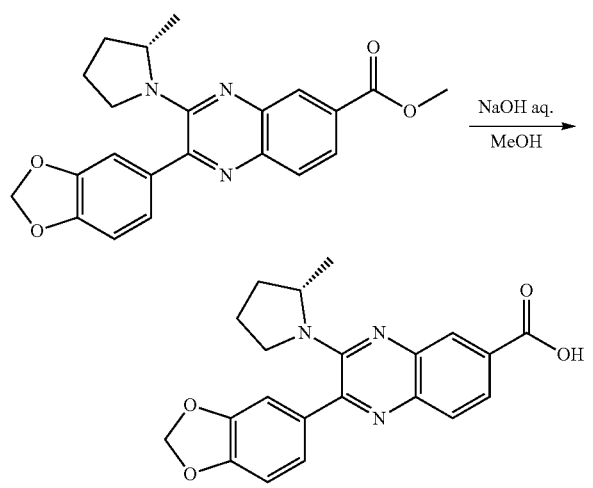

Into a 50-mL round-bottom flask, was placed a solution of methyl 2-(benzo[d][1,3]dioxol-5-yl)-3-((S)-2-methylpyrrolidin-1-yl)quinoxaline-6-carboxylate (94 mg, 0.24 mmol, 1.00 equiv) in methanol (15 mL). This was followed by the addition of a solution of sodium hydroxide (58.9 mg, 1.47 mmol, 5.00 equiv) in water (3 mL) dropwise with stirring. The resulting solution was stirred for 5 hr at 50° C. in an oil bath. The resulting mixture was concentrated under vacuum. The resulting solution was diluted with H$_2$O. The pH value of the aqueous solution was adjusted to 3-4 with 1N aqueous hydrogen chloride. The resulting solids were collected by filtration. The crude product (100 mg) was purified by Prep-HPLC with the following conditions (1#-Waters 2767-2): Column, SunFire Prep C18, 19*150 mm Sum; mobile phase, water with 0.05% TFA and CH$_3$CN (10% CH$_3$CN up to 80% in 8.5 min, hold 80% in 1 min, up to 100% in 0.1 min, hold 100% in 0.8 min); Detector, UV 220&254 nm. This resulted in 40 mg (44%) of 2-(benzo[d][1,3]dioxol-5-yl)-3-((S)-2-methylpyrrolidin-1-yl)quinoxaline-6-carboxylic acid as a yellow solid.

LC-MS:(ES, m/z): 378 [M+H]$^+$ $^1$H NMR (400 MHz, DMSO, ppm) 13.05 (s, 1H), 8.23 (s, 1H), 7.91-7.90 (t, J=2 Hz, 2H), 7.30-7.23 (t, J=14 Hz, 2H), 7.07-7.05 (d, J=8 Hz, 1H), 6.13-6.12 (d, J=4 Hz, 2H), 4.27-4.22 (m, 1H), 3.16-3.10 (m, 1H), 3.02-2.98 (m, 1H), 2.13 (s, 1H), 1.79 (s, 1H), 1.62-1.50 (m, 2H), 1.33-1.24 (m, 3H).

EXAMPLE 84

2-(1H-Indol-5-yl)-3-(isopropyl(methyl)amino)quinoxaline-6-carboxylic Acid

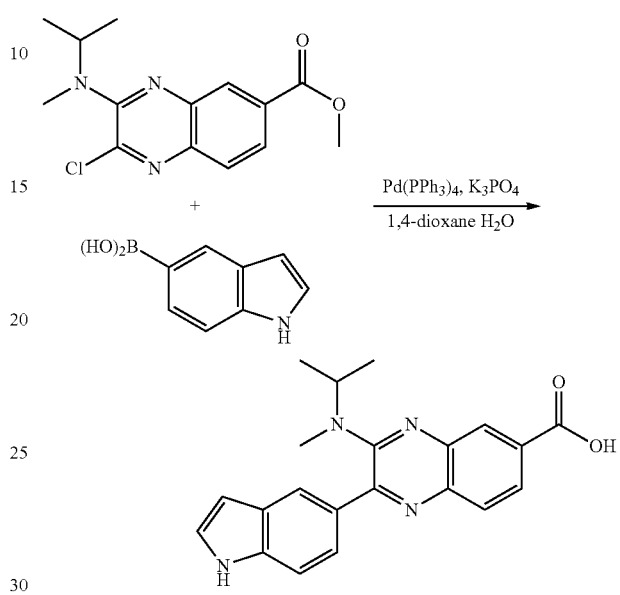

Into a 10-mL sealed tube, was placed methyl 2-chloro-3-(isopropyl(methyl)amino)quinoxaline-6-carboxylate (60 mg, 0.20 mmol, 1.00 equiv), 1H-indol-5-ylboronic acid (100 mg, 0.62 mmol, 3.05 equiv), Pd(PPh$_3$)$_4$ (23.6 mg, 0.02 mmol, 0.10 equiv), K$_3$PO$_4$ (174 mg, 0.82 mmol, 4.01 equiv), 1,4-dioxane/H$_2$O (4/1 mL). The resulting solution was stirred for overnight at 100° C. in an oil bath. The resulting mixture was concentrated under vacuum. The residue was applied onto a silica gel column with dichloromethane/methanol (10:1). The crude product (60 mg) was purified by Prep-HPLC with the following conditions (1#-Waters 2767-2): Column, SunFire Prep C18, 19*150 mm Sum; mobile phase, water with 0.05% TFA and CH$_3$CN (30% CH$_3$CN up to 55% in 8 min, hold 55% in 3 min, up to 100% in 0.1 min, hold 100% in 0.9 min); Detector, UV 220&254 nm. This resulted in 25 mg (33%) of 2-(1H-indol-5-yl)-3-(isopropyl(methyl)amino)quinoxaline-6-carboxylic acid as a red solid.

LC-MS:(ES, m/z): 361 [M+H]$^+$ $^1$H-NMR (300 MHz, DMSO, ppm) δ 11.305 (s, 1H), 8.254 (s, 1H), 8.124 (s, 1H), 7.923-7.920 (d, J=0.9 Hz, 2H), 7.668-7.662 (m, 1H), 7.530-7.501 (d, J=8.7 Hz, 1H), 7.439-7.421 (t, J=2.7 Hz, 1H), 6.559 (s, 1H), 4.263-4.175 (m, 1H), 2.704 (s, 3H), 1.013-0.990 (d, J=6.9 Hz, 6H).

EXAMPLE 85

3-(Isopropyl(methyl)amino)-2-(4-(trifluoromethoxy)phenyl)quinoxaline-6-carboxylic Acid

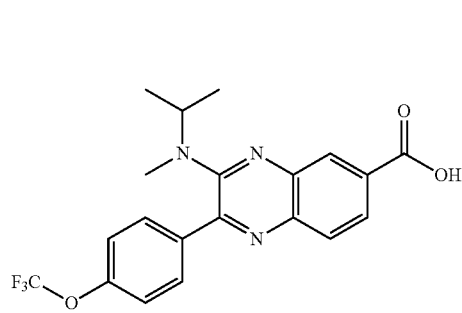 [SMILES: CC(C)N(C)c1nc2cc(C(=O)O)ccc2nc1-c1ccc(OC(F)(F)F)cc1]

Step 1. Methyl 3-(isopropyl(methyl)amino)-2-(4-(trifluoromethoxy)phenyl)quinoxaline-6-carboxylate

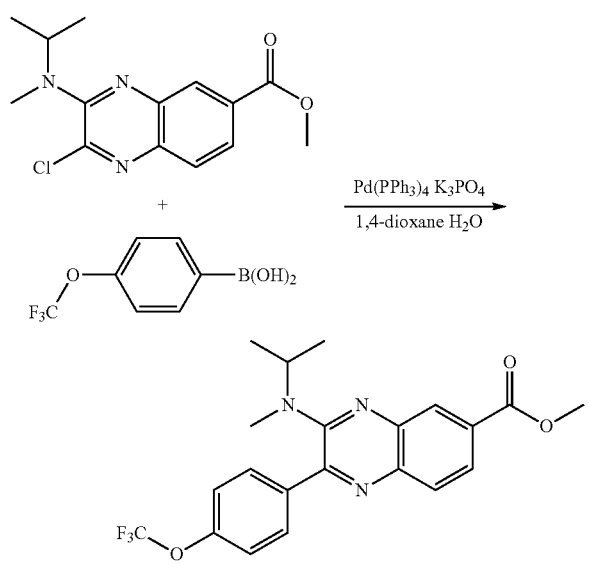

Into a 10-mL sealed tube, was placed methyl 2-chloro-3-(isopropyl(methyl)amino)quinoxaline-6-carboxylate (200 mg, 0.68 mmol, 1.00 equiv), 4-(trifluoromethoxy)phenylboronic acid (280 mg, 1.36 mmol, 1.99 equiv), Pd(PPh$_3$)$_4$ (157 mg, 0.14 mmol, 0.20 equiv), K$_3$PO$_4$ (577 mg, 2.73 mmol, 4.01 equiv), 1,4-dioxane (4 mL). The resulting solution was stirred for overnight at 100° C. in an oil bath. The resulting mixture was concentrated under vacuum. The residue was purified by silica gel column chromatography with ethyl acetate/petroleum ether (1:40). This resulted in 120 mg (42%) of methyl 3-(isopropyl(methyl)amino)-2-(4-(trifluoromethoxy)phenyl)quinoxaline-6-carboxylate as a yellow solid.

Step 2. 3-(isopropyl(methyl)amino)-2-(4-(trifluoromethoxy)phenyl)quinoxaline-6-carboxylic Acid

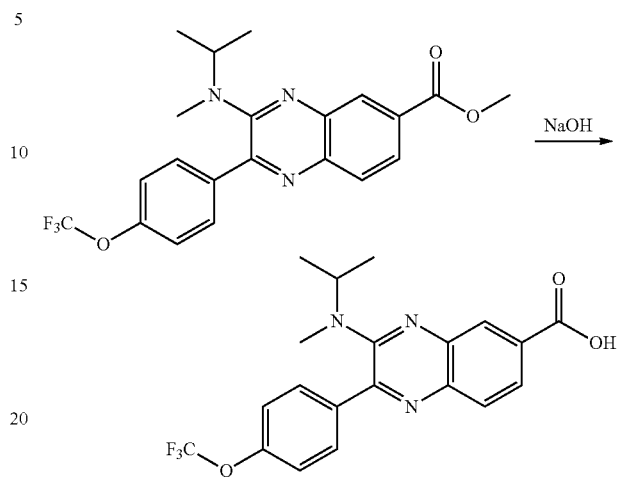

Into a 50-mL round-bottom flask, was placed a solution of methyl 3-(isopropyl(methyl)amino)-2-(4-(trifluoromethoxy)phenyl)quinoxaline-6-carboxylate (120 mg, 0.29 mmol, 1.00 equiv) in methanol (15 mL), sodium hydroxide (57 mg, 1.43 mmol, 4.98 equiv), H$_2$O (2 mL). The resulting solution was stirred for 2 hr at 50° C. in an oil bath. The resulting mixture was concentrated under vacuum and diluted with 20 mL of H$_2$O. The pH value of the aqueous solution was adjusted to 4-5 with hydrogen chloride (2.5 mol/L). The resulting solids were collected by filtration. The crude product (100 mg) was purified by Prep-HPLC with the following conditions (1#-Waters 2767-1): Column, SunFire Prep C18, 19*150 mm Sum; mobile phase, water with 0.05% TFA and CH$_3$CN (65% CH$_3$CN up to 85% in 8 min, up to 100% in 2 min); Detector, UV 220 254 nm. This resulted in 70 mg (60%) of 3-(isopropyl(methyl)amino)-2-(4-(trifluoromethoxy)phenyl)quinoxaline-6-carboxylic acid as a yellow solid.

LC-MS:(ES, m/z): 406 [M+H]$^+$ $^1$H NMR (300 MHz, DMSO, ppm) δ 8.273 (s, 1H), 8.033-7.955 (m, 4H), 7.552-7.525 (d, J=8.1 Hz, 2H), 4.202-4.114 (m, 1H), 2.667 (s, 3H), 1.052-1.030 (d, J=6.6 Hz, 6H).

EXAMPLE 86

2-(4-Cyanophenyl)-3-(isopropyl(methyl)amino)quinoxaline-6-carboxylic Acid

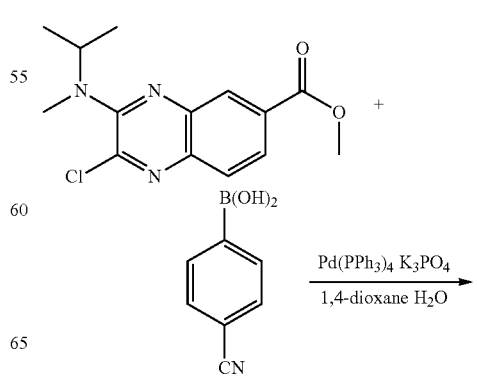

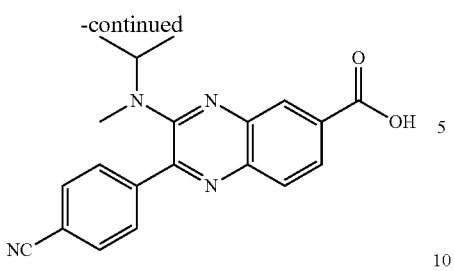

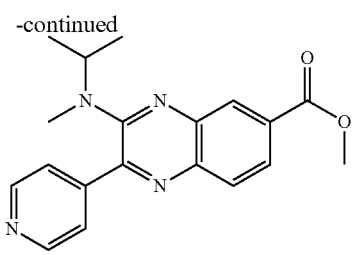

Into a 10-mL sealed tube, was placed methyl 2-chloro-3-(isopropyl(methyl)amino)quinoxaline-6-carboxylate (150 mg, 0.51 mmol, 1.00 equiv), 4-cyanophenylboronic acid (150 mg, 1.02 mmol, 1.99 equiv), Pd(PPh$_3$)$_2$Cl$_2$ (36 mg, 0.05 mmol, 0.10 equiv), K$_3$PO$_4$ (433 mg, 2.04 mmol, 3.99 equiv), 1,4-dioxane/H$_2$O (4/1 mL). The resulting solution was stirred for overnight at 100° C. in an oil bath. The resulting mixture was concentrated under vacuum. The residue was applied onto a silica gel column with dichloromethane/methanol (10:1). The resulting crude product (100 mg) was purified by Prep-HPLC under the following conditions (1 #-Waters 2767-1): Column, SunFire Prep C18, 19*150 mm 5 um; mobile phase, water with 0.05% TFA and CH$_3$CN (48% CH$_3$CN up to 68% in 8 min, up to 100% in 2 min); Detector, uv 220 254 nm. This resulted in 22 mg (12%) of 2-(4-cyanophenyl)-3-(isopropyl(methyl)amino) quinoxaline-6-carboxylic acid as a yellow solid.

LC-MS:(ES, m/z): 347 [M+H]$^+$ $^1$H-NMR (300 MHz, DMSO, ppm) δ 13.242 (s, 1H), 8.276-8.273 (d, J=0.9 Hz, 2H), 8.052-7.931 (m, 6H), 4.211-4.123 (m, 1H), 2.647 (s, 3H), 1.060-1.038 (d, J=6.6 Hz, 6H).

EXAMPLE 87

3-(Isopropyl(methyl)amino)-2-(pyridin-4-yl)quinoxaline-6-carboxylic Acid

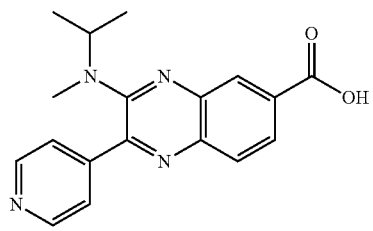 [SMILES: CC(C)N(C)c1nc2cc(C(=O)O)ccc2nc1-c1ccncc1]

Step 1. Methyl 3-(isopropyl(methyl)amino)-2-(pyridin-4-yl)quinoxaline-6-carboxylate

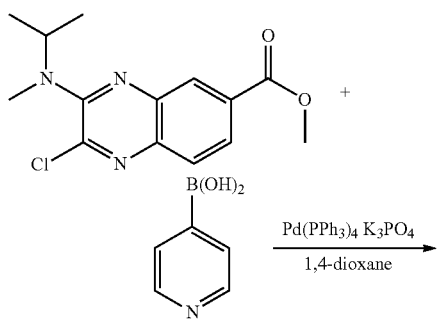

Into a 10-mL sealed tube, was placed methyl 2-chloro-3-(isopropyl(methyl)amino)quinoxaline-6-carboxylate (150 mg, 0.51 mmol, 1.00 equiv), pyridin-4-ylboronic acid (124.5 mg, 1.02 mmol, 1.99 equiv), Pd(PPh$_3$)$_4$ (59 mg, 0.05 mmol, 0.10 equiv), K$_3$PO$_4$ (433 mg, 2.04 mmol), 1,4-dioxane (4 mL). The resulting solution was stirred for overnight at 50° C. in an oil bath under nitrogen atmosphere. The resulting mixture was concentrated under vacuum. The residue was purified by silica gel column chromatography with EA/PE (1:40). This resulted in 50 mg (29%) of methyl 3-(isopropyl (methyl)amino)-2-(pyridin-4-yl)quinoxaline-6-carboxylate as a yellow solid.

LC-MS:(ES, m/z): 337 [M+H]$^+$

Step 2. 3-(isopropyl(methyl)amino)-2-(pyridin-4-yl) quinoxaline-6-carboxylic Acid Into a 10-mL sealed tube, was placed a solution of methyl 3-(isopropyl(methyl)amino)-2-(pyridin-4-yl)quinoxaline-6-carboxylate (50 mg, 0.15 mmol, 1.00 equiv) in methanol (15 mL), sodium hydroxide (30 mg, 0.75 mmol, 5.04 equiv), water (2 mL). The resulting solution was stirred for 2 hr at 50° C. in an oil bath. The resulting mixture was concentrated under vacuum and diluted with 20 mL of H$_2$O. The pH value of the aqueous solution was adjusted to 4-5 with hydrogen chloride (2 mol/L). The resulting solids were collected by filtration. This resulted in 22 mg (44%) of 3-(isopropyl (methyl)amino)-2-(pyridin-4-yl)quinoxaline-6-carboxylic acid as a yellow solid.

LC-MS:(ES, m/z): 323 [M+H]$^+$ $^1$H-NMR (300 MHz, DMSO, ppm) δ 8.791-8.771 (d, J=6.0 Hz, 2H), 8.279-8.276 (d, J=0.9 Hz, 1H), 8.007-7.938 (m, 2H), 7.870-7.849 (d, J=6.3 Hz, 2H), 4.250-4.162 (m, 1H), 2.657 (s, 3H), 1.081-1.059 (d, J=6.6 Hz, 6H).

EXAMPLE 88

2-(H-Imidazo[1,2-a]pyridin-6-yl)-3-(isopropyl(methyl)amino)quinoxaline-6-carboxylic Acid

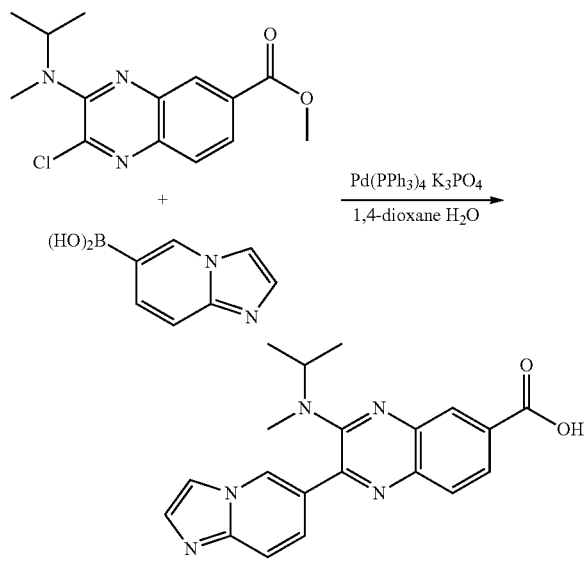

Into a 10-mL sealed tube, was placed methyl 2-chloro-3-(isopropyl(methyl)amino)quinoxaline-6-carboxylate (70 mg, 0.24 mmol, 1.00 equiv), H-imidazo[1,2-a]pyridin-6-ylboronic acid (59 mg, 0.36 mmol, 1.53 equiv), Pd(PPh$_3$)$_4$ (28 mg, 0.02 mmol, 0.10 equiv), K$_3$PO$_4$ (200 mg, 0.94 mmol, 3.96 equiv), 1,4-dioxane/H$_2$O (4/1 mL). The resulting solution was stirred for overnight at 100° C. in an oil bath. The resulting mixture was concentrated under vacuum. The residue was purified by silica gel column chromatography with dichloromethane/methanol (30:1). The resulting crude product (80 mg) was purified by Prep-HPLC under the following conditions (1 #-Waters 2767-5): Column, SunFire Prep C18, 19*150 mm Sum; mobile phase, water with 0.05% TFA and CH$_3$CN (15% CH$_3$CN up to 37% in 9 min, up to 100% in 1 min, down to 15% in 1 min); Detector, uv 254 nm. This resulted in 26 mg (30%) of 2-(H-imidazo[1,2-a]pyridin-6-yl)-3-(isopropyl(methyl)amino)quinoxaline-6-carboxylic acid as a yellow solid.

LC-MS:(ES, m/z): 362 [M+H]$^+$ $^1$H-NMR (300 MHz, DMSO, ppm) δ 9.422 (s, 1H), 8.451 (s, 1H), 8.309 (s, 1H), 8.273-8.250 (d, J=6.9 Hz, 1H), 8.145 (s, 1H), 8.041-7.998 (m, 3H), 4.243-4.177 (m, 1H), 2.741 (s, 3H), 1.098-1.082 (d, J=4.8 Hz, 6H).

EXAMPLE 89

2-(Benzofuran-2-yl)-3-(isopropyl(methyl)amino)quinoxaline-6-carboxylic Acid

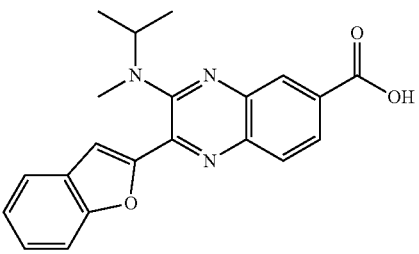 [SMILES: CC(C)N(C)c1nc2cc(C(=O)O)ccc2nc1-c1cc2ccccc2o1]

Step 1. Methyl 2-(benzofuran-2-yl)-3-(isopropyl(methyl)amino)quinoxaline-6-carboxylate

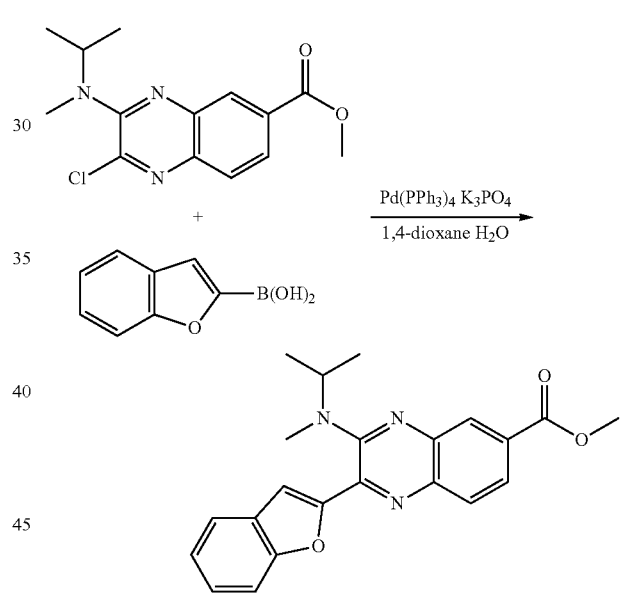

Into a 10-mL sealed tube, was placed methyl 2-chloro-3-(isopropyl(methyl)amino)quinoxaline-6-carboxylate (200 mg, 0.68 mmol, 1.00 equiv), benzofuran-2-ylboronic acid (220 mg, 1.36 mmol, 1.99 equiv), Pd(PPh$_3$)$_4$ (157 mg, 0.14 mmol, 0.20 equiv), K$_3$PO$_4$ (577 mg, 2.73 mmol, 4.01 equiv), 1,4-dioxane (4 mL). The resulting solution was stirred for overnight at 100° C. in an oil bath. The resulting mixture was concentrated under vacuum. The residue was applied onto a silica gel column with ethyl acetate/petroleum ether (1:40). This resulted in 160 mg (63%) of methyl 2-(benzofuran-2-yl)-3-(isopropyl(methyl)amino)quinoxaline-6-carboxylate as a yellow solid.

LC-MS:(ES, m/z): 376 [M+H]$^+$

Step 2. 2-(Benzofuran-2-yl)-3-(isopropyl(methyl) amino)quinoxaline-6-carboxylic Acid

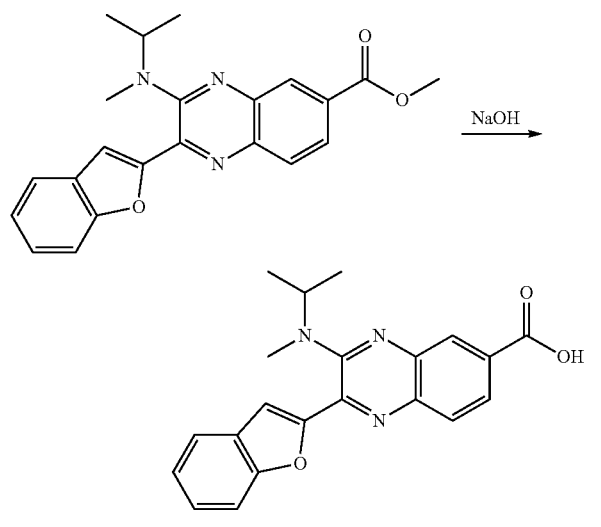

Into a 50-mL round-bottom flask, was placed a solution of methyl 2-(benzofuran-2-yl)-3-(isopropyl(methyl)amino) quinoxaline-6-carboxylate (160 mg, 0.43 mmol, 1.00 equiv) in methanol (20 mL), sodium hydroxide (85 mg, 2.12 mmol, 4.99 equiv), water (2 mL). The resulting solution was stirred for 2 hs at 50° C. in an oil bath. The resulting mixture was concentrated under vacuum. The resulting solution was diluted with 20 mL of H₂O. The pH value of the aqueous solution was adjusted to 4-5 with hydrogen chloride (2.5 M). The resulting solids were collected by filtration. The crude product (120 mg) was purified by Prep-HPLC with the following conditions (1 #-Waters 2767-1): Column, XbridgePrep Shield RP 18, Sum, 19*150 mm; mobile phase, water with 0.05% TFA and CH₃CN (58% CH3CN up to 78% in 8 min, up to 100% in 2 min); Detector, UV 220 254 nm. This resulted in 70 mg (45%) of 2-(benzofuran-2-yl)-3-(isopropyl(methyl)amino)quinoxaline-6-carboxylic acid as a yellow solid.

LC-MS:(ES, m/z): 362 [M+H]⁺

¹H-NMR (300 MHz, DMSO, ppm) δ 13.250 (s, 1H), 8.275-8.272 (d, J=0.9 Hz, 1H), 8.034-7.962 (m, 2H), 7.826-7.702 (m, 3H), 7.482-7.328 (m, 2H), 4.254-4.167 (m, 1H), 2.836 (s, 3H), 1.180-1.158 (d, J=6.6 Hz, 6H).

The following compounds may generally be made via a modified version of the schemes shown.

Scheme IV.

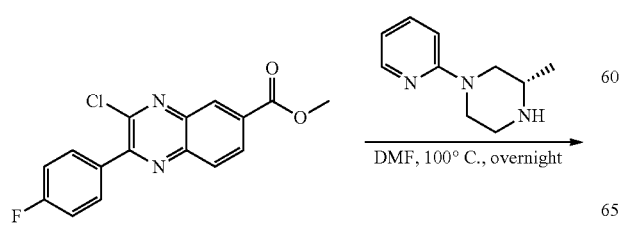

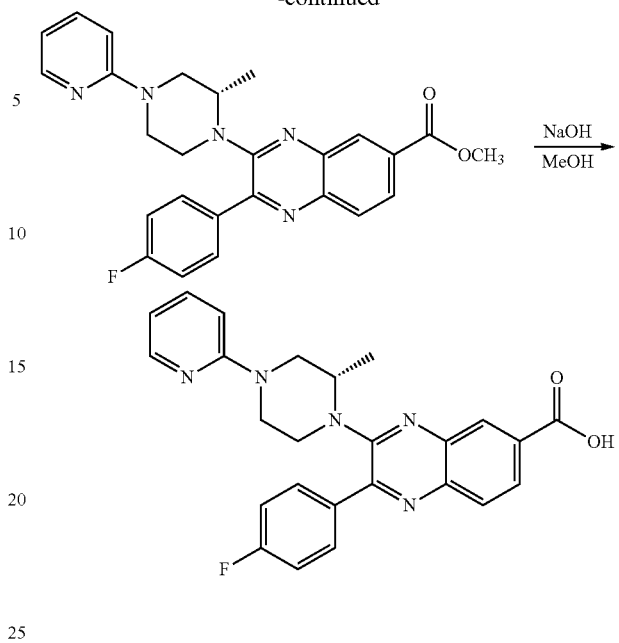

EXAMPLE 90

(S)-2-(4-Fluorophenyl)-3-(2-methyl-4-(pyridin-2-yl) piperazin-1-yl)quinoxaline-6-carboxylic Acid

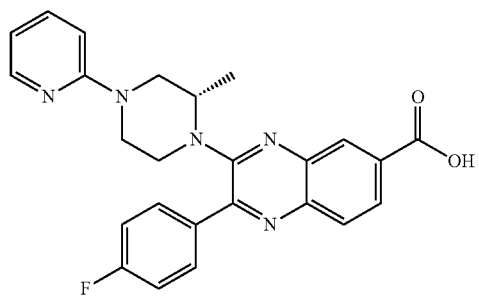 [SMILES: C[C@H]1CN(c2ccccn2)CCN1c1nc2cc(C(=O)O)ccc2nc1-c1ccc(F)cc1]

LC-MS:(ES, m/z): 444 [M+H].

EXAMPLE 91

(S)-2-(4-Fluorophenyl)-3-(2-methylpiperidin-1-yl) quinoxaline-6-carboxylic Acid

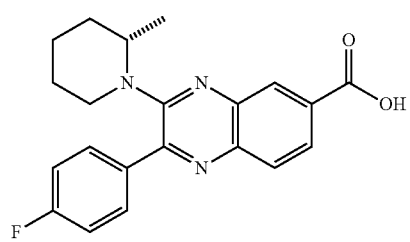 [SMILES: C[C@H]1CCCCN1c1nc2cc(C(=O)O)ccc2nc1-c1ccc(F)cc1]

EXAMPLE 92

3-(Cyclopropyl(methyl)amino)-2-(4-fluorophenyl)quinoxaline-6-carboxylic Acid

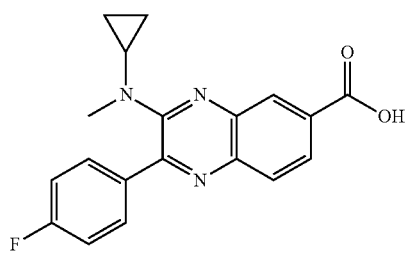 [SMILES: CN(c1nc2cc(C(=O)O)ccc2nc1-c1ccc(F)cc1)C1CC1]

LC-MS:(ES, m/z): 338 [M+H].

EXAMPLE 93

(R)-2-(4-Fluorophenyl)-3-(2-(methoxymethyl)pyrrolidin-1-yl)quinoxaline-6-carboxylic Acid

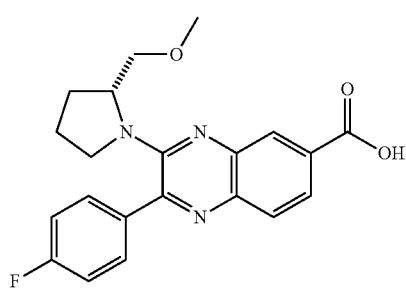 [SMILES: COC[C@H]1CCCN1c1nc2cc(C(=O)O)ccc2nc1-c1ccc(F)cc1]

LC-MS:(ES, m/z): 382 [M+H].

EXAMPLE 94

(S)-3-(2-Methyl-4-(pyridin-2-yl)piperazin-1-yl)-2-phenylquinoxaline-6-carboxylic Acid

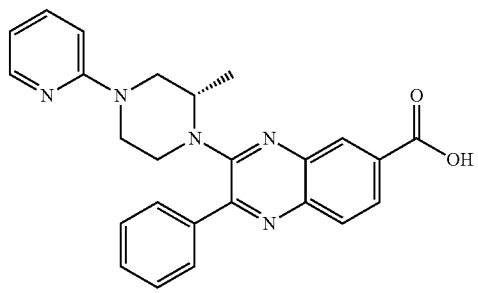 [SMILES: C[C@H]1CN(c2ccccn2)CCN1c1nc2cc(C(=O)O)ccc2nc1-c1ccccc1]

LC-MS:(ES, m/z): 426 [M+H].

EXAMPLE 95

2-(Benzo[d][1,3]dioxol-5-yl)-3-(3,4-dihydroquinolin-1(2H)-yl)quinoxaline-6-carboxylic Acid

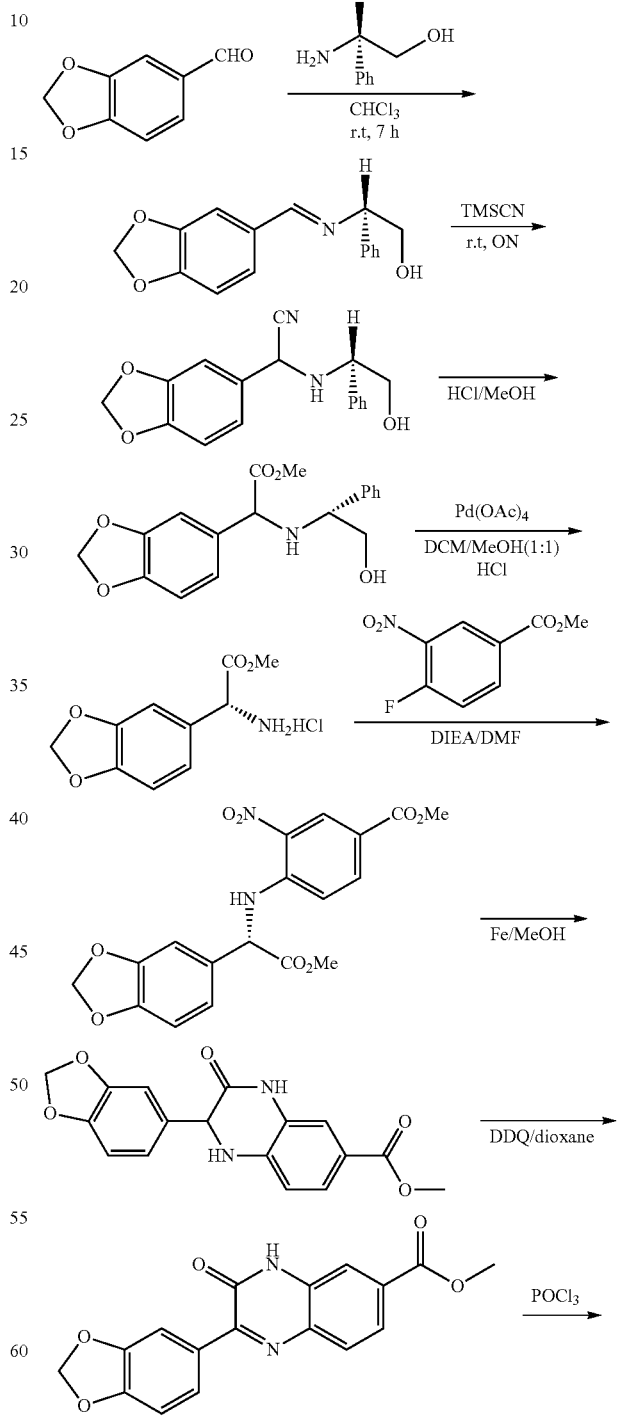

217
-continued
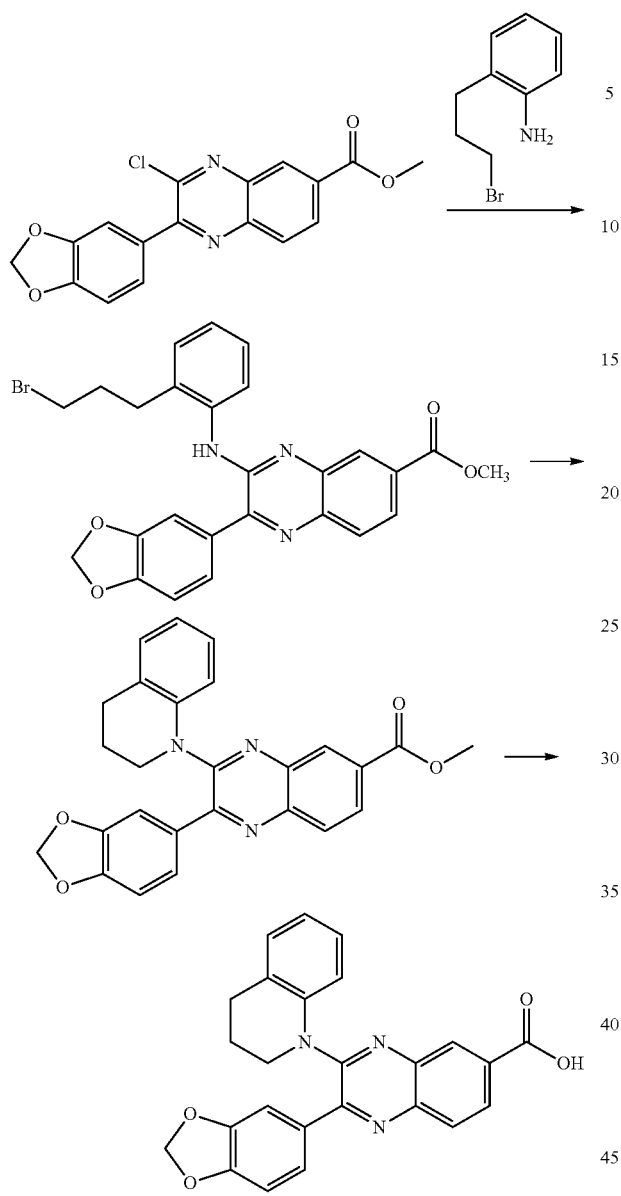
LC-MS:(ES, m/z): 426 [M+H].
¹H-NMR (300 MHz, CDCl₃): 8.70 (s, 1H), 8.22 (d, J=8.6 Hz, 1H), 8.11 (d, J=8.6 Hz, 1H), 7.32 (d, J=8.4 Hz, 1H), 7.29 (1H), 7.06 (m, 1H), 6.88 (m, 1H), 6.86-6.67 (m, 4H), 5.95 (s, 2H), 3.87 (br t, 2H), 2.84 (br t, 2H), 2.09 (br t, 2H).
218
EXAMPLE 96
3-(Octahydroquinolin-1(2H)-yl)-2-phenylquinoxaline-6-carboxylic Acid
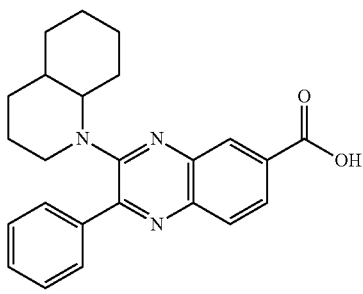 [SMILES: O=C(O)c1ccc2nc(-c3ccccc3)c(N3CCCC4CCCCC43)nc2c1]
LC-MS:(ES, m/z): 388 [M+H].
EXAMPLE 97
3-(Isopropyl(methyl)amino)-2-(pyridin-3-yl)quinoxaline-6-carboxylic Acid
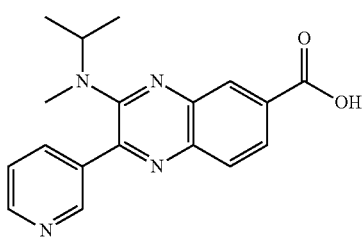 [SMILES: CC(C)N(C)c1nc2cc(C(=O)O)ccc2nc1-c1cccnc1]
LC-MS:(ES, m/z): 323 [M+H].
EXAMPLE 98
2-(Furan-2-yl)-3-(isopropyl(methyl)amino)quinoxaline-6-carboxylic Acid
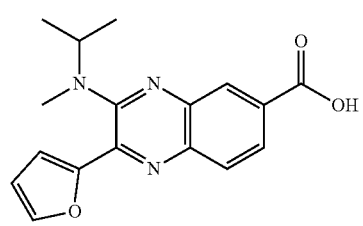 [SMILES: CC(C)N(C)c1nc2cc(C(=O)O)ccc2nc1-c1ccco1]
LC-MS:(ES, m/z): 312 [M+H].

EXAMPLE 99

3-(Isopropyl(methyl)amino)-2-(quinolin-3-yl)quinoxaline-6-carboxylic Acid

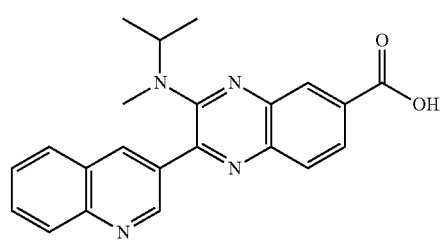 [SMILES: CC(C)N(C)c1nc2cc(C(=O)O)ccc2nc1-c1cnc2ccccc2c1]

LC-MS:(ES, m/z): 373 [M+H].

EXAMPLE 100

3-(Isopropyl(methyl)amino)-2-(4-morpholinophenyl)quinoxaline-6-carboxylic Acid

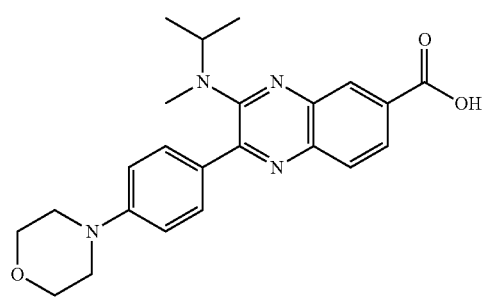 [SMILES: CC(C)N(C)c1nc2cc(C(=O)O)ccc2nc1-c1ccc(N2CCOCC2)cc1]

LC-MS:(ES, m/z): 407 [M+H].

EXAMPLE 101

3-(1,1-Dioxidothiomorpholino)-2-(4-fluorophenyl)quinoxaline-6-carboxylic Acid

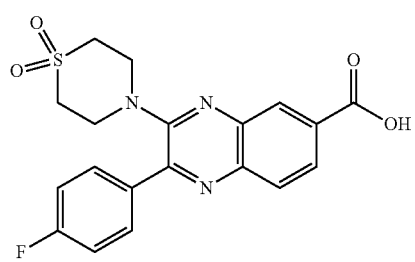 [SMILES: O=C(O)c1ccc2nc(-c3ccc(F)cc3)c(N3CCS(=O)(=O)CC3)nc2c1]

LC-MS:(ES, m/z): 402 [M+H].

EXAMPLE 102

3-(1,1-Dioxidothiomorpholino)-2-phenylquinoxaline-6-carboxylic Acid

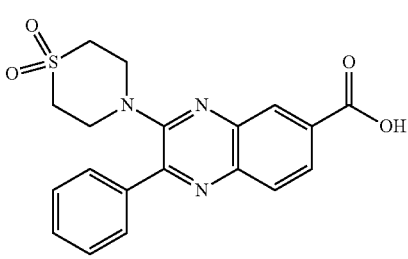 [SMILES: O=C(O)c1ccc2nc(-c3ccccc3)c(N3CCS(=O)(=O)CC3)nc2c1]

LC-MS:(ES, m/z): 384 [M+H].

EXAMPLE 103

2-(4-Fluorophenyl)-3-(3-oxopiperazin-1-yl)quinoxaline-6-carboxylic Acid

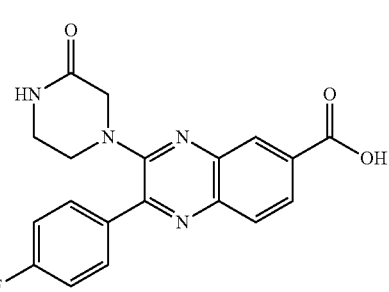

LC-MS:(ES, m/z): 367 [M+H].

EXAMPLE 104

2-(4-Fluorophenyl)-3-(methyl(piperidin-4-yl)amino)quinoxaline-6-carboxylic Acid

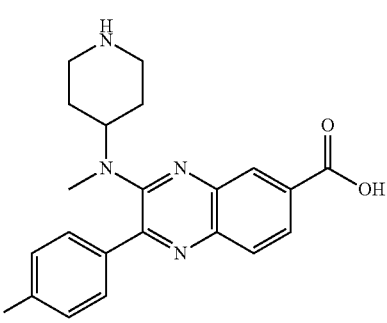

LC-MS:(ES, m/z): 331 [M+H].

EXAMPLE 105

2-(4-Fluorophenyl)-3-(methyl(tetrahydro-2H-pyran-4-yl)amino)quinoxaline-6-carboxylic Acid

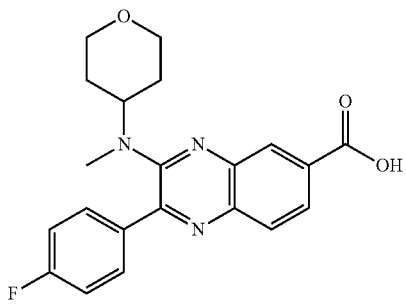 [SMILES: CN(c1nc2cc(C(=O)O)ccc2nc1-c1ccc(F)cc1)C1CCOCC1]

LC-MS:(ES, m/z): 382 [M+H].

EXAMPLE 106

3-(Cyclopentyl(methyl)amino)-2-(4-fluorophenyl)quinoxaline-6-carboxylic Acid

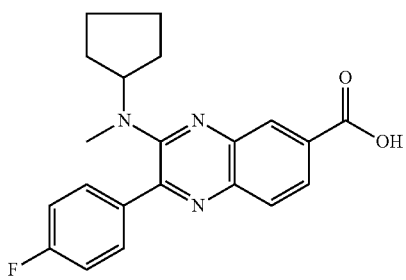 [SMILES: CN(c1nc2cc(C(=O)O)ccc2nc1-c1ccc(F)cc1)C1CCCC1]

LC-MS:(ES, m/z): 366 [M+H].

EXAMPLE 107

3-(Isopropyl(methyl)amino)-2-(5-methylthiophen-2-yl)quinoxaline-6-carboxylic Acid

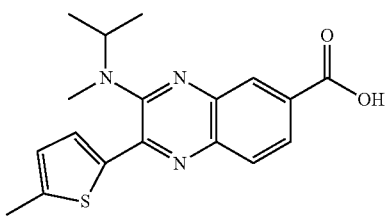 [SMILES: Cc1ccc(-c2nc3ccc(C(=O)O)cc3nc2N(C)C(C)C)s1]

EXAMPLE 108

3-(Isopropyl(methyl)amino)-2-(thiophen-2-yl)quinoxaline-6-carboxylic Acid

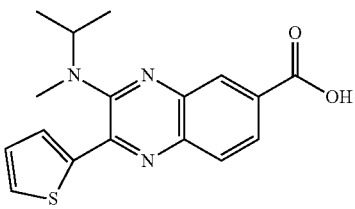

LC-MS:(ES, m/z): 328 [M+H].

EXAMPLE 109

3-(Isopropyl(methyl)amino)-2-(6-methoxypyridin-3-yl)quinoxaline-6-carboxylic Acid

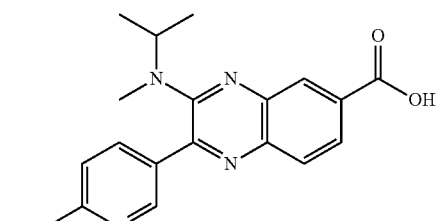

LC-MS:(ES, m/z): 353 [M+H].

EXAMPLE 110

2-(Furan-2-yl)-3-(isopropyl(methyl)amino)quinoxaline-6-carboxylic Acid

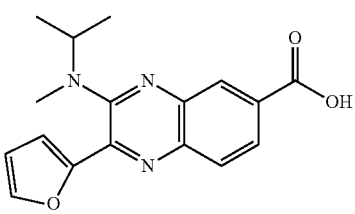 [SMILES: CC(C)N(C)c1nc2cc(C(=O)O)ccc2nc1-c1cccs1]

LC-MS:(ES, m/z): 312 [M+H].

EXAMPLE 111

2-(4-Fluorophenyl)-3-(4-(N-methylacetamido)piperidin-1-yl)quinoxaline-6-carboxylic Acid

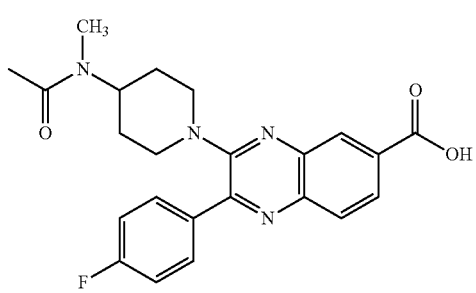 [SMILES: CC(=O)N(C)C1CCN(c2nc3cc(C(=O)O)ccc3nc2-c2ccc(F)cc2)CC1]

LC-MS:(ES, m/z): 423 [M+H].

EXAMPLE 112

2-(4-Fluorophenyl)-3-(4-methyl-3-oxopiperazin-1-yl)quinoxaline-6-carboxylic Acid

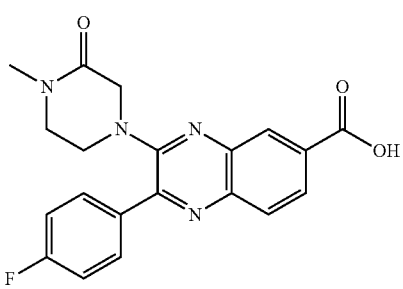 [SMILES: CN1CCN(c2nc3cc(C(=O)O)ccc3nc2-c2ccc(F)cc2)CC1=O]

LC-MS:(ES, m/z): 381 [M+H].

EXAMPLE 113

2-(1H-Indol-6-yl)-3-(isopropyl(methyl)amino)quinoxaline-6-carboxylic acid

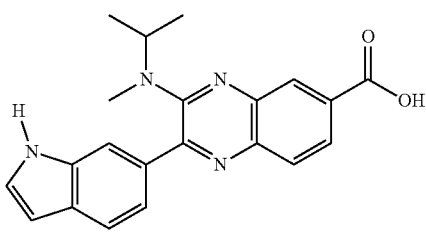

LC-MS:(ES, m/z): 361[M+H].

EXAMPLE 114

2-(1H-Indol-2-yl)-3-(isopropyl(methyl)amino)quinoxaline-6-carboxylic Acid

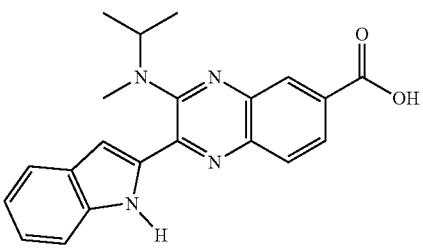 [SMILES: CC(C)N(C)c1nc2cc(C(=O)O)ccc2nc1-c1cc2ccccc2[nH]1]

LC-MS:(ES, m/z): 361[M+H].

The following compounds can generally be made using the methods known in the art and described above. It is expected that these compounds when made will have activity similar to those that have been made in the examples above.

2-phenyl-3-(2,3,4,5-tetrahydro-1H-benzo[b]azepin-1-yl)quinoxaline-6-carboxylic acid 2-(4-fluorophenyl)-3-(2,3,4,5-tetrahydro-1H-benzo[b]azepin-1-yl)quinoxaline-6-carboxylic acid (S)-3-(sec-butyl(methyl)amino)-2-(4-fluorophenyl)quinoxaline-6-carboxylic acid 3-(sec-butyl(methyl)amino)-2-(furan-3-yl)quinoxaline-6-carboxylic acid 3-(isopropyl(methyl)amino)-2-(1H-pyrazol-4-yl)quinoxaline-6-carboxylic acid 3-(isopropyl(methyl)amino)-2-(6-methoxypyridin-3-yl)quinoxaline-6-carboxylic acid 2-(1H-indazol-6-yl)-3-(isopropyl(methyl)amino)quinoxaline-6-carboxylic acid 3-(isopropyl(methyl)amino)-2-(1-methyl-1H-indazol-6-yl)quinoxaline-6-carboxylic acid 2-(1-(tert-butoxycarbonyl)-1H-indol-2-yl)-3-(isopropyl(methyl)amino)quinoxaline-6-carboxylic Acid 2-(1-(tert-butoxycarbonyl)-5-methoxy-1H-indol-2-yl)-3-(isopropyl(methyl)amino) quinoxaline-6-carboxylic acid 3-(isopropyl(methyl)amino)-2-(5-methoxy-1H-indol-2-yl)quinoxaline-6-carboxylic acid 2-(5-fluoro-1H-indol-2-yl)-3-(isopropyl(methyl)amino)quinoxaline-6-carboxylic acid 2-(5-bromopyridin-3-yl)-3-(isopropyl(methyl)amino)quinoxaline-6-carboxylic acid 2-(1H-indazol-5-yl)-3-(isopropyl(methyl)amino)quinoxaline-6-carboxylic acid 3-(isopropyl(methyl)amino)-2-(3-(trifluoromethyl)-1H-pyrazol-4-yl)quinoxaline-6-carboxylic acid 2-(6-(tert-butoxycarbonylamino)pyridin-3-yl)-3-(isopropyl(methyl)amino)quinoxaline-6-carboxylic acid 2-(5-fluoropyridin-2-yl)-3-(isopropyl(methyl)amino)quinoxaline-6-carboxylic acid 3-(isopropyl(methyl)amino)-2-(5-(trifluoromethyl)pyridin-2-yl)quinoxaline-6-carboxylic acid 3-(isopropyl(methyl)amino)-2-(6-(trifluoromethyl)pyridin-3-yl)quinoxaline-6-carboxylic acid 2-(5-cyanopyridin-2-yl)-3-(isopropyl(methyl)amino)quinoxaline-6-carboxylic acid 3-(isopropyl(methyl)amino)-2-(6-(pyrrolidin-1-yl)pyridin-3-yl)quinoxaline-6-carboxylic acid 2-(6-fluoropyridin-3-yl)-3-(isopropyl(methyl)amino)quinoxaline-6-carboxylic acid (S)-2-(benzofuran-2-yl)-3-(2-methylpyrrolidin-1-yl)quinoxaline-6-carboxylic acid 2-(benzofuran-2-yl)-3-(cyclopropyl(methyl)amino)quinoxaline-6-carboxylic acid 2-(5-fluorobenzofuran-2-yl)-3-(isopropyl(methyl)amino)quinoxaline-6-carboxylic acid 2-(5-chlorobenzofuran-2-yl)-3-(isopropyl(methyl)amino)quinoxaline-6-carboxylic acid 2-(benzofuran-2-yl)-3-(sec-butyl(methyl)amino)quinoxaline-6-carboxylic acid The activity of the compounds in Examples 1-114 as PASK modulators is illustrated in the following assays. The other compounds listed above, which have not yet been made and/or tested, are predicted to have activity in these assays as well.

Biochemical Assay for hPASK Activity

PAS Kinase Luminescence Assay

One assay for purified hPASK activity utilizes the Kinase-Glo Luminescent Kinase Assay (Promega), which quantifies the amount of ATP remaining in solution following kinase reaction. The assay is carried out in a 96-well plate format and is performed by adding a volume of Kinase-Glo Reagent (Promega, catalog #V3771) equal to the volume of solution in the well of a completed kinase reaction. Kinase-Glo reagent contains Luciferase and its substrate. After addition to a kinase reaction it allows to measure luminescence. The amount of ATP left in solution at the time of Kinase-Glo Plus addition is directly proportional to the luminescence that is measured in each well, and inversely correlated with kinase activity.

Purified hPASK from insect cells (0.02 g) is added to a 50 L reaction mix containing 40 mM HEPES (pH 7.0), 100 mM KCl, 5 mM MgCl$_2$, 1 mM DTT and 1 g of MBP protein. Inhibitory compounds are then added and the mixture is incubated for 10 min at 25° C. before adding 5 L of ATP (at desired concentration). The reaction is allowed to proceed at 25° C. for 1 hour before adding 50 L of Kinase-Glo reagent. The luminescence is measured as soon as 10 minutes after Kinase-Glo reagent is added.

Results are shown below in Table 1.

TABLE 1

| Example # | IC$_{50}$ Kinase Domain<br>+ indicates ≤10 μm<br>− indicates ≥10 μm |
|---|---|
| 11 | + |
| 16 | + |
| 17 | + |
| 18 | + |
| 19 | + |
| 20 | + |
| 21 | + |
| 22 | − |
| 23 | + |
| 24 | + |
| 25 | + |
| 26 | + |
| 27 | + |
| 28 | + |
| 29 | + |
| 30 | + |
| 31 | + |

PASK ATP Radiochemical Assay

Purified PASK (UniProt #Q96RG2; human recombinant N-terminal GST tagged construct, residues 879-1323) from insect cells (final concentration 5 nM) is added to freshly prepared Base Reaction Buffer containing 20 mM HEPES (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO and Myelin Basic Protein (2 μM final). Test compounds in DMSO are then added and the mixture, followed by delivery of $^{33}$P-ATP (specific activity 0.01 μCi/μl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results for this assay are shown below in Table 2. NT indicates that the compound was not tested.

TABLE 2

| Example # | IC$_{50}$ Kinase Domain<br>+ indicates ≤10 um<br>− indicates ≥10 um |
|---|---|
| 1 | + |
| 2 | + |
| 3 | + |
| 4 | − |
| 5 | − |
| 6 | + |
| 7 | + |
| 8 | + |
| 9 | + |
| 10 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | NT |
| 23 | NT |
| 24 | + |
| 25 | NT |
| 26 | + |
| 27 | NT |
| 28 | − |
| 29 | − |
| 30 | + |
| 31 | + |
| 32 | + |
| 40 | + |
| 43 | + |
| 46 | + |
| 51 | + |
| 52 | + |
| 55 | + |
| 57 | + |
| 58 | + |
| 65 | + |
| 66 | + |
| 63 | + |
| 64 | + |
| 72 | + |
| 74 | + |
| 75 | + |
| 76 | + |
| 77 | + |
| 78 | + |
| 79 | + |
| 80 | + |
| 81 | + |
| 83 | + |
| 84 | + |
| 87 | + |

TABLE 2-continued

| Example # | IC$_{50}$ Kinase Domain<br>+ indicates ≤10 um<br>− indicates ≥10 um |
|---|---|
| 88 | + |
| 89 | + |

PAS Kinase FRET Assay

The aim of the FRET assay is to determine the inhibition potential of test compounds on targeted kinase. This assay platform provides a homogenous screening method for measuring kinase activity by quantitating the amount of phospho-substrate in solution following a kinase reaction.

In the presence of kinase and ATP, the Ulight-peptide is phosphorylated and captured by an anti-phospho-substrate antibody, which brings the Eu chelate donor and Ulight acceptor dyes into close proximity. Upon excitation at 340 nm, the Eu chelate transfers its energy to the Ulight dye, resulting in a fluorescent light emission at 665 nm.

Titration of kinase at 1 mM ATP was achieved via the following protocol. After making serial three-fold dilutions of PASK (Invitrogen) in reaction buffer across the plate; 5 µl of kinase dilution and 5 µl substrate/ATP mix were added to the wells of the white Optiplate-384 (PerkinElmer). The contents of the plate were and incubated at RT for 1 h. The reaction was stopped by adding 5 µl of stop solution to each test well followed by mixing and incubation at RT for 10 minutes. 5 µl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the EC$_{50}$. Titration of ATP at the EC$_{50}$ concentration of kinase to determine ATP Km,app. was performed using the following method. After making serial dilutions of ATP (Invitrogen), 5 µl of ATP dilution and 5 µl substrate/kinase mix were added to the wells of the white Optiplate-384 (PerkinElmer). The contents of the plate were and incubated at RT for 1 h. The reaction was stopped by adding 5 µl of stop solution to each test well followed by mixing and incubation at RT for 10 minutes. 5 µl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the EC$_{50}$ as the ATP Km,app.

Compound screening was done via the following method. 10 mM stock solution of test compound in DMSO was prepared by dissolving test compound in DMSO at RT for 1 hour, and then sonicating at 100% output for 8 minutes. If compound is not soluble under this condition, it was diluted to 3 mM. Kinase reaction buffer was prepared containing 10 mM MgCl$_2$, 50 mM HEPES, 1 mM EGTA, 0.01% TWEEN-20, 2 mM DTT. Serial dilutions of the test compounds were prepared at 4× final assay concentrations using Freedom EVO200® dispensing system as follows: 12×10$^{-5}$ M 4×10$^{-5}$ M, 1.33×10$^{-5}$ M, 4.44×10$^{-6}$ M, 1.48×10$^{-6}$ M, 4.92×10$^{-7}$ M, 1.65×10$^{-7}$ M, 5.48×10$^{-7}$ M, 1.82×10$^{-8}$ M, 6.09×10$^{-9}$, 2.03×10$^{-9}$ M. Test compounds (2.5 µl at 4× the final assay concentration) was added to wells using Freedom EVO200® dispensing system. As a positive control, 2.5 µl of positive compound was added to assay wells, and 2.5 µl of DMSO to assay wells as vehicle control. Kinase solution was prepared in reaction buffer at 2× final assay concentration. Kinase solution (5 µl) was added to each well of the assay plate. The substrate and ATP solution was prepared in kinase reaction buffer at 4× final assay concentration. The kinase reaction was started by adding 2.5 µl of substrate+ATP mix solution to each well of the assay plate. The plate is mixed on a plate shaker; then covered and allowed to react for 2 hours in the dark at 25° C. without shaking. The reaction was stopped by adding 5 µl of stop solution to each test well followed by mixing and incubation at RT for 10 minutes in the dark. 5 µl of detection mix (detection antibody diluted in detection buffer) was added; the contents of the plate were mixed and then incubated in the dark for 1 hour at RT. The signal was recorded at TR-FRET mode (665 nm/615 nm).

Results are shown below in Table 3.

TABLE 3

| Example # | IC$_{50}$ Kinase Domain<br>+ indicates ≤10 um<br>− indicates ≥10 um |
|---|---|
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 65 | + |
| 59 | + |
| 60 | + |
| 61 | + |
| 66 | + |
| 67 | + |
| 68 | + |
| 62 | + |
| 63 | + |
| 64 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | − |
| 83 | + |
| 84 | + |
| 85 | + |
| 86 | + |
| 87 | + |
| 88 | + |

TABLE 3-continued

| Example # | IC$_{50}$ Kinase Domain<br>+ indicates ≤10 um<br>− indicates ≥10 um |
|---|---|
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | − |
| 102 | − |
| 103 | + |
| 104 | + |
| 105 | + |
| 106 | + |
| 107 | + |
| 108 | + |
| 111 | + |
| 112 | + |

In Vivo Assays

A selected compound disclosed above ("Subject Compound"), Example 57, has been tested in two models of dyslipidemia. This compound, thought to be a specific PASK inhibitor, was expected to reproduce important phenotypic features of the PASK−/− mouse (31) in a mouse high fat dietary model and in a rat high fructose dietary model. All values given below are averages over the treatment groups.

Mouse High Fat Dietary Model

A standard model of human hyperlipidemia and insulin resistance is the mouse fed a high fat diet for several weeks (31, 33). Additionally, since hepatic lipid synthesis is known to be regulated by food consumption, the fast/re-feed cycle of Horton et al. (32) was incorporated into the chronic high fat diet model. The compound was evaluated in this model as an agent to restore insulin sensitivity and lower blood lipids. The chronic high fat diet was fed to mice to simulate a standard Western diet which is elevated in calories from high fat and carbohydrate intake. This and similar models of dietary induced obesity, insulin insensitivity and elevated serum lipids and cholesterol are used as mouse and rat models of human pathology including hyperlipidemia, type II diabetes, atherosclerosis, obesity, cardiovascular and liver disease. These models have been used as excellent predictors of efficacy in human clinical trials (PPAR and FXR agonists).

The farnesoid X receptor (FXR) is a ligand-activated transcription factor and a member of the nuclear receptor superfamily. This receptor has been shown to have crucial roles in controlling bile acid homeostasis, lipoprotein and glucose metabolism, hepatic regeneration, intestinal bacterial growth and the response to hepatotoxins. WAY-362450 is an agonist of the FXR and has been shown to reduce serum triglycerides and cholesterol in several models of hyperlipidemia and protects against the development of atherosclerotic plaque formation in mouse atherosclerosis models and liver inflammation and fibrosis in a murine model of non-alcoholic steatohepatitis (33, 34, 35, 36). While the mechanism of action of FXR agonists is clearly distinct from PASK inhibition, WAY-362450 has been used as a positive control compound producing physiologically beneficial changes in glucose and lipid metabolism resembling inhibition of PASK. Throughout these in vivo assays, WAY-362450 has been used as a control compound, and will be referred to as such.

The study design is shown in Table 4.

TABLE 4

| Group | Test Article | Dose Level (mg/kg) | Dose Concentration (mg/mL) |
|---|---|---|---|
| 1 | Vehicle | 0 | 0 |
| 2 | Subject Compound | 30 | 3 |
| 3 | Subject Compound | 100 | 10 |
| 4 | Control | 30 | 3 |

Male C57Bl6 mice were obtained from Jackson Laboratories and had been fed a high fat diet (60% kcal fat) for eight weeks. The mice were fed an identical high fat diet (Research Diet D12492) upon arrival and during the study. All mice were treated with the subject compound at 30 or 100 mg/kg, control compound (WAY-362450) at 30 mg/kg or vehicle by oral gavage daily for three days. On the final day, 10 animals from each group began an 24 hour fast and then were sacrificed (fasted groups 1a,2a,3a,4a). Alternatively, 10 animals from each group underwent a 24 hour fast followed by a 12 hour re-feed period with the same high fat diet ad libitum and then were sacrificed (re-fed groups 1b,2b,3b,4b).

Body weights were monitored at the start and end of the protocol. After completing the fast or fast/re-feed conditions, the mice were given avertin for anesthesia by intraperitoneal administration. Whole blood was collected by cardiac puncture and the mice were terminated by cervical dislocation. Livers were collected surgically, weighed and immediately frozen in liquid nitrogen. The blood was placed in Li-heparin treated tubes, centrifuged to collect plasma and the plasma frozen.

The plasma was analyzed by standard colorimetric assays for glucose, insulin, triglycerides and cholesterol. Frozen liver samples were pulverized and extracted in ethanolic KOH and analyzed for liver triglycerides and cholesterol.

After completing the dosing schedule and the fast/re-feed cycle, vehicle treated animals weighed 29.2 g. Treatment with the subject compound at 30 mg/kg or 100 mg/kg reduced body weight in a dose dependent manner by 2.7% and 5.1%, respectively. The control compound (WAY-362450) at 30 mg/kg also reduced body weight by 6.5% as compared to the Vehicle with Fast/Re-feed group. Additionally, vehicle treated mice which were fasted only (no re-feed) weighed 27.3 g at the completion of the study. The subject compound also decreased body weight in fasted only animals by 1.8% and 5.1%, similar to the dose responsive reduction in body weight in the fasted and re-fed animals. The control compound decreased body weight in the fasted only animals by 4% compared to the Vehicle Fasted group.

Liver weights were measured in mice that were treated with vehicle, the subject compound or the control compound and fasted or fasted and re-fed. Vehicle treated mice that were fasted and re-fed displayed mean terminal liver weights of 1.2 g and 0.9 g for fast/re-feed and fasted only mice, respectively. The subject compound at 30 and 100 mg/kg caused a trend of dose dependent reductions in liver weights of about 7-9%. The effects of the control compound treatment at 30 mg/kg on liver weight were identical to those of the subject compound at the same dose.

The subject compound also caused dose related reductions in plasma glucose and insulin levels compared to vehicle treated mice in both the fasted and re-fed groups. These effects were similar or greater than those produced by treatment with the control compound. Vehicle mice which underwent the complete fast and re-feed cycle exhibited plasma glucose levels of 104 mg/dl and the subject compound decreased glucose by up to 21% at the highest dose (100 mg/kg). The control compound increased plasma glucose by 7.6%. In the fasted only mice, vehicle treated mice displayed a mean circulating plasma glucose concentration of 116 mg/dl and the subject compound decreased glucose by 30% and 43% in a dose related manner. The control compound caused a 19% reduction in fasted mice.

Plasma insulin concentrations were decreased by treatment with the subject compound dose dependently (10% and 28% at 30 and 100 mg/kg) in the fasted and re-fed mice compared to vehicle controls (2.32 IU/ml). Insulin was also reduced in the control compound treated mice which underwent the fast and re-feed cycle by 22% compared to vehicle mice. In the fasted only mice, final plasma insulin concentrations were 2.12 µIU/ml and this control level was decreased by up to 26% by the subject compound (30 and 100 mg/kg) and 39% by the control compound (30 mg/kg).

In the high fat fed mouse model, the subject compound dosed orally at 30 and 100 mg/kg per day for three days caused a dose-related reduction in body weight in the fasted and re-fed states. Additionally, the PASK inhibitor induced a concentration dependent decrease in liver weights in the fasted state with a similar trend in the re-fed state. These changes in body and liver weights were similar or equivalent to those produced by exposure to the control compound. Moreover, the subject compound treatment produced dose-dependent decreases in plasma glucose and insulin levels. These effects were noted in the fasted and re-fed states and were comparable or greater than that caused by the control compound exposure. Reductions in body weight, liver weight, plasma glucose and insulin concentrations are indicative of insulin resensitization and utility in correcting the phenotype of type II diabetes.

Rat High Fructose Model with Fast/Re-Feed

Another standard model of human hyperlipidemia and insulin resistance is the rat fed a high fructose diet for several weeks (33). Additionally, since hepatic lipid synthesis is known to be regulated by food consumption, the fast/reefed cycle of Horton et al. (32) was incorporated into the chronic high fructose diet model. A compound disclosed above was evaluated in this model as an agent to restore insulin sensitivity and lower blood lipids.

The study design is shown in Table 5.

TABLE 5

| Group | Test Article | Dose Level (mg/kg) | Dose Concentration (mg/mL) |
|---|---|---|---|
| 1 | Vehicle | 0 | 0 |
| 2 | Subject Compound | 30 | 3 |
| 3 | Subject Compound | 100 | 10 |
| 4 | Control | 30 | 3 |

Eight week old male Sprague Dawley rats were purchased from Harlan, Inc. The rats weighed 200-225 g upon arrival and were divided into groups as detailed in Table 2 and were immediately placed on a high fructose diet (60% kcal fructose; Open Source Diet #D00111301) ad libitum for three weeks. During the last week of feeding the high fructose diet, the rats were dosed with vehicle (5% solutol, 8% β cyclo-dextrin), subject compound at 30 mg/kg or 100 mg/kg or the control compound at 30 mg/kg by oral gavage once daily for 7 days. On the final day, all animals were placed on a 12 fast followed by a 12 re-feed period on the high fructose diet ad libitum. Body weights were monitored throughout the protocol. After completing the fast or fast/re-feed conditions, the rats were given avertin for anesthesia by intraperitoneal administration. Whole blood was collected by cardiac puncture and the rats were terminated by cervical dislocation. Livers were collected surgically, weighed and immediately frozen in liquid nitrogen. The blood was placed in Li-heparin treated tubes, centrifuged to collect plasma and the plasma frozen.

The plasma was analyzed by standard colorimetric assays for glucose, insulin, triglycerides and cholesterol.

As seen in FIG. 1, there was a significant increase in body weight of the control compound treated group compared to the Vehicle control group over the course of the drug treatment period of 7 days. Rats treated with the subject compound at 30 mg/kg displayed a modest increase in body weight relative to the Vehicle group. and animals treated with the subject compound at 100 mg/kg exhibited a modest decrease in body weight relative to the Vehicle group.

Liver weights from the high fructose diet rats treated with the subject compound and the control compound were measured. There was a small increase in liver weight in the the control compound treated rats of about 2 g, and only a slight trend of a dose related reduction in liver weights in the subject compound treated rats. The maximal reduction in liver weight observed at the 100 mg/kg dose of the subject compound in the rat high fructose model was about 4%. On the other hand, the control compound increased liver weights in these animals by about 15%.

The subject compound also caused dose related reductions in plasma glucose and insulin levels compared to vehicle treated rats. These effects were similar or greater than those produced by treatment with the control compound. Vehicle treated rats on the high fructose diet displayed mean plasma glucose and insulin concentrations of 205 mg/dl and 42.1 µIU/ml after the fast and re-feed cycle. Rats exposed to the subject compound for 7 days showed a decrease in plasma glucose of 21.5% and 26.3% in 30 and 100 mg/kg treated groups, respectively, compared to vehicle. The control compound did not alter plasma glucose concentrations. Insulin levels were reduced by 15.4% and 31.4% by subject compound exposure while the control compound rat insulin levels were decreased by 63.2%.

Subject compound treatment caused a clear dose-dependent reduction in plasma triglycerides and a slight trend to reduce plasma cholesterol as compared to vehicle control rats. Triglyceride and cholesterol levels in the vehicle rats fed the high fructose diet with fast and re-feed were 387 mg/dl and 69 mg/dl, respectively. The subject compound caused a 25.1% reduction in triglycerides in the 30 mg/kg group and a 54.3% reduction in the 100 mg/kg group. The control compound also decreased plasma triglycerides by 68% as compared to vehicle rats. Cholesterol concentrations were decreased by 5.7 and 10% in the subject compound-treated rats with 30 and 100 mg/kg treatment. However, the control compound increased plasma cholesterol by 17% with 30 mg/kg treatment.

The subject compound dosed orally at 30 and 100 mg/kg per day for seven days caused a dose-related reduction in body weight in the rats fed a high fructose diet with fast/re-feed. Additionally, the PASK inhibitor induced a slight trend for a concentration dependent decrease in liver weights in the rats. The control compound treatment caused an increase in body weight and liver weight in this model. The subject compound treatment produced dose-dependent decreases in plasma glucose and insulin levels. The subject compound greatly reduced plasma triglyceride concentrations and slightly reduced plasma cholesterol levels in a dose-related fashion in high fructose fed rats. All of these metabolic effects of the subject compound were comparable or greater than those caused by the control compound exposure. Reductions in body weight, liver weight, plasma glucose and insulin concentrations are indicative of insulin resensitization and utility in correcting the phenotype of type II diabetes. The dose related decreases in plasma triglycerides and cholesterol suggest an anti-hyperlipidemic profile.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for inhibiting purine-analog sensitive kinase (PASK) comprising contacting PASK with a compound of structural Formula I:

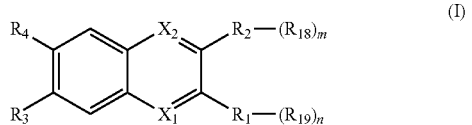

or a pharmaceutically acceptable salt, or ester thereof, wherein:

$X_1$ and $X_2$ are each N;

$R_1$ and $R_2$ are each independently selected from the group consisting of alkyl, cycloalkyl, heterocycloalkyl, aryl, heteroaryl, and $NR_5R_6$, any of which may be optionally substituted, with the proviso that at least one of $R_1$ or $R_2$ is $NR_5R_6$;

$R_3$ is hydrogen;

$R_4$ is selected from the group consisting of $COOR_7$, $NO_2$, $CONR_8R_9$, $CONR_{10}OR_{11}$, and tetrazolyl;

$R_5$ and $R_6$ are each independently selected from the group consisting of hydrogen, $C_1$-$C_6$ alkyl, $C_1$-$C_6$ alkenyl, $C_1$-$C_6$ alkynyl, $C_1$-$C_7$ cycloalkyl, $C_1$-$C_7$ heterocycloalkyl, aryl, heteroaryl, aralkyl, and heteroaralkyl, any of which may be optionally substituted; or taken together, $R_5$ and $R_6$ may form a heterocycloalkyl or heteroaryl, either of which may be optionally substituted;

$R_7$, $R_8$, $R_9$, $R_{10}$, and $R_{11}$ are each independently selected from the group consisting of hydrogen, $C_1$-$C_6$ alkyl, aryl, heteroaryl, aralkyl and heteroaralkyl, any of which may be optionally substituted;

$R_{18}$ and $R_{19}$ are independently selected from the group consisting of cycloalkyl, heterocycloalkyl, aryl, and heteroaryl, any of which may be optionally substituted; and m and n are each independently an integer from 0 to 2.

* * * * *